(12) United States Patent
Pachynski et al.

(10) Patent No.: US 11,938,193 B2
(45) Date of Patent: Mar. 26, 2024

(54) COMPOSITIONS COMPRISING CHEMERIN AND METHODS OF USE THEREOF

(71) Applicant: Washington University, St. Louis, MO (US)

(72) Inventors: Russell Pachynski, St. Louis, MO (US); Holbrook Kohrt, Palo Alto, CA (US); Jason Yonehiro, Palo Alto, CA (US); Brian Zabel, Palo Alto, CA (US)

(73) Assignee: Washington University, St. Louis, MO (US)

( * ) Notice: Subject to any disclaimer, the term of this patent is extended or adjusted under 35 U.S.C. 154(b) by 370 days.

(21) Appl. No.: 16/068,890

(22) PCT Filed: Jan. 9, 2017

(86) PCT No.: PCT/US2017/012725
§ 371 (c)(1),
(2) Date: Jul. 9, 2018

(87) PCT Pub. No.: WO2017/120589
PCT Pub. Date: Jul. 13, 2017

(65) Prior Publication Data
US 2019/0008982 A1  Jan. 10, 2019

Related U.S. Application Data

(60) Provisional application No. 62/276,595, filed on Jan. 8, 2016.

(51) Int. Cl.
| | |
|---|---|
| A61K 47/68 | (2017.01) |
| A61K 45/06 | (2006.01) |
| A61P 35/00 | (2006.01) |
| C07K 14/47 | (2006.01) |
| C07K 14/52 | (2006.01) |
| A61K 38/00 | (2006.01) |

(52) U.S. Cl.
CPC .......... *A61K 47/6813* (2017.08); *A61K 45/06* (2013.01); *A61K 47/6849* (2017.08); *A61K 47/6869* (2017.08); *A61P 35/00* (2018.01); *C07K 14/4702* (2013.01); *C07K 14/52* (2013.01); *C07K 14/521* (2013.01); *A61K 38/00* (2013.01); *C07K 2319/00* (2013.01); *C07K 2319/33* (2013.01); *C07K 2319/50* (2013.01)

(58) Field of Classification Search
CPC combination set(s) only.
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,173,414 A | 12/1992 | Lebkowski et al. | |
| 5,264,618 A | 11/1993 | Felgner et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 7,198,951 B2 | 4/2007 | Gao et al. | |
| 7,939,313 B2 | 5/2011 | Heyduk et al. | |
| 2004/0086966 A1* | 5/2004 | Wittamer | A61P 21/00 435/69.1 |
| 2005/0107583 A1 | 5/2005 | Jiang et al. | |
| 2005/0276812 A1* | 12/2005 | Ebens | C07K 16/28 530/391.1 |
| 2007/0213510 A1 | 9/2007 | Wittamer et al. | |
| 2010/0150950 A1* | 6/2010 | Coccia | A61P 37/02 435/375 |
| 2010/0189727 A1 | 7/2010 | Rodeck et al. | |
| 2013/0039888 A1 | 2/2013 | McCarty et al. | |
| 2013/0074199 A1 | 3/2013 | Spiegelman et al. | |
| 2013/0336925 A1 | 12/2013 | Alvarez et al. | |
| 2015/0202291 A1 | 7/2015 | Bosch et al. | |
| 2015/0218280 A1 | 8/2015 | Epstein et al. | |

FOREIGN PATENT DOCUMENTS

| | | |
|---|---|---|
| WO | 199513365 A1 | 5/1995 |
| WO | 199513392 A1 | 5/1995 |
| WO | 199617947 A1 | 6/1996 |
| WO | 199706243 A1 | 2/1997 |
| WO | 199708298 A1 | 3/1997 |
| WO | 199709441 A2 | 3/1997 |
| WO | 199721825 A1 | 6/1997 |

(Continued)

OTHER PUBLICATIONS

Pachynski et al. (JEM, 209(8): 1427-1435, 2012).*
Pachynski et al. (J. Exp. Med., 209(8): 1427-1435, 2012).*
Altschul, S. et al., "Basic Local Alignment Search Tool," J. Mo. Biol., 1990, pp. 403-410, vol. 215, Academic Press Limited.
Altschul, S. et al., "Gapped BLAST and PSI-BLAST: a new generation of protein database search programs," Nucl. Acid Res., 1997, pp. 3389-3402, vol. 25, No. 17, Oxford University Press.
Carter, B., "Adeno-associated virus vectors," Current Opin. Biotechnol., Oct. 1992, pp. 533-539, vol. 3, No. 5.

(Continued)

*Primary Examiner* — Nelson B Moseley, II
(74) *Attorney, Agent, or Firm* — Polsinelli PC

(57) ABSTRACT

The present disclosure provides compositions comprising chemerin and the methods of use thereof. The compositions of the disclosure are useful in the treatment of cancer.

17 Claims, 72 Drawing Sheets
(47 of 72 Drawing Sheet(s) Filed in Color)
Specification includes a Sequence Listing.

(56) References Cited

FOREIGN PATENT DOCUMENTS

| WO | | 199911764 | A2 | | 3/1999 | | |
|----|----|-----------|----|----|--------|----|----|
| WO | WO | 2004/027045 | | * | 4/2004 | | |
| WO | | 200183692 | A2 | | 11/2011 | | |
| WO | WO | 2014/025199 | | * | 2/2014 | ............. | C07K 19/00 |

OTHER PUBLICATIONS

Clark, K. et al., "A stable cell line carrying adenovirus-inducible rep and cap genes allows for infectivity titration of adeno-associated virus vectors," Gene Ther., Dec. 1996, pp. 1124-1132, vol. 3, No. 12.

Duque, S. et al., "Intravenous Administration of Self-complementary AAV9 Enables Transgene Delivery to Adult Motor Neurons," Mol. Ther., Jul. 2009, pp. 1187-1196, vol. 17, No. 7.

Foust, K. et al., "Intravascular AAV9 preferentially targets neonatal neurons and adult astrocytes," Nature Biotechnol., Jan. 2009, pp. 59-65, vol. 27, No. 1.

Gao, G. et al., "Clades of Adeno-Associated Viruses Are Widely Disseminated in Human Tissues," J. Virol., Jun. 2004, pp. 6381-6388, vol. 78, No. 12.

GenBank accession No. ACM47221.1, Jul. 27, 2010, 1 pg.
GenBank accession No. ACX51147.1, Aug. 3, 2010, 1 pg.
GenBank accession No. AKQ62908.1, Jul. 21, 2015, 1 pg.
GenBank accession No. AKR17020.1, Jul. 30, 2015, 1 pg.
GenBank accession No. CAG46789.1, Oct. 16, 2008, 2 pgs.
GenBank accession No. CR541992.1, Oct. 16, 2008, 2 pgs.
GenBank accession No. CR542026.1, Jul. 26, 2016, 2 pgs.
GenBank accession No. NM_002889.3, Aug. 19, 2018, 4 pgs.
GenBank accession No. NP_001013445.1, May 27, 2018, 3 pgs.
GenBank accession No. NP_001127631.1, May 28, 2018, 1 pg.
GenBank accession No. NP_001135487.1, Oct. 29, 2016, 1 pg.
GenBank accession No. NP_001231216.1, May 31, 2018, 2 pgs.
GenBank accession No. NP_002880.1, May 31, 2018, 2 pgs.
GenBank accession No. NP_082128.1, Jun. 2, 2018, 3 pgs.

Hermonat, P. et al., "Use of adeno-associated virus as a mammalian DNA cloning vector: Transduction of neomycin resistance into mammalian tissue culture cells," PNAS, Oct. 1984, pp. 6466-6470, vol. 81.

International Search Report and Written Opinion dated Mar. 31, 2017 from related International Patent Application No. PCT/US2017/012725; 16 pgs.

Kaplitt, M. et al., "Safety and tolerability of gene therapy with an adeno-associated virus (AAV) borne GAD gene for Parkinson's disease: an open label, phase I trial," Lancet, Jun. 23, 2007, pp. 2097-2105, vol. 369.

Karlin, S. et al., "Methods for assessing the statistical significance of molecular sequence features by using general scoring schemes," PNAS, Mar. 1990, pp. 2264-2268, vol. 87.

Kim, J. et al., "Chemerin Suppresses Ovarian Follicular Development and Its Potential Involvement in Follicular Arrest in Rats Treated Chronically With Dihydrotestosterone," Endocrinology, Aug. 2013, pp. 2912-2923, vol. 154, No. 8.

Kolate, A. et al., "PEG—A versatile conjugating ligand for drugs and drug delivery systems," J. Controlled Release, Oct. 2014, pp. 67-81, vol. 192.

Laughlin, C. et al., "Cloning of infectious adeno-associated virus genomes in bacterial plasmids," Gene, Jul. 1983, pp. 65-73, vol. 23, No. 1.

Lebkowski, J. et al., "Adeno-Associated Virus: a Vector System for Efficient Introduction and Integration of DNA into a Variety of Mammalian Cell Types," Mol. Cell Biol., Oct. 1988, pp. 3988-3996, vol. 8, No. 10.

Lin, W. et al., "Reduced Expression of Chemerin is Associated with a Poor Prognosis and a Lowed Infiltration of Both Dendritic Cells and Natural Killer Cells in Human Hepatocellular Carcinoma," Clin. Lab., 2011, pp. 879-885, vol. 57, Nos. 11-12.

Lin, P-C. et al., "Epigenomic Alterations in Localized and Advanced Prostate Cancer," Neoplasia, Apr. 2013, pp. 373-383, vol. 15, No. 4.

Marks, W. et al., "Safety and tolerability of intraputaminal delivery of CERE-120 (adeno-associated virus serotype 2-neurturin) to patients with idiopathic Parkinson's disease: an open-label, phase I trial," Lancet Neurol., May 2008, pp. 400-408, vol. 7.

Mclaughlin, S. et al., "Adeno-Associated Virus Transduction Vectors: Analysis of Proviral Structures," J. Virol., Jun. 1988, pp. 1963-1973, vol. 62, No. 6.

Muzyczka, N., "Use of Adeno-Associated Virus as a General Transduction Vector for Mammalian Cells," In: Muzcyczka, M. (eds) Viral Expression Vectors. Current Topics in Microbiology and Immunology, 1992, pp. 97-129, vol. 158, Springer, Berlin Heidelberg.

Pacak, C. et al., "Recombinant Adeno-Associated Virus Serotype 9 Leads to Preferential Cardiac Transduction In Vivo," Circ. Res., Aug. 16, 2006, e3-e9, vol. 99.

Pachynski, R. et al., "The chemoattractant chemerin suppresses melanoma by recruiting natural killer cell antitumor defenses," J. Exp. Med., 2012, pp. 1427-1435, vol. 209, No. 8, The Rockefeller University Press.

Paul, R. et al., "Increased Viral Titer Through Concentration of Viral Harvests from Retroviral Packaging Lines," Human Gene Therapy, Oct. 1993, pp. 609-615, vol. 4. No. 5.

Perrin, P. et al., "An experimental rabies vaccine produced with a new BHK-21 suspension cell culture process: use of serum-free medium and perfusion-reactor system," Vaccine, 1995, pp. 1244-1250, vol. 13, No. 13.

Rossi, A. et al., "Analysis of protein-ligand interactions by fluorescence polarization," Europe PMC Funders Group. Author Manuscript, Sep. 3, 2011, pp. 1-43, published in final edited form as: Nat. Protoc., Mar. 2011, pp. 365-387, vol. 6, No. 3.

Ruffing, M. et al., "Mutations in the carboxy terminus of adeno-associated virus 2 capsid proteins affect viral infectivity: lack of an RGD integrin-binding motif," J. Gen. Virol., 1994, pp. 3385-3392, vol. 75, SGM, Great Britain.

Samulski, R. et al., "Cloning of adeno-associated virus into pBR322: Rescue of intact virus from the recombinant plasmid in human cells," PNAS, Mar. 1982, pp. 2077-2081, vol. 79.

Samulski, R. et al., "Helper-Free Stocks of Recombinant Adeno-Associated Viruses: Normal Integration Does Not Require Viral Gene Expression," J. Virol., Sep. 1989, pp. 3822-3828, vol. 63, No. 9.

Senapathy, P. et al., "Molecular Cloning of Adeno-associated Virus Variant Genomes and Generation of Infectious Virus by Recombination in Mammalian Cells," J. Biol. Chem., Apr. 10, 1984, pp. 4661-4666, vol. 259, No. 7.

Srivastava, A. et al., "Nucleotide Sequence and Organization of the Adeno-Associated Virus 2 Genome," J Virol, Feb. 1983, pp. 555-564, vol. 45, No. 2.

Tratschin, J-D. et al., "A Human Parvovirus, Adeno-Associated Virus, as a Euraryotic Vector: Transient Expression and Encapsidation of the Procaryotic Gene for Chloramphenicol Acetyltransferase," Mol. Cell. Biol., Oct. 1984, pp. 2072-2081, vol. 4, No. 10.

Tratschin, J-D. et al., "Adeno-Associated Virus Vector for High Frequency Integration, Expression, and Rescue of Genes in Mammalian Cells," Mol. Cell. Biol., Nov. 1985, pp. 3251-3260, vol. 5, No. 11.

Wang, Z. et al., "Adeno-associated virus serotype 8 efficiently delivers genes to muscle and heart," Nat. Biotechnol., Mar. 2005, pp. 321-328, vol. 23, No. 3.

Worgall, S. et al., "Treatment of Late Infantile Neuronal Ceroid Lipofuscinosis by CNS Administration of a Serotype 2 Adeno-Associated Virus Expressing CLN2 cDNA," Hum. Gene Ther, May 2008, pp. 463-474, vol. 19, Mary Ann Liebert, Inc.

Zincarelli, C. et al., "Analysis of AAV Serotypes 1-9 Mediated Gene Expression and Tropism in Mice After Systemic Injection," Mol. Ther., Jun. 2008, pp. 1073-1080, vol. 16, No. 6.

Moore, James E., et al., Chemokine Transport Dynamics and Emerging Recognition of Their Role in Immune Function, Curr Opin Biomed Eng., Mar. 2018, vol. 5, pp. 90-95.

* cited by examiner

COMPOSITIONS COMPRISING CHEMERIN AND METHODS OF USE THEREOF

CROSS REFERENCE TO RELATED APPLICATIONS

This application claims the benefit of U.S. Provisional Application No. 62/276,595, filed Jan. 8, 2016, and International Application No. PCT/US17/12725, filed Jan. 9, 2017 the disclosures of which are hereby incorporated by reference in their entirety.

GOVERNMENTAL RIGHTS

This invention was made with government support under grant number CA169354 awarded by National Institutes of Health. The government has certain rights in the invention.

FIELD OF THE INVENTION

The present disclosure provides compositions comprising chemerin and the methods of use thereof. The compositions of the disclosure are useful in the treatment of cancer.

BACKGROUND OF THE INVENTION

Chemerin is a tumor suppressive cytokine that acts by recruiting host immune defenses. Additionally, chemerin is downregulated in many cancers. For example, in prostate cancer, RARRES2 (the gene that encodes chemerin) has been found to be one of the most downregulated genes when comparing normal prostate tissue to prostate cancer. Thus, novel methods are needed to increase the level of chemerin in tumors.

SUMMARY OF THE INVENTION

In an aspect, the disclosure provides a polynucleotide sequence encoding a polypeptide, the polypeptide comprising chemerin linked via a linker to a targeting moiety, wherein the targeting moiety is capable of directing the chemerin to a target site on a cell.

In another aspect, the disclosure provides an isolated polypeptide sequence encoded by a polynucleotide sequence of the disclosure.

In still another aspect, the disclosure provides a vector comprising a polynucleotide sequence of the disclosure.

In still yet another aspect, the disclosure provides a composition comprising a chemerin linked via a linker to a targeting moiety, wherein the targeting moiety is capable of directing the chemerin to a target site on a cell.

In a different aspect, the disclosure provides a method to deliver a chemerin to a target cell, the method comprising contacting a target cell with a composition of the disclosure.

In other aspects, the disclosure provides a method to recruit immune cells to a tumor in a subject, the method comprising administering to the subject a composition comprising a chemerin linked via a linker to a targeting moiety, wherein the targeting moiety is capable of directing the chemerin to a target site on a cancer cell of the tumor.

In still other aspects, the disclosure provides a method to increase phosphatase and tensin homolog (PTEN) expression in a tumor in a subject, the method comprising administering to the subject a composition comprising a chemerin linked via a linker to a targeting moiety, wherein the targeting moiety is capable of directing the chemerin to a target site on a cancer cell of the tumor.

In still yet other aspects, the disclosure provides a method to treat, stabilize or prevent cancer in a subject, the method comprising administering to the subject a composition comprising a chemerin linked via a linker to a targeting moiety, wherein the targeting moiety is capable of directing the chemerin to a target sit on a cancer cell of a tumor and thereby recruiting immune cells to the tumor.

BRIEF DESCRIPTION OF THE FIGURES

The application file contains at least one drawing executed in color. Copies of this patent application with color drawing(s) will be provided by the Office upon request and payment of the necessary fee.

(FIG. 1A) Control or chemerin-expressing B16 melanoma growth in C57BL/6 mice. (FIG. 1B) Total CD45+ TIL in tumors at day 17. (FIG. 1C) TIL subset analysis of control vs chemerin-expressing tumors at day 17. On average, the frequency of conventional DC (Lin$^-$B220$^-$CD11c$^+$), T cells, and NK cells was increased in chemerin-expressing tumors, with a concomitant decrease in the percentage of myeloid derived suppressor cells (MDSC, Lin$^-$CD11 b$^+$GR1$^+$) and pDC (Lin$^-$B220$^+$CD11c$^{int}$PDCA1$^+$) which are considered tolerogenic. Significance of differences in sample groups was determined using the unpaired Student's t-test. *p<0.05

(FIG. 2A, FIG. 2B) prostate cancer, (FIG. 2C) lung cancer, (FIG. 2D) breast cancer, (FIG. 2E) colon cancer, and (FIG. 2F) melanoma.

FIG. 15D depicts that the B16 CD20+ cells express CD20 (light blue).

FIG. 16C depicts that the B16 CD20+ cells express CD20 (orange).

FIG. 21A shows the control (saline injection) where B16 CD20+ cells are light blue and B16 WT cells are darker blue. FIG. 21B shows injection with the fusion protein where B16 CD20+ cells are cyan and B16 WT cells are black. FIG. 21C depicts that the B16 CD20+ cells express CD20 (purple).

FIG. 22A show the amount of CD20 expression with B16 CD20+ cells in cyan and B16 WT cells in red. FIG. 22B shows the amount of AF647 cells B16 CD20+ cells in purple, B16 WT cells in black and B16 unstained cells in dotted line.

(FIG. 29A) Real-time RT-PCR results of PTEN mRNA expression in prostate cancer cells treated with vehicle (Control) or 6 nM recombinant chemerin (rChem). PTEN Expression is normalized to GAPDH loading control for each sample (*$P<0.01$, n=4). (FIG. 29B) Real-time RT-PCR results of PTEN mRNA expression in Ewing sarcroma (SKES) and osteosarcoma (U2OS) cells treated with PBS (Control) or 6 nM recombinant chemerin. PTEN Expression is normalized to GAPDH loading control for each sample (*$P<0.01$, n=4). (FIG. 29C) Representative western blots for PTEN protein expression in RWPE-1 no treatment (NT), PC3, and DU145 cells treated with vehicle (Control) or 6 nM Chemerin for 48 h. (FIG. 29D) Representative western blot for PTEN protein expression in SKES and U2OS cells treated with PBS (Control) or 3 nM or 6 nM Chemerin for 48 h. (FIG. 29E) Quantified western blot results showing PTEN protein expression in control or Chemerin treated PC3 cells. Normalized to Actin or GAPDH loading control for each respective sample (*$P<0.05$, n=3). (FIG. 29F) Quantified western blot results for PTEN protein expression in PBS (Control) or Chemerin treated U2OS sarcoma cells. Each sample is normalized to GAPDH loading control. Each sample set was independently repeated three times (*$P<0.05$, n=3).

(FIG. 30A, FIG. 30B, FIG. 30C) Real-time RT-PCR results of PTEN mRNA expression in DU145 (FIG. 30A), SKES (FIG. 30B), U2OS (FIG. 30C) cancer cells transfected with the following groups: Mock (no siRNA), Control siRNA (non-specific sequence), or CMKLR1 siRNA. Following transfection, each respective group was treated with PBS (Control) or 6 nM recombinant chemerin. PTEN expression is normalized to GAPDH loading control for each sample (*$P<0.01$, n=4. NS=No significant difference). (FIG. 30D, FIG. 30E, FIG. 30F) Representative western blot for PTEN protein expression in the transfected DU145 (FIG. 30D), SKES (FIG. 30E), U2OS (FIG. 30F) cell subsets treated with PBS or 6 nM chemerin for 48 h. (FIG. 30G, FIG. 30H, FIG. 30I) Quantified western blot results showing PTEN protein expression in PBS or Chemerin treated DU145 (FIG. 30G), SKES (FIG. 30H), U2OS (FIG. 30I) cells following transfection. Sample expression is normalized to GAPDH loading control (*$P<0.05$, n=3).

(FIG. 31A) DU145, (FIG. 31B) SKES, (FIG. 31C) U2OS. (FIG. 31D, FIG. 31D) Representative 4× images showing tumor cell invasion normalized to baseline cell migration, No matrigel matrix and No FBS (n=4). The following groups were compared: No matrigel–No FBS, No matrigel–CM+10% FBS, 1 mg/mL matrigel+cells treated with 48 h PBS, or 1 mg/mL matrigel+cells treated with 48 h 6 nM recombinant human chemerin (rHchemerin). Scale bar=100 µm. (FIG. 31F) Quantified tumor cell invasion results for each respective tumor cell line comparing matrigel invasion in cells treated with PBS (vehicle) or 6 nM rChemerin for 48 h. Following treatment, cells were allowed to migrate for 24 h. Cells were fixed with methanol and stained with 0.1% Crystal violet. After imaging, cells were lysed with 10% acetic acid. To quantify, each sample absorbance was read in duplicate at 590 nm. Each respective absorbance is normalized to the baseline migration when using a no matrigel and no FBS control setup (*$P<0.05$, n=4). The invaded or migrated cells attached to the other side of the insert membrane were imaged under a light microscope (Nikon) in four random fields. Three independent experiments were performed for each subset and condition. Numbers of invasive or migrated cells under different treatments were normalized to the negative control, consisting of no matrigel and no FBS driven gradient. They were expressed as a means of invasion compared to the control±SEM.

(FIG. 32A, FIG. 32B, FIG. 32D, FIG. 32E, FIG. 32G, FIG. 32H) Representative 4× images showing tumor cell invasion of PBS or rChemerin treated (FIG. 32A, FIG. 32B) DU145, (FIG. 32D, FIG. 32E) U2OS, and (FIG. 32F, FIG. 32H) SKES cells transfected with Mock (no siRNA), Control siRNA, or CMKLR1 siRNA. Each sample set and condition were performed in triplicate wells. Overall migration was normalized to baseline cell migration using No matrigel matrix and No FBS gradient (n=3). Each of the following groups were compared: No matrigel–No FBS, No matrigel–CM+10% FBS, 1 mg/mL matrigel+cells treated with 48 h PBS, or 1 mg/mL matrigel+cells treated with 48 h 6 nM recombinant human chemerin (rHchemerin). Scale bar=100 µm. (FIG. 32C, FIG. 32F, FIG. 32I) Quantified tumor cell invasion results for each subset of transfected (FIG. 32C) DU145, (FIG. 32F) U2OS, and (FIG. 32I) SKES cells. Each set was treated with either PBS (vehicle) or 6 nM Chemerin for 48 h. Following treatment, cells were allowed to migrate for 24 h. Cells were fixed with methanol and stained with 0.1% Crystal violet. After imaging, cells were lysed with 10% acetic acid. As previously described, the relative sample absorbance was read in duplicate at 590 nm. Each respective sample absorbance is normalized to baseline migration using the no matrigel and no FBS control (*$P<0.05$, n=4. NS=No significant difference).

(FIG. 33A) RWPE-1, (FIG. 33B) PC3, (FIG. 33C) DU145. (FIG. 33D) Repesentative Western blot for CMKLR1 expression, normalized to GAPDH loading control. (FIG. 33E) SKES, (FIG. 33F) U2OS, (FIG. 33G) HT-1080 Fibrosarcoma cells. (FIG. 33H) Representative Western blot for CMKLR1 expression, normalized to actin loading control.

(FIG. 35A, FIG. 35B, FIG. 35E, FIG. 35F) Western blot analysis for CMKLR1 expression after transfection with siRNA. Loading control bands are probed with anti-GAPDH antibody on the same blot. DU145 (FIG. 35A), PC3 (FIG. 35B), SKES (FIG. 35E), and U2OS (FIG. 35F) cells were transfected with either control siRNA or siRNA against CMKLR1. Relative band intensity was quantified and analyzed based on results from three independent experiments, and presented as a ratio to the baseline CMKLR1 expression in non-transfected cells (n=3). (FIG. 35C, FIG. 35D, FIG. 35G, FIG. 35H) Western blot analysis for CMKLR1 expression. Transfection of CMKLR1 siRNA, but not control siRNA, resulted in a significant decrease in CMKLR1 expression. *$P<0.01$ compared to non-transfected (NT) cells.

(FIG. 37A) DU145, (FIG. 37B) PC3, (FIG. 37C) SKES, (FIG. 37D) U2OS.

DETAILED DESCRIPTION OF THE INVENTION

Figure 1A:
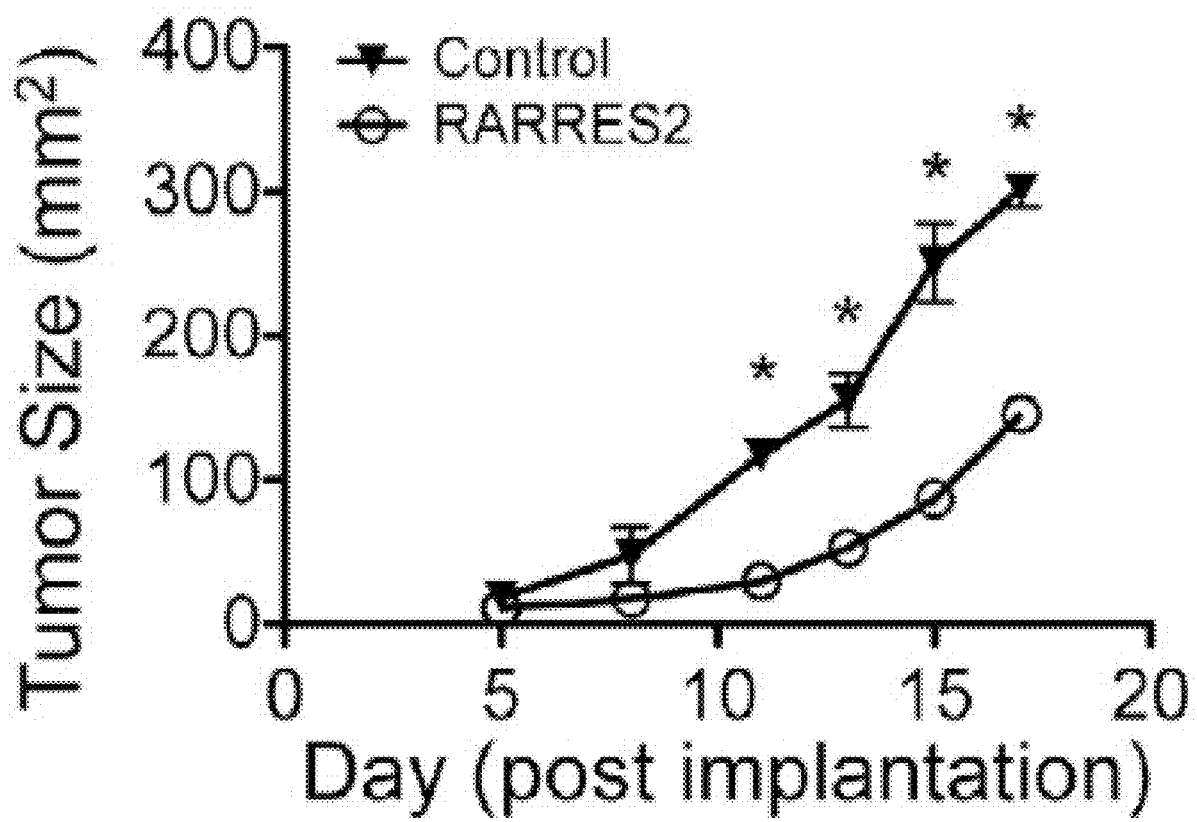
FIG. 1A, FIG. 1B and FIG. 1C depict graphs showing that chemerin is tumor suppressive and favorably alters tumor infiltrating leukocyte profiles.

The disclosure describes a novel fusion protein comprising a targeting moiety, such as a single chain variable fragment (scFv), linked to chemerin. The targeting moiety binds a specific protein, typically a surface protein that is specific or unique to a particular tumor. The fusion protein may also comprise a linker. In some instances the linker is cleavable via specific proteases that are upregulated in the tumor microenvironment. As chemerin is a leukocyte chemoattractant, the presence of chemerin in the tumor microenvironment recruits immune cells. These immune cells may then activate and lyse the cells of the tumor. Additionally, it has been discovered that chemerin can upregulate PTEN expression. PTEN is a tumor suppressor gene that is very commonly downregulated, mutated, or lost in tumors and contributes to tumor formation and/or progression. Accordingly, a fusion protein of the disclosure may also be used in treating a tumor.

Specific aspects of the invention are described in detail below.

I. COMPOSITION

In an aspect, the disclosure provides a composition comprising chemerin linked to a targeting moiety, wherein the targeting moiety is capable of directing the chemerin to a target site on a cell. The composition may further comprise a linker to connect chemerin to the targeting moiety. Chemerin, the targeting moiety and the linker are described in greater detail below. It should be understood that chemerin as described in detail below can be linked to any of the targeting moieties described in detail below in the absence or presence of any of the linkers described below. In another aspect, the disclosure provides a polynucleotide sequence encoding chemerin, a targeting moiety, and optionally a linker and a vector comprising the polynucleotide sequence. In still another aspect, the disclosure provides a polypeptide encoded by a polynucleotide of the disclosure.

(a) Chemerin

As used herein "chemerin", also referred to as retinoic acid receptor responder protein 2 (RARRES2), tazarotene-induced gene 2 protein (TIG2), or RAR-responsive protein TIG2, is a 14 kDa chemoattractant protein that acts as a ligand for the G protein-coupled receptor CMKLR1 (also known as ChemR23). In humans, chemerin is encoded by the RARRES2 gene. The term chemerin includes the active or inactive version of chemerin. The inactive version of chemerin, or pro-form may also be termed "prochemerin." Prochemerin is activated through cleavage of the C-terminus by inflammatory and coagulation serine proteases. The term chemerin also includes variants of chemerin such a truncated or mutated forms of chemerin, provided the truncated or mutated form of chemerin functions as the active version of chemerin (i.e. chemoattractant). The sequence information for the full length human chemerin amino acid sequence can be found using, for example, the GenBank accession number CAG46789.1 or NP_002880.1. The sequence information for the full length human chemerin gene sequence can be found using, for example, the GenBank Gene ID number 5919 or the full length human chemerin mRNA sequence can be found using, for example, the GenBank accession number CR542026.1 or CR541992.1 or NM_002889.3.

A skilled artisan will appreciate that chemerin may be found in a variety of species. Non-limiting examples include mouse (NP_018128.1), cattle (ACM47221.1), boar (ACX51147.1), goat (AKR17020.1), rat (NP_001013445.1), chicken (AKQ62908.1), hamster (NP_001231216.1), orangutan (NP_001127631.1), and frog (NP_001135487.1). It is appreciated that the present disclosure is directed to analogs of chemerin in other organisms and is not limited to the human analog. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the disclosure. Equally, BLAST protein searches may be performed with the BLASTX program to obtain amino acid sequences that are homologous to a polypeptide of the disclosure. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to chemerin.

In one embodiment, chemerin comprises the amino acid sequence set forth in SEQ ID NO:1 (MRRLLIPLALWL-GAVGVGVAELTEAQRRGLQVA-LEEFHKHPPVQWAFQETSVESAVD TPFPAGIFVR-LEFKLQQTSCRKRDWKKPECKVRPNGRKRKCLACI KLGSEDKVLGRLV HCPIETQVLRE-AEEHQETQCLRVQRAGEDPHSFYFPGQFAFSKAL-PRS). SEQ ID NO:1 is human prochemerin comprising a 20-amino acid hydrophobic signal peptide. In another embodiment, chemerin comprises the amino acid sequence set forth in SEQ ID NO:2 (ELTEAQRRGLQVA-LEEFHKHPPVQWAFQETSVESAVDTPFPAGIFVR-LEFKLQQTSC RKRDWKKPECKVRPN-GRKRKCLACIKLGSEDKVLGRLVHCPIETQVLREAE EHQETQ CLRVQRAGEDPHSFYFPGQFAFSKALPRS). SEQ ID NO:2 is mature human prochemerin with the signal peptide removed. In still another embodiment, chemerin comprises the amino acid sequence set forth in SEQ ID NO:2, wherein 1 to 10 amino acids are absent from the C-terminus. The cleavage of amino acids from the C-terminus of chemerin represents the active from of chemerin. In certain embodiments, 5, 6, 7, 8 or 9 amino acids are absent from the C-terminus of SEQ ID NO:2. In a specific embodiment, 6 amino acids are absent from the C-terminus of SEQ ID NO:2. In another specific embodiment, chemerin comprises the amino acid sequence set forth in SEQ ID NO:3 (ELTEAQRRGLQVALEEFHKHPPVQWAFQETSVESAV-DTPFPAGIFVRLEFKLQQTSC RKRDWKKPECKVRPN-GRKRKCLACIKLGSEDKVLGRLVHCPIETQVLRE-AEEHQETQ CLRVQRAGEDPHSFYFPGQFAFS). SEQ ID NO:3 is mature human chemerin with the signal peptide removed. In still another specific embodiment, chemerin comprises the amino acid sequence set forth in SEQ ID NO:22 (ELSETQRRSLQVA-LEEFHKHPPVQLAFQEIGVDRAEEVLFSAGTFVR-LEFKLQQTNCP KKDWKKPECTIKPNGRRRKCLA-CIKMDPKGKILGRIVHCPILKQGPQDPQELQCIKIAQ AGEDPHGYFLPGQFAFSRALRTK). SEQ ID NO:22 is mature mouse prochemerin. In still yet another specific embodiment, chemerin comprise the amino acid sequence set forth in SEQ ID NO:23 (ELSETQRRSLQVA-LEEFHKHPPVQLAFQEIGVDRAEEVLFSAGTFVR-LEFKLQQTNCP KKDWKKPECTIKPN-GRRRKCLACIKMDPKGKILGRIVHCPILKQGPQDPQE LQCIKIAQ AGEDPHGYFLPGQFAFS). SEQ ID NO:23 is mature mouse chemerin.

In an embodiment, chemerin is a sequence comprising at least 80% identity to SEQ ID NO:1, SEQ ID NO:2, SEQ ID NO:3, SEQ ID NO:22 or SEQ ID NO:23. For example, the chemerin may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO: 1, SEQ ID NO:2, SEQ ID NO:3, SEQ ID NO:22 or SEQ ID NO:23.

In certain embodiments, chemerin may be PEGylated for improved systemic half-life and reduced dosage frequency. In an embodiment, PEG may be added to chemerin. As such, a composition of the disclosure may comprise chemerin comprising PEG. In an embodiment, PEG may be selected from the group consisting of PEG-10K, PEG-20K and PEG-40K. Methods of conjugating PEG to a protein are standard in the art. For example, see Kolate et al, *Journal of Controlled Release* 2014; 192(28): 67-81, which is hereby incorporated by reference in its entirety. Still further, chemerin may be modified to remove T cell epitopes. T cell epitopes can be the cause of an immunogenicity issue upon administration of a composition to a subject. Through their presentation to T cells, they activate the process of anti-drug antibody development. Preclinical screening for T cell epitopes may be performed in silico, followed by in vitro and in vivo validation. T cell epitope-mapping tools such as EpiMatrix can be highly accurate predictors of immune response. Deliberate removal of T cell epitopes may reduce immunogenicity. Other means of improving the safety and efficacy of a composition of the disclosure by reducing their immunogenicity include humanization and PEGylation.

(b) Targeting Moiety

As used herein, a "targeting moiety" is a polypeptide that is able to direct the entity to which it is attached (e.g. a chemerin) to a target site. Target sites may include, but are not limited to, the cell surface, a cell-surface protein, polypeptide, glycoprotein, lipid, or sugar residue, and an intracellular vesicle. A targeting moiety specifically binds to a target site on a target cell. The phrase "specifically binds" herein means a targeting moiety binds to a target site with an affinity ($K_d$) in the range of at least 0.1 mM to 1 pM, or in the range of at least 0.1 pM to 200 nM, or in the range of at least 0.1 pM to 10 nM. Methods of determining whether a targeting moiety binds to a target site are known in the art. For instance, see the Rossi and Taylor, *Nature Protocols* 2011; 6: 365-387.

In certain embodiments, a target site is on a cancer cell. Accordingly, a targeting moiety is a polypeptide that is able to direct the entity to which it is attached (e.g. a chemerin) to a target site on a cancer cell. A target site on a cancer cell may be a tumor-specific antigen (TSA) or a tumor-associated antigen (TAA). As used herein, a "tumor-specific antigen" is a protein, polypeptide, glycoprotein, lipid, sugar residue, etc. that is only present on tumor cells and not on any other cell. As used herein, a "tumor-associated antigen" is a protein, polypeptide, glycoprotein, lipid, sugar residue, etc. which is present on some tumor cells and also some normal cells. Without wishing to be bound by theory, in general, a TAA on a cancer cell may also be found on a normal cell, however, in the cancer cell the TAA is overexpressed relative to the expression of that same TAA on a normal cell. In an embodiment, a "target site on a cancer cell" is a protein, polypeptide, glycoprotein, lipid, sugar residue, etc. that is embedded within the plasma membrane surface of the cancer cell. In a specific embodiment, a "target site on a cancer cell" is a protein that is embedded within the plasma membrane surface of the cancer cell. A "protein that is embedded within the plasma membrane surface" may also be referred to as a receptor. Non-limiting examples of proteins associated with cancer cells include those listed in Table A. In certain embodiments, the target site on a cancer cell may be selected from the group consisting of CD20, HER2, EGFR, PSCA and PSMA. In another specific embodiment, the target site on a cancer cell is CD20. In still another specific embodiment, the target site on a cancer cell is PSCA.

TABLE A

| 3H11 | BDLF3 | CDCA1 | EGFRvIII | GLUT receptor | KIT | MMP9 | PAR1 | RSL1D1 | TEKT5 |
|---|---|---|---|---|---|---|---|---|---|
| 5T4 | BFR2 | CDCP1 | EI24 | Glypican-3 | KLF4 | MMP25 | PAR4 | RTKN | TEX101 |
| αvβ3-integrin | BGLF4 | CDH3 | EIF4EBP1 | GML | KLHL41 | MOB3B | $P2Y_2$ | RUNX1 | TEX14 |
| A1BG | BHLF1 | CDK2AP1 | ELF3 | GNA11 | KLK10 | MORC1 | PCM1 | RUNX2 | TEX15 |
| A33 | BHRF1 | CDK4 | ELF4 | GNAQ | KMT2D | MPHOSPH1 | PCNXL2 | RYK | TF |
| A4GALT | BILF1 | CDK7 | ELOVL4 | GNB2L1 | KOC1 | MPP3 | PDGFB | S1P | TFDP3 |
| AACT | BILF2 | CDKN1A | EMP1 | GOLGA5 | K-ras | MPL | PDGFRA | SAGE1 | TFE3 |
| AAG | BIN1 | CDKN2A | ENAH | gp100 | KRIT1 | MRAS | PEPP2 | SART2 | TGFBR1 |
| ABCB1 | BING-4 | CEA | Endosialin | gp75 | KU-CT-1 | MRP1 | PGF | SART3 | TGFBR2 |
| ABI1 | BIRC7 | CEACAM1 | ENO1 | Gp96 | KW-12 | MRP3 | PGK1 | SASH1 | THEG |
| ABI2 | BLLF1 | CENPK | ENO2 | GPAT2 | KW-2 | MRPL28 | PGRMC1 | sCLU | TIPRL |

TABLE A-continued

| | | | | | | | | | |
|---|---|---|---|---|---|---|---|---|---|
| ABL1 | BLLF2 | CEP162 | ENO3 | GPATCH2 | KW-5 (SEBD4) | MRPL30 | PHLDA3 | SCP-1 | TLR2 |
| ABL-BCR | BMI1 | CEP290 | ENTPD5 | GPM6a | KW-7 | MRPS11 | PHLPP1 | SCRN1 | TMEFF1 |
| ABLIM3 | BMLF1 | CEP55 | EP2 | GPNMB | L1CAM | MSLN | PIAS1 | SDCBP | TMEFF2 |
| ABLL | BMPR1B | CFL1 | EP4 | GPR143 | L53 | MTA1 | PIAS2 | SDF-1 | TMEM108 |
| ABTB1 | BMRF1 | CH3L2 | EpCAM | GPR161 | L6 | MTA2 | PIK3CA | SDHD | TMEM127 |
| ACACA | BNLF2a | CHEK1 | EPHA2 | GPR30 | LAG3 | MTA3 | PIK3CD | SEC31A | TMPRSS12 |
| ACBD4 | BNLF2b | CK2 | EPHA3 | GPR89A | Lage-1 | MTCP1 | PIK3R2 | SEC63 | TNC |
| ACO1 | BNRF1 | CLCA2 | EPHB2 | GRB2 | LATS1 | MTSS1 | PIM1 | Semaphorin 4D | TNFRSF17 |
| ACRBP | BRAF1 | CLOCK | EPHB4 | GRP75 | LATS2 | MUC-1 | PIM2 | SEMG1 | TNFSF15 |
| ACTHR | BRD4 | CLPP | EPHB6 | GRP78 | LCMT2 | MUC-2 | PIM3 | SEPT2 | TNK2 |
| ACTL6A | BRDT | CMC4 | EPS8 | GRPR | LCP1 | MUC-5AC | PIR | SFN | TOMM34 |
| ACTL8 | BRI3BP | CML66 | ERBB3 | GUCY1A3 | LDHC | MUM1 | PIWIL1 | SH2B2 | TOP2A |
| ACTN4 | BRINP1 | CO-029 | ERBB4 | H3F3A | LDLR | MUM2 | PIWIL2 | SH2D1B | TOP2B |
| ACVR1 | BRLF1 | COTL1 | EREG | HAGE | LEMD1 | MYB | PKN3 | SH3BP1 | TOR3A |
| ACVR1B | BTBD2 | COX6B2 | ERG | hANP | Lengsin | MYC | PLA2G16 | SHB | TP73 |
| ACVR2B | BUB1B | CPSF1 | ERVK-18 | HBEGF | LETMD1 | MYCL | PLAC1 | SHC3 | TPA1 |
| ACVRL1 | BVRF2 | CPXCR1 | ERVK-19 | hCG-beta | LGALS3BP | MYCLP1 | PLAG1 | SIRT2 | TPGS2 |
| ACS2B | BXLF1 | CREBL2 | ESR1 | HDAC1 | LGALS8 | MYCN | PLAUR | SIVA1 | TPI1 |
| ACSL5 | BZLF1 | CREG1 | ETA | HDAC2 | LH receptor | MYD88 | PLEKHG5 | SKI | TPL2 |
| ADAM-15 | C15orf60 | Cripto | ETAA1 | HDAC3 | LIN7A | MYEOV | PLK3 | SLBP | TPM4 |
| ADAM17 | CA 125 | CRISP2 | ETB | HDAC4 | LIPI | MYO1B | PLS3 | SLC22A10 | TPO |
| ADAM2 | CA 19-9 | CRK | ETS1 | HDAC5 | LIV-1 | NA17-A | PLVAP | SLC25A47 | TPPP2 |
| ADAM29 | CA195 | CRKL | ETS2 | HDAC6 | LLGL1 | NA88-A | PLXNB1 | SLC3A2 | TPR |
| ADAM7 | CA9 | CRLF2 | ETV1 | HDAC7 | LMO1 | NAE1 | PLXNB2 | SLC35A4 | TPTE |
| ADAP1 | CABYR | CT45 | ETV5 | HDAC8 | LMO2 | Napsin-A | PML | SLC45A3 | TRAF5 |
| ADFP | CADM4 | CT45A2 | ETV6 | HDAC9 | LMP1 | NAT6 | PML-RARA | SLC4A1AP | TRAG-3 |
| ADGRA3 | CAGE1 | CT45A3 | EVI5 | HEATR1 | LMP2 | NBAS | POTEA | SLCO6A1 | Transferrin receptor |
| ADGRF1 | CALCA | CT45A4 | EWSR1 | Hepsin | LOC59346 | NBPF12 | POTEB | SLITRK6 | TRGC2 |
| ADGRF2 | CALR3 | CT45A5 | EYA2 | Her2/neu | LOXL2 | NCOA4 | POTEC | Sm23 | TRIM24 |
| ADGRL2 | CAN | CT46 | EZH2 | HERC2 | LPA | NDC80 | POTED | SMAD5 | TRIM37 |
| ADHFE1 | CASC3 | CT47 | FABP7 | HERV-K104 | LRP1 | NDUFC2 | POTEE | SMAD6 | TRIM68 |
| ADORA2B | CASC5 | CT47B1 | FAM133A | HEXB | LRRN2 | Nectin-4 | POTEG | SMO | TRPM8 |
| AEN | CASP5 | CTAGE2 | FAM13A | HEXIM1 | LTF | NEK2 | POTEH | Smoothened | TSGA10 |
| AFF1 | CASP8 | cTAGE5 | FAM46D | HGRG8 | LTK | NEMF | PP2A | Smt3B | TSH receptor |
| AFF4 | CaSR | CTCFL | FAM58BP | HIPK2 | LU | NENF | PPAPDC1B | SNRPD1 | TSP50 |
| AFP | CBFA2T2 | CTDSP2 | FANCG | HJURP | LZTS1 | NEURL1 | PPFIA1 | SOS1 | TSPAN6 |
| AGAP2 | CBFA2T3 | CTGF | FATE1 | HMGB1 | LYN | NFIB | PPIG | SOX-2 | TSPY1 |
| AGO1 | CBL | CTLA4 | FBXO39 | HMOX1 | M6PR | NFKB2 | PPP2R1B | SOX-6 | TSPY2 |
| AGO3 | CBLB | CTNNA2 | FBXW11 | HNRPL | MAEA | NF-X1 | PPYR1 | SPA17 | TSPY3 |
| AGO4 | CC3 | CTNNB1 | FCHSD2 | HOM-TES-85 | MAEL | NFYC | PRAME | SPACA3 | TSPYL1 |
| AGR2 | CCDC110 | CTNND1 | FER | HORMAD1 | MAF | NGAL | PRDX5 | SPAG1 | TSSK6 |
| AIFM2 | CCDC33 | CTSH | FES | HORMAD2 | MAFF | NKG2D-L1 | PRKAA1 | SPAG17 | TTC23 |
| AIM2 | CCDC36 | CTTN | FEV | HPSE | MAFG | NKG2D-L2 | PRKCI | SPAG4 | TTK |
| AKAP-13 | CCDC6 | CXCR2 | FGF10 | HPV16 E6 | MAFK | NKG2D-L3 | PRM1 | SPAG6 | TULP2 |
| AKAP-3 | CCDC62 | CXCR4 | FGF23 | HPV16 E7 | MAGE-A1 | NKG2D-L4 | PRM2 | SPAG8 | TUSC2 |
| AKAP-4 | CCDC83 | CXorf48 | FGF3 | HPV18 E6 | MAGE-A10 | NLGN4X | PRMT3 | SPAG9 | TVHUSC |
| AKIP1 | CCL13 | CXorf61 | FGF4 | HPV18 E7 | MAGE-A11 | NLRP4 | PRMT6 | SPANXA1 | TWEAK |
| AKT1 | CCL2 | CYP1B1 | FGF5 | HRAS | MAGE-A12 | NMB-R | PDL1 | Span-Xb | TXNIP |
| AKT2 | CCL7 | CYP3A3 | FGFR1 | HS7C | MAGE-A2 | NNMT | PROM1 | SPAN-Xc | TYMS |
| AKT3 | CCNA1 | CypB | FGFR2 | HSC54 | MAGE-A2B | NOL4 | PRSS54 | SPANXD | TYR |
| ALDH1A1 | CCNA2 | CYR61 | FGFR3 | HSD17B13 | MAGE-A3 | NOTCH2 | PRSS55 | SPANXE | U2 snRNP B |
| ALK | CCNB1 | CS1 | FGFR4 | HSP105 | MAGE-A4 | NOTCH3 | PRTN3 | SPANXN1 | U2AF1 |
| ALKBH1 | CCND1 | CSAG1 | FGR | HPS27 | MAGE-A5 | NOTCH4 | PRUNE | SPANXN2 | UBD |
| ALPK1 | CCNE2 | CSDE1 | FLI1 | HSP54 | MAGE-A6 | NOV | PRUNE2 | SPANXN3 | UBE2A |
| ALPP | CCNI | CSF1 | FLOT2 | HSP60 | MAGE-A8 | NPM1 | PSA | SPANXN4 | UBE2V1 |
| AMIGO2 | CCNL1 | CSF1R | FLT3 | HSP70 | MAGE-A9 | NPY1R | PSCA | SPANXN5 | UBE4B |
| ANG2 | CCK1 | CSF3R | FMNL1 | HSP71 | MAGE-B1 | NPY2R | PSMA | SPATA19 | UBR5 |
| ANKRD45 | CCK2 | CSK | FMOD | HSPA1A | MAGE-B2 | NPY5R | PSMD10 | SPEF2 | UBXD5 |
| ANO1 | CCR2 | CSK23 | FMR1NB | HSPA2 | MAGE-B3 | NR6A1 | PSP-94 | SPI1 | UFL1 |
| ANP32A | CD105 | DAPK3 | FN1 | HSPA5 | MAGE-B4 | N-RAS | PTEN | SPINLW1 | URI1 |
| ANXA2 | CD123 | DAZ1 | Fn14 | HSPA9B | MAGE-B5 | NRCAM | PTH-rP | SPO11 | URLC10 |
| APC | CD13 | DCAF12 | FNIP2 | HSPB1 | MAGE-B6 | NRP1 | PTK6 | SRC | UROC1 |
| APEH | CD133 | DCT | Folate receptor | HSPB9 | MAGE-C1 | NSE1 | PTPN20A | SRPX | USP2 |
| APOA2 | CD137 | DCUN1D1 | FOLR1 | HSPD1 | MAGE-C2 | NSE2 | PTPRK | SSPN | USP4 |
| APOD | CD138 | DCUN1D3 | FOS | HST-2 | MAGE-C3 | NTRK1 | PTPRR | SSX-1 | VAV1 |
| APOL1 | CD157 | DDR1 | FosB | HT001 | mammaglobin-A | NUAK1 | PTPRZ | SSX-2 | VEGFR1 |
| AR | CD16A | DDX3X | FOSL1 | hTERT | MANF | NUGGC | PTTG-1 | SSX-3 | VEGFR2 |
| ARAF | CD178 | DDX43 | FOXM1 | HUS1 | MAP2K2 | NXF2 | PTTG2 | SSX-4 | VHL |
| ARF4L | CD19 | DDX6 | FOXO1 | IDH1 | MAP2K7 | NXF2B | PTTG3 | SSX-5 | VIM |
| ARHGEF5 | CD194 | DEDD | FOXO3 | IDO1 | MAP3K7 | NY-BR-1 | PXDNL | SSX-6 | VWA5A |
| ARID3A | CD2 | DEK | FRAT1 | IER3 | MAP4K5 | NY-ESO-1 | RAB11FIP3 | SSX-7 | WHSC2 |
| ARID4A | CD20 | DENR | Frizzled | IGF1R | MART1 | NY-MEL-1 | RAB8A | SSX-9 | WISP1 |
| ARL6IP5 | CD21 | DEPDC1 | FRMD3 | IGFS11 | MART-2 | OCA2 | RAD1 | ST18 | WNK2 |
| ARMC3 | CD22 | DFNA5 | FSTL3 | IL13RA2 | MAS1 | ODF1 | RAD17 | STAT1 | WNT10B |
| ARMC8 | CD229 | DGAT2 | FTHL17 | IMP-3 | MC1R | ODF2 | RAD51C | STEAP1 | WNT3 |

TABLE A-continued

| | | | | | | | | | |
|---|---|---|---|---|---|---|---|---|---|
| ARTC1 | CD23 | DHFR | FUNDC2 | ING3 | MCAK | ODF3 | RAF1 | STK11 | WNT-5a |
| ARX | CD27 | dJ383J4.1 | FUS | INPPL1 | MCF2 | ODF4 | RAGE-1 | STK25 | WT1 |
| AT1 | CD28 | DKK1 | FUT1 | INTS6 | MCF2L | OGG1 | RAP1A | STK3 | VWVP1 |
| ATAD2 | CD30 | DKK3 | FUT3 | IRAK2 | MCL1 | OGT | RARA | STN | XAGE-1 |
| ATIC | CD317 | DKKL1 | FYN | IRF4 | MCTS1 | OIP5 | RASSF10 | SUPT7L | XAGE-2 |
| AURKC | CD33 | DLEU1 | GAB2 | IRS4 | MCSP | OS9 | RB1 | Survivin | XAGE-3 |
| AXIN1 | CD350 | DMBT1 | GADD45G | ITGA5 | MDM2 | OTOA | RBL2 | SUV39H1 | XAGE-4 |
| AXL | CD36 | DMRT1 | GAGE-1 | ITGB8 | MDM4 | OX40 | RBM46 | SYCE1 | XAGE-5 |
| β1AR | CD37 | DNAJB8 | GAGE12B/C/D/E | ITPA | ME1 | OX40L | RBP4 | SYCP1 | XBP1 |
| β2AR | CD4 | DNAJC8 | GAGE12F | ITPR2 | ME491 | P4HB | RCAS1 | SYT | XPO1 |
| B1 | CD40 | DNMT3A | GAGE12G | JAK2 | MECOM | P53 | RCVRN | TA-4 | XRCC3 |
| B2 | CD40L | DPPA2 | GAGE12H | JAK3 | MELK | P56-LCK | RECQL4 | TACC1 | YB-1 |
| BAAT | CD45 | DR4 | GAGE12I | JARID1B | MEN1 | PA2G4 | RET | TAF1B | YEATS4 |
| BAFF | CD47 | DR5 | GAGE12J | JAZF1 | MERTK | PAGE1 | RGS22 | TAF4 | YES1 |
| BAGE-1 | CD51 | DRG1 | GAGE-2 | JNK1 | MET | PAGE2 | RGS5 | TAF7L | YKL-40 |
| BAGE-2 | CD52 | DSCR8 | GAGE-3 | JNK2 | MFGE8 | PAGE2B | RHAMM | TAG-1 | ZBTB7A |
| BAGE-3 | CD55 | E2F3 | GAGE-5 | JNK3 | MFHAS1 | PAGE3 | RhoC | TAL1 | ZBTB7C |
| BAGE-4 | CD6 | E2F6 | GAGE-6 | JTB | MFI2 | PAGE4 | RL31 | TAL2 | ZEB1 |
| BAGE-5 | CD61 | E2F8 | GAGE-7 | JUN | MGAT5 | PAGE5 | RNASET2 | TAPBP | ZFYVE19 |
| BAI1 | CD70 | EBNA1 | GAGE-8 | JUP | mGluRs | PAK2 | RNF43 | TATI | ZNF165 |
| BAL | CD74 | EBNA2 | GALGT2 | K19 | Midkine | PANO1 | RNF8 | TAX1BP3 | ZNF185 |
| BALF2 | CD75 | EBNA3 | GAS7 | KAAG1 | MIF | PAP | RON | TBC1D3 | ZNF217 |
| BALF4 | CD79B | EBNA4 | GATA-3 | Kallikrein4 | MKI67 | PAPOLG | Ropporin-1A | TBP-1 | ZNF320 |
| BALF5 | CD80 | EBNA6 | GBU4-5 | KAT6A | MLH1 | PARK2 | ROR1 | TCL1A | ZNF395 |
| BARF1 | CD86 | EBNA-LP = EBNA5 | GCDFP-15 | KCND2 | MLL | PARK7 | RPA1 | TCL1B | ZNF645 |
| BBRF1 | CD87 | ECT2 | GDI2 | KDM1A | MLLT1 | PARP12 | RPL10A | TDHP | ZUBR1 |
| BCAN | CD8a | ECTL2 | GFAP | KDM5A | MLLT10 | PASD1 | RPL7A | TDRD1 | ZW10 |
| BCAP31 | CD8b | EDAG | GFI1 | KIAA0100 | MLLT11 | PAX3 | RPS2 | TDRD4 | ZWINT |
| BCL-2 | CD95 | EEF2 | Ghrelin | KIAA0336 | MLLT3 | PAX5 | RPS6KA5 | TDRD6 | |
| BCL2L1 | CD98 | EFNA1 | GHSR | KIAA1199 | MLLT4 | PBF | RPSA | | |
| BCL6 | CDC123 | EFS | GIPC1 | KIAA1641 | MLLT6 | PBK | RQCD1 | | |
| BCL9 | CDC2 | EFTUD2 | GITR | KIF11 | MMP14 | PBX1 | RRAS2 | | |
| BCR | CDC27 | EGFL7 | GKAP1 | KIF1B | MMP2 | PCDC1 | | | |
| BCRF1 | CDC73 | EGFR | GLI1 | KIF20A | MMP7 | | | | |

Non-limiting examples of suitable targeting moieties that bind to a target site on a cancer cell include agents selected from the group consisting of an aptamer, a thioaptamer, an antibody, an antibody fragment, a double-stranded DNA sequence, an antigen, modified nucleic acids, nucleic acid mimics, a polynucleotide, a peptide nucleic acid, a locked nucleic acid, a phosphorodiamidate morpholino oligomer (PMO), a ligand, a ligand fragment, a receptor, a receptor fragment, a protein, a polypeptide, a peptide, a coenzyme, a coregulator, an allosteric molecule, and an ion. The term "aptamer" refers to a polynucleotide, generally a RNA or a DNA that has a useful biological activity in terms of biochemical activity, molecular recognition or binding attributes. Usually, an aptamer has a molecular activity such as binding to a target molecule at a specific epitope (region). It is generally accepted that an aptamer, which is specific in its binding to any polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In an embodiment, a targeting moiety that binds to a target site on a cancer cell may be an antibody. The term 37 antibody' includes the term "monoclonal antibody". "Monoclonal antibody" refers to an antibody that is derived from a single copy or clone, including e.g., any eukaryotic, prokaryotic, or phage clone. Monoclonal antibodies can be produced using e.g., hybridoma techniques well known in the art, as well as recombinant technologies, phage display technologies, synthetic technologies or combinations of such technologies and other technologies readily known in the art. Further by "antibody" is meant a functional monoclonal antibody, or an immunologically effective fragment thereof; such as an Fab, Fab', or F(ab')2 fragment thereof. As long as the protein retains the ability specifically to bind its intended target, it is included within the term "antibody." Also included within the definition "antibody" for example are single chain forms, generally designated Fv, regions, of antibodies with this specificity. These scFvs are comprised of the heavy and light chain variable regions connected by a linker. Methods of making and using scFvs are known in the art. Additionally, included within the definition "antibody" are single-domain antibodies, generally designated sdAb, which is an antibody fragment consisting of a single monomeric variable antibody domain. A sdAb antibody may be derived from camelids ($V_HH$ fragments) or cartilaginous fishes ($V_{NAR}$ fragments). As used herein "humanized antibody" includes an antibody that is composed partially or fully of amino acid sequence sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for the protein on the cancer cell is maintained or enhanced in the context of fully human germline framework regions or framework regions that are substantially human. In certain embodiments, an antibody is a scFv. In a specific embodiment, an antibody is a CD20 scFv. In another specific embodiment, an antibody is a PSCA scFv.

In one embodiment, a CD20 scFV antibody comprises the amino acid sequence set forth in SEQ ID NO:4 (QVQLQQPGAELVKPGASVKMSCKASGYTFTSYN-MHWVKQTPGRGLEWIGAIYPGNG DTSYN-QKFKGKATLTADKSSSTAYMQLSSLTSEDSAVYY-CARSTYYGGDWYFNVWG AGTTVTVSAGGGGSGGGGSGGGGSQIVLSQSPAIL-SASPGEKVTMTCRASSSVSYIH WFQQKPGSSPKPWI-YATSNLASGVPVRFSGSGSGTSYSLTISRVEAE-DAATYYCQQW TSNPPTFGGGTKLEIK). In another specific embodiment, a CD20 scFV antibody consists of SEQ ID NO:4. In an embodiment, a CD20 scFV antibody is a sequence comprising at least 80% identity to SEQ ID NO:4. For example, the CD20 scFV antibody may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:4.

In another embodiment, a PSCA scFv antibody comprises the amino acid sequence set forth in SEQ ID NO:5 (EVQLQQSGPELKKPGTSVRISCK-TSGYTFTEYTIHWVKQSHGKSLEWIGNINPNNGGT TYNQKFEDKATLTVDKSSSTAYMELRSLTSED-SAVYYCAAGWNFDYWGQGTTLTVSS SGGGGSGGGGSGGGGSDI-VMTQSHKFMSTSVGDRVSIICK-ASQDVGTAVDWYQQKP GQSPKLLIYWAST-RHTGVPDRFTGSGSGTDFTLTITNVQSEDLADYFCQ QYNSYPLTF GAGTMLDLK). In another specific embodiment, a PSCA scFV antibody consists of SEQ ID NO:5. In an embodiment, a PSCA scFV antibody is a sequence comprising at least 80% identity to SEQ ID NO:5. For example, the PSCA scFV antibody may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:5.

(c) Linker

In an aspect, a composition of the disclosure further comprises a linker. The linker may be used to connect chemerin to the targeting moiety. It is to be understood that linking chemerin to the targeting moiety will not adversely affect the function of chemerin or the targeting moiety. Suitable linkers include amino acid chains and alkyl chains functionalized with reactive groups for coupling to both chemerin and the targeting moiety or combinations thereof.

In an embodiment, the linker may include amino acid side chains, referred to as a peptide linker. Amino acid residue linkers are usually at least one residue and can be 50 or more residues, but alone do not specifically bind to the target protein. In an embodiment, a linker may be about 1 to about 10 amino acids. In another embodiment, a linker may be about 10 to about 20 amino acids. In still another embodiment, a linker may be about 20 to about 30 amino acids. In still yet another embodiment, a linker may be about 30 to about 40 amino acids. In different embodiments, a linker may be about 40 to about 50 amino acids. In other embodiments, a linker may be more than 50 amino acids. For instance, a linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. In a specific embodiment, a linker is about 5 to about 15 amino acids. In another specific embodiment, a linker is about 9 amino acids.

Any amino acid residue may be used for the linker provided the linker does not specifically bind to the target protein. Typical amino acid residues used for linking are glycine, serine, alanine, leucine, tyrosine, cysteine, lysine, glutamic and aspartic acid, or the like. For example, a linker may be $(G)_n$, $(G)_nA(G)_n$, $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. Accordingly, n may be 1, 2, 3, 4, 5, 6, 7, 8, 9, 10, 11, 12, 13, 14, 15, 16, 17, 18, 19 or 20. Thus, in certain embodiments, a linker includes, but is not limited to, $(G)_n$, $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. In a specific embodiment, a linker may be $(G)_nA(G)_n$. In another specific embodiment, a linker is SEQ ID NO:6 (GGGGAGGGG). A linker may comprise one or more epitope tags. For instance, a linker may comprise 1, 2, 3, 4, 5, 6, 7 or 8 epitope tags. Non-limiting examples of epitope tags include FLAG tag, HA tag, His tag, Myc tag and V5 tag.

In certain embodiments, the linker may comprise a cleavable peptide. It is important that the chemerin remain extracellular to recruit immune cells. Thus a cleavable peptide linker may be important when the binding affinity of the targeting moiety is high thereby increasing internalization of the chemerin. A "cleavable peptide" as used herein is a peptide that comprises a site susceptible to cleavage by an enzyme. In certain embodiments, the enzyme is an enzyme that is associated with a disease or condition. Non-limiting examples of a disease or condition include cancer, cardiovascular disease, arthritis, viral, bacterial, parasitic or fungal infection, Alzheimer's disease, emphysema, thrombosis, hemophilia, stroke, organ dysfunction, any inflammatory condition, vascular disease, parenchymal disease, or a pharmacologically-induced state. In a specific embodiment, the disease or condition is cancer. Non-limiting examples of sites susceptible to cleavage include a MMP sensitive site, a caspase-sensitive site, a kallikrein sensitive site, a cathepsin sensitive site, a plasminogen activator sensitive site and/or an ADAM sensitive site. In certain embodiments, the cleavable peptide comprises a caspase-sensitive site. Caspases, or cysteine-aspartic proteases or cysteine-dependent aspartate-directed proteases, are a family of cysteine proteases that play essential roles in apoptosis (programmed cell death), necrosis, and inflammation. There are two types of apoptotic caspases: initiator (apical) caspases and effector (executioner) caspases. Initiator caspases (e.g., caspase-2, caspase-8, caspase-9, and caspase-10) cleave inactive pro-forms of effector caspases, thereby activating them. Effector caspases (e.g., caspase-3, caspase-6, caspase-7) in turn cleave other protein substrates within the cell, to trigger the apoptotic process. In an embodiment, the cleavable peptide comprises a caspase-3 or caspase-7 sensitive site. In certain embodiments, the cleavable peptide comprises a MMP sensitive site. MMPs (matrix metalloproteinases) are zinc-dependent endopeptidases capable of degrading all kinds of extracellular matrix proteins, but also can process a number of bioactive molecules. MMPs are known to be involved in the cleavage of cell surface receptors, the release of apoptotic ligands (such as the FAS ligand), and chemokine/cytokine inactivation. MMPs are also thought to play a major role on cell behaviors such as cell proliferation, migration (adhesion/dispersion), differentiation, angiogenesis, apoptosis, and host defense. MMPs may be classified based on their functional activity. Non-limiting examples of suitable MMPs for which a sensitive site may be designed include collagenases (MMP1, MMP8, MMP13), matrilysin (MMP7, MMP26), metalloelastase (MMP12), gelatinases (MMP2, MMP9), enamelysin (MMP20), stromelysins (MMP3, MMP10, MMP11), membrane-type MMPs (MMP14, MMP15, MMP16, MMP17, MMP24, MMP25), and other (MMP19, MMP21, MMP23A, MMP23B, MMP27, MMP28). In an embodiment, the cleavable peptide comprises a MMP2 or MMP9 sensitive site (PLGLAG—SEQ ID NO:7). In another embodiment, the cleavable peptide comprises a MMP1 sensitive site. In still another embodiment, the cleavable peptide comprises a MMP10 sensitive site. The cleavable peptide site utilized may be chosen based on the cancer targeted. For example, if the cancer targeted is head and neck cancer, the cleavable peptide may comprise a MMP10 sensitive site. Alternatively, if the cancer targeted is prostate cancer, the cleavable peptide may comprise a MMP2 or MMP9 sensitive site.

In another embodiment, an alkyl chain linking group may be coupled to the chemerin by reacting the terminal amino group or the terminal carboxyl group with a functional group on the alkyl chain, such as a carboxyl group or an activated ester. Subsequently the targeting moiety is attached to the alkyl chain to complete the formation of the complex by reacting a second functional group on the alkyl chain with an appropriate group on the targeting moiety. The second functional group on the alkyl chain is selected from substituents that are reactive with a functional group on the targeting moiety while not being reactive with the chemerin. For example, when the targeting moiety incorporates a functional group, such as a carboxyl group or an activated ester, the second functional group of the alkyl chain linking group can be an amino group or vice versa. It will be appreciated that formation of the conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis may be used. It will be appreciated that linking groups may alternatively be coupled first to the targeting moiety and then to the chemerin.

An alternative chemical linking group to an alkyl chain is polyethylene glycol (PEG), which is functionalized in the same manner as the alkyl chain described above. Such a linker may be referred to as a heterobifunctional PEG linker or a homobifunctional PEG linker. Non-limiting examples of heterobifunctional PEG linkers include: O-(2-Aminoethyl)-O'-[2-(biotinylamino)ethyl]octaethylene glycol; 0-(2-Aminoethyl)-O'-(2-carboxyethyl)polyethylene glycol hydrochloride $M_p$ 3000; O-(2-Aminoethyl)-O'-(2-carboxyethyl)polyethylene glycol 5,000 hydrochloride $M_p$ 5,000; O-(2-Aminoethyl)polyethylene glycol 3,000 Mp 3,000; O-(2-Aminoethyl)-O'-(2-(succinylamino)ethyl)polyethylene glycol hydrochloride $M_p$ 10,000; O-(2-Azidoethyl)heptaethylene glycol; O-[2-(Biotinylamino)ethyl]-O'-(2-carboxyethyl)undecaethylene glycol; 21-[D(+)-Biotinylamino]-4,7,10,13,16,19-hexaoxaheneicosanoic acid; O-(2-Carboxyethyl)-O'-[2-(Fmoc-amino)-ethyl]heptacosaethylene glycol; O-(2-Carboxyethyl)-O'-(2-mercaptoethyl)heptaethylene glycol; O-(3-Carboxypropyl)-O'-[2-(3-mercaptopropionylamino)ethyl]-polyethylene glycol $M_w$ 3000; O-(3-Carboxypropyl)-O'-[2-(3-mercaptopropionylamino)ethyl]-polyethylene glycol $M_w$ 5000; O—[N-(3-Maleimidopropionyl)aminoethyl]-O'-[3-(N-succinimidyloxy)-3-oxopropyl]heptacosaethylene glycol; and O-[2-(3-Tritylthiopropionylamino)ethyl]polyethylene glycol $M_p$ 3,000. Non-limiting examples of homobifunctional PEG linkers include: MAL-PEG-MAL (Bifunctional Maleimide PEG Maleimide); OPSS-PEG-OPSS (OPSS: orthopyridyl disulfide; PDP-PEG-PDP); HS-PEG-SH (Bifunctional Thiol PEG Thiol); SG-PEG-SG (Bifunctional PEG Succinimidyl Glutarate NHS ester); SS-PEG-SS (Bifunctional PEG Succinimidyl Succinate NHS ester); GAS-PEG-GAS (Bifunctional PEG Succinimidyl ester NHS-PEG-NHS); SAS-PEG-SAS (Bifunctional PEG Succinimidyl ester NHS-PEG-NHS); Amine-PEG-Amine (Bifunctional PEG Amine NH2-PEG-NH2); AC-PEG-AC (Bifunctional Acrylate PEG Acrylate); ACA-PEG-ACA (Bifunctional Polymerizable PEG Acrylate Acrylamide); Epoxide-PEG-Epoxide (Bifunctional PEG Epoxide or EP); NPC-PEG-NPC (Bifunctional NPC PEG, Nitrophenyl Carbonate); Aldehyde-PEG-Aldehyde (ALD-PEG-ALD, bifunctional PEG propionaldehyde); AA-PEG-AA (Acid-PEG-Acid, AA-acetic acid or carboxyl methyl); GA-PEG-GA (Acid-PEG-Acid, GA: Glutaric acid); SA-PEG-SA (Bifunctional PEG carboxylic acid-Succinic Acid); GAA-PEG-GAA (Bifunctional PEG carboxylic acid, Glutaramide Acid); SAA-PEG-SAA (Bifunctional PEG carboxylic acid, Succinamide Acid); Azide-PEG-Azide (Bifunctional PEG azide, N3-PEG-N3); Alkyne-PEG-Alkyne (Bifunctional alkyne or acetylene PEG); Biotin-PEG-Biotin (Bifunctional biotin PEG linker); Silane-PEG-Silane (Bifunctional silane PEG); Hydrazide-PEG-Hydrazide (Bifunctional PEG Hydrazide); Tosylate-PEG-Tosylate (Bifunctional PEG Tosyl); and Chloride-PEG-Chloride (Bifunctional PEG Halide).

Additionally, the linker may comprise a combination of linkers described herein. For example, the linker may comprise an amino acid linker and a cleavable peptide linker. Specifically, the linker may comprise a glycine linker and a cleavable peptide comprising a MMP sensitive site. More specifically, the linker may comprise a glycine linker and a cleavable peptide comprising a MMP2 or MMP9 sensitive site. In a specific embodiment, the linker comprises SEQ ID NO:8 (GGGGAGGGGPLGLAG).

In certain embodiments, a linker may be modified for improved systemic half-life and reduced dosage frequency. In an embodiment, N-glycans are added to a linker. While the biological function is typically determined by the protein component, carbohydrates can play a role in molecular stability, solubility, in vivo activity, serum half-life, and immunogenicity. The sialic acid component of carbohydrate in particular, can extend the serum half-life of protein therapeutics. Accordingly, new N-linked glycosylation consensus sequences may be introduced into desirable positions in the peptide backbone to generate proteins with increased sialic acid containing carbohydrate, thereby increasing in vivo activity due to a longer serum half-life. In another embodiment, PEG is added to a linker. Methods of conjugating PEG to a protein are standard in the art. For example, see Kolate et al, *Journal of Controlled Release* 2014; 192 (28): 67-81, which is hereby incorporated by reference in its entirety. In an embodiment, a composition comprises a linker comprising PEG and/or one or more N-glycans. In an embodiment, PEG is selected from the group consisting of PEG-10K, PEG-20K and PEG-40K.

Another aspect of the disclosure involves cross-linking the chemerin and targeting moiety of the disclosure to improve their pharmacokinetic, immunogenic, diagnostic, and/or therapeutic attributes. Cross-linking involves joining two molecules by a covalent bond through a chemical reaction at suitable site(s) (e.g., primary amines, sulfhydryls) on the chemerin and targeting moiety. In an embodiment, the chemerin and targeting moiety may be cross-linked together. The cross-linking agents may form a cleavable or non-cleavable linker between the chemerin and the targeting moiety. Cross-linking agents that form non-cleavable linkers between the chemerin and the targeting moiety may comprise a maleimido- or haloacetyl-based moiety. According to the present disclosure, such non-cleavable linkers are said to be derived from maleimido- or haloacetyl-based moiety. Cross-linking agents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), -κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester [AMAS], succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). These cross-linking agents form non-cleavable linkers derived from maleimido-based moieties. Cross-linking agents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP). These cross-linking agents form non-cleavable linkers derived from haloacetyl-based moieties. Cross-linking agents that form non-cleavable linkers between the chemerin and the targeting moiety may comprise N-succinimidyl 3-(2-pyridyldithio)propionate, 4-succinimidyl-oxycarbonyl-α-methyl-alpha-(2-pyridyldithio)-toluene (SMPT), N-succinimidyl-3-(2-pyridyldithio)-butyrate (SDPB), 2-iminothiolane, or acetylsuccinic anhydride.

(d) Chemerin Construct

In an aspect, the present disclosure provides a chemerin construct. A chemerin construct of the disclosure is a polynucleotide sequence encoding a polypeptide, the polypeptide comprising chemerin linked to a targeting moiety, wherein the targeting moiety is capable of directing the chemerin to a target site on a cell. As used herein, the terms "polynucleotide sequence of the disclosure" and "chemerin construct" are interchangeable. The present disclosure also provides isolated polypeptides encoded by chemerin constructs, vectors comprising chemerin constructs, and isolated cells comprising said vectors.

i. Polynucleotide Sequence

A chemerin construct of the disclosure is a polynucleotide sequence encoding a polypeptide, the polypeptide comprising chemerin linked to a targeting moiety, wherein the targeting moiety is capable of directing the chemerin to a target site on a cell. In certain embodiments, the polynucleotide sequence of the disclosure may encode a polypeptide that further comprises a linker linking chemerin to the targeting moiety. In some embodiments, a chemerin construct of the disclosure is a polynucleotide sequence encoding a polypeptide, the polypeptide comprising chemerin attached via a linker to a targeting moiety, wherein the targeting moiety is capable of directing the chemerin to a target site on a cell. In certain embodiments, the target site is a target protein on the surface of a cell. In other embodiments, the targeting moiety is selected from the group consisting of an antibody or fragment thereof, an aptamer, or a binding domain derived from a target protein ligand. In another embodiment, the cell is a cancer cell.

Each of the above embodiments may optionally comprise a signal peptide and/or a purification moiety. When present, typically the polynucleotide sequence encoding the signal peptide is at the N-terminus of the chemerin construct and the polynucleotide sequence encoding the purification moiety is at the C-terminus of the chemerin construct. Alternatively, the polynucleotide sequence encoding the signal peptide and the polynucleotide sequence encoding the purification moiety are both at the N-terminus of the chemerin construct. The choice of polynucleotide sequence encoding the signal peptide can and will vary depending on a variety factors including, but not limited to, the desired cellular location and type of cell. Suitable polynucleotide sequence encoding signal peptides are known in the art, as are polypeptide sequences encoded therefrom. In a specific embodiment, the signal peptide comprises SEQ ID NO:9 (MEWSWVFLFFLSVTTGVHS). Similarly, the choice of purification moiety can and will vary. Suitable purification moieties are known in the art, as are the polynucleotide sequences encoding them. In a specific embodiment, the purification moiety is a histidine tag. In another embodiment, the purification moiety is a 10× histidine tag.

In each of the above embodiments, a "chemerin" may be as described in detail above in Section I(a), a "targeting moiety" may be as described in detail above in Section I(b), and a "linker" may be as described in detail above in Section I(c), each of which are hereby incorporated by reference into this section.

In one embodiment, a polynucleotide sequence comprises SEQ ID NO: 10. The polynucleotide sequence of SEQ ID NO:10 encodes for a polypeptide comprising a signal peptide, a 10 histidine tag, a scFv CD20 antibody, a glycine linker and mature chemerin.

In another embodiment, a polynucleotide sequence comprises SEQ ID NO:11. The polynucleotide sequence of SEQ ID NO:11 encodes for a polypeptide comprising a scFv CD20 antibody, a glycine linker and mature chemerin.

In still another embodiment, a polynucleotide sequence comprises SEQ ID NO: 12. The polynucleotide sequence of SEQ ID NO:12 encodes for a polypeptide comprising a signal peptide, a 10 histidine tag, a scFv CD20 antibody, a glycine linker and prochemerin.

In still yet another embodiment, a polynucleotide sequence comprises SEQ ID NO:13. The polynucleotide sequence of SEQ ID NO:13 encodes for a polypeptide comprising a scFv CD20 antibody, a glycine linker and prochemerin.

Polynucleotide sequences of the disclosure may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the disclosure. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

ii. Polypeptide Sequence

In another aspect, the present disclosure provides one or more isolated polypeptide(s) encoded by a polynucleotide sequence of the disclosure. Polynucleotide sequences of the disclosure are described in detail in Section I(d)i, and are hereby incorporated by reference into this section. An isolated polypeptide of the disclosure comprises chemerin linked to a targeting moiety, wherein the targeting moiety is capable of directing the chemerin to a target site on a cell. In certain embodiments, a polypeptide of the disclosure may further comprise a linker linking chemerin to the targeting moiety. In one embodiment, an isolated polypeptide may comprise chemerin attached to a targeting moiety via a linker stretching between the C-terminus of the chemerin to the N-terminus of the targeting moiety. In another embodiment, an isolated polypeptide may comprise a chemerin attached to a targeting moiety via by a linker stretching between the C-terminus of the targeting moiety to the N-terminus of the chemerin.

In one embodiment, a polypeptide sequence comprises SEQ ID NO: 14. The polypeptide comprises a signal peptide, a 10 histidine tag, a scFv CD20 antibody, a glycine linker and mature chemerin.

In another embodiment, a polypeptide sequence comprises SEQ ID NO:15. The polypeptide comprises a scFv CD20 antibody, a glycine linker and mature chemerin.

In still another embodiment, a polypeptide sequence comprises SEQ ID NO: 16. The polypeptide comprises a signal peptide, a 10 histidine tag, a scFv CD20 antibody, a glycine linker and prochemerin.

In still yet another embodiment, a polypeptide sequence comprises SEQ ID NO:17. The polypeptide comprises a scFv CD20 antibody, a glycine linker and prochemerin.

In a different embodiment, a polypeptide sequence comprises SEQ ID NO:18. The polypeptide comprises a signal peptide, a scFv PSCA antibody, a glycine linker and prochemerin.

In another different embodiment, a polypeptide sequence comprises SEQ ID NO:19. The polypeptide comprises a signal peptide, a scFv PSCA antibody, a glycine linker and mature chemerin.

In still another different embodiment, a polypeptide sequence comprises SEQ ID NO:20. The polypeptide comprises a signal peptide, a scFv PSCA antibody, a glycine linker, a MMP2/9 sensitive linker and prochemerin.

In still yet another embodiment, a polypeptide sequence comprises SEQ ID NO:21. The polypeptide comprises a signal peptide, a scFv PSCA antibody, a glycine linker, a MMP2/9 sensitive linker, and mature chemerin.

Isolated polypeptides of the disclosure may be produced from nucleic acids molecules using molecular biological methods known to in the art. Generally speaking, a polynucleotide sequence encoding the polypeptide is inserted into a vector that is able to express the polypeptide when introduced into an appropriate host cell. Appropriate host cells include, but are not limited to, bacterial, yeast, insect, and mammalian cells. Once expressed, polypeptides may be obtained from cells using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the disclosure may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises a purification moiety.

iii. Vector

In another aspect, the present disclosure provides a vector comprising a chemerin construct of the disclosure. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

In a specific embodiment, the vector is an expression vector. The vector may have a high copy number, an intermediate copy number, or a low copy number. The copy number may be utilized to control the expression level for the chemerin construct, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Expression vectors typically contain one or more of the following elements: promoters, terminators, ribosomal binding sites, and IRES. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. A promoter may be constitutive, inducible/repressible or cell type specific. In certain embodiments, the promoter may be constitutive. Non-limiting examples of constitutive promoters include CMV, UBC, EF1α, SV40, PGK, CAG, CBA/CAGGS/ACTB, CBh, MeCP2, U6 and H1. In other embodiments, the promoter may be an inducible promoter. The inducible promoter may be selected from the group consisting of tetracycline, heat shock, steroid hormone, heavy metal, phorbol ester, adenovirus E1A element, interferon, and serum inducible promoters. In different embodiments, the promoter may be cell type specific.

Expression of the nucleic acid molecules may be regulated by a second nucleic acid sequence so that the molecule is expressed in a host transformed with the recombinant DNA molecule. For example, expression of the nucleic acid molecules may be controlled by any promoter/enhancer element known in the art.

A nucleic acid encoding a chemerin construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

In some embodiments, the vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

An expression vector encoding a chemerin construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding a chemerin construct that is introduced to the cell may be linear or circular, may be single-stranded or double-stranded, and may be DNA, RNA, or any modification or combination thereof.

An expression construct encoding a chemerin construct may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

Upon introduction into the cell, an expression construct encoding a chemerin construct may be integrated into a chromosome. In some embodiments, integration of the expression construct encoding a chemerin construct into a cellular chromosome may be achieved with a mobile element. The mobile element may be a transposon or a retroelement. A variety of transposons are suitable for use. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include adeno-associated viruses and retroviruses. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. A variety of retroviruses are suitable for use. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

Integration of an expression construct encoding a chemerin construct into a chromosome of the cell may be random. Alternatively, integration of an expression construct encoding a chemerin construct may be targeted to a particular sequence or location of a chromosome. In general, the general environment at the site of integration may affect whether the integrated expression construct encoding a chemerin construct is expressed, as well as its level of expression. The virus may be altered to have tropism for a specific cell type. For example, the virus may be altered to have tropism for cancer cells.

Cells transfected with the expression construct encoding a chemerin construct generally will be grown under selection to isolate and expand cells in which the nucleic acid has integrated into a chromosome. Cells in which the expression construct encoding a chemerin construct has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

In certain embodiments, a vector-comprising a chemerin construct of the disclosure is an adeno-associated viral (AAV) vector. Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication, encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus, making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., J. Virol., 78: 6381-6388 (2004). Advances in the delivery of AAV6 and AAV8 have made possible the transduction by these serotypes of skeletal and cardiac muscle following simple systemic intravenous or intraperitoneal injections. See, Pacak et al., *Circ. Res.*, 99(4): 3-9 (1006) and Wang et al., *Nature Biotech.*, 23(3): 321-328 (2005). The use of some serotypes of AAV to target cell types within the central nervous system, though, has required surgical intraparenchymal injection. See, Kaplitt et al., *Lancet* 369: 2097-2105 (2007); Marks et al., *Lancet Neurol* 7: 400-408 (2008); and Worgall et al., *Hum Gene Ther* (2008).

An adeno-associated viral (AAV) vector is a plasmid comprising a recombinant AAV genome. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In an exemplary embodiment, a vector is based on the AAV2 serotype. In another exemplary embodiment, a vector is based on the AAV9 serotype (see, for example, Foust et al., *Nature Biotechnology*, 27: 59-65 (2009); Duque et al., *Mol. Ther.* 17: 1187-1196 (2009); Zincarelli et al., *Mol. Ther.*, 16: 1073-1080 (2008); and U.S. Patent Publication No. 20130039888).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production. The disclosure thus provides packaging cells that produce infectious rAAV.

In another aspect, the disclosure provides rAAV (i.e., infectious encapsidated rAAV particles) comprising a rAAV genome of the disclosure. In some embodiments, the rAAV genome is a self-complementary genome.

iv. Isolated Cell

In another aspect, the present disclosure provides an isolated cell comprising a vector of the disclosure. The cell may be a prokaryotic cell or a eukaryotic cell. Appropriate cells include, but are not limited to, bacterial, yeast, insect, and mammalian cells.

In some embodiments, the isolated host cell comprising a vector of the disclosure may be used to produce a polypeptide encoded by a chemerin construct of the disclosure. Generally, production of a polypeptide involves transfecting isolated host cells with a vector comprising a chemerin construct and then culturing the cells so that they transcribe and translate the desired polypeptide. The isolated host cells may then be lysed to extract the expressed polypeptide for subsequent purification. "Isolated host cells" are cells which have been removed from an organism and/or are maintained in vitro in substantially pure cultures. A wide variety of cell types can be used as isolated host cells, including both prokaryotic and eukaryotic cells. Isolated cells include, without limitation, bacterial cells, fungal cells, yeast cells, insect cells, and mammalian cells.

In one embodiment, the isolated host cell is characterized in that after transformation with a vector of the disclosure, it produces the desired polypeptide for subsequent purification. Such a system may be used for protein expression and purification as is standard in the art. In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp., *Stenotrophomonas* sp., *Micrococcus* sp., *Neisseria* sp., *Bdellovibrio* sp., *Hemophilus* sp., *Klebsiella* sp., *Proteus mirabilis, Enterobacter cloacae, Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

Particularly useful bacterial host cells for protein expression include Gram negative bacteria, such as *Escherichia coli, Pseudomonas fluorescens, Pseudomonas haloplanctis, Pseudomonas putida* AC10, *Pseudomonas pseudoflava, Bartonella henselae, Pseudomonas syringae, Caulobacter crescentus, Zymomonas mobilis, Rhizobium meliloti, Myxococcus xanthus* and Gram positive bacteria such as *Bacillus subtilis, Corynebacterium, Streptococcus cremoris, Streptococcus lividans,* and *Streptomyces lividans. E. coli* is one of the most widely used expression hosts. Accordingly, the techniques for overexpression in *E. coli* are well developed and readily available to one of skill in the art. Further, *Pseudomonas fluorescens,* is commonly used for high level production of recombinant proteins (i.e. for the development bio-therapeutics and vaccines).

Particularly useful fungal host cells for protein expression include *Aspergillis oryzae, Aspergillis niger, Trichoderma reesei, Aspergillus nidulans, Fusarium graminearum.*

Particularly useful yeast host cells for protein expression include *Candida albicans, Candida maltose, Hansenula polymorpha, Kluyveromyces fragilis, Kluyveromyces lactis, Pichia guillerimondii, Pichia pastoris, Saccharomyces cerevisiae, Schizosaccharomyces pombe,* and *Yarrowia lipolytica.*

Particularly useful mammalian host cells for protein expression include Chinese hamster ovary (CHO) cells, HeLa cells, baby hamster kidney (BHK) cells, monkey kidney cells (COS), human hepatocellular carcinoma cells (eg. Hep G2), human embryonic kidney cells, *Bos primigenius,* and *Mus musculus.* Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

In another embodiment, the host cell may be in vivo; i.e., the cell may be disposed in a subject. Accordingly, a polypeptide of the disclosure is expressed from a host cell in the subject. In certain embodiments, a host cell in a subject may be a cancer cell. In an embodiment, an AAV vector may be used to express a polypeptide of the disclosure in a host cell disposed in a subject.

(e) Pharmaceutical Compositions

The present disclosure also provides pharmaceutical compositions. The pharmaceutical composition comprises a polynucleotide, polypeptide, vector or isolated cell of the invention which is detailed above, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, an active ingredient of the disclosure is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, an active ingredient of the disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethyl indocarbocyanine perchloarate, 1,1'-dioleyl-3,3,3',3'-tetramethyl indo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying an active ingredient of the disclosure (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828, 837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, an active ingredient of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. An active ingredient of the disclosure may be encapsulated in a microemulsion by any method generally known in the art.

In yet another embodiment, an active ingredient of the disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate an active ingredient of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. METHODS

In an aspect, the disclosure provided a method to deliver a chemerin to a target cell. The method comprises contacting a target cell with a composition comprising a chemerin linked to a targeting moiety, wherein the targeting moiety is capable of directing the chemerin to a target site on a cell. Alternatively, the method comprises contacting a target cell with a polypeptide encoded by a polynucleotide of the disclosure. A target site may be a target protein on the surface of a cancer cell. The chemerin may be linked to a targeting moiety via a linker. The linker may be a cleavable linker such that upon binding of the targeting moiety to a target protein on the surface of a cancer cell, the chemerin is released from the targeting moiety via cleavage of the linker.

In another aspect, the disclosure provides a method to recruit immune cells to a tumor in a subject. The method comprises administering to the subject a composition comprising a chemerin linked to a targeting moiety, wherein the targeting moiety is capable of directing the chemerin to a target site on a cancer cell of the tumor. The target site may be a protein on the surface of a cancer cell. Alternatively, the method comprises administering to the subject a polypeptide encoded by a polynucleotide of the disclosure. Chemerin is known to bind to the G-protein coupled receptor CMKLR1 (chemokine like receptor 1), CCRL2 (chemokine receptor-like 2) and GPR1 (G protein-coupled receptor 1) found on cells. Non-limiting examples of cells that express CCRL2 include vascular endothelial cells, neutrophils, monocytes and macrophages. Non-limiting examples of cells that express CMKLR1 include innate immune cells such as dendritic cells, macrophages, monocytes, and natural killer cells. Accordingly, the presence of chemerin at or near the surface of a cancer cell of the tumor recruits immune cells to the tumor. The presence of immune cells may result in tumor cell lysis. In an embodiment, the presence of immune cells may result in about 10% to about 100% lysis of tumor cells. In another embodiment, the presence of immune cells may result in about 20% to about 80% lysis of tumor cells. In still another embodiment, the presence of immune cells may result in greater than 40% lysis of tumor cells. For example, the presence of immune cells may result in greater than 40%, greater than 45%, greater than 50%, greater than 55%, greater than 60%, greater than 65%, greater than 70%, greater than 75%, greater than 80%, greater than 85%, greater than 90%, greater than 95%, or greater than 99% lysis of tumor cells. The lysis of tumor cells may be measured using any standard assay (e.g., caspase assays, TUNEL and DNA fragmentation assays, cell permeability assays, and Annexin V assays).

In still another aspect, the disclosure provides a method to increase phosphatase and tensin homolog (PTEN) expression in a tumor in a subject. The method comprises administering to the subject a composition comprising a chemerin linked to a targeting moiety, wherein the targeting moiety is capable of directing the chemerin to a target site on a cancer cell of the tumor. The target site may be a target protein on the surface of a cancer cell. Alternatively, the method comprises administering to the subject a polypeptide encoded by a polynucleotide of the disclosure. PTEN is a tumor suppressor gene that is commonly downregulated, mutated, or lost in tumors and contributes to tumor formation and/or progression. Accordingly, it is advantageous to increase PTEN expression in tumors. Administration of a chemerin construct of the disclosure may increase PTEN expression by at least about 1.2-fold, at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, at least about 13-fold, at least about 14-fold, at least about 15-fold, or at least about 20-fold relative to baseline. In certain embodiments, administration of a chemerin construct of the disclosure may increase PTEN expression by at least about 1.2-fold, at least about 1.5-fold, at least about 2-fold, or at least about 2.5-fold relative to baseline. As used herein "baseline" is the level of PTEN expression in the tumor of the subject in the absence of a chemerin construct. Alternatively, the increase in PTEN expression may be measured using p-value. Accordingly, administration of a chemerin construct of the disclosure may increase PTEN expression when the p-value is less than 0.1, less than 0.05, less than 0.01, less than 0.005, or less than 0.001 when compared to baseline.

In still yet another aspect, the disclosure provides a method to decrease WNT/β-catenin pathway expression in a tumor in a subject. The method comprises administering to the subject a composition comprising a chemerin linked to a targeting moiety, wherein the targeting moiety is capable of directing the chemerin to a target site on a cancer cell of the tumor. The target site may be a target protein on the surface of a cancer cell. Alternatively, the method comprises administering to the subject a polypeptide encoded by a polynucleotide of the disclosure. The WNT/β-catenin pathway is active in multiple tumor types and thus being able to target pharmacologically the WNT/β-catenin pathway is an anti-tumor strategy. Administration of a chemerin construct of the disclosure may decrease WNT/β-catenin pathway expression by at least about 1.2-fold, at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, at least about 13-fold, at least about 14-fold, at least about 15-fold, or at least about 20-fold relative to baseline. In certain embodiments, administration of a chemerin construct of the disclosure may decrease WNT/β-catenin pathway expression by at least about 1.2-fold, at least about 1.5-fold, at least about 2-fold, or at least about 2.5-fold relative to baseline. As used herein "baseline" is the level of WNT/β-catenin pathway expression in the tumor of the subject in the absence of a chemerin construct. Alternatively, the decrease in WNT/β-catenin pathway expression may be measured using p-value. Accordingly, administration of a chemerin construct of the disclosure may decrease WNT/β-catenin pathway expression when the p-value is less than 0.1, less than 0.05, less than 0.01, less than 0.005, or less than 0.001 when compared to baseline.

In a different aspect, the disclosure provides a method to treat, stabilize or prevent cancer in a subject. The method comprises administering to the subject a composition comprising a chemerin linked to a targeting moiety, wherein the targeting moiety is capable of directing the chemerin to a target site on a cancer cell of a tumor and thereby recruiting immune cells to the tumor. The target site may be a target protein on the surface of a cancer cell. Alternatively, the method comprises administering to the subject a polypeptide encoded by a polynucleotide of the disclosure. The presence of immune cells results in tumor cell lysis thereby decreasing the number of tumor cells. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. The inventors have shown that a composition of the disclosure recruits immune cells to the site of a tumor, wherein the immune cells specifically lyse tumor cells thereby reducing the amount of tumor cells. In a desired embodiment, the percent of tumor or cancerous cells surviving the treatment is at least 20, 30, 40, 50, 60, 70, 80, 90 or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a composition of the invention is at least 2, 5, 10, 15, 20, 25, 30, 35, 40, 45 or 50-fold greater than the decrease in the number of non-tumor or non-cancerous cells. Desirably, the methods of the present invention result in a decrease of 20, 30, 40, 50, 60, 50, 80, 90 or 100% in the size of a tumor or in the number of cancerous cells, as determined using standard methods. Desirably, at least 20, 30, 40, 50, 60, 70, 80, 90, or 95% of the treated subjects have a complete remission in which all evidence of the tumor or cancer disappears. Desirably, the tumor or cancer does not reappear or reappears after at least 1, 2, 3, 4, 5, 10, 15, or 20 years.

The composition, chemerin, targeting moiety, linker, polynucleotide and polypeptide are as described in Section I. The subject, administration and tumor are described below.

(a) Administration

In certain aspects, a pharmacologically effective amount of a composition of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, intratumoral, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. Pheresis may be used to deliver a composition of the invention. In certain embodiments, a composition of the invention may be administered via an infusion (continuous or bolus).

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

Effective peripheral systemic delivery by intravenous or intraperitoneal or subcutaneous or intratumoral injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable response (e.g., an immunostimulatory, an anti-angiogenic response, a cytotoxic response, tumor regression). Actual dosage levels of active ingredients in a therapeutic composition of the invention can be varied so as to administer an amount of the active ingredient(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. For example, a dose may range from about 1 mg/kg to about 200 mg/kg, about 1 mg/kg to about 100 mg/kg, about 1 mg/kg to about 75 mg/kg, about 1 mg/kg to about 50 mg/kg, about 1 mg/kg to about 25 mg/kg, about 5 mg/kg to about 100 mg/kg, about 5 mg/kg to about 75 mg/kg, about 5 mg/kg to about 50 mg/kg, about 5 mg/kg to about 25 mg/kg, about 10 mg/kg to about 100 mg/kg, about 10 mg/kg to about 75 mg/kg, about 10 mg/kg to about 50 mg/kg, or about 10 mg/kg to about 25 mg/kg. Alternatively, the dose may be about 1 mg/kg, about 5 mg/kg, about 10 mg/kg, about 15 mg/kg, about 20 mg/kg, about 25 mg/kg, about 30 mg/kg, about 40 mg/kg, about 50 mg/kg, about 75 mg/kg, about 100 mg/kg, about 125 mg/kg, about 150 mg/kg, about 175 mg/kg or about 200 mg/kg.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In other embodiments, a dose may be administered weekly. For example, a dose may be administered weekly, every 2 weeks, every 3 weeks, every 4 weeks, every 5 weeks, or every 6 weeks. In still other embodiments, a dose may be administered monthly. For example, a dose may be administered monthly, every 2 months, every 3 months, every 4 months, every 5 months, every 6 months, every 7 months, every 8 months, every 9 months, every 10 months, every 11 months, or every 12 months.

Duration of treatment could range from a single dose administered on a one-time basis to a life-long course of therapeutic treatments. The duration of treatment can and will vary depending on the subject and the cancer to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The timing of administration of the treatment relative to the disease itself and duration of treatment will be determined by the circumstances surrounding the case. Treatment could begin immediately, such as at the time of diagnosis, or treatment could begin following surgery. Treatment could begin in a hospital or clinic itself, or at a later time after discharge from the hospital or after being seen in an outpatient clinic.

Although the foregoing methods appear the most convenient and most appropriate and effective for administration of a composition of the invention, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

A composition of the disclosure may also be administered in combination with standard treatment for cancer. Standard treatment may depend on the type and severity of the cancer, as well as the general condition of the subject. Standard treatment of cancer consists primarily of radiation, surgery, chemotherapy and/or targeted therapy. Standard treatment algorithms for each cancer may be found via the National Comprehensive Cancer Network (NCCN) guidelines (www.nccn.org/professionals/physician_gls/f_guidelines.asp). In a specific embodiment, a composition of the disclosure may be administered in combination with checkpoint inhibitors. Non-limiting examples of checkpoint inhibitors include pembrolizumab (Keytruda®), nivolumab (Opdivo®), ipilimumab (Yervoy®), atezolizumab (Tecentriq®) pidilizumab, MPDL3280A, AMP-514, MED14736, MSB0010718C, AUNP 12, and BMS-936559/MDX-1105.

(b) Tumor

A composition of the disclosure may be used to deliver chemerin to a cancer cell or treat a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, the neoplasm or cancer may be selected from the group consisting of melanoma, kidney cancer, bladder cancer, lung cancer, breast cancer, colon cancer, prostate cancer and blood cancer. As used herein, a "blood cancer" is a cancer that affects the blood, bone marrow and lymphatic system. There are three main groups of blood cancer: leukemia, lymphoma and myeloma. The four broad classification of leukemia are: acute lymphocytic leukemia (ALL), acute myelogenous leukemia (AML), chronic lymphocytic leukemia (CLL) and chronic myelogenous leukemia (CML). Lymphomas are divided into two categories: Hodgkin lymphoma and non-Hodgkin lymphoma. Most non-Hodgkin lymphomas are B-cell lymphomas, and either grow quickly (high-grade) or slowly (low-grade). There are 14 types of B-cell non-Hodgkin lymphomas. The rest are T-cell lymphomas, named after a different cancerous white blood cell, or lymphocyte. Because myeloma frequently occurs at many sites in the bone marrow, it is often referred to as multiple myeloma. In a specific embodiment, the neoplasm or cancer is a CD20+ lymphoma.

(c) Subject

A suitable subject includes a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Chemerin: A Tumor Suppressive Chemoattractant

Chemerin (RARRES2; retinoic acid responder-2) is a widely expressed, endogenous non-chemokine ligand for the G-protein coupled receptor chemokine-like receptor-1 (CMKLR1), expressed in macrophages, DCs, and highly cytotoxic NK cells, with similar expression in the mouse. Chemerin is a known chemoattractant for these CMKLR1+ cells, and acts to recruit these cells to sites of inflammation along its concentration gradient. Thus, the chemerin/CMKLR1 axis may play a key role in the rapid recruitment of cells of the innate immune system.

Figure 1B:
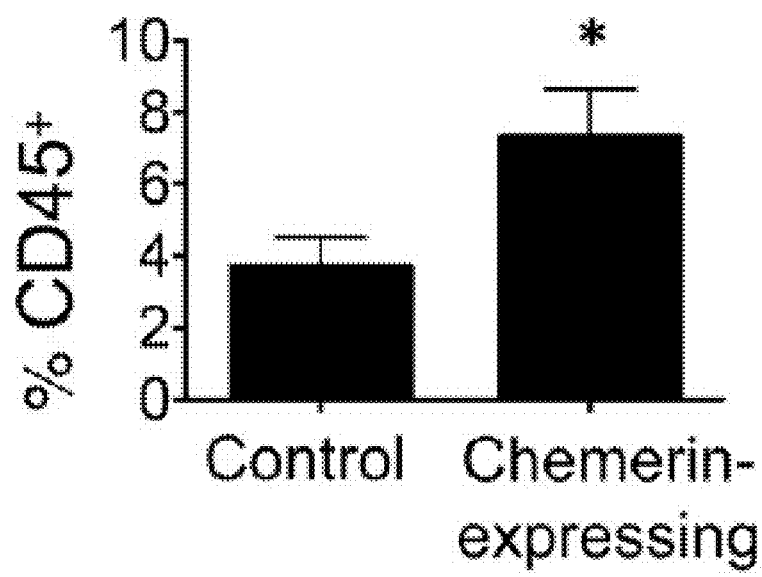
Figure 1C:
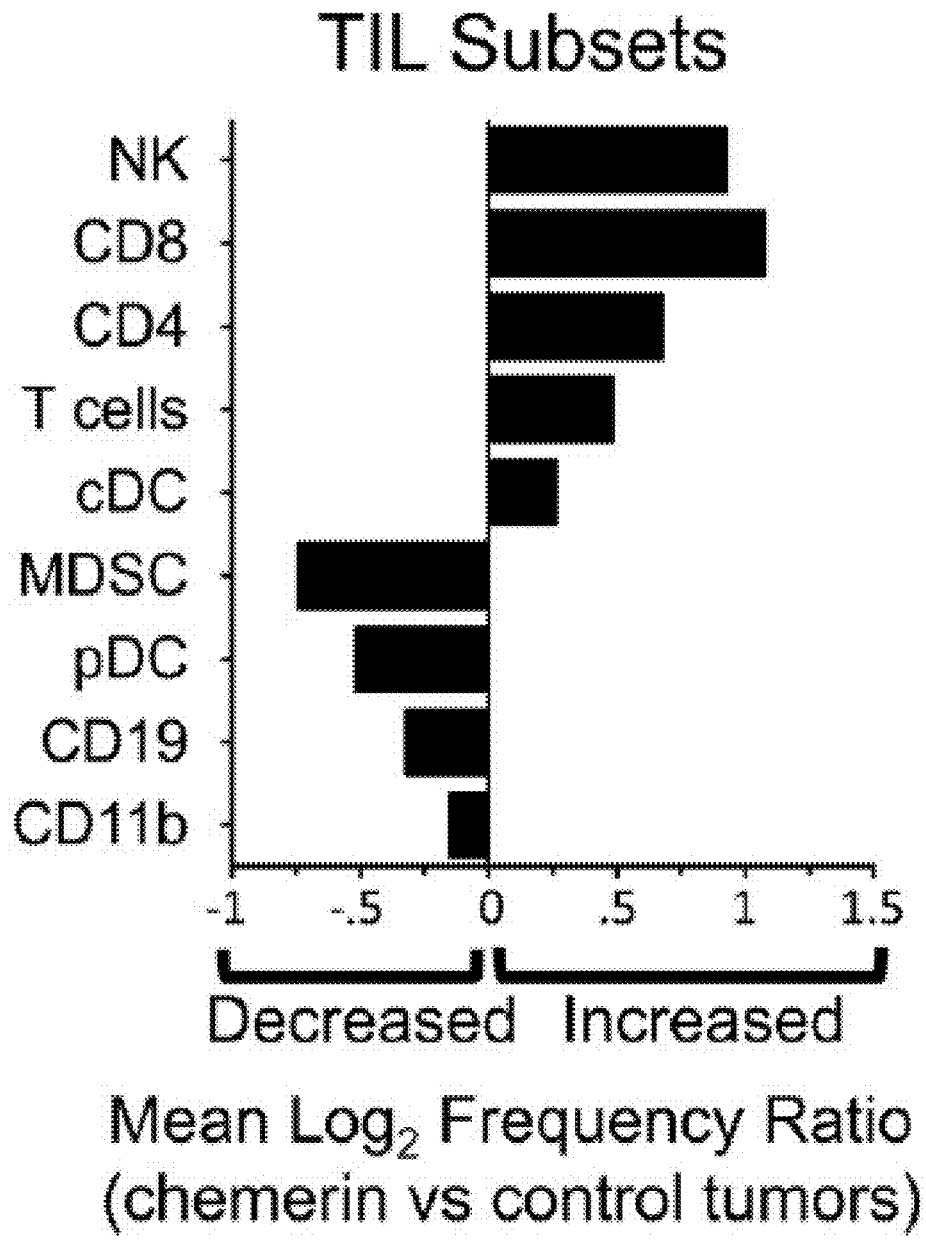
Figure 2A:
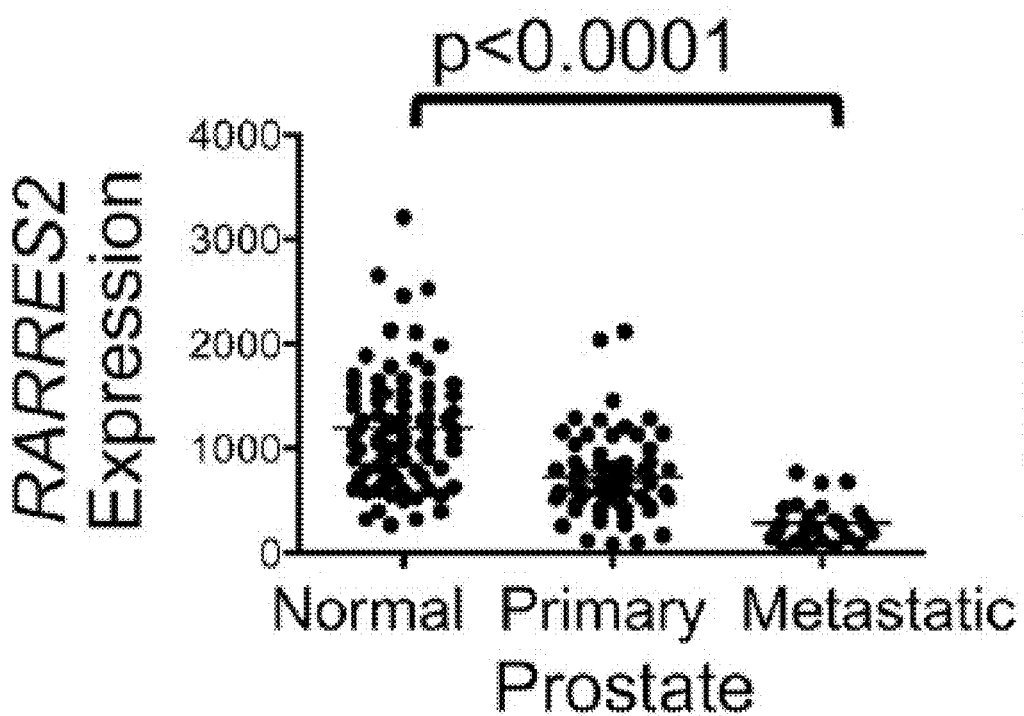
FIG. 2A, FIG. 2B, FIG. 2C, FIG. 2D, FIG. 2E and FIG. 2F depict graphs showing that RARRES2 is downregulated in human tumors. Microarray data from the GEO (Gene Expression Omnibus) database was modified to show the relative expression (calculated signal intensities) for RARRES2 (chemerin-encoding gene). Evaluating RARRES2 expression in normal and cancerous (primary or metastatic) human primary tissues. Individual tissue samples are represented as dots, and bars represent mean. Significance of differences in RARRES2 expression in sample groups was determined using the unpaired Student's t-test.
Figure 2B:
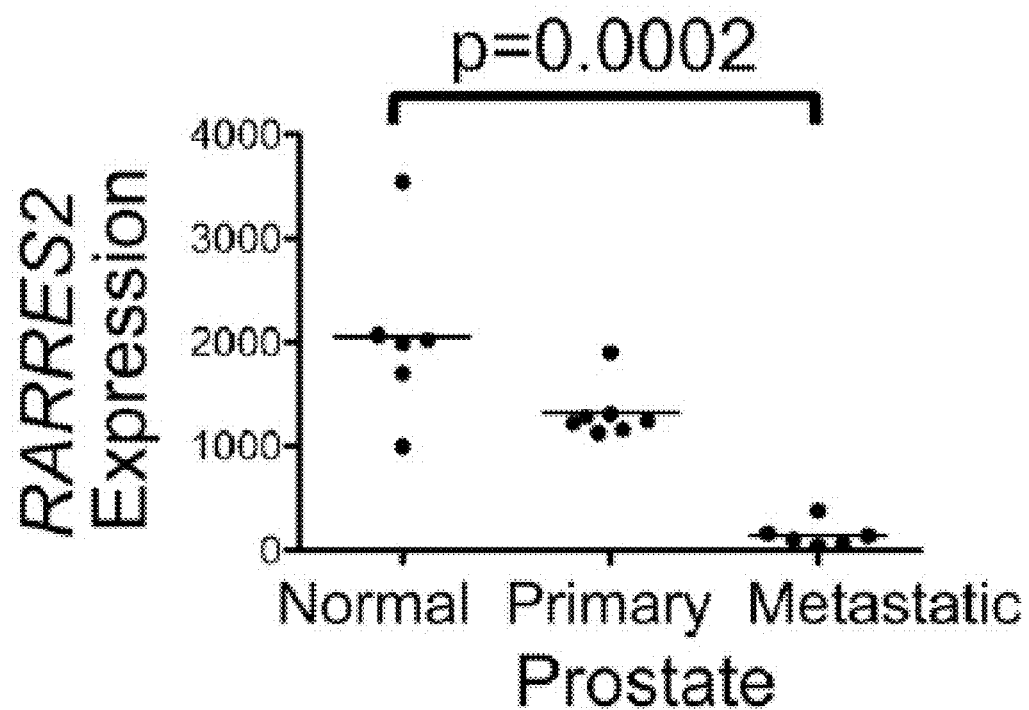
Figure 2C:
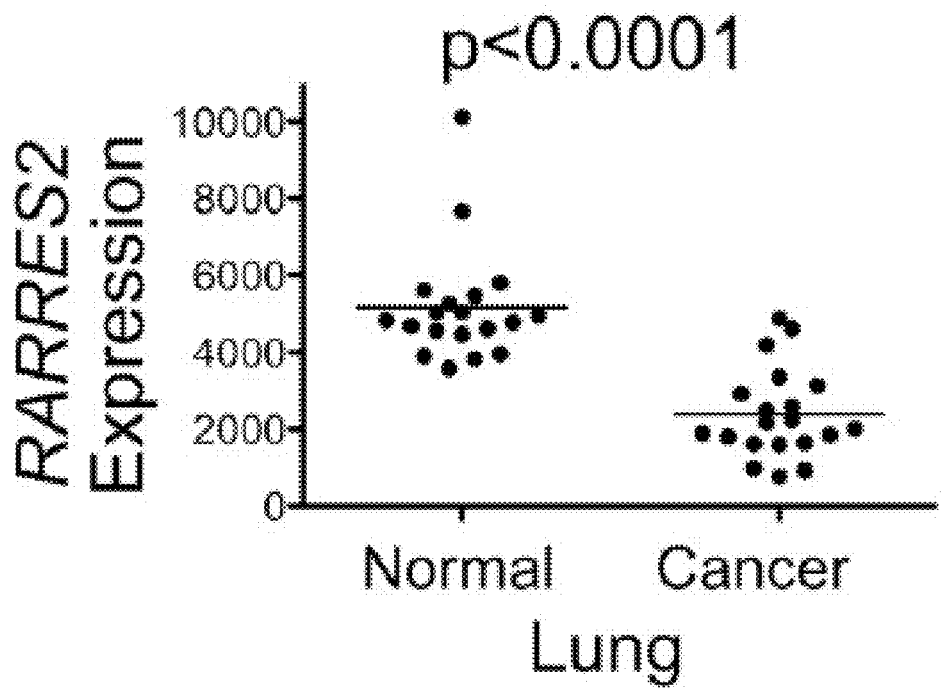
Figure 2D:
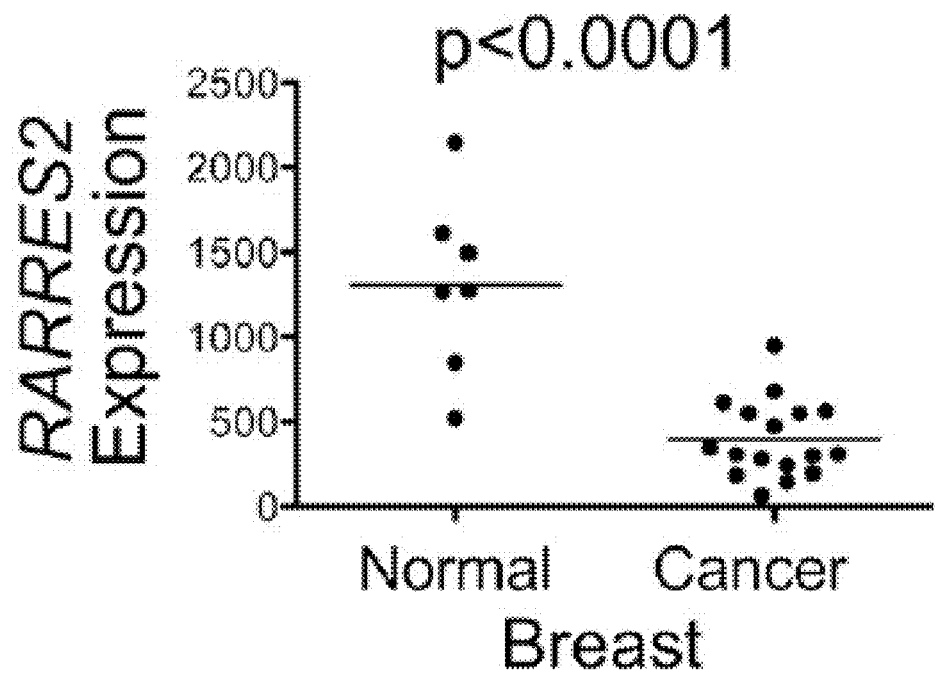
Figure 2E:
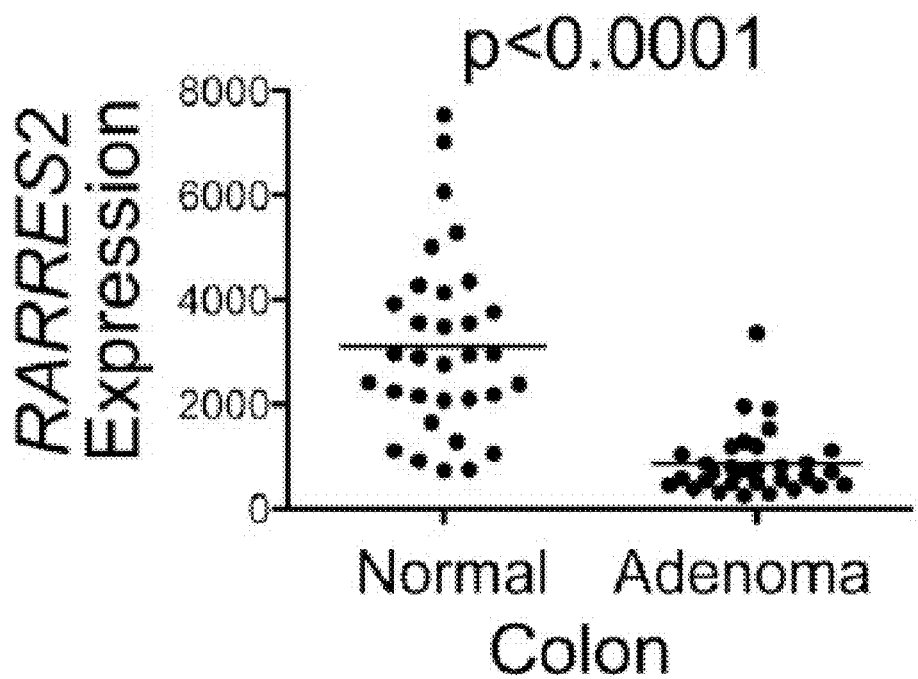
Figure 2F:
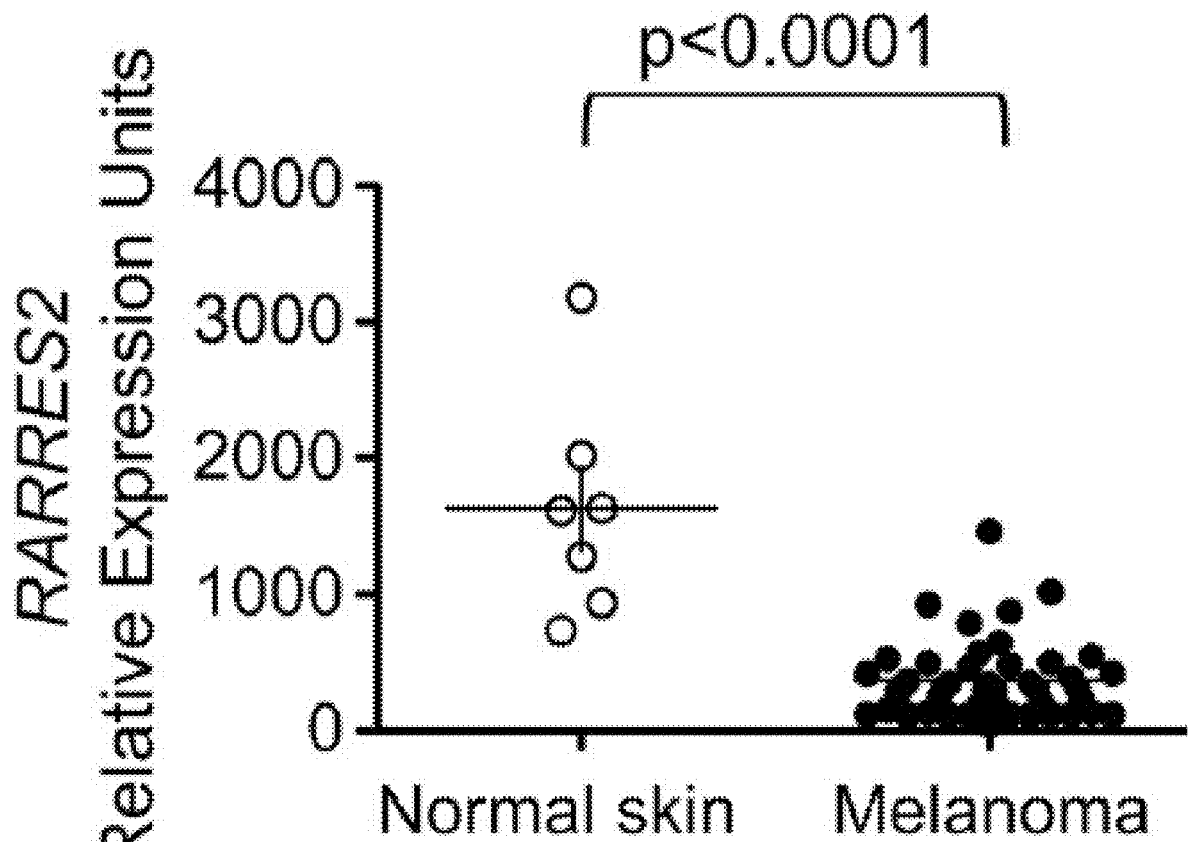

In our melanoma models, chemerin-expressing tumors grew significantly more slowly than control tumors (FIG. 1A), while chemerin itself had no effect on tumor cell proliferation or phenotype in vitro. There was a significant increase in CD45+ infiltrating immune cells in chemerin-expressing tumors (FIG. 1B), and a subsequent favorable skewing of the tumor infiltrating leukocytes (TIL) within the tumor microenvironment (TME) (FIG. 1C), notably NK and T cells. Importantly, the ratio of NK and T cells (putative effector cells) to MDSC or plasmacytoid DC (putative suppressor cells) was significantly increased. Chemerin's anti-tumor effects were mediated by NK cells in this model, as depletion abrogated the effect, while absence of T and B cells had no impact. NK cells have potent anti-tumor activity, and can also reciprocally activate dendritic cells, as well as macrophages to augment anti-tumor activity. We hypothesized that, as chemerin recruits innate immune cells, it may be downregulated as a means of immune evasion and/or escape.

Example 2. RARRES2 in Human Cancer

Given the potential role of chemerin/RARRES2 in controlling leukocyte migration into tumors, we then asked whether this was differentially regulated in human cancer compared with normal tissue (FIG. 2A, FIG. 2B, FIG. 2C, FIG. 2D, FIG. 2E, FIG. 2F). We investigated the expression of RARRES2 in human melanoma and prostate, lung, breast, and colon cancer. Strikingly, RARRES2 was significantly downregulated in all human tumor tissues tested. Interestingly, a stepwise downregulation of RARRES2 correlates with malignant progression (FIG. 2A, FIG. 2B), consistent with our hypothesis that chemerin downregulation is a potential mechanism of tumor immune evasion, and supporting the relevance of the hypothesis to prostate cancer. Our data, using quantitative PCR as well as IHC on tissue microarrays shows that chemerin/RARRES2 is downregulated in malignant prostate tissues (not shown).

Downregulation of RARRES2 has been reported in studies of several specific tumor types in man, including prostate, colon, adrenocortical, and skin carcinomas. Importantly, downregulation of RARRES2 was associated with loss of chemerin protein and development of malignancy in an immunohistochemical study of human squamous cell skin cancer. Thus, we hypothesize that chemerin acts as a natural tumor suppressive cytokine in prostate cancer and, further, that tumors may downregulate it as a means of immune evasion.

Example 3. Tumor Chemerin/RARRES2 Correlates with Survival

Figure 3:
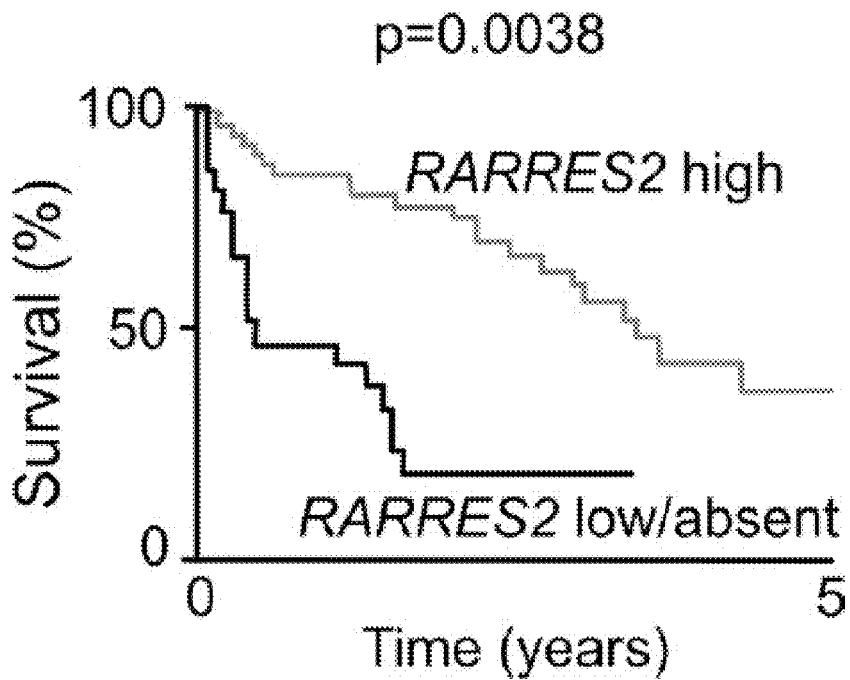
FIG. 3 depicts a graph showing that higher RARRES2 expression correlates with improved prognosis in human melanoma. RARRES2 mRNA gene expression and clinical data were analyzed for 2 large patient cohorts with malignant melanoma. Association between RARRES2 expression and clinical outcome was assessed by examining continuous expression of RARRES2 in relation to overall survival as measured by log-likelihood P values within a univariate Cox regression model. Patients were separately analyzed for overall survival by Kaplan-Meier analysis, and stratified into high- and low-RARRES2 groups based on comparison of expression level relative to an idealized threshold within each cohort. Multiple hypothesis testing correction for optimal threshold selection was addressed using 1000-fold cross-validation within each study; for corresponding the Kaplan Meier strata depicted as survival curves (line graph, left), only these corrected log-rank p-values are reported. Affymetrix microarray data were processed starting with CEL files, with Entrez Gene probe set summarization using CustomCDF version 12 and normalization using MAS 5.0 linear scaling method.

Higher expression or RARRES2 correlated with better outcomes in clinical studies of melanoma (FIG. 3). Two additional studies in hepatocellular carcinoma (HCC) and non-small cell lung cancer (NSCLC) also show correlation of chemerin expression in tumor biopsies with improved overall survival, suggesting the presence of chemerin within the tumor microenvironment is associated with improved clinical outcomes. Importantly, these two studies also stained for tumor-infiltrating immune cells (eg natural killer and dendritic cells), and showed that the increased levels of chemerin in the tumors correlated with an increase in these infiltrating immune cells, suggesting a role for chemerin in this regard. Our studies suggest that chemerin impairs tumor growth in vivo, and thus that growth inhibition reflects an alteration in the host environment rather than a direct effect on the malignant cells themselves.

Example 4. Chemerin Constructs

Figure 4:
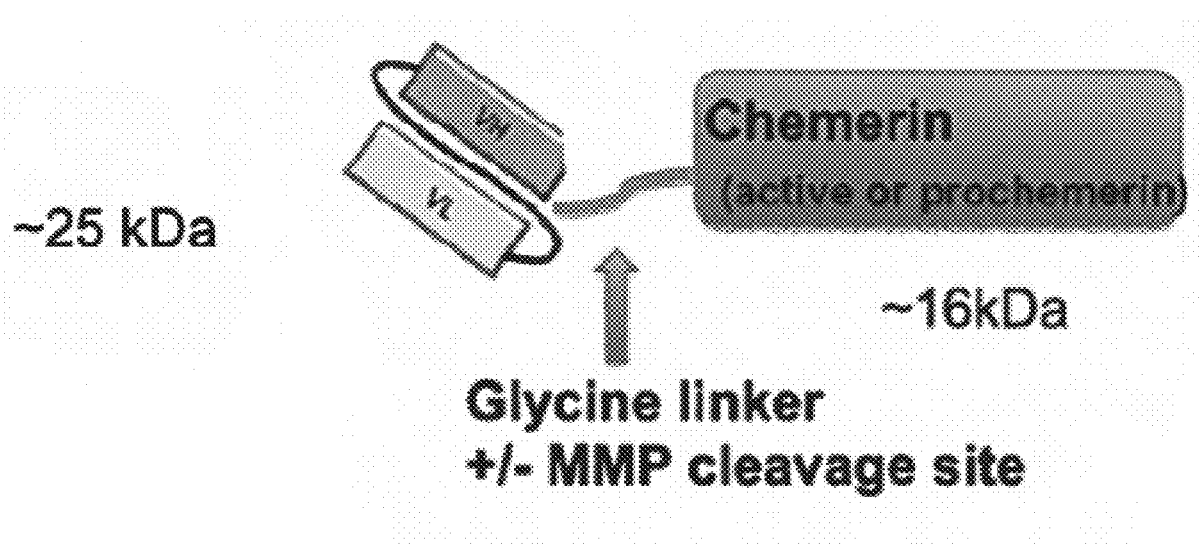
FIG. 4 depicts a schematic of a chemerin fusion protein. In the schematic, chemerin (active or prochemerin) is linked to anti-human CD20 scFv (or a ligand to other tumor antigens) via a glycine and/or MMP cleavage site linker.

A fusion protein comprising chemerin linked to a scFv antibody was designed. Specifically, mature chemerin or prochemerin was linked to a CD20 scFv antibody. However, once proof of concept has been shown, other targeting ligands may be used to direct chemerin to the site of the tumor. The chemerin construct also included a glycine linker with or without a MMP cleavage site (FIG. 4). The cleavage site can be cleaved by matrix metalloproteinases (MMPs) upregulated in tumors thereby releasing chemerin into the extracellular space once the fusion protein has bound to the target tumor cell. It is important that chemerin remain extracellular to perform its chemoattractant functions.

A construct comprising CD20 scFV, a glycine linker and mature chemerin or prochemerin was developed. The mature chemerin construct comprises SEQ ID NO:10 and the prochemerin construct comprises SEQ ID NO:12. The polypeptides expressed from SEQ ID NO:10 and SEQ ID NO:12 are SEQ ID NO:14 and SEQ ID NO:16, respectively.

CHO cells were seeded in a shake flask 24 hours before transfection, and were grown using serum-free chemically defined media. The DNA expression constructs comprising SEQ ID NO:10 or SEQ ID NO:12 were transiently transfected into 0.1 liter of suspension CHO cells. After 24 hours, cells were counted to obtain the viability and viable cell count, and titer was measured by ForteBio Octet. Additional readings were taken throughout the transient transfection production run. The culture was harvested at day 7.

The conditioned media supernatant harvested from the transient transfection production run was clarified by centrifuge spinning. Filtration using a 0.2 μm membrane filter was performed. The protein was purified using anti-His affinity chromatography. After purification and filtration, 0.05 mg of CD20 scFv-Human mature chemerin and 0.02 mg of CD20 scFv-Human prochemerin protein was obtained. SDS PAGE analysis was performed and the gel was stained with SimplyBlue SafeStain solution.

The CD20 scFv-Human mature chemerin and CD20 scFv-Human prochemerin proteins were cloned into a high expression mammalian vector system and a small-scale (0.1 liter) transient production was completed in CHO cells. The protein was purified by His-tag purification and 0.05 mg of CD20 scFv-Human bioactive chemerin and 0.02 mg of CD20 scFv-Human PROchemerin protein was obtained.

Example 5. In Vitro Evaluation of Chemerin Fusion Protein

Figure 5:
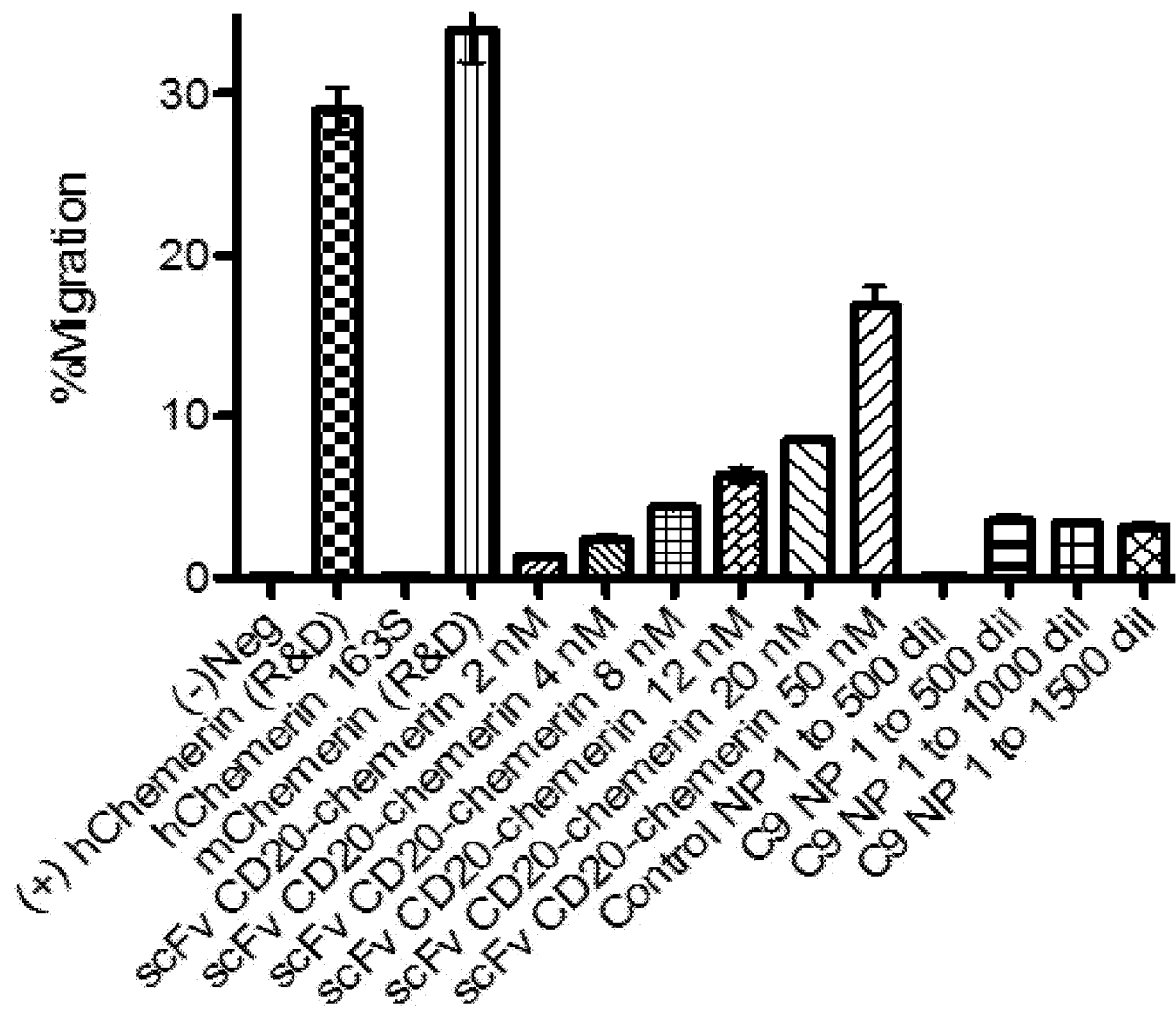
FIG. 5 depicts a graph shows that scFv CD20-chemerin fusion protein results in significant recruitment of CMKLR1+ cells.

A chemotaxis assay was performed to assess the functionality of the chemerin portion of the fusion protein. A 96-well chemotaxis assay was conducted for 1.75 hours at 37° C. The percent migration of input cells was calculated as a measure of chemerin activity. Recombinant human chemerin, mouse chemerin and scFv CD20-chemerin at 50 nM all showed significant recruitment of CMKLR1+ cells (FIG. 5).

Figure 6:
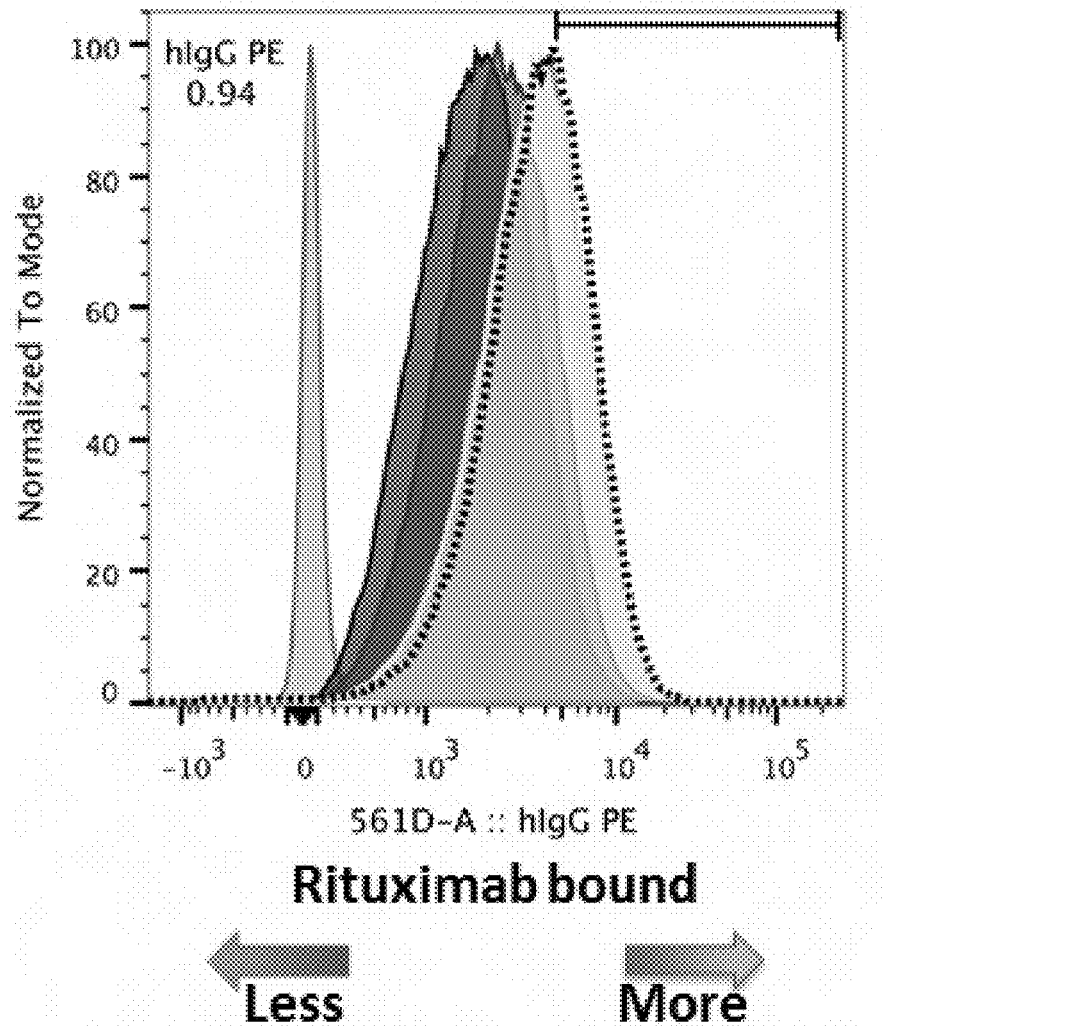
FIG. 6 depicts a flow cytometry plot showing that scFv CD20-chemerin fusion protein competes with rituximab for binding to CD20 positive cells.

Next, a competitive binding assay with the chemerin fusion protein was conducted. CD20+ Raji human lymphoma cells were used. The cells were preincubated with fusion protein. Rituximab was then added. An anti-human IgG antibody was used to detect bound rituximab. Functional binding of the scFv CD20-chemerin fusion protein should compete with rituximab for CD20 binding and reduce FACS signal. In fact, scFv CD20-chemerin at 15 μg/ml (purple) bound to CD20 and showed the most rituximab displacement (FIG. 6). Rituximab only, with no scFv CD20-chemerin added, is shown in the dotted line. There was no consistent correlation between CD20-chemerin concentration and rituximab displacement.

Figure 7:
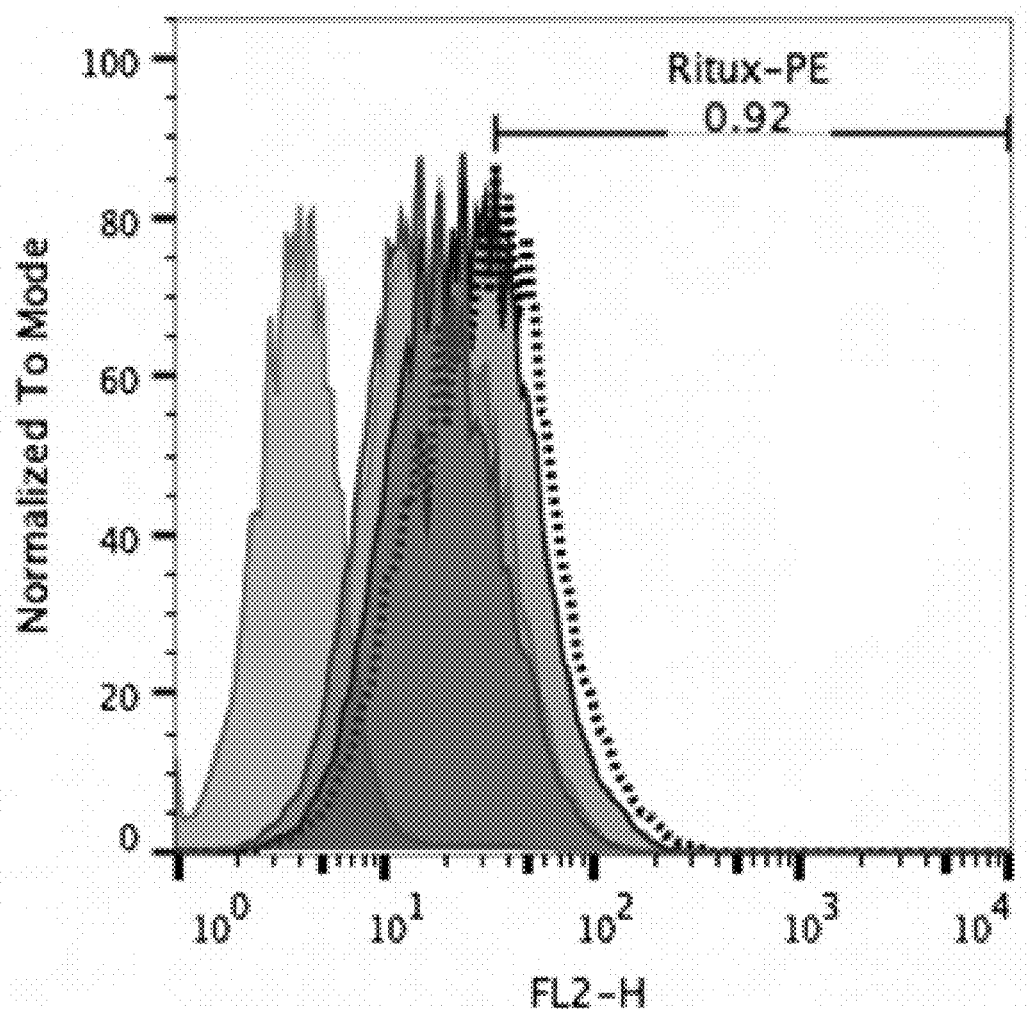
FIG. 7 depicts a second experiment showing a flow cytometry plot showing that scFv CD20-chemerin fusion protein competes with rituximab for binding to CD20 positive cells.

The competitive binding assay was repeated at 4° C. Raji cells were preincubated for 30 minutes with nothing or scFv CD20-chemerin at 3.75 μg/ml, 7.5 μg/ml, or 15 μg/ml. Rituximab was then added to a final concentration of 1 μg/ml and incubated for 30 minutes at 4° C. Following this incubation, anti-human IgG-PE was added and incubated for 20 minutes at 4° C. Less rituximab was bound in all the scFv CD20-chemerin groups suggesting that the fusion protein competes with rituximab binding to Raji cells (FIG. 7).

Example 6. In Vivo Evaluation of Chemerin Fusion Protein

To evaluate the activity of the chemerin fusion protein in vivo, B16 melanoma was engineered to express human CD20 on its surface. There is 73% homology between mouse and human CD20, with most of the differences occurring in in the extracellular domain. Anti-human CD20 antibody production takes approximately 10-14 days and the adaptive response takes approximately 3-5 days thereby allowing a treatment window in the immunocompetent mice. Murine CMKLR1 (dez) can bind and mediate chemotaxis to human chemerin in vitro. L12dez cells chemotax to human chemerin. Thus, scFv CD20-chemerin fusion protein may be able to recruit murine leukocytes into B16 hCD20+ tumors.

Figure 8:
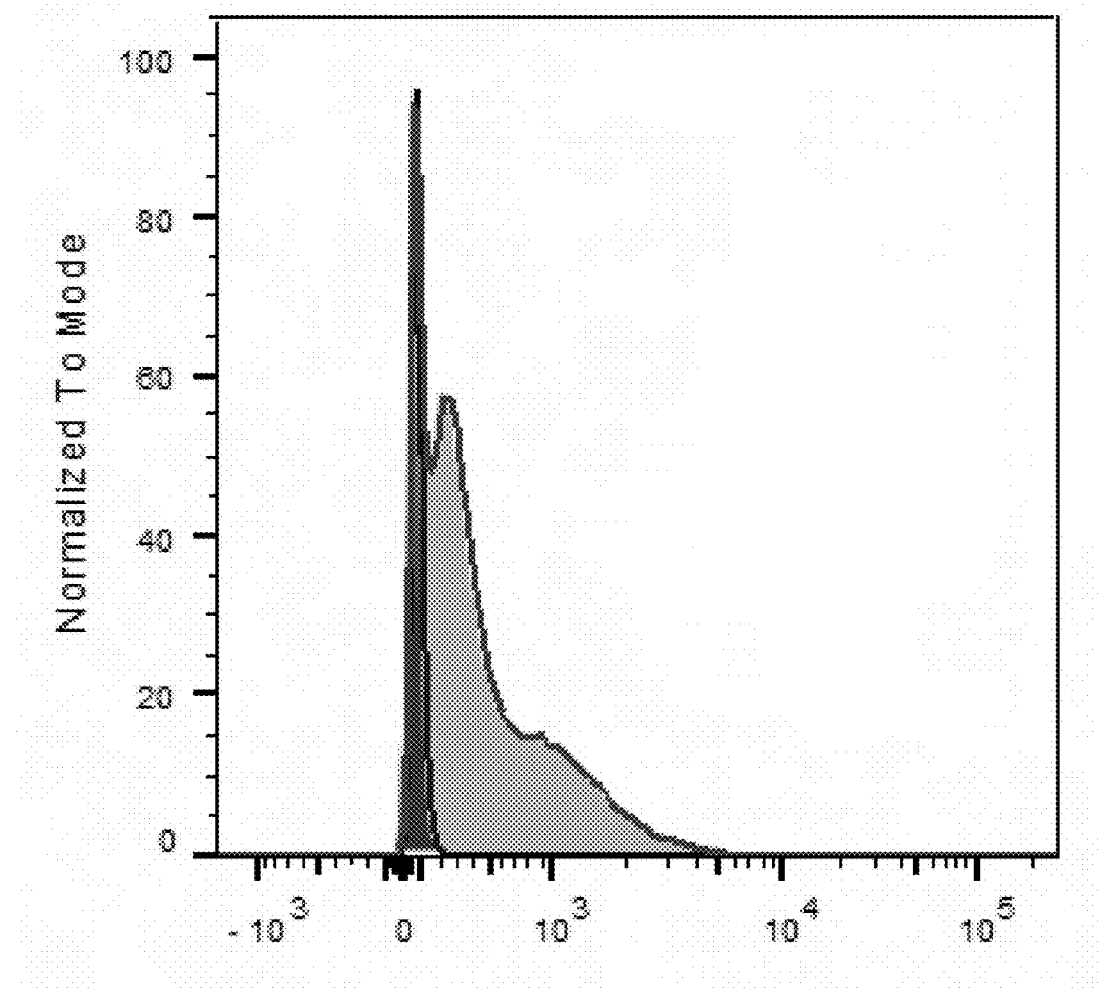
FIG. 8 depicts a flow cytometry plot showing human CD20 expression in B16 melanoma cells engineered to expression human CD20.
Figure 9:
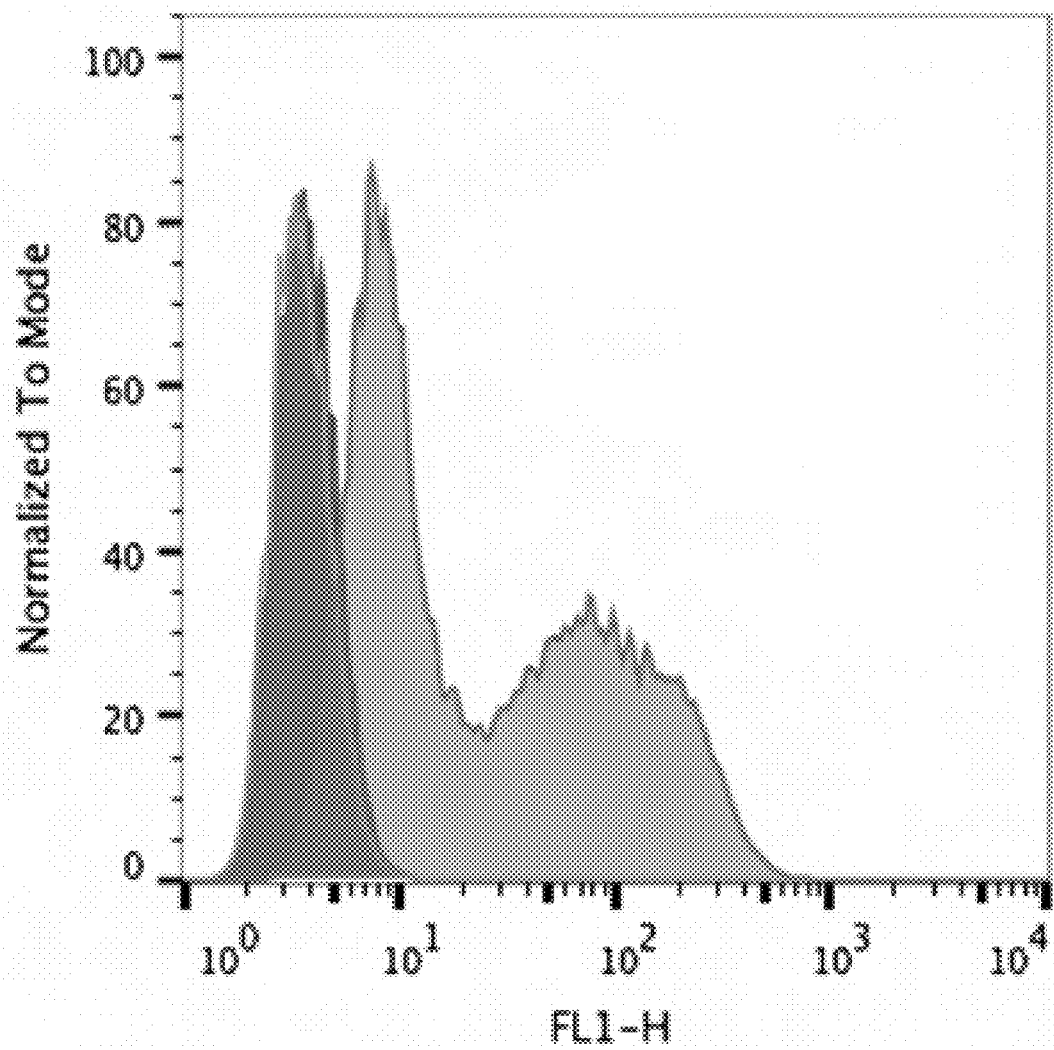
FIG. 9 depicts a flow cytometry plot showing that after 2 sorts the number of CD20 expressing cells isolated increases.
Figure 10:
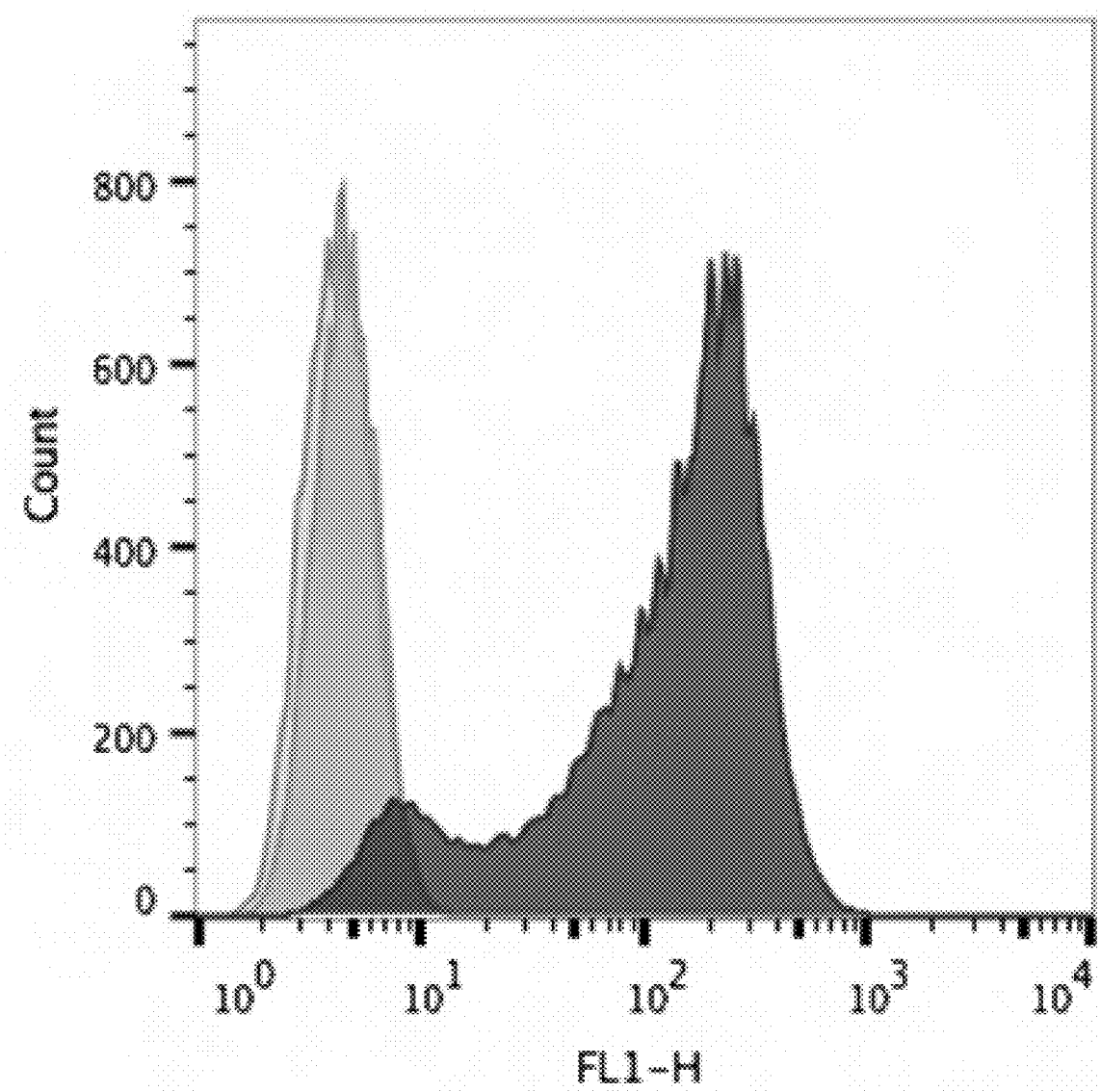
FIG. 10 depicts a flow cytometry plot showing that after 3 sorts the number of CD20 expressing cells isolated increases even further.
Figure 11:
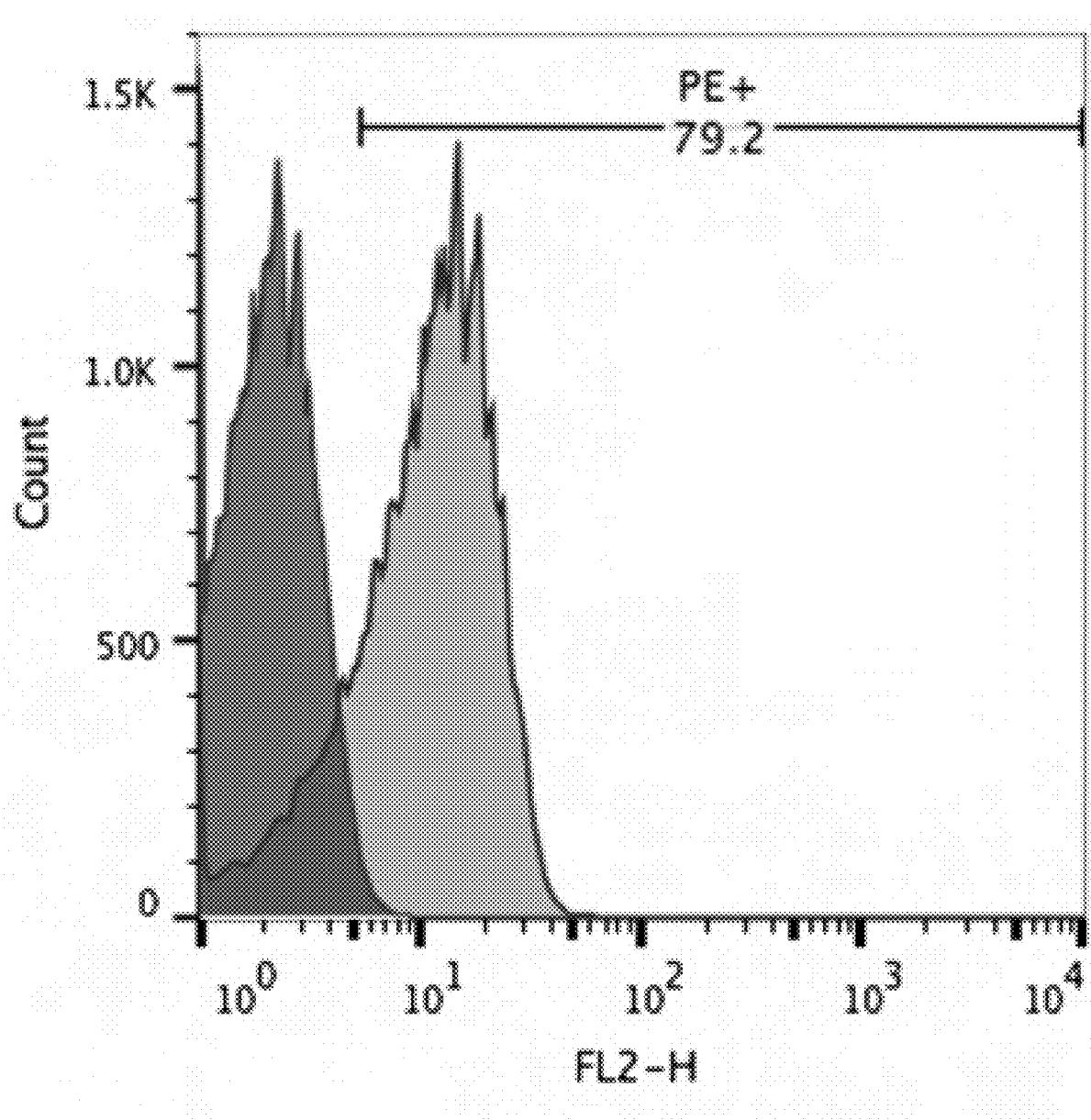
FIG. 11 depicts a flow cytometry plot showing that the majority of peripheral human NK cells express CMKLR1 (blue).

First it was confirmed that the B16 melanoma cells transfected with human CD20 expressed human CD20 (FIG. 8). After two sorts of the transfected B16 melanoma cells, it was confirmed that they expressed human CD20 (FIG. 9). After three sorts, cells with robust expression of human CD20 were obtained (FIG. 10). Fresh human NK cells were then isolated and stained with anti-human CMKLR1-PE. It was determined that the majority of peripheral human NK cells express CMKLR1 (FIG. 11).

Figure 12:
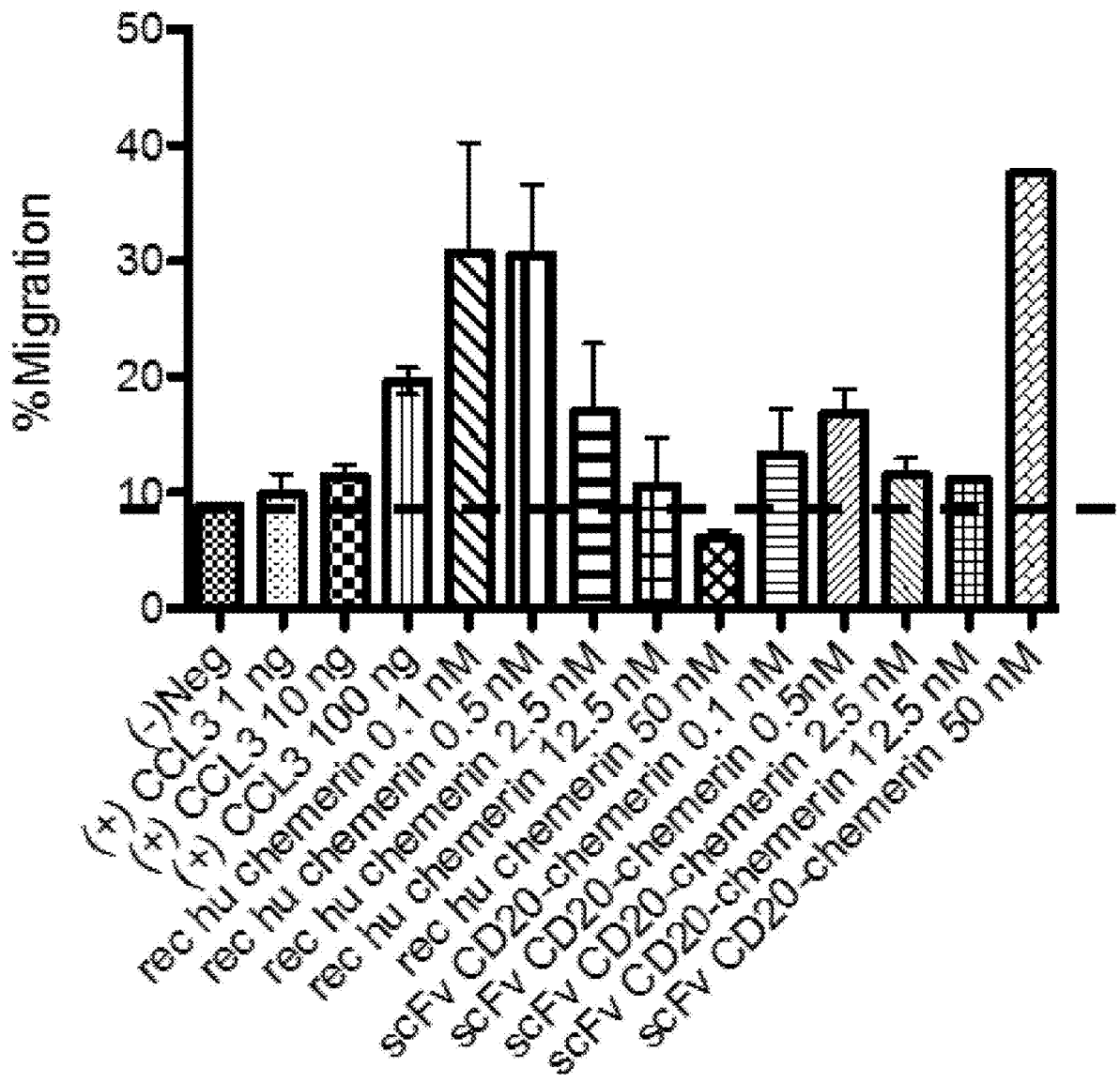
FIG. 12 depicts a graph showing that CD20-chemerin fusion protein recruits human NK cells in vitro.
Figure 13:
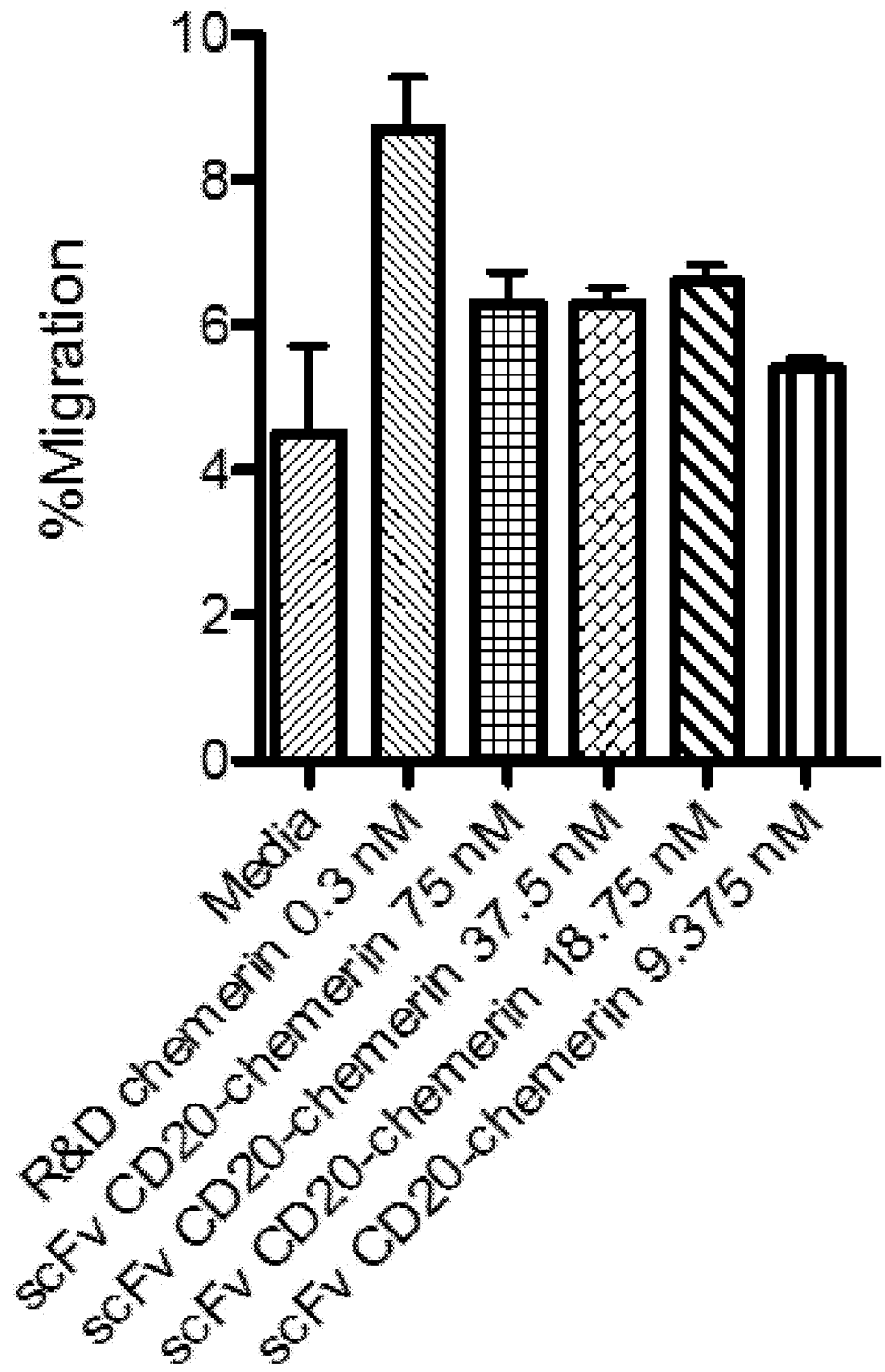
FIG. 13 depicts a graph showing that additional concentrations of CD20-chemerin fusion protein recruit human NK cells in vitro.

The migration assay discussed in Example 4 was then used to evaluate the ability of the fusion protein to recruit human NK cells in vitro. It was found that the scFv CD20-chemerin fusion protein significantly recruited NK cells at 50 nM (FIG. 12). The experiment was repeated with lower concentrations of fusion protein. The results showed that scFv CD20-chemerin caused migration of human NK cells (FIG. 13).

Figure 14:
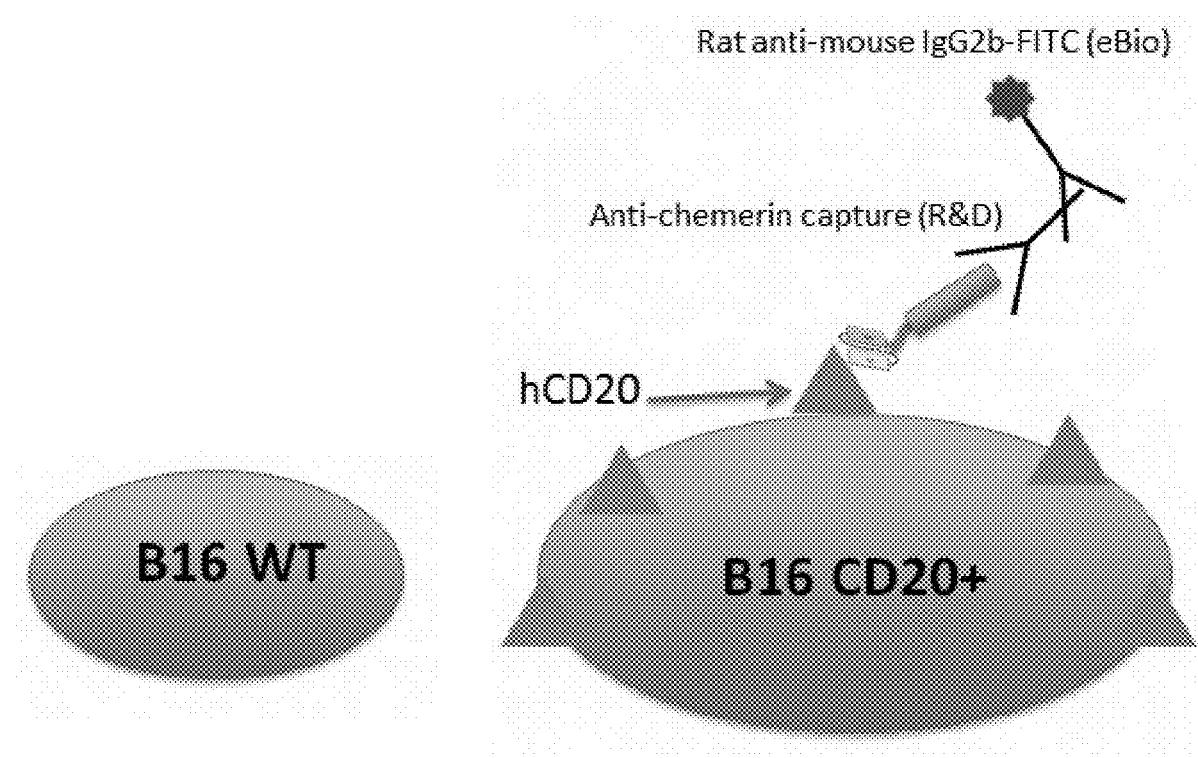
FIG. 14 depicts a FACS detection scheme used to detect fusion protein binding to CD20+ cells.
Figure 15A:
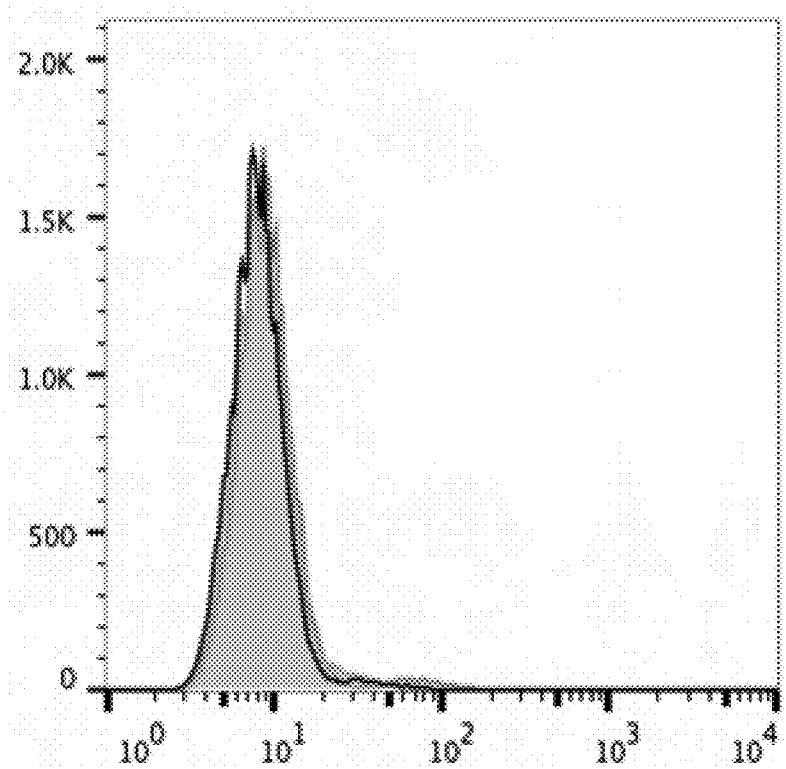
FIG. 15A, FIG. 15B, FIG. 15C and FIG. 15D depict flow cytometry plots showing that the scFv CD20-chemerin fusion protein selectively binds CD20. The scFv CD20-chemerin fusion protein selectively binds to B16 CD20+ cells (FIG. 15B) but does not appreciably bind to B16 WT cells (FIG. 15A). The scFv CD20-chemerin fusion protein group is indicated in cyan. Further, there is a dose response of scFv CD20-chemerin fusion protein binding to B16 CD20+ cells. scFv CD20-chemerin fusion protein (FIG. 15C). Green 1000 ng/ml; red 100 ng/ml; purple 10 ng/ml.
Figure 15B:
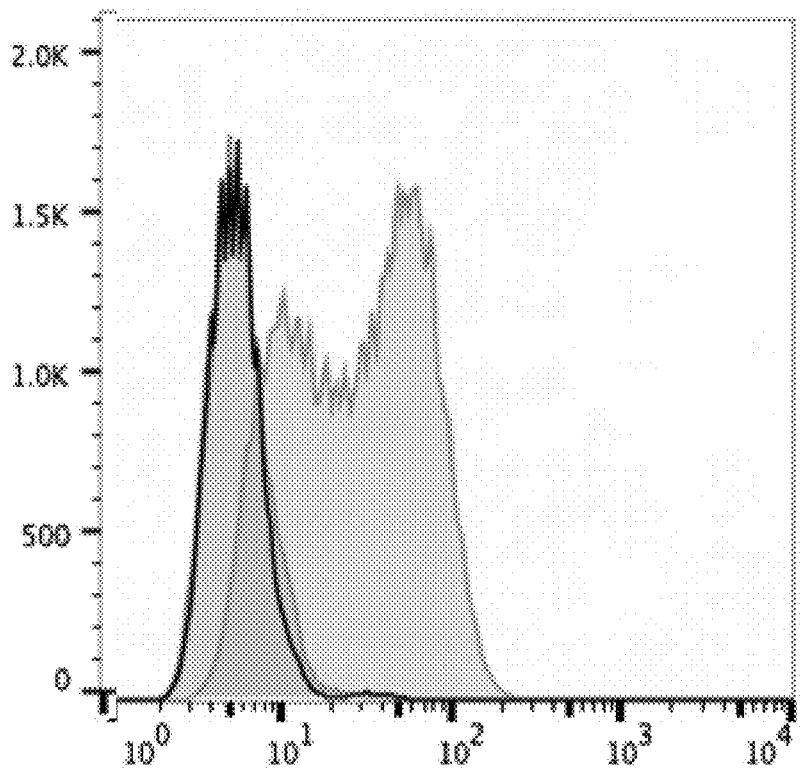
Figure 15C:
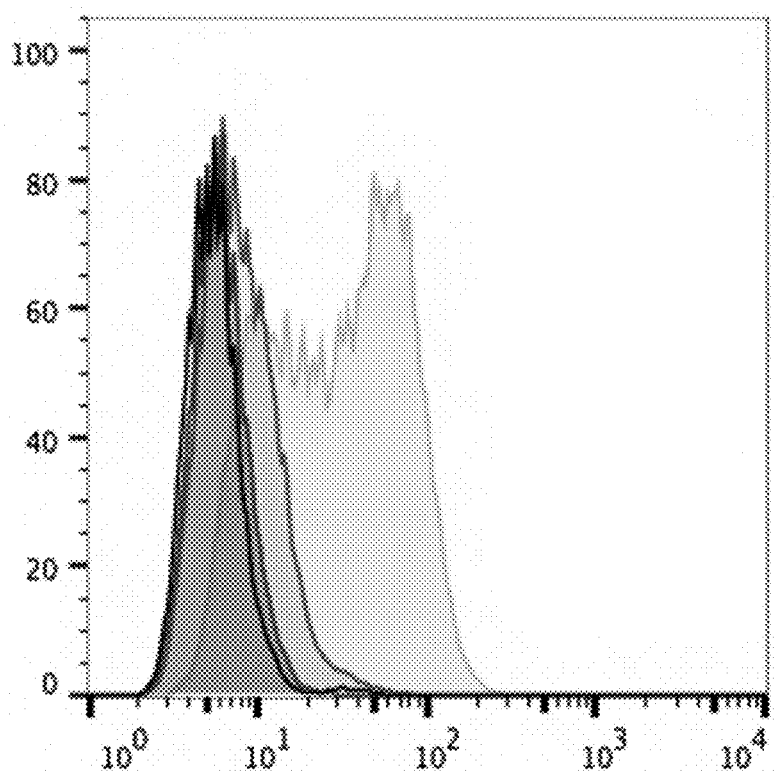
Figure 15D:
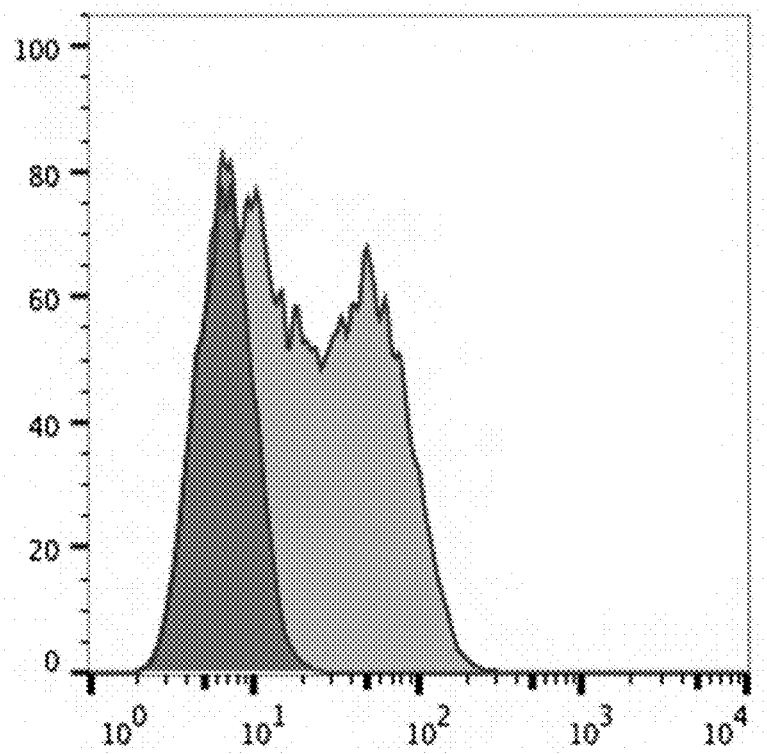
Figure 16A:
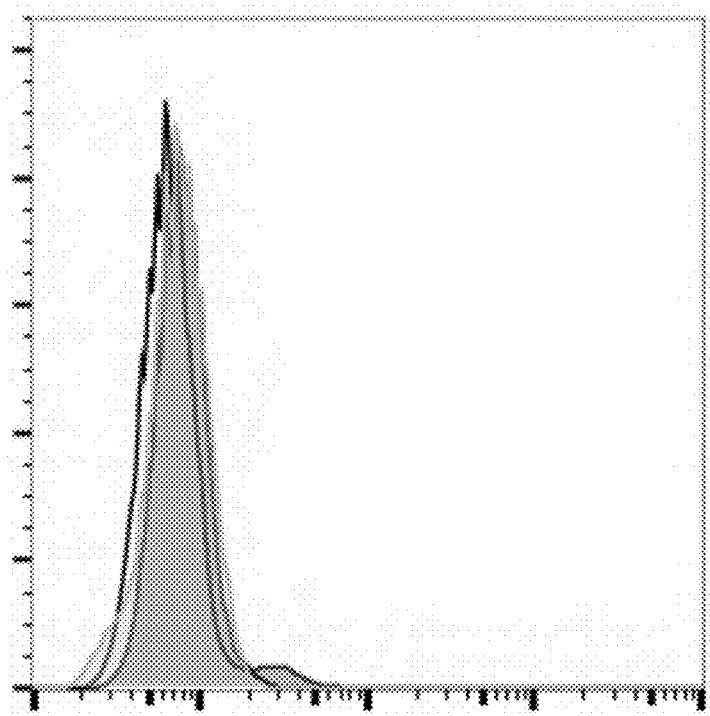
FIG. 16A, FIG. 16B and FIG. 16C depict flow cytometry plots from a second experiment showing that the scFv CD20-chemerin fusion protein selectively binds CD20. The scFv CD20-chemerin fusion protein selectively binds to B16 CD20+ cells (FIG. 16B) but does not appreciably bind to B16 WT cells (FIG. 16A). The scFv CD20-chemerin fusion protein group is indicated in orange.
Figure 16B:
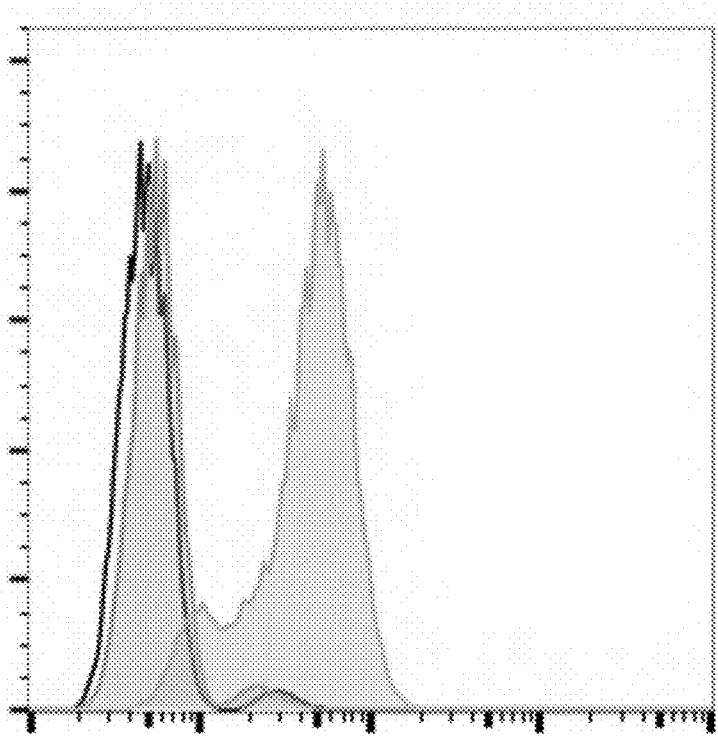
Figure 16C:
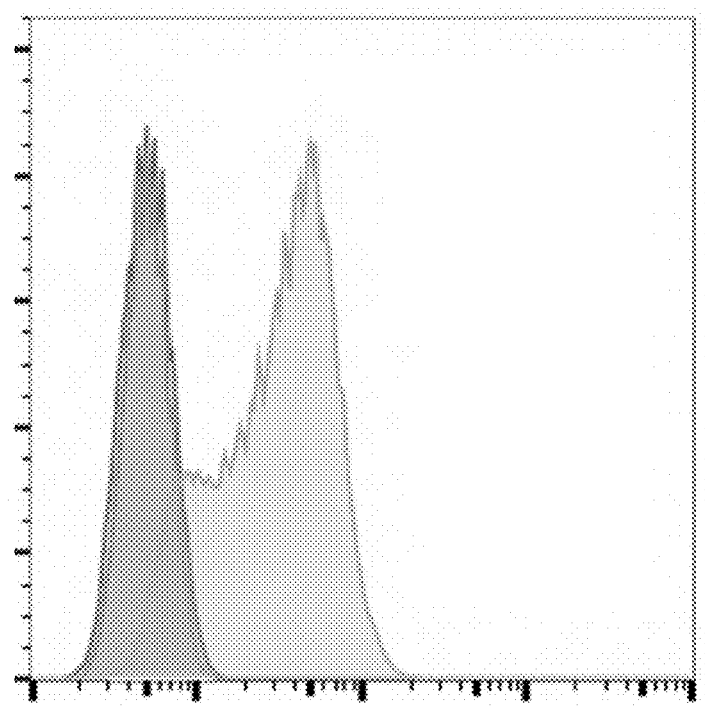
Figure 17:
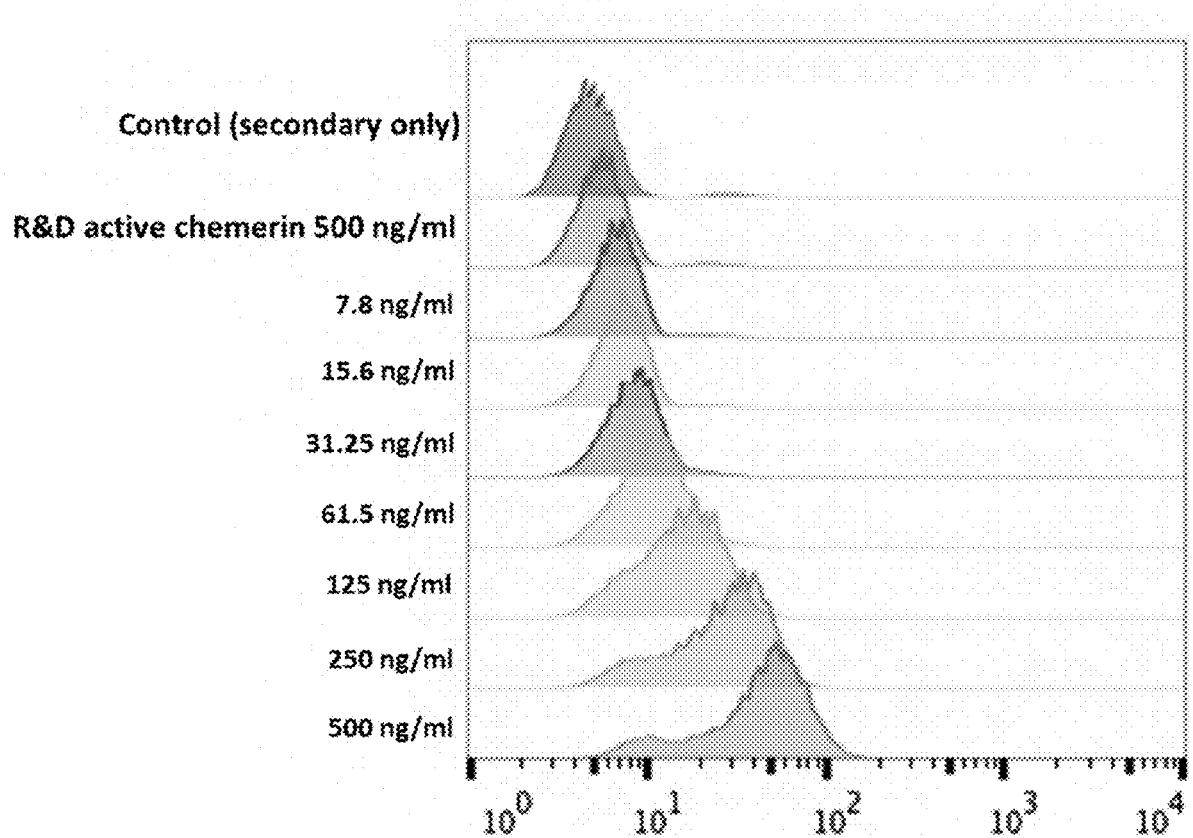
FIG. 17 depicts flow cytometry plots demonstrating the dose response of the scFv CD20-chemerin fusion protein binding to B16 CD20+ cells.
Figure 18:
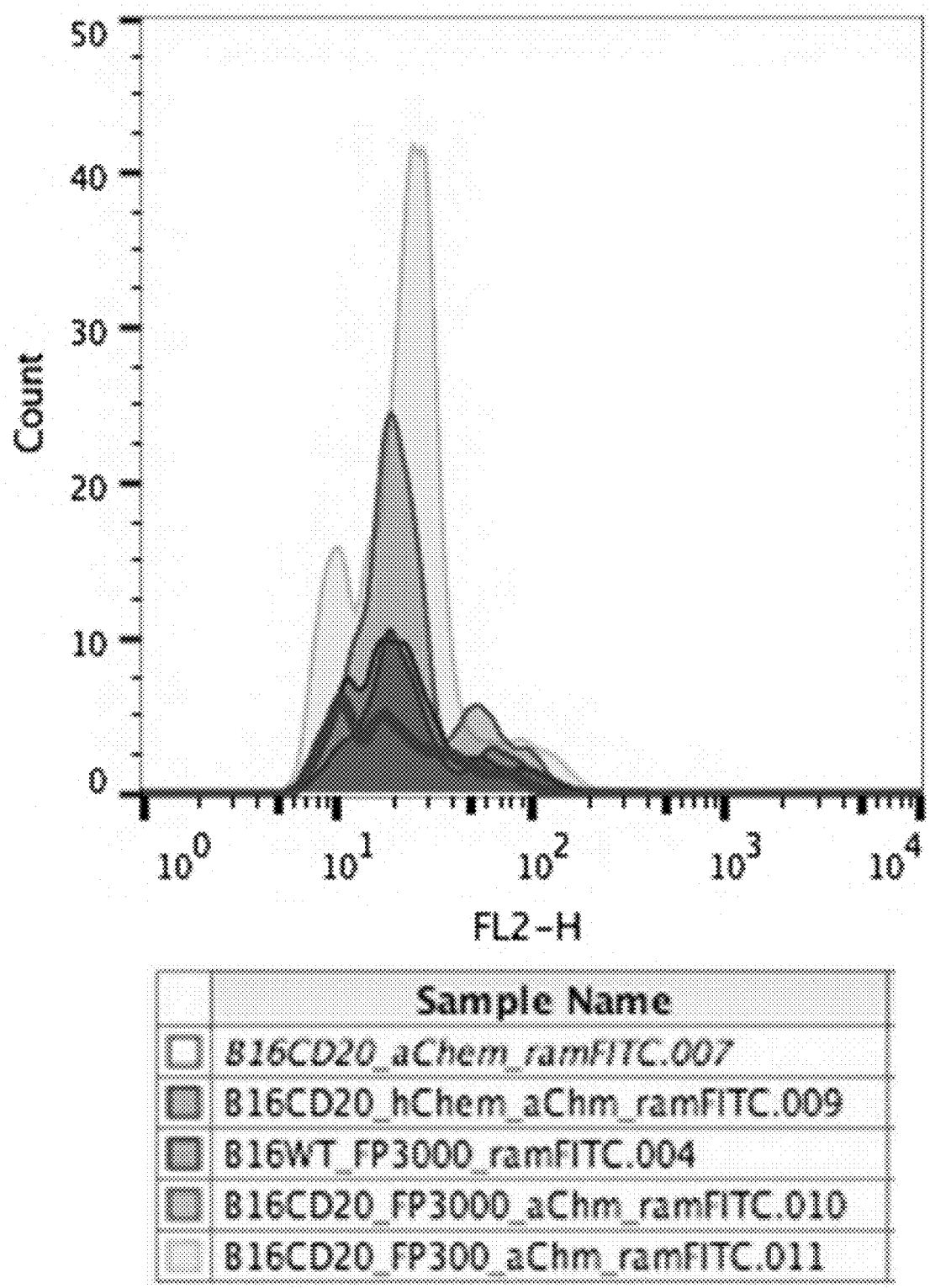
FIG. 18 depicts a flow cytometry plot showing the selective binding of scFv CD20-chemerin fusion protein to CD20+ B16 tumors.

The binding of the scFv CD20-chemerin fusion protein to B16 melanoma cells expressing human CD20 was evaluated by FACS as depicted in FIG. 14. Using the triple sorted B16 CD20+ cells (FIG. 15D), scFv CD20-chemerin selectively bound to the CD20 expressing B16 cells (FIG. 15B) but not the WT B16 cells (FIG. 15A). The unconjugated human recombinant chemerin was administered at 1000 ng/ml. A dose response was also observed when the scFv CD20-chemerin was administered at 1000 ng/ml, 100 ng/ml and 10 ng/ml (FIG. 15C). The cells were incubated with the various proteins for 15 minutes at 4° C. The study was repeated, confirming that the scFv CD20-chemerin fusion protein selectively bound B16 cells expressing CD20 (FIG. 16A, FIG. 16B, FIG. 16C). Additional concentrations of scFv CD20-chemerin were evaluated and a dose response curve was detected (FIG. 17). It was also demonstrated that the scFv CD20-chemerin fusion protein selectively bound to CD20+ B16 tumors. B16 WT or B16 hCD20+ cells were incubated with nothing, human recombinant chemerin or scFv CD20-chemerin fusion protein at either 300 or 3000 ng/ml. The fusion protein groups demonstrated a significant increase in stained cells relative to untreated or chemerin alone (FIG. 18).

Example 7. Evaluation of Chemerin Fusion Protein on In Vivo Tumor Targeting

Figure 19:
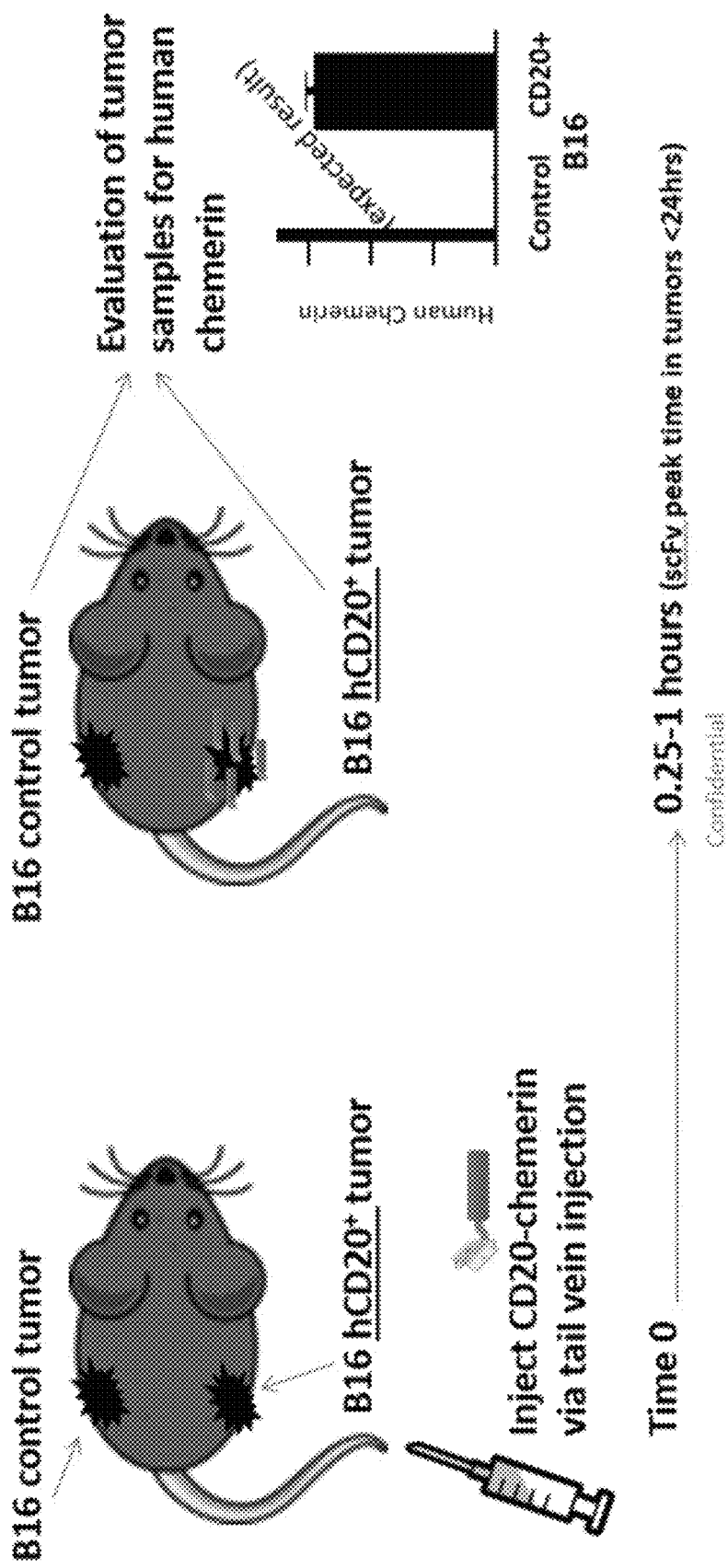
FIG. 19 depicts a schematic of the experimental design for the in vivo demonstration of tumor targeting of the chemerin fusion protein.
Figure 20:
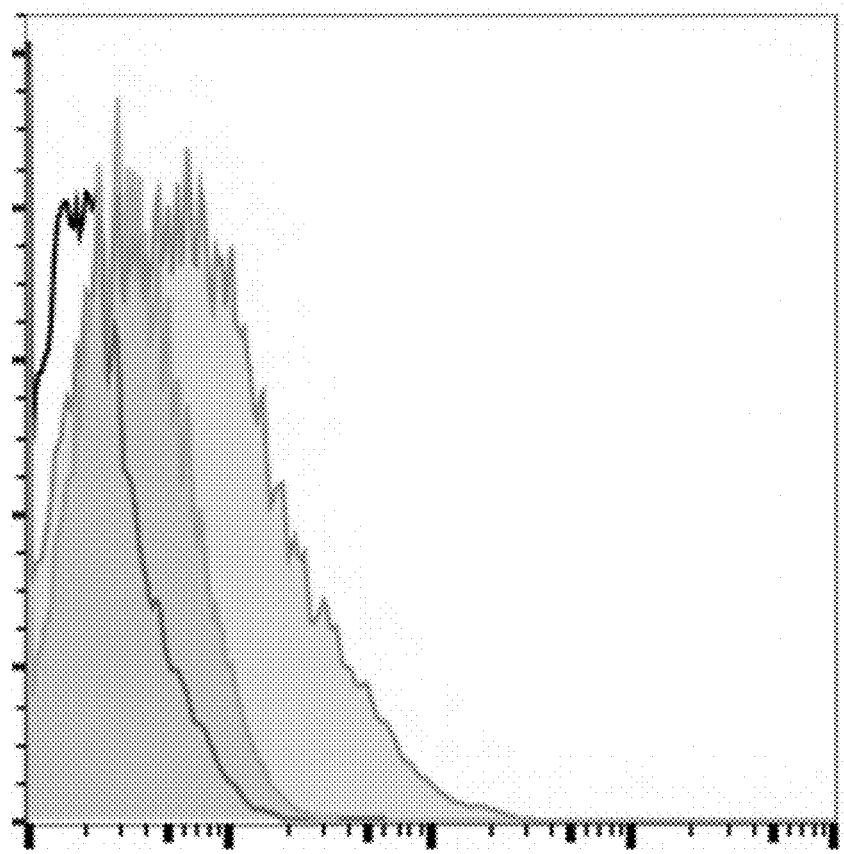
FIG. 20 depicts a flow cytometry plot showing the binding of the rituximab control to B16 hCD20+ cells. Cyan is B16 CD20+ cells, Orange is B16 CD20+ with isotype control, and Black is B16 WT cells.
Figure 21A:
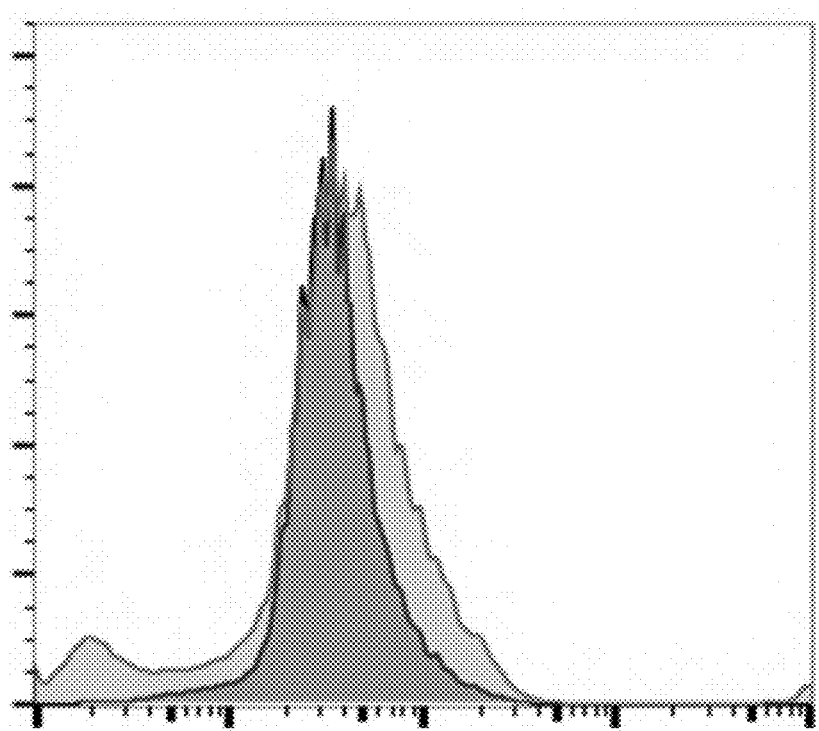
FIG. 21A, FIG. 21B and FIG. 21C depict a flow cytometry plots showing the binding of the scFv CD20-chemerin fusion protein to B16 hCD20+ cells.
Figure 21B:
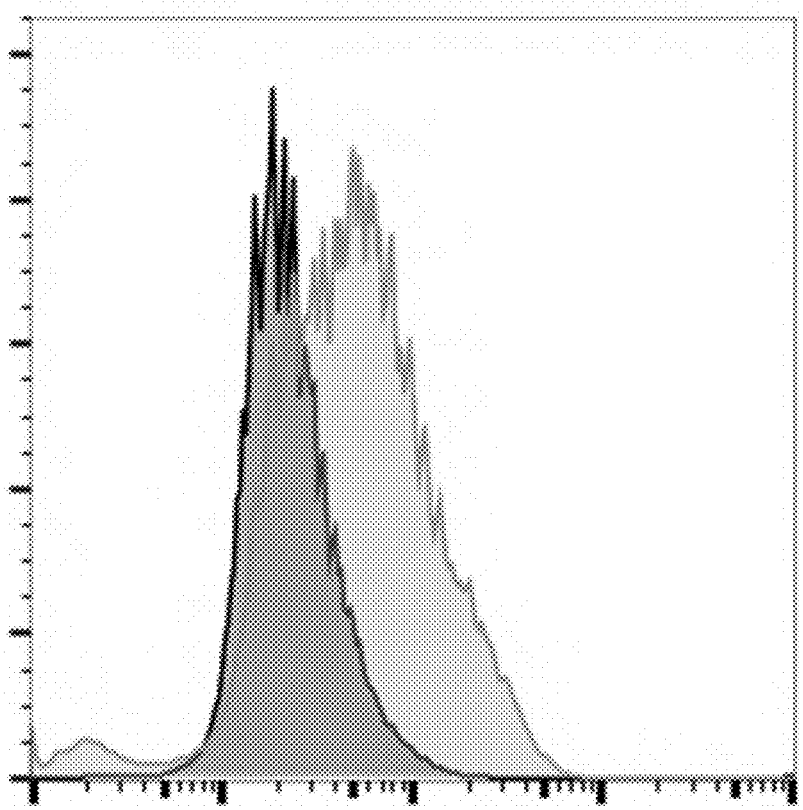
Figure 21C:
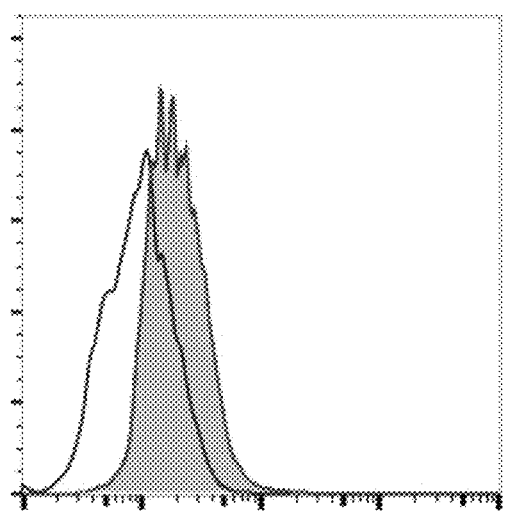

Mice were injected in their right flank and left flank with either $4\times10^6$ cells of B16 control cells or B16 hCD20+ cells. The tumor was allowed to grow for 4 days and then the mice are injected with scFv CD20-chemerin protein via tail injection. At various timepoints, the samples are evaluated for human chemerin (FIG. 19). In a second experiment, mice were injected retro-orbitally with saline, rituximab (10 mg/kg) or scFv CD20-chemerin fusion protein (4 mg/kg). Blood was collected pre-injection and at 15 minutes and 30 minutes post-injection. Mice were then sacrifices and the tumor was harvested at 30 minutes post-injection. A single suspension of the tumor was made and stained for FACS. Anti-chemerin antibody and IgG2b-FITC secondary antibody were used for detection. In the rituximab control, rituximab bound to the B16 hCD20+ tumor but not the B16 WT tumor (FIG. 20). It was also observed in the scFv CD20-chemerin treated mice, that scFv CD20-chemerin selectively bound to the B16 hCD20+ tumor cells (FIG. 21B). The control mice were treated with saline only (FIG. 21A).

Example 8. Labeled scFv CD20-Chemerin Fusion Protein

Figure 22A:
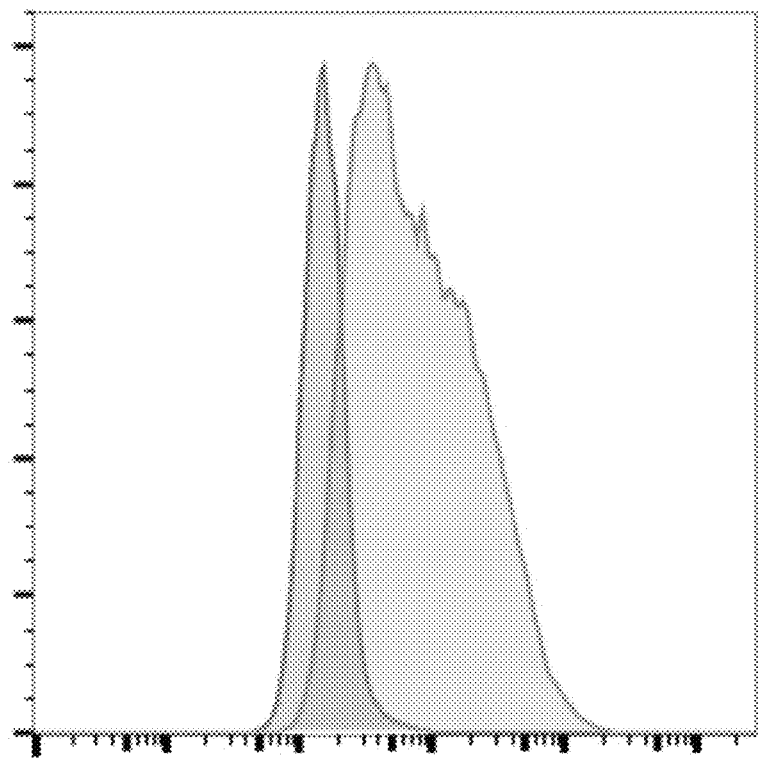
FIG. 22A and FIG. 22B depict flow cytometry plots showing binding of the scFv CD20-chemerin fusion protein labeled with AF-647 to B16 CD20+ cells.
Figure 22B:
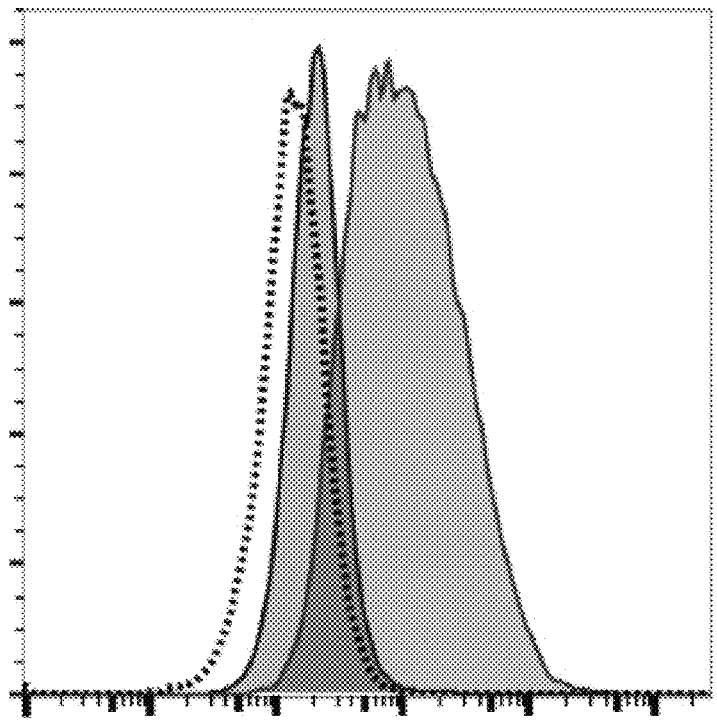
Figure 23:
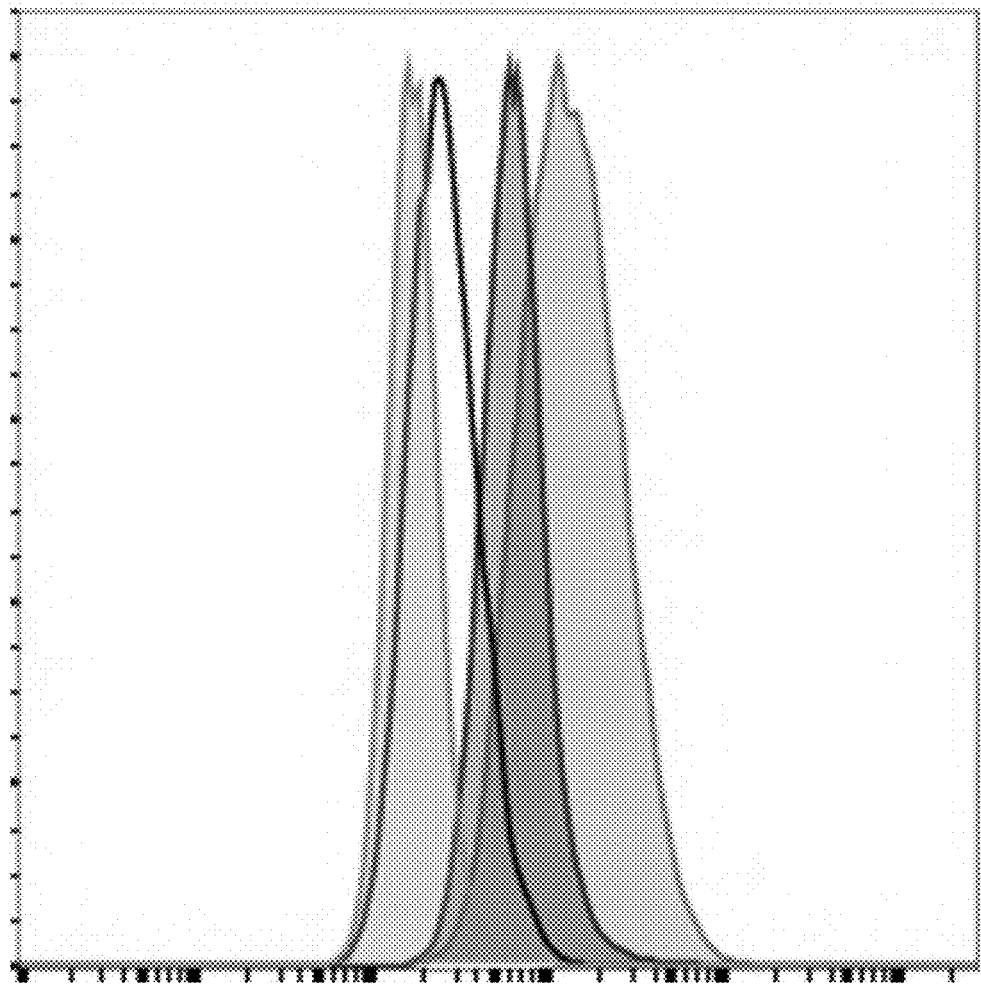
FIG. 23 depicts a flow cytometry plot showing that some background staining is observed with unlabeled fusion protein on WT cells. B16 CD20+ cells are red, B16 WT cells are blue, B16 unstained cells are grey, and B16 cells stained with secondary antibody only are white.
Figure 24:
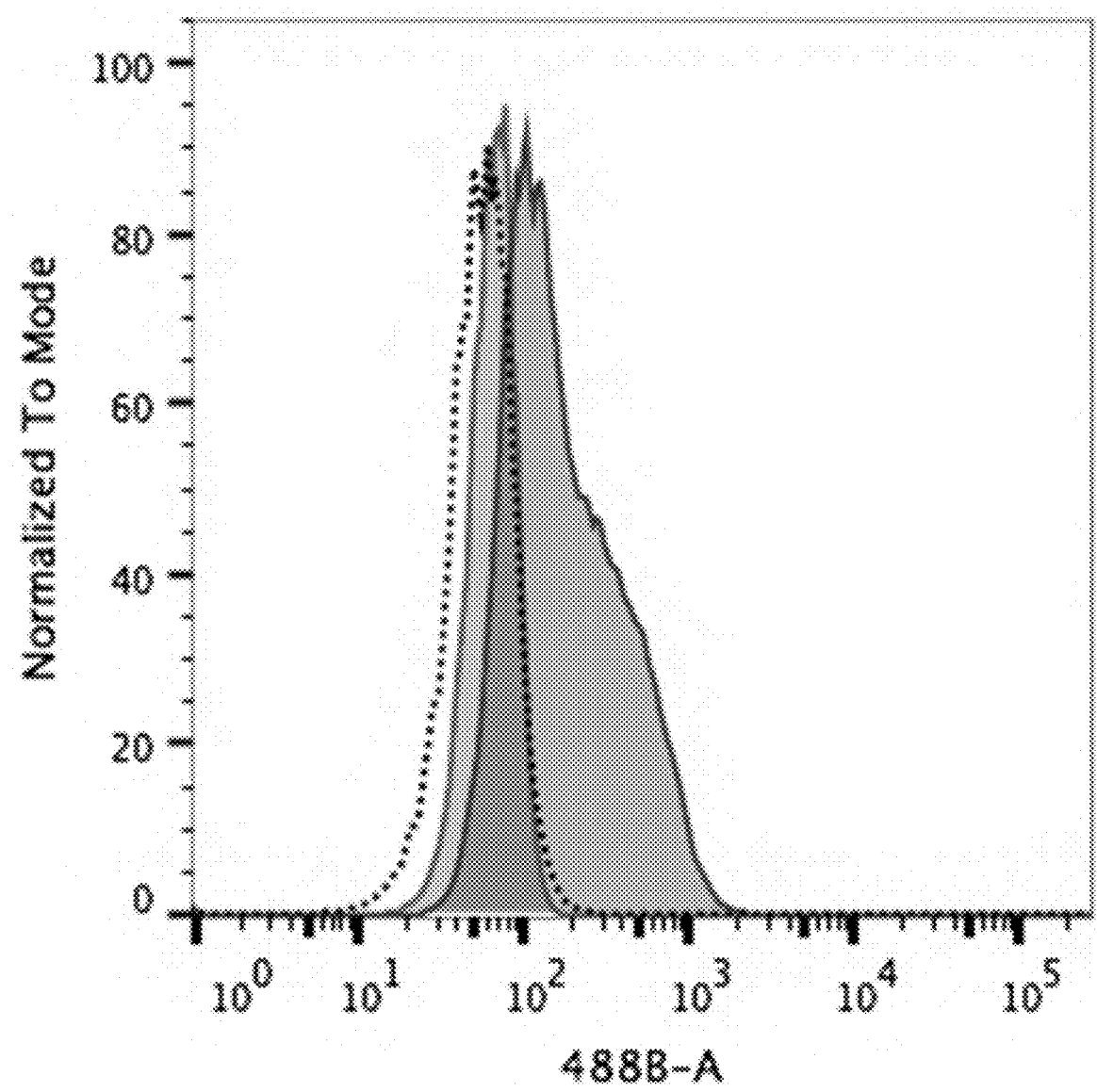
FIG. 24 depicts a flow cytometry plot showing binding of the labeled fusion protein to B16 CD20+ cells. B16 CD20+ cells are purple, B16 WT cells are red, B16 unstained cells are dotted line.
Figure 25:
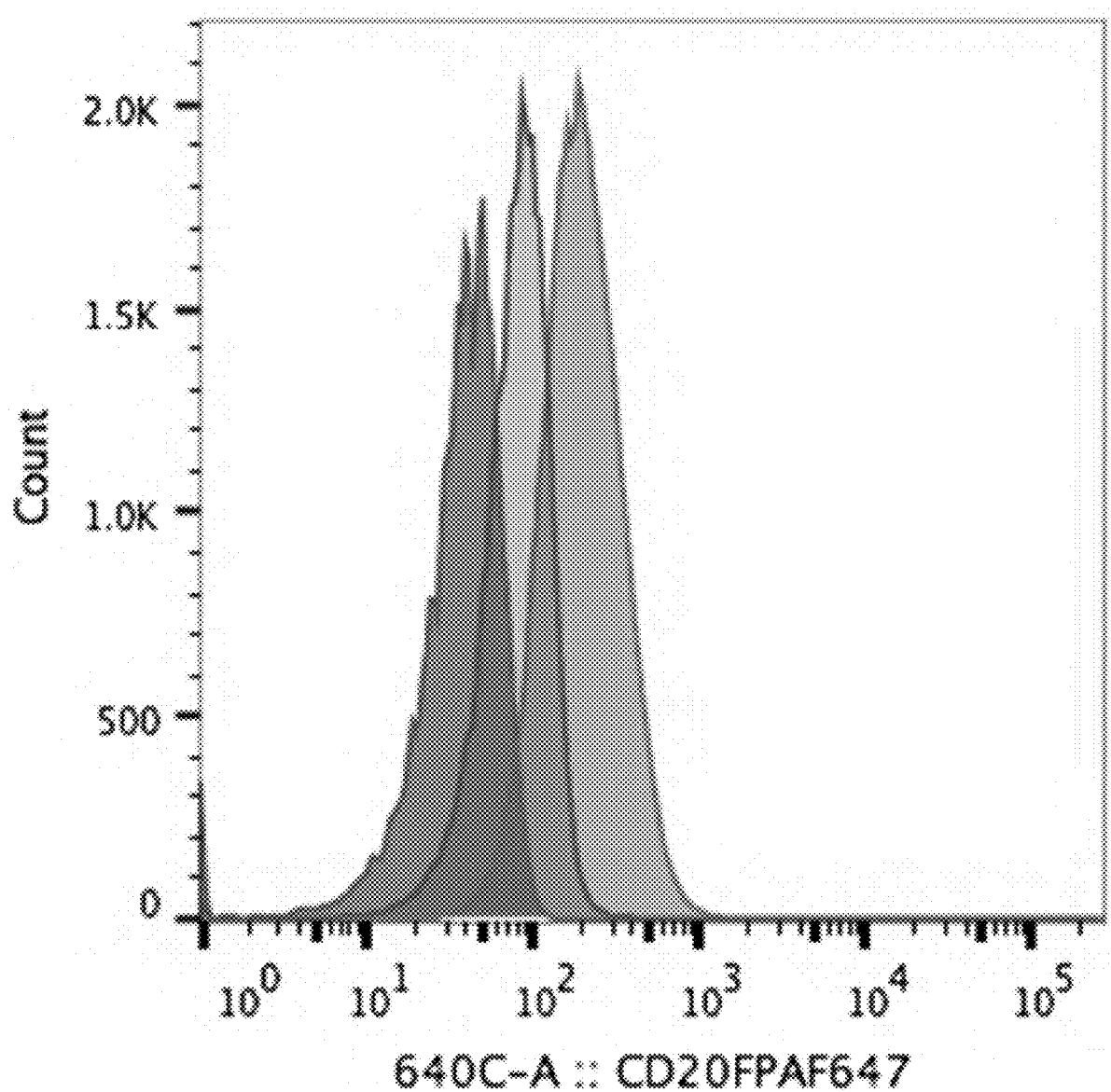
FIG. 25 depicts a flow cytometry plot showing in vitro staining of B16 WT or B16 hCD20+ tumor cells with AF647-labeled chemerin fusion protein. Increased specific staining of B16 hCD20 cells compared to B16 WT cells was observed. B16 CD20+ cells are purple, B16 WT cells are red, B16 unstained cells are grey.
Figure 26:
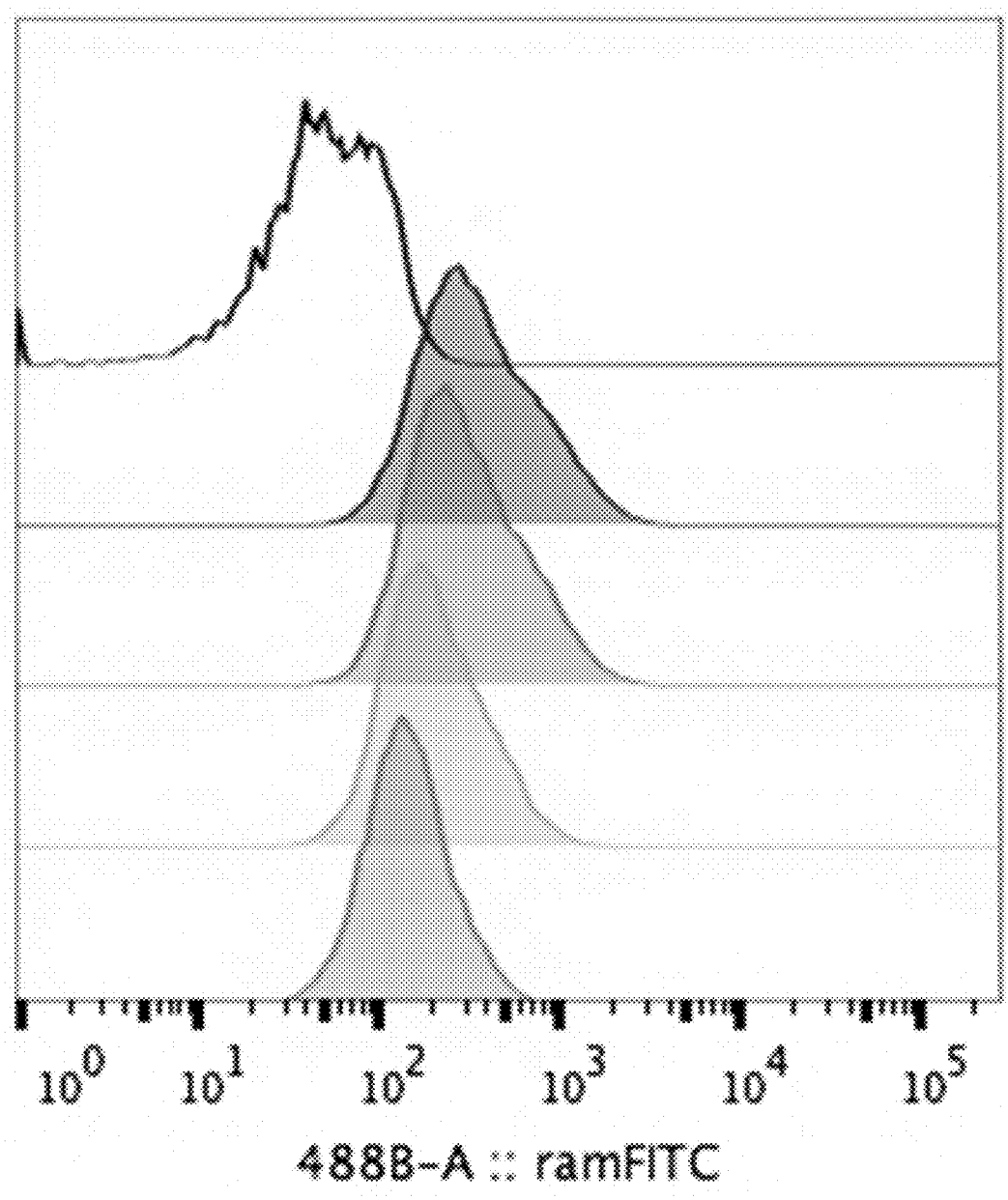
FIG. 26 depicts flow cytometry plots showing in vitro staining of CD20+ tumor cells with conditioned supernatant from 293 cells transduced to express the scFv CD20-chemerin fusion protein. Black line has no primary, purple is undiluted scFv CD20-chemerin supernatant, red is 1:2 dilution; light orange is 1:4 dilution; light red is 1:8 dilution.
Figure 27:
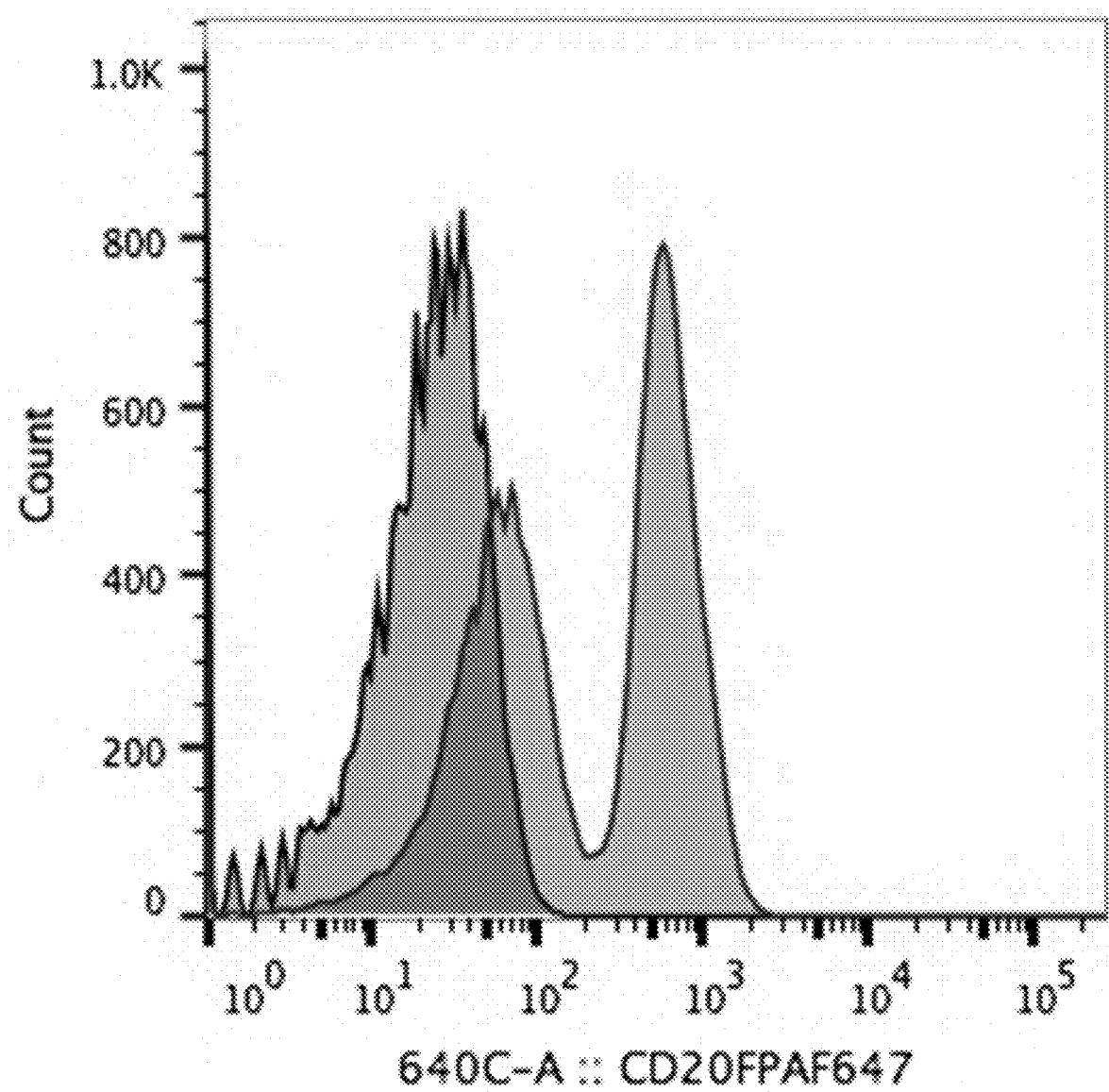
FIG. 27 depicts a flow cytometry plot showing that Raji (human B cell lymphoma CD20+ cell line) stained with AF647 fluorescently labeled CD20-chemerin fusion protein in vitro. Raji cells stained with AF647 labeled fusion protein are purple and isotype control is gray.

The scFv CD20-chemerin fusion protein was then labeled with Life Technologies AF-647. The yield of labeled protein was approximately 10-fold less compared to the yield of unlabeled protein. However, the labeled protein still selectively binds to B16 CD20+ cells (FIG. 22B). FIG. 23 also shows that the labeled protein selectively bound to B16 CD20+ cells. However, some background staining with the unlabeled fusion protein on WT cells was observed. In vitro staining of B16 WT or B16 hCD20+ tumor cells with AF647-labeled chemerin fusion protein showed increased specific staining of B16 hCD2 cells compared to B16 WT cells (FIG. 24, FIG. 25). further, in vitro staining of CD20+ tumor cells with conditioned supernatant from 293 cells transduced to express the scFv CD20-chemerin fusion protein demonstrated a dose response in cell staining (FIG. 26). Additionally, the Raji (human B cell lymphoma CD20+ cell line) stained with AF647 fluorescently labeled CD20-chemerin fusion protein in vitro (FIG. 27).

Example 9. CD20-Chemerin Fusion Protein Recruits Human CD56+ NK Cells In Vitro

Figure 28:
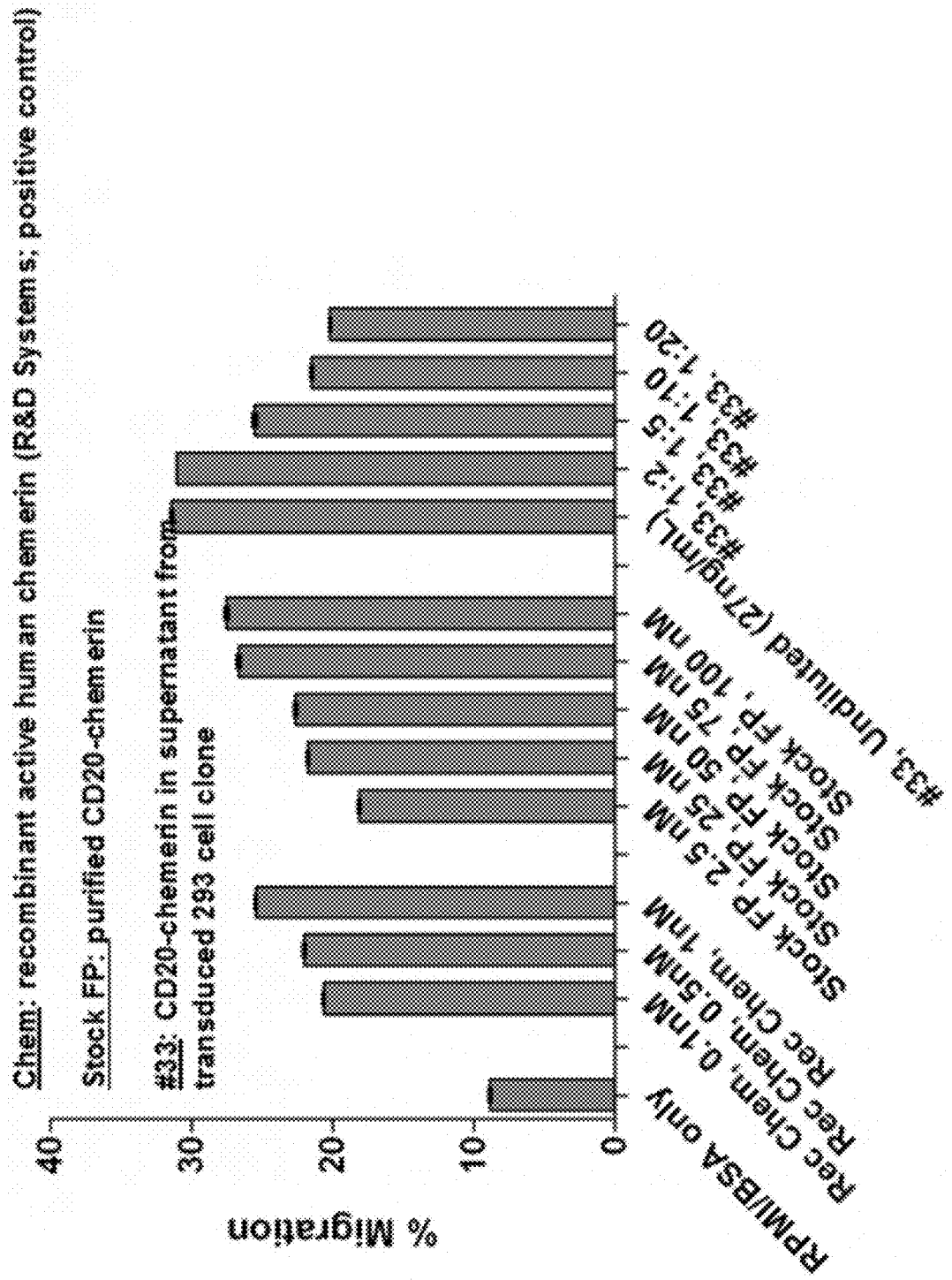
FIG. 28 depicts a graph showing that the CD20-chemerin fusion protein recruits human CD56+ NK cells in vitro.

The ability of the scFv CD20-chemerin fusion protein to recruit NK cells was evaluated. A migration assay was performed as described above. Cells were incubated with recombinant human chemerin, purified scFv CD20-chemerin fusion protein or scFv CD20-chemerin fusion protein from the supernatant of 293 cells transduced to express the protein. The results demonstrated that both fusion protein preparations recruited NK cells (FIG. 28).

Future plans include systemic administration of the fusion protein via tail vein injection and evaluation of the ability of the fusion protein to preferentially concentrate at a CD20+ tumor. Additionally, tumors will be evaluated at later timepoints and tumor infiltrating leukocytes will be analyzed. Further, fusion proteins to target different tumor types will be developed, such as HER2 for breast and EGFR for head and neck and colon cancer.

Example 10. The Leukocyte Chemoattractant, Chemerin, Upregulates PTEN Via CMKLR1 in Human Tumors The influence of chemerin on the content of PTEN activity in tumor lines was examined. It was shown that exogenous chemerin treatment significantly upregulates PTEN mRNA and protein expression using both prostate and sarcoma tumor lines. Interestingly, chemerin proved to significantly slow tumor migration in each of the tumor lines. This data suggest an important role for RARRES2/chemerin in the PTEN signaling cascade, a commonly dysregulated signaling pathway leading to tumor cell survival and proliferation. Thus, it is hypothesized that chemerin facilitates increased PTEN activity via CMKLR1 binding. The experimental studies described herein focus on the chemerin-driven upregulation of PTEN activity and its direct effect on effective immunotherapy strategies.

Exogenous Chemerin Exposure Upregulates PTEN Expression in Multiple Cancer Cell Lines.

Figure 29A:
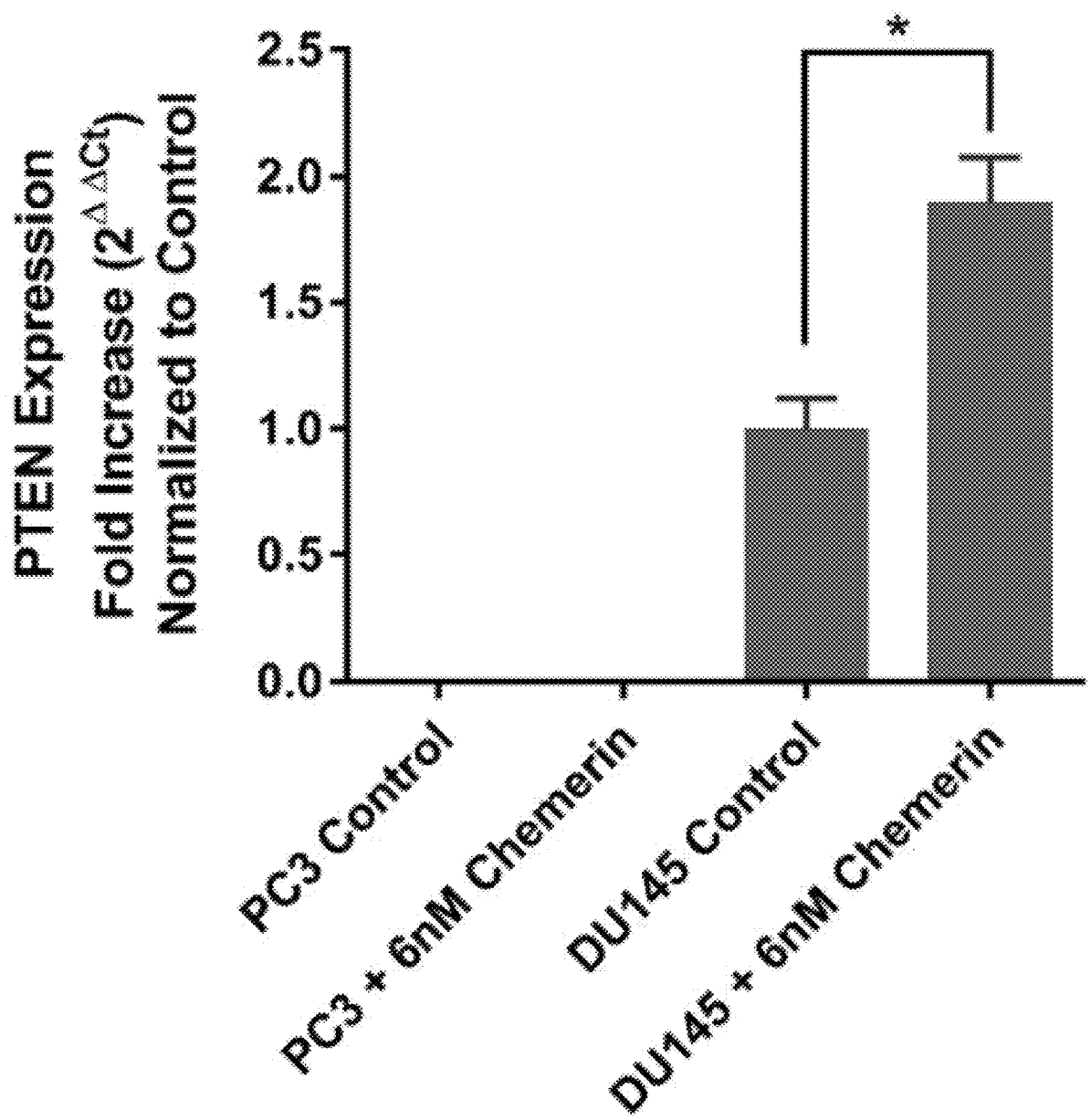
FIG. 29A, FIG. 29B, FIG. 29C, FIG. 29D, FIG. 29E, FIG. 29F and FIG. 29G depict graphs and immunoblots showing that recombinant chemerin upregulates PTEN expression in tumor cells.
Figure 29B:
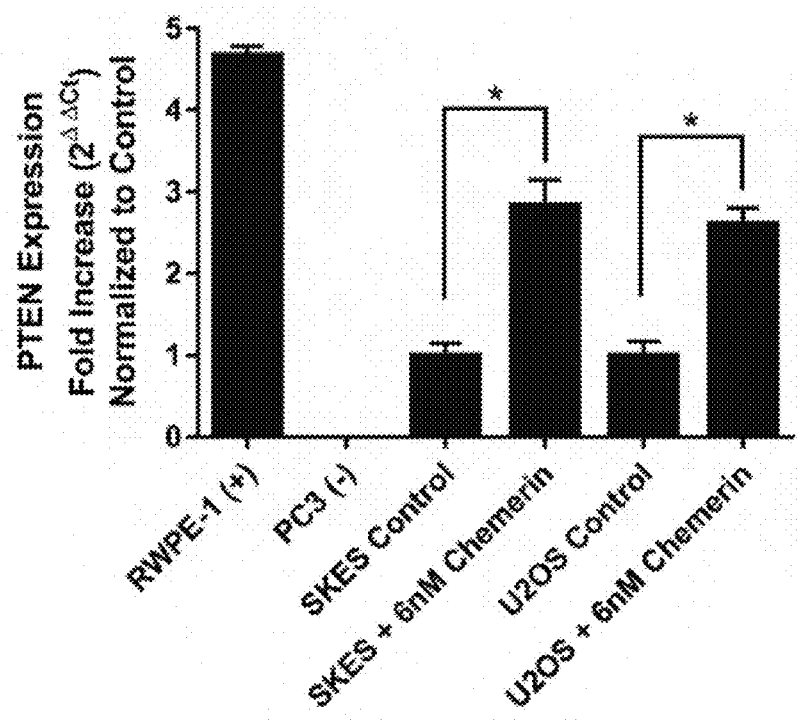

To interrogate the mechanisms associated with chemerin-mediated PTEN expression, CMKLR1 expression is confirmed in the tumor cell lines using flow cytometry and western blot analysis (FIG. 33). PC3 (FIG. 33B) and DU145 (FIG. 33C) PCa cells exhibited low levels of CMKLR1 expression, similar to RWPE-1 (FIG. 33A), or normal prostate cells. Also, the sarcoma cell lines, SKES (FIG. 33E) and U2OS (FIG. 33F), significantly expressed CMKLR1 compared to the little to no CMKLR1 expression seen in the HT-1080 cell line (FIG. 33G), a type of fibrosarcoma cell line. Next, the prostate and sarcoma tumor cell lines were incubated with 6 nM recombinant chemerin protein for 48 hours, where media and chemerin reagents were changed daily. Next, the effect of chemerin on overall PTEN mRNA expression was investigated. PTEN mRNA expression was quantified for each cell line and treatment using quantitative real-time RT-PCR analysis. PTEN expression was normalized to GAPDH loading control for each sample. In the chemerin treated groups, the results show that PTEN mRNA expression was significantly upregulated over the vehicle alone treated cells (n=4, P<0.01). In the PC3 cells, the PTEN genomic sequence is deleted and no PTEN was detected using RT-PCR analysis (FIG. 29A). There was an approximately two fold increase in PTEN mRNA expression in the DU145, SKES, and U2OS cells after chemerin incubation (FIG. 29A, FIG. 29B). This data suggest chemerin plays a direct role in activating PTEN signaling in these human cancer cell lines. PTEN is commonly lost or mutated in malignant tissue types and novel upregulation due to chemerin exposure may lead to slowed or inhibited tumor cell activity.

Figure 29C:
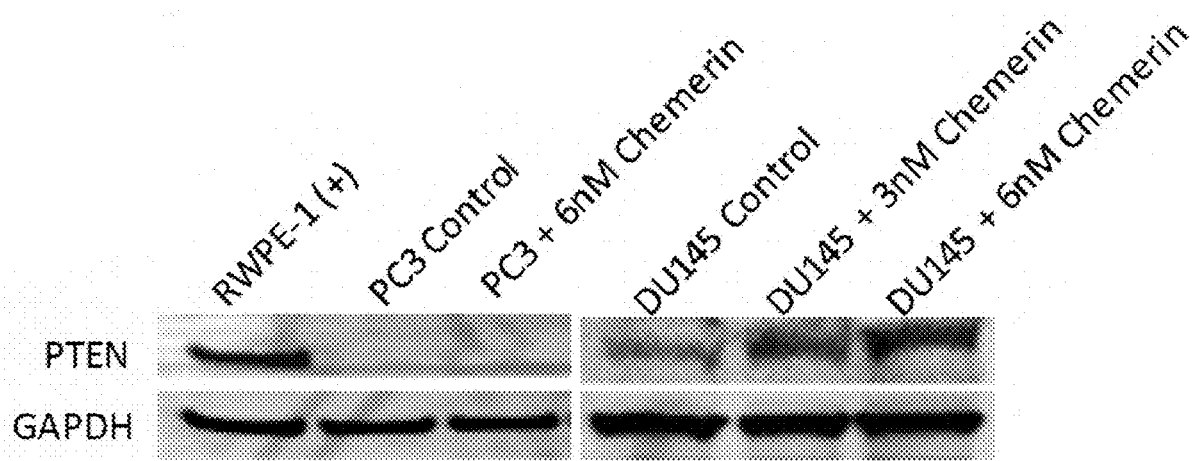
Figure 29D:
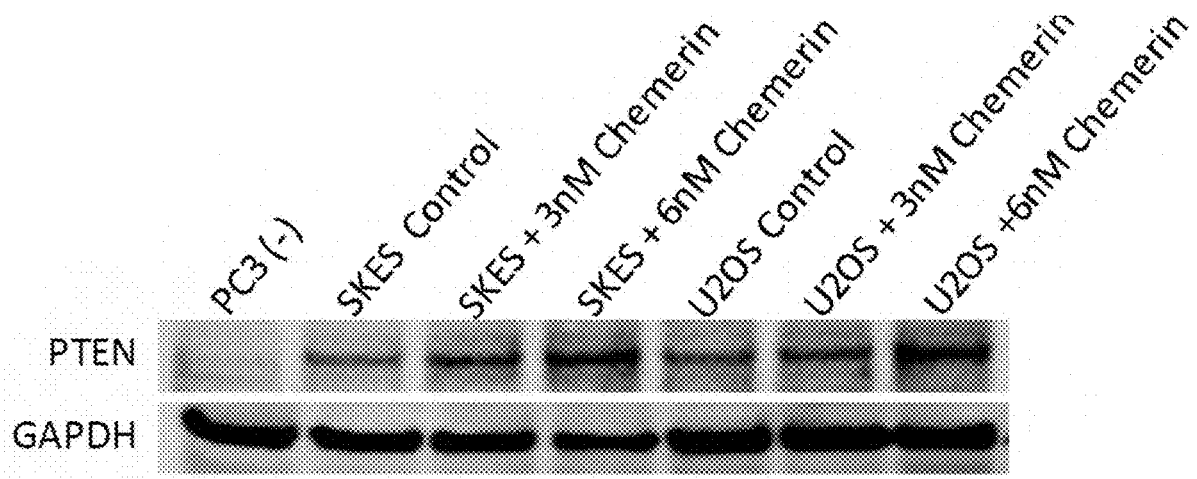
Figure 29E:
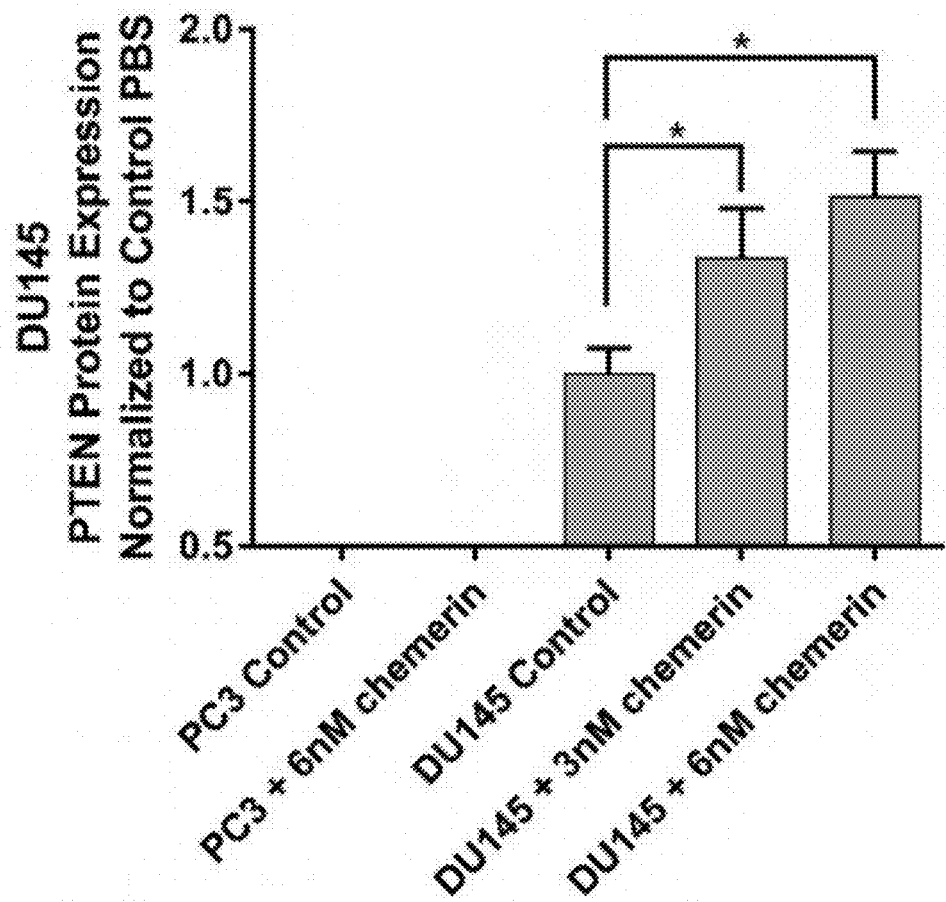
Figure 29F:
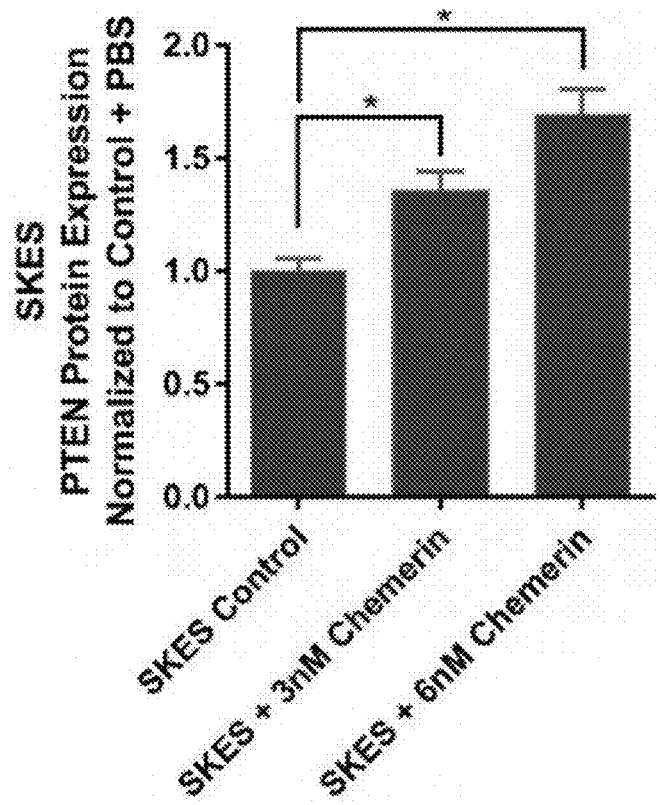
Figure 29G:
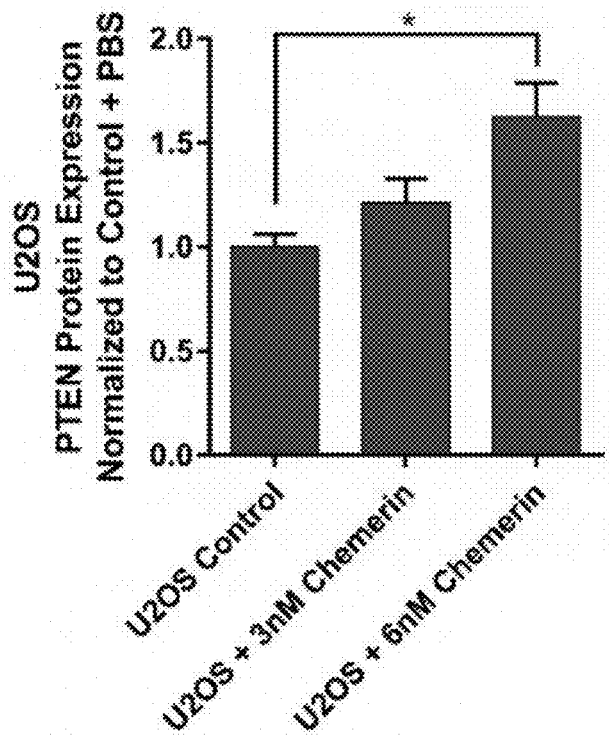
Figure 30A:
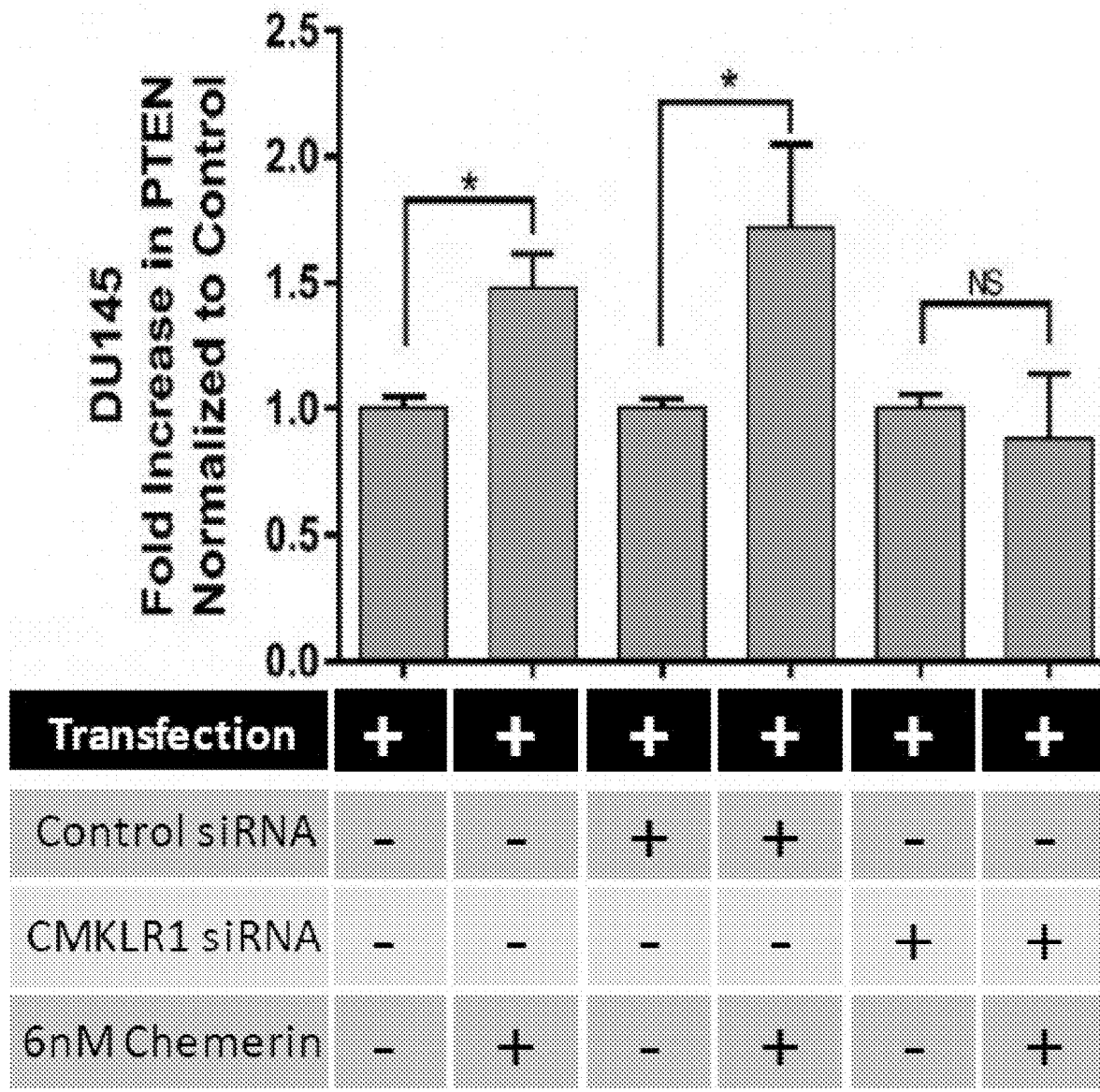
FIG. 30A, FIG. 30B, FIG. 30C, FIG. 30D, FIG. 30E, FIG. 30F, FIG. 30G, FIG. 30H and FIG. 30I depict graphs and immunoblots showing CMKLR1 knockdown mitigates chemerin's affect on upregulating PTEN expression in tumor cells.
Figure 30B:
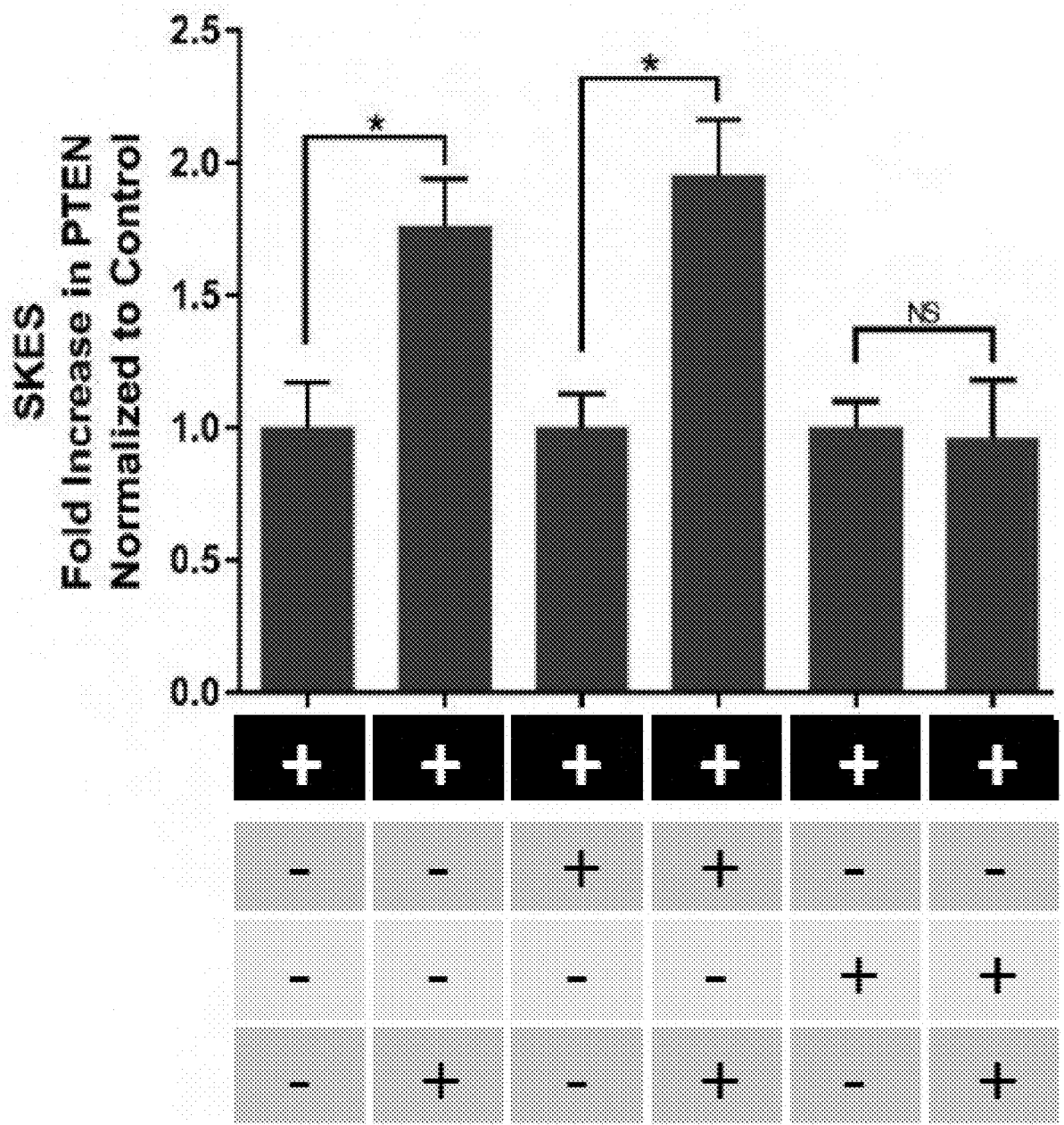
Figure 30C:
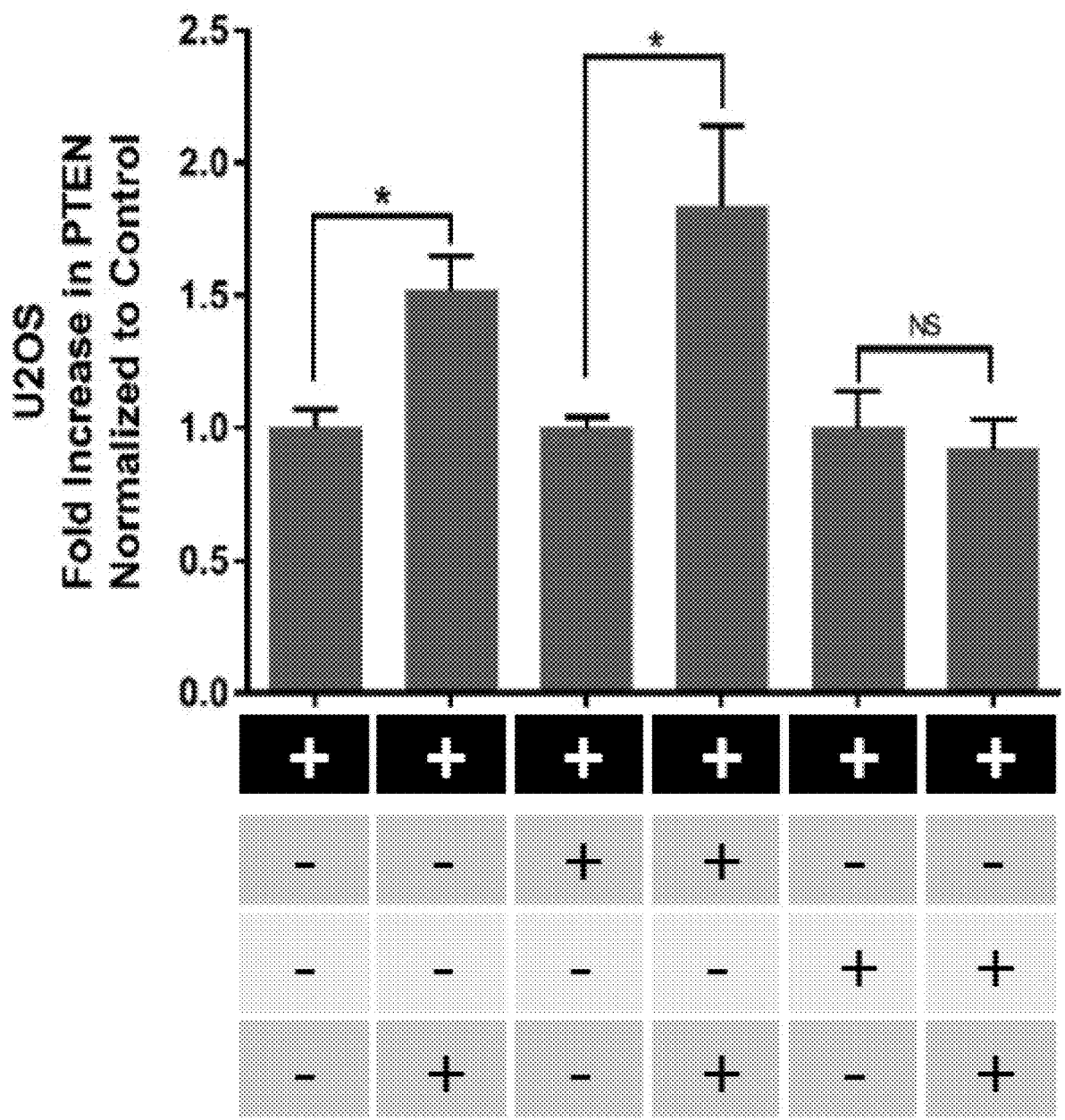
Figure 30D:
Figure 30E:
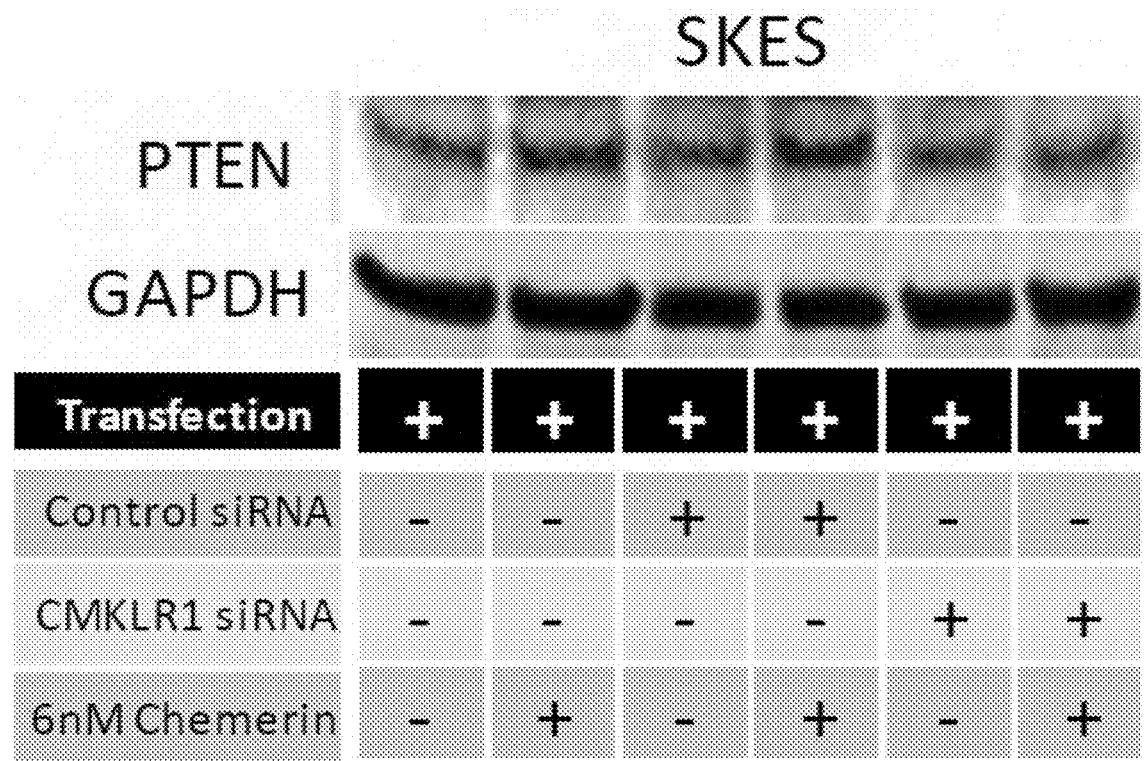
Figure 30F:
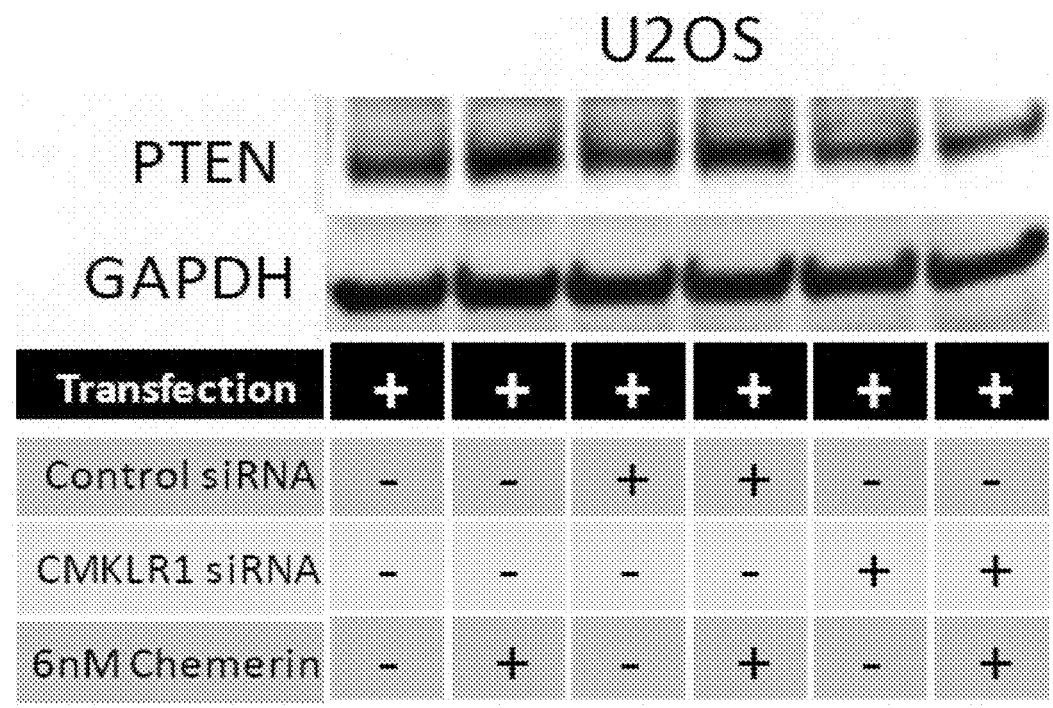
Figure 30G:
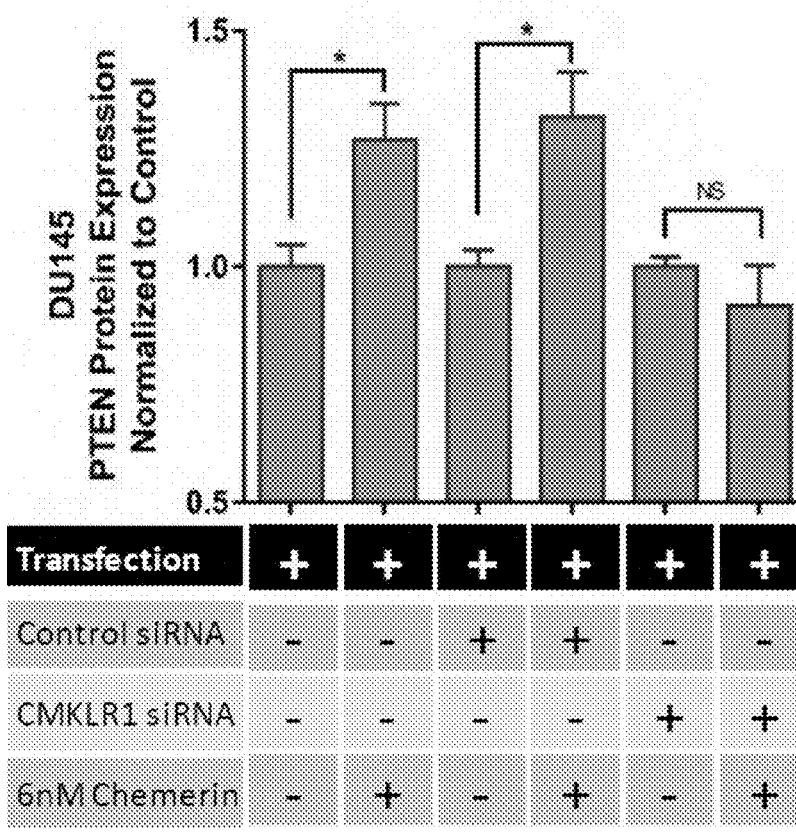
Figure 30H:
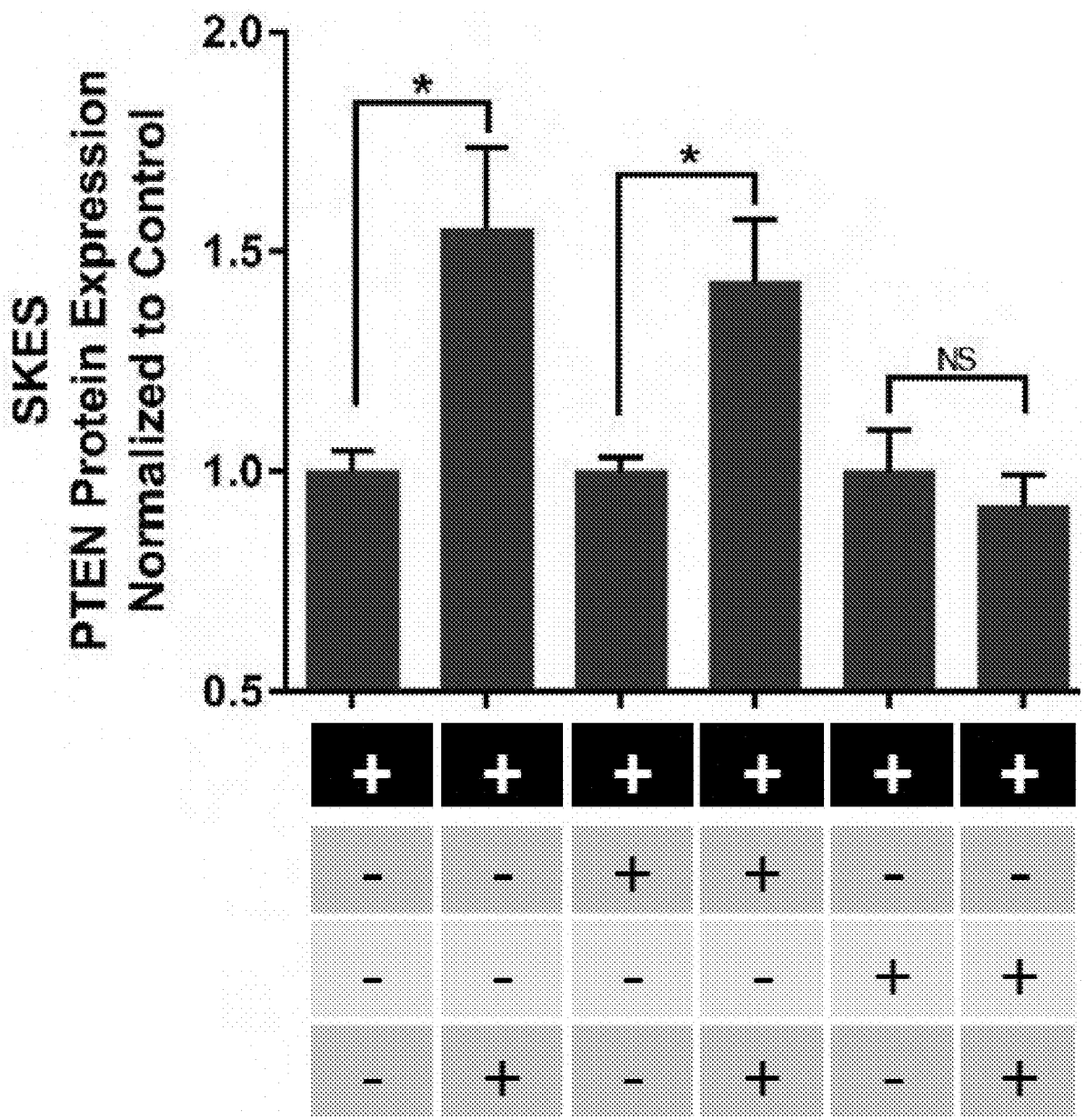
Figure 30I:
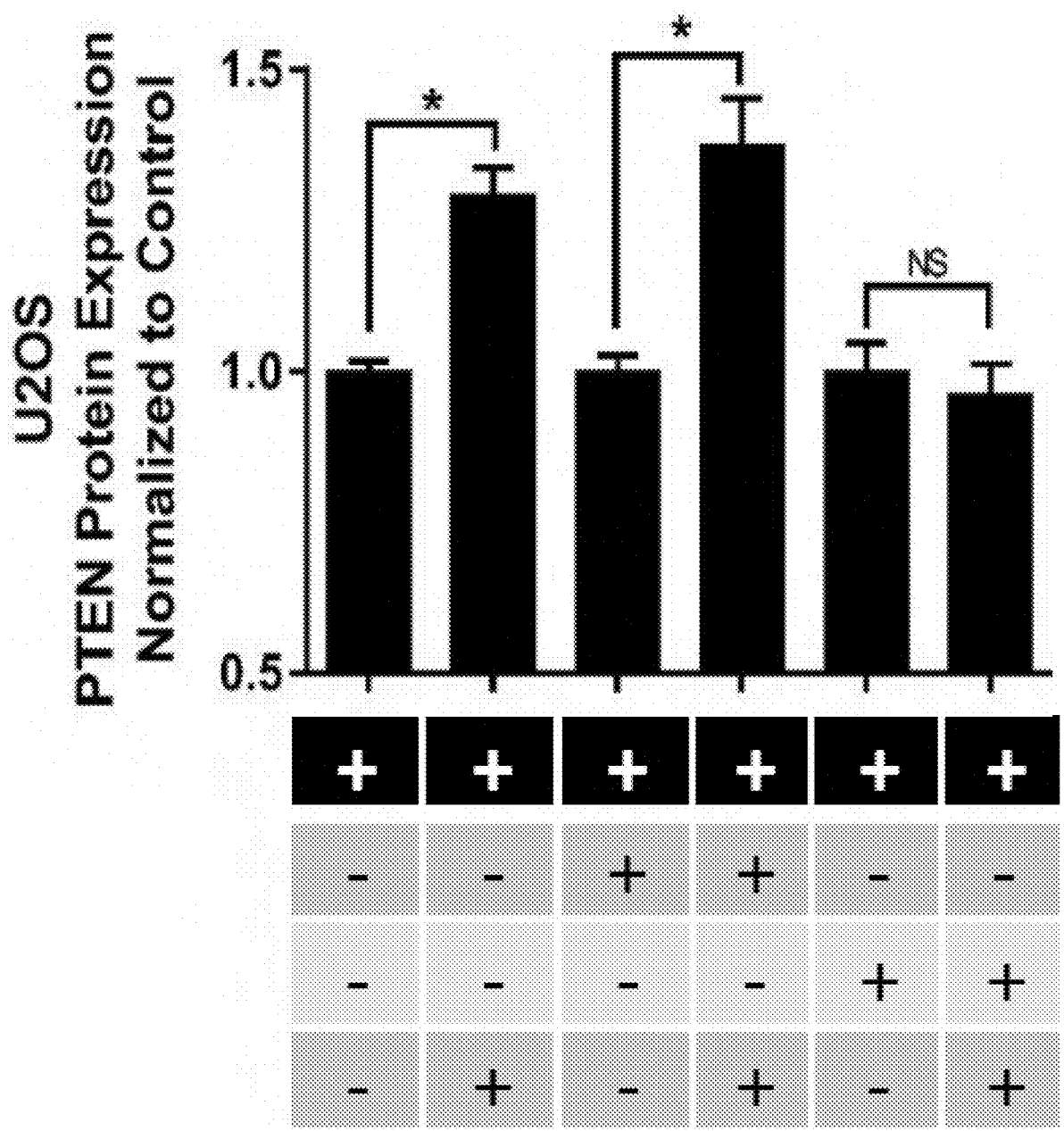
Figure 36:
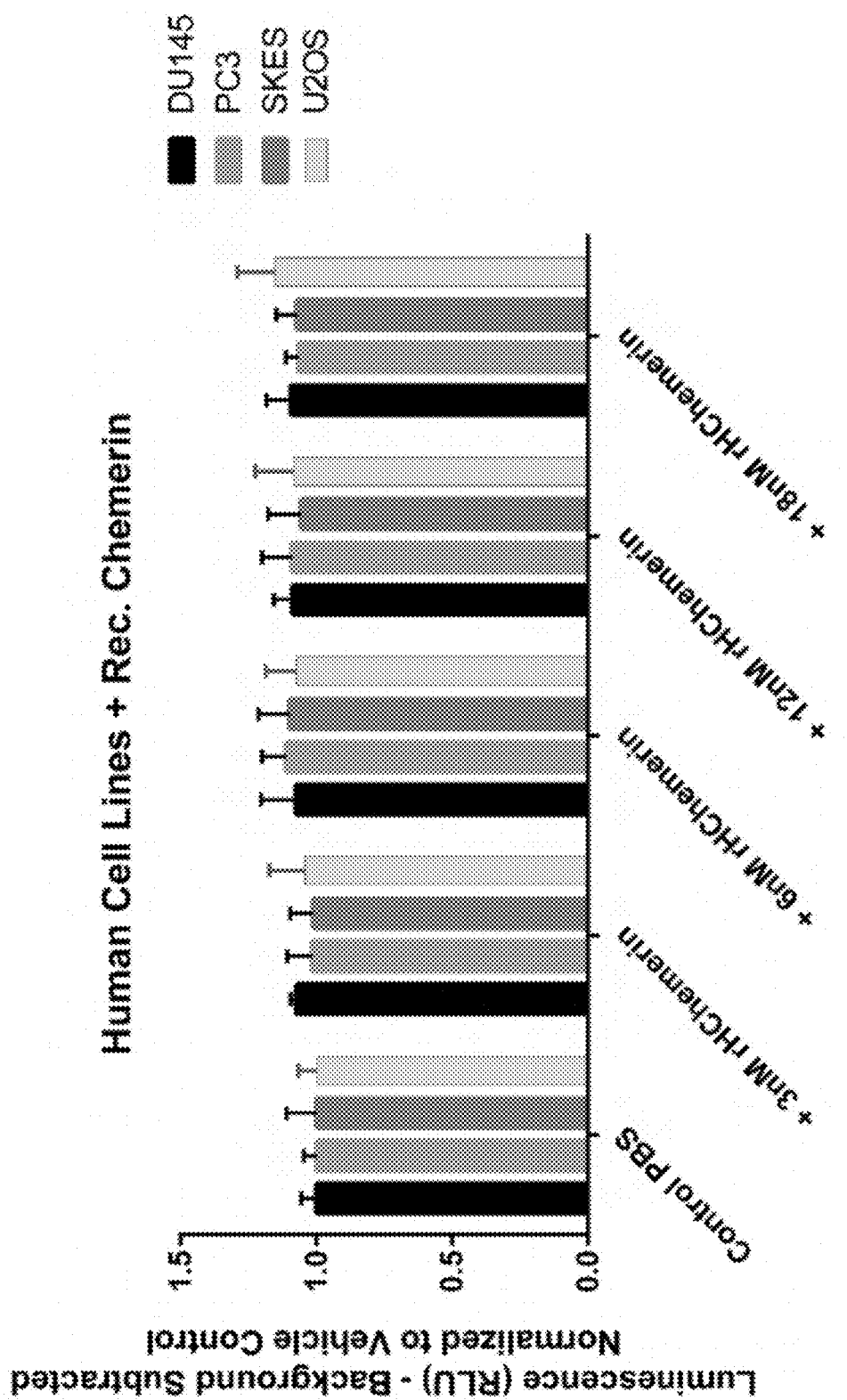
FIG. 36 depicts a graph showing caspase activation in response to varying chemerin concentrations. Each cell line was treated with varying chemerin concentrations (PBS, 3 nM, 6 nM, 12 nM, and 18 nM chemerin) for 72 h. Triplicate wells were then assessed for caspase-3 and -7 expression in each respective sample set (n=4). Results show that chemerin does not induce significant changes in caspase activation after 72 h chemerin incubation. *P<0.01, compared to the PBS treated cells for each respective cell line.
Figure 37A:
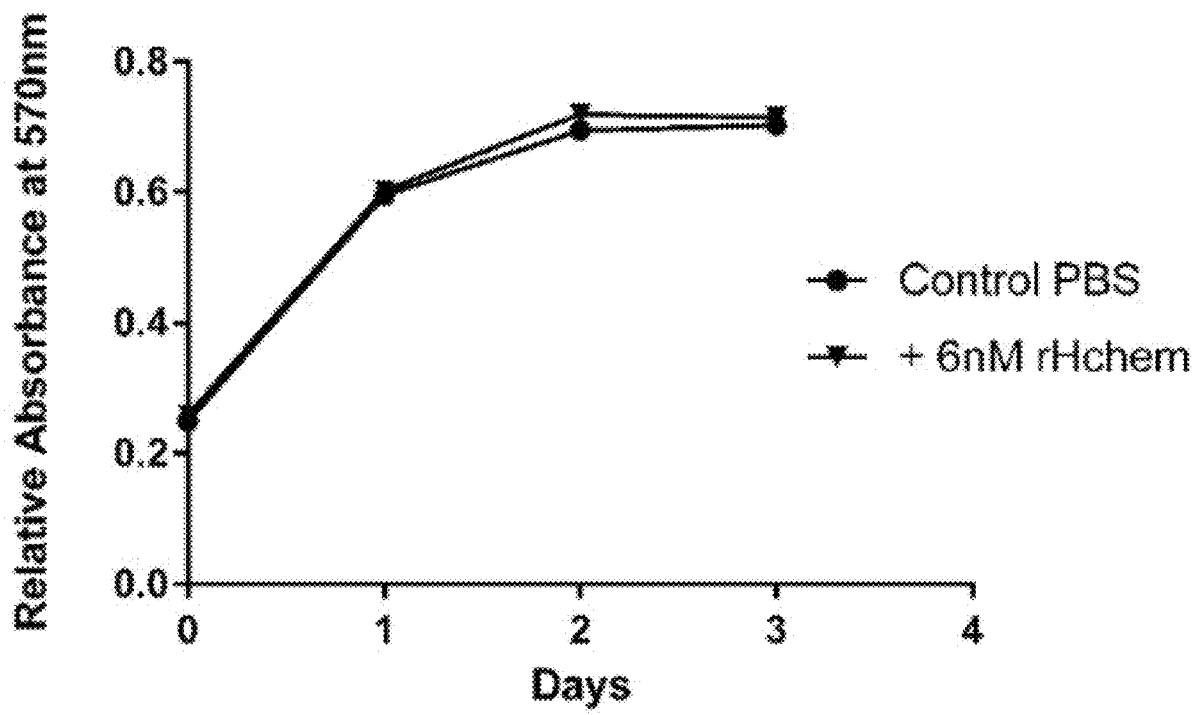
FIG. 37A, FIG. 37B, FIG. 37C and FIG. 37D depicts graphs assessing the effect of chemerin incubation on tumor cell proliferation. Each cell line was treated with PBS or 6 nM chemerin concentration for 72 h. Each day, triplicate wells were incubated with Alamar blue, and the absorbance was read, correlating to total number of cells per well (n=3). Results show that chemerin does not affect overall cell proliferation over a 72 h chemerin incubation. *P<0.01, compared to the paired PBS treated cells for each cell line.
Figure 37B:
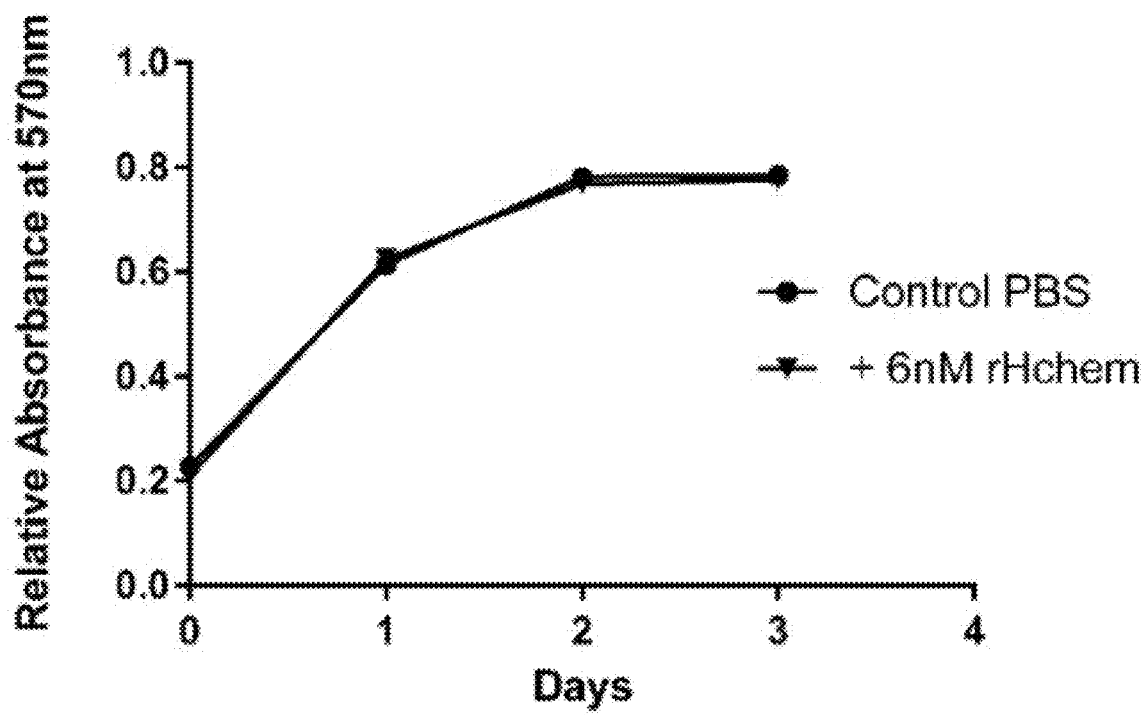
Figure 37C:
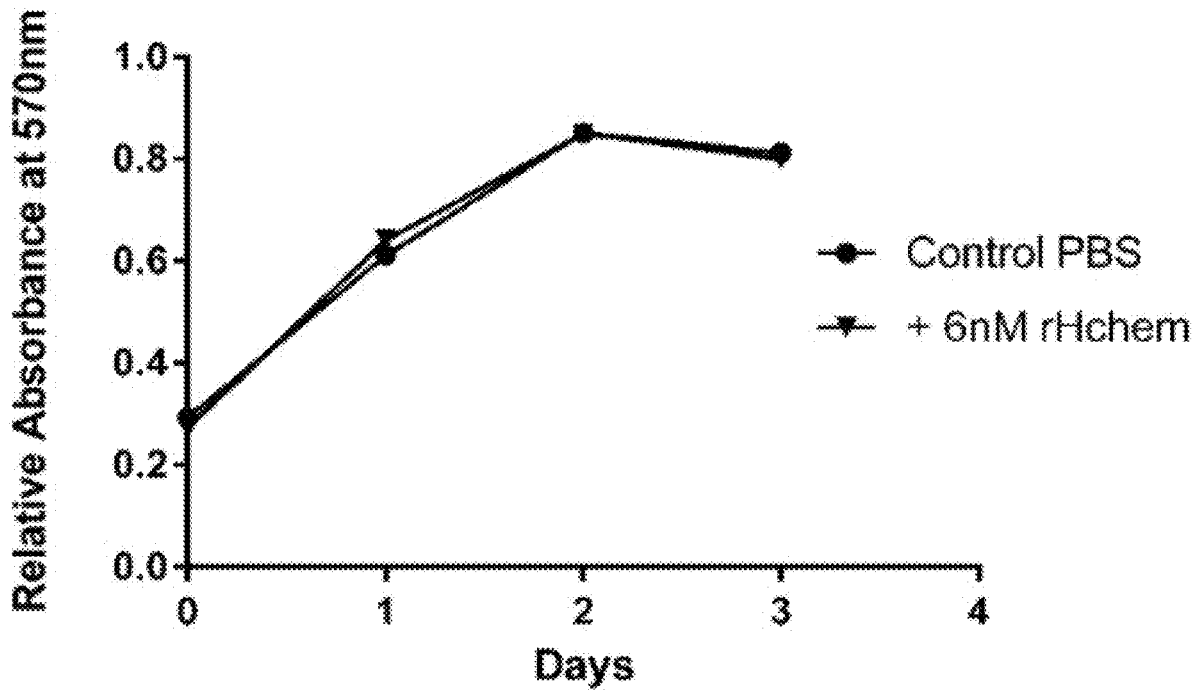
Figure 37D:
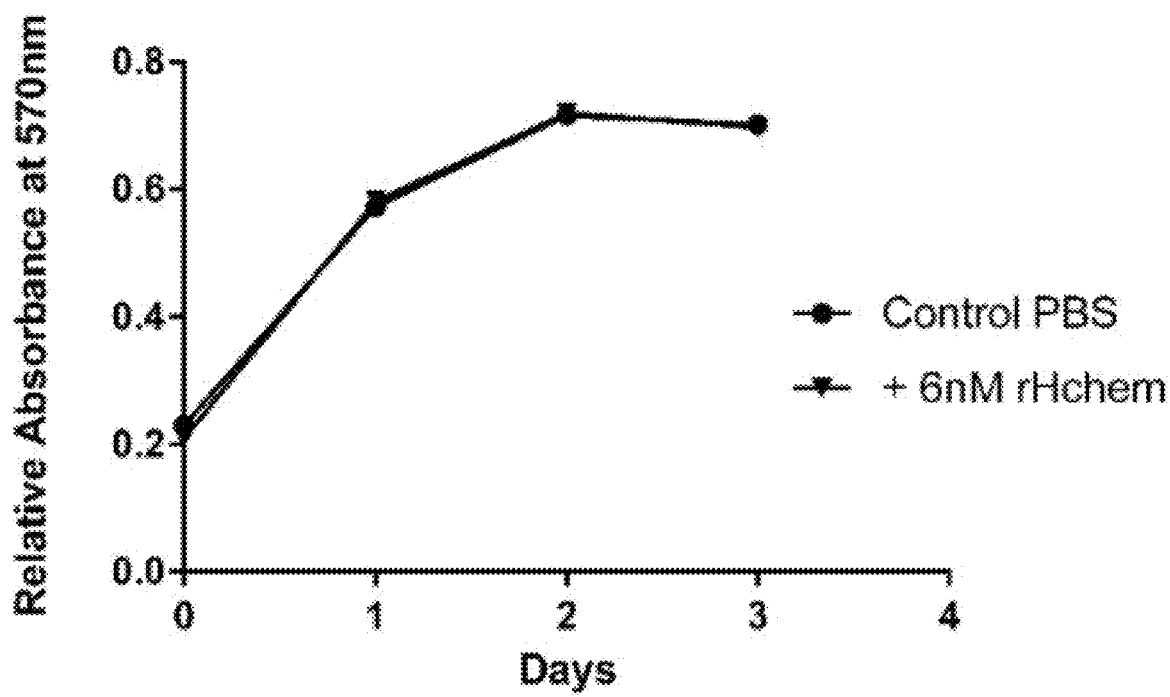

Following the chemerin-induced PTEN mRNA upregulation, the previous experiments were repeated to investigate PTEN protein expression for each sample set. Once again, PC3 cells do not express PTEN mRNA and no protein was found (FIG. 29C). Western blot analysis showed a significant increase in PTEN protein expression related to 6 nM chemerin treatment compared to the PBS control (FIG. 29C, FIG. 29D). After quantifying the Western results, PTEN protein was approximately increased 1.52 fold in DU145 cells, 1.6 fold increase in U2OS cells, and 1.67 fold increase in SKES cells compared to the control cells (n=3, P<0.05). Thus, these protein expression results correlate with an upregulation in PTEN transcription due to chemerin treatment. Moreover, exogenous chemerin incubation did not affect cell apoptosis (caspase activation) or significantly alter tumor cell proliferation between the chemerin and control vehicle groups after a 72 hour exposure (FIG. 36, FIG. 37).

Figure 34:
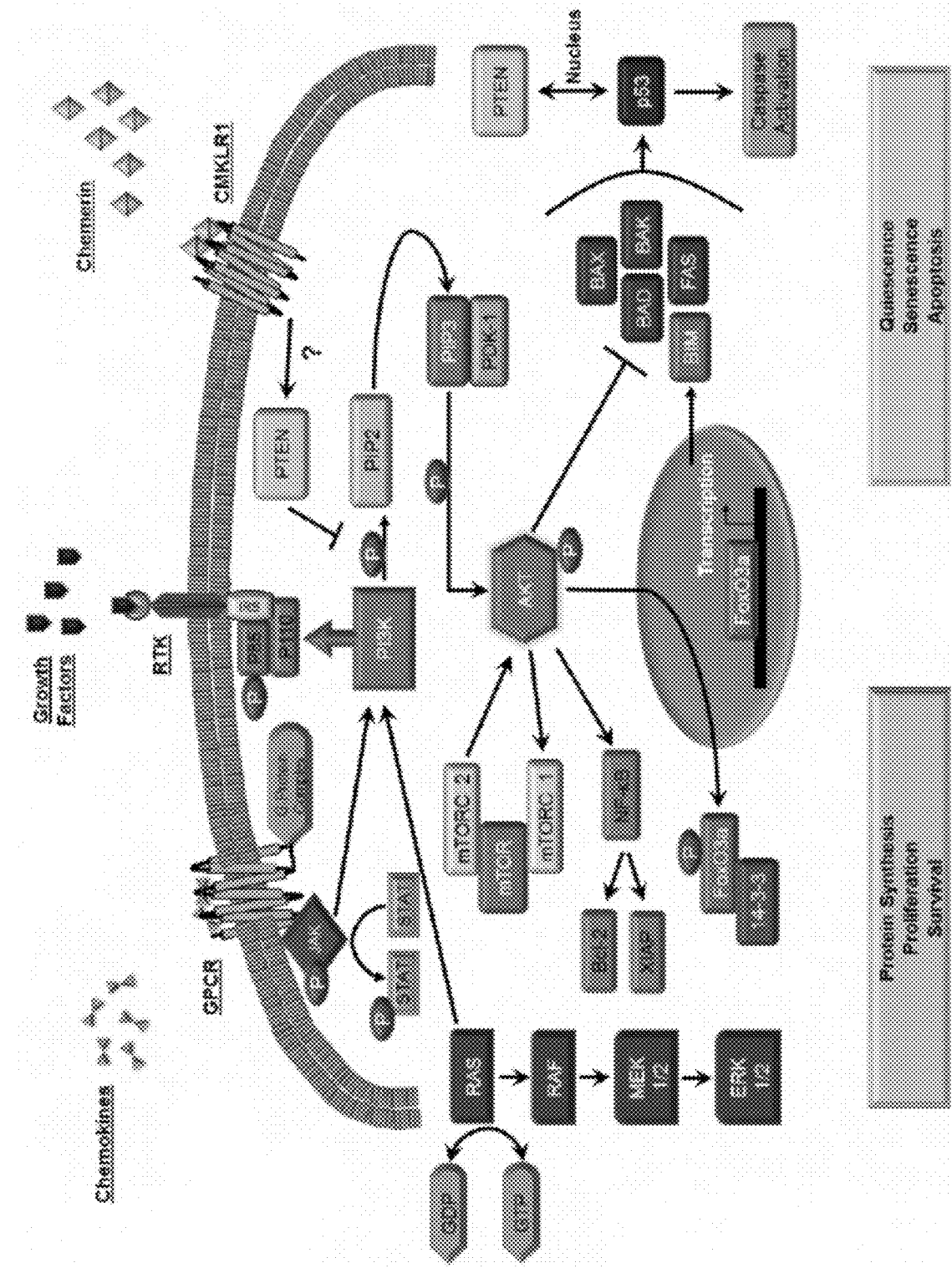
FIG. 34 depicts a PI3K/Akt/PTEN signaling cascade schematic. A current understanding of the PI3K pathways and how it is regulated by PTEN.
Figure 35A:
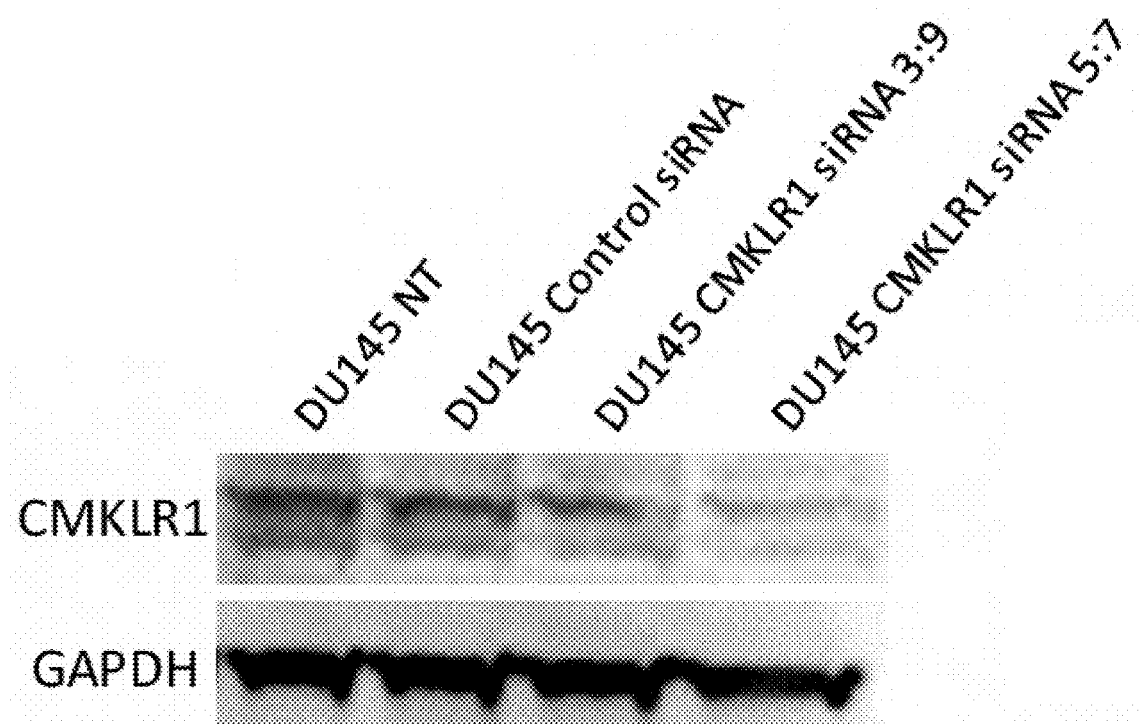
FIG. 35A, FIG. 35B, FIG. 35C, FIG. 35D, FIG. 35E, FIG. 35F, FIG. 35G and FIG. 35H depict graph sand immunoblots showing knockdown of CMKLR1 expression in human cells.
Figure 35B:
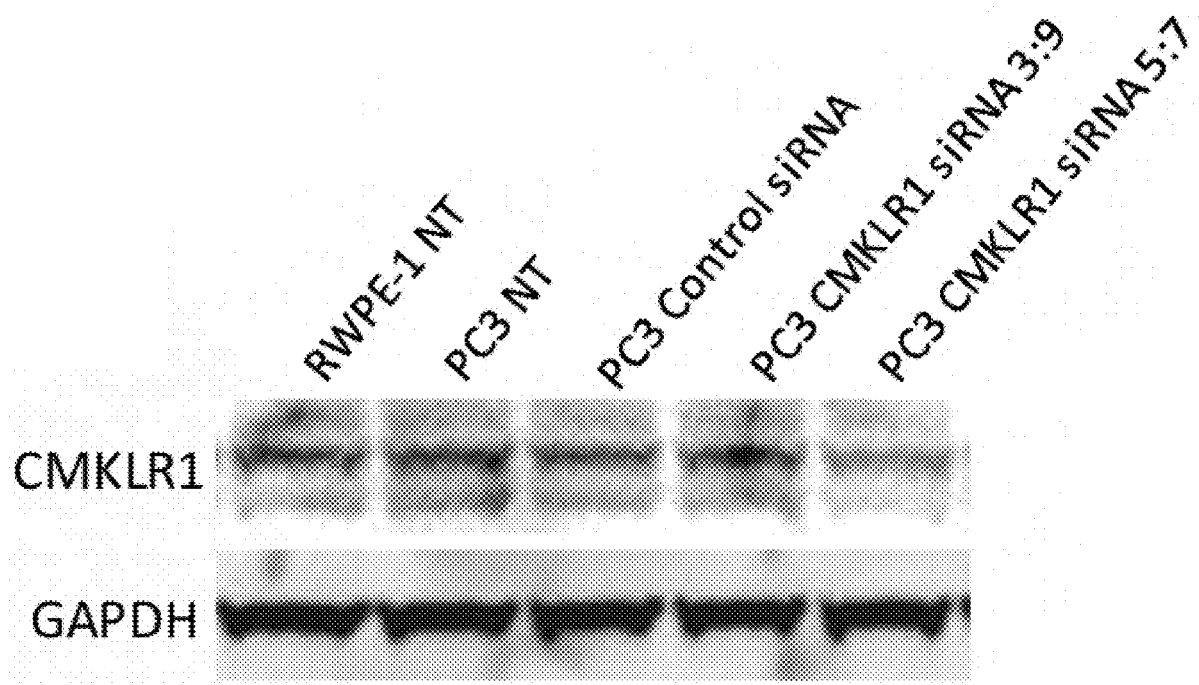
Figure 35C:
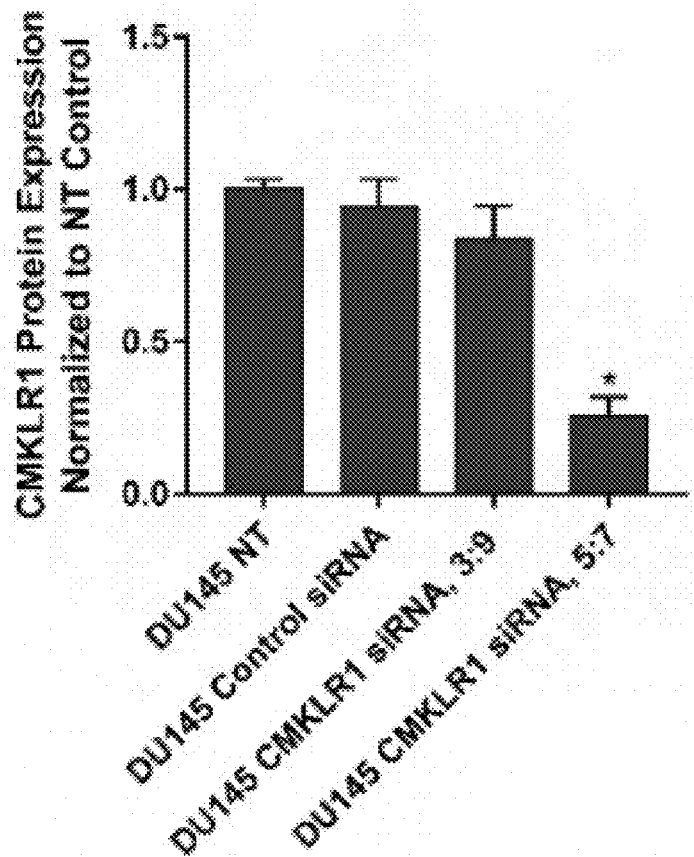
Figure 35D:
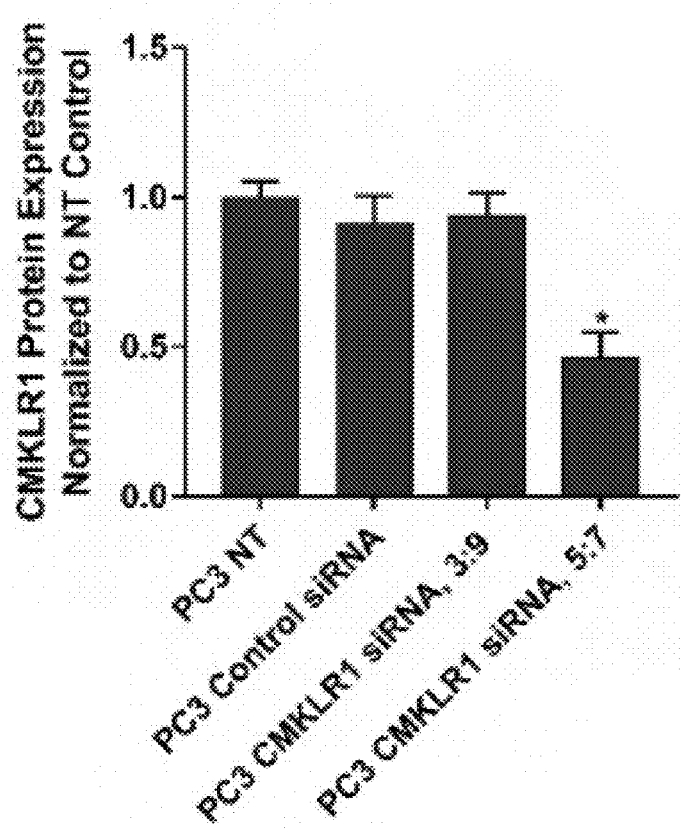
Figure 35E:
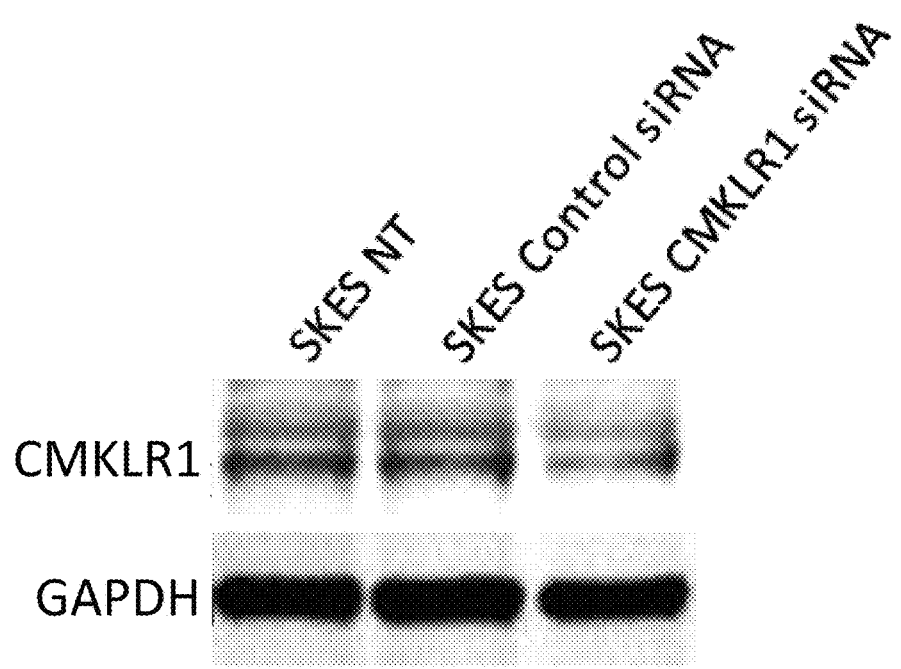
Figure 35F:
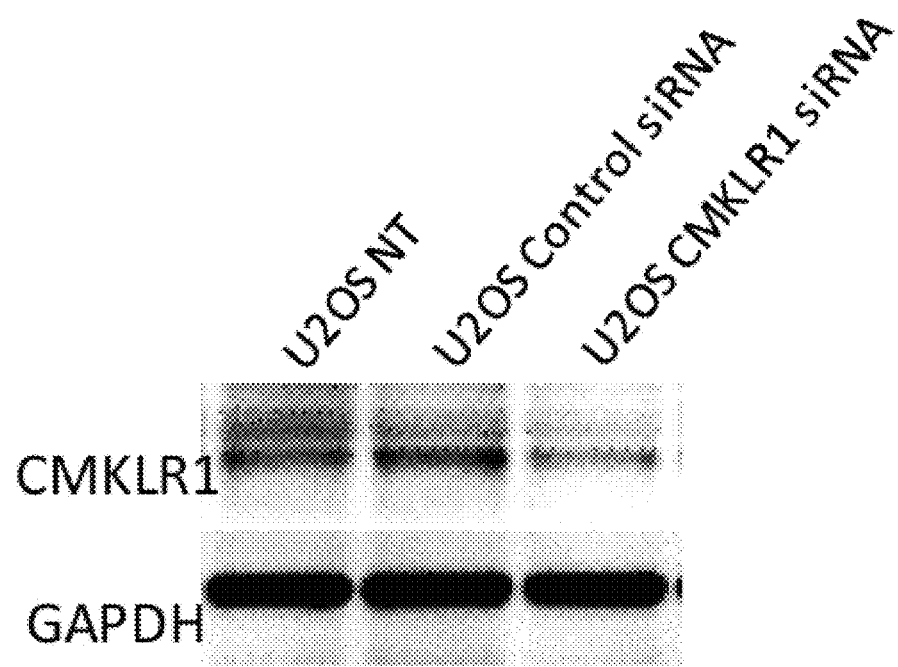
Figure 35G:
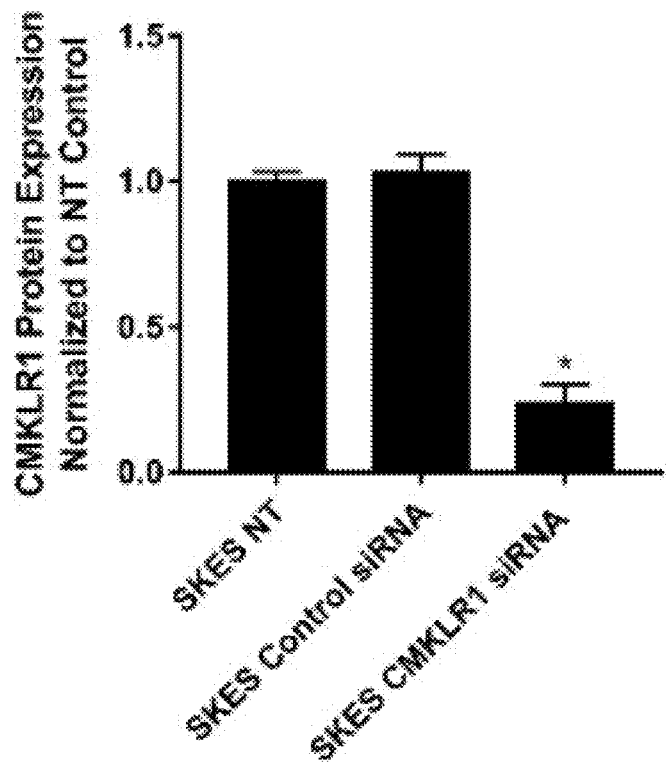
Figure 35H:
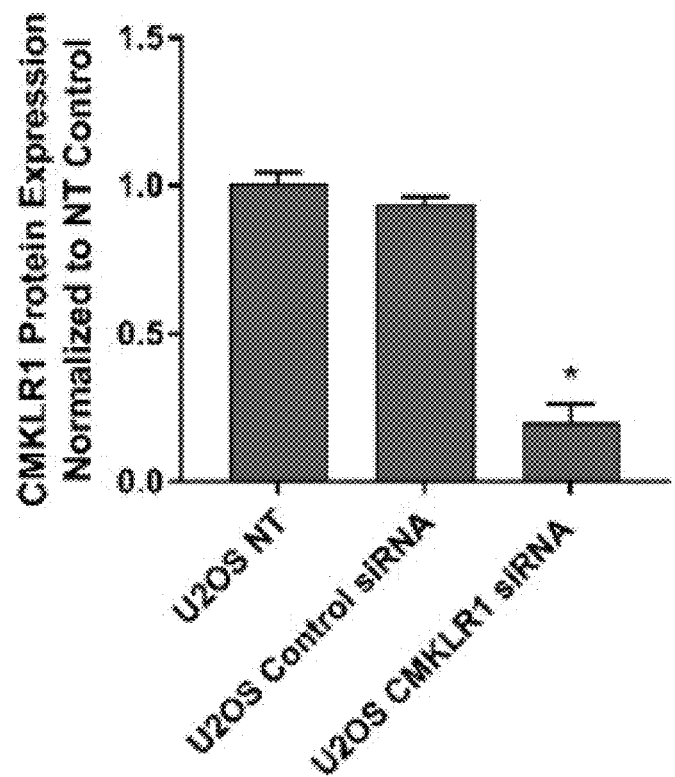

Overall, recombinant chemerin incubation lead to a significant increase in PTEN mRNA and protein expression compared to the vehicle control alone treated tumor cell lines. These results suggest chemerin, at least in part, plays a role in the PTEN activation pathway. Therefore, there may be a potential link between chemerin and PTEN signaling via CMKLR1, one of chemerin's main signaling G protein-coupled receptors (FIG. 34).

Figure 38:
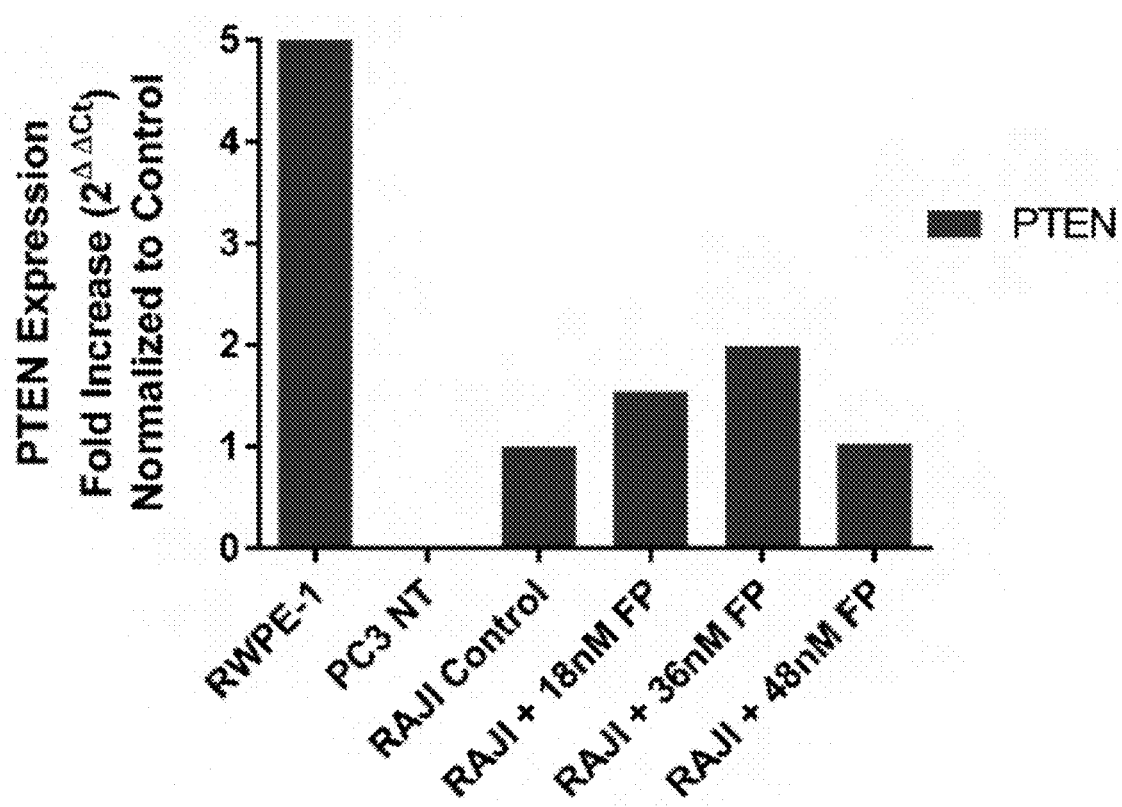
FIG. 38 depicts a graph showing that the chemerin fusion protein increases PTEN expression in RAJI cells.

The utility of the chemerin fusion protein described in the examples above in increasing PTEN expression in tumor cells was examined. RAJI cells were treatment with different concentration of fusion protein at 48 hours. Quantitative PCR was then performed on the samples to determine the level of PTEN expression. FIG. 38 demonstrates that the fusion protein increases PTEN expression in RAJI cells. PTEN is a tumor suppressor gene that is very commonly down regulated, mutated, or lost in tumors and contributes to tumor formation and/or progression, so it is very advantageous to increase the PTEN expression in tumors using the disclosed fusion protein.

CMKLR1 Knockdown Affects Chemerin-Induced PTEN Signaling.

Mechanistic studies were needed to further elucidate this chemerin-PTEN interplay in tumor cells. The potential link between chemerin and PTEN signaling was further investigated through a primary chemerin receptor, CMKLR1. After CMKLR1 siRNA knockdown, the effect of chemerin on increased PTEN expression was lost. Compared to the results using non-transfected cells, mock and control siRNA-A transfected cells demonstrated a significant increase in PTEN expression following exogenous chemerin treatment (FIG. 30). On the other hand, CMKLR1 siRNA knockdown completely mitigated the chemerin-induced increase in PTEN expression. This data further supports the hypothesis that chemerin binds CMKLR1 in order to elicit augmented PTEN expression and activity via CMKLR1.

Additionally, the effect of chemerin on PTEN phosphatase activity in each tumor cell line was investigated. PTEN phosphatase activity modulates PI3K-induced PIP3 phosphate, which is required for subsequent cell survival and proliferation. Here, it is shown that exogenous chemerin upregulates PTEN expression in human cancer cell lines via CMKLR1 binding (FIG. 30). Specifically, the ability of PTEN to dephosphorylate a key PI3K pathway constituent, $PIP_3$ phosphate, was investigated after vehicle control or chemerin incubation. Protein lysates were collected following each 48 h experiment for PTEN immunoprecipitation. PTEN-IP protein samples were incubated with $PIP_3$ phosphate and free phosphate was quantified using a malachite green assay. Further study showed increased PTEN phosphatase activity after 48 hour chemerin exposure, which supports the previous experimental data showing increased overall PTEN expression. However, CMKLR1 knockdown mitigated the amplified PTEN phosphatase activity in the presence of chemerin (FIG. 31). This result supports the results showing chemerin incubation led to increased PTEN expression and activity. Overall, a key mechanistic role of CMKLR1 in the chemerin-PTEN signaling cascade is demonstrated.

Changes in PTEN Expression Due to Chemerin Lead to Decreased Tumor Invasion.

Figure 31A:
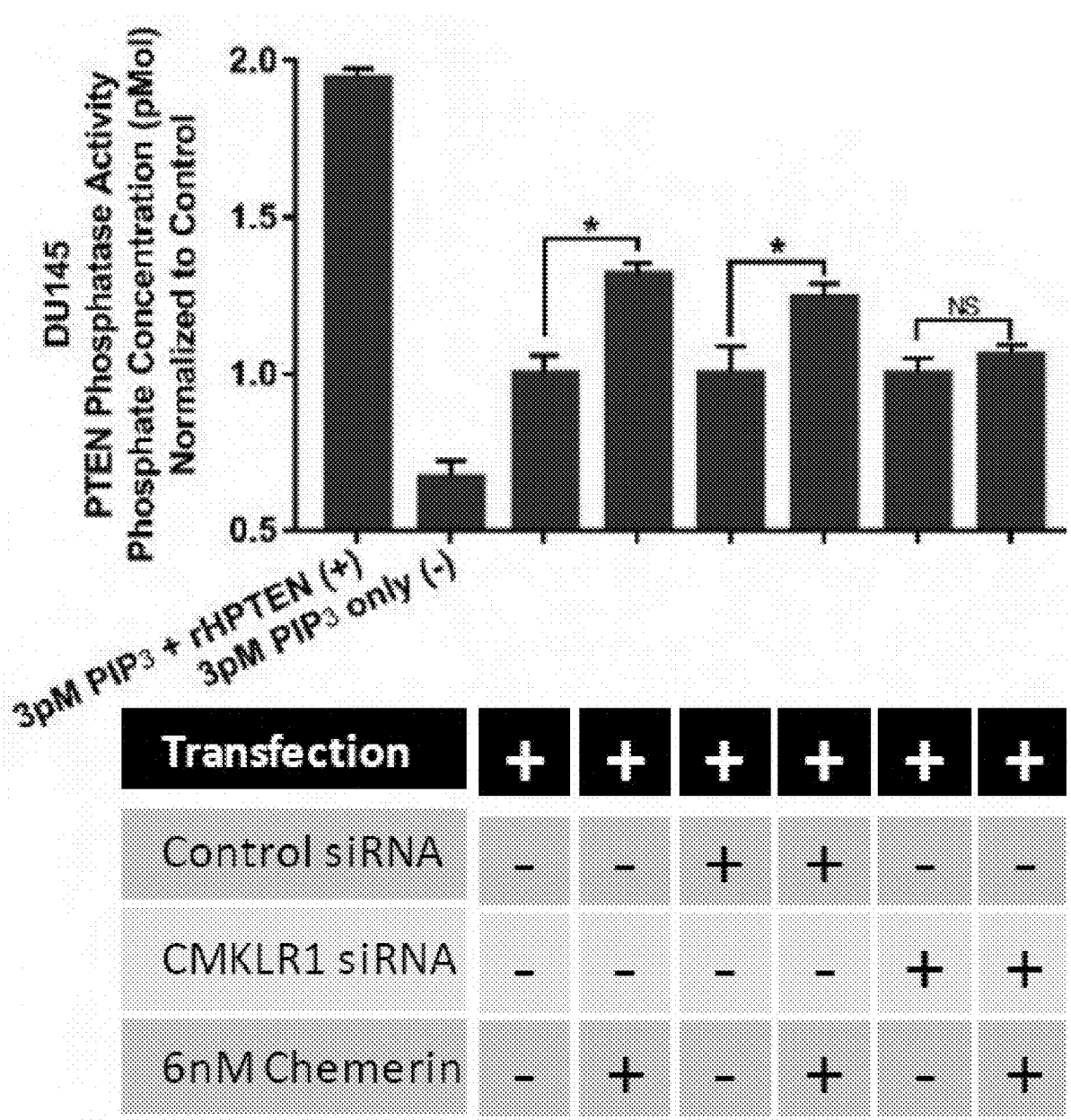
FIG. 31A, FIG. 31B, FIG. 31C, FIG. 31D, FIG. 31E and FIG. 31F depict graphs and images showing increased PTEN phosphatase activity and diminished tumor cell invasion with chemerin incubation via CMKLR1. DU145, SKES, US0S cells transfected with Mock (no siRNA), Control siRNA, or CMKLR1 siRNA were treated with either PBS or 6 nM chemerin for 48 h. Protein samples were collected after each experiment using an IP lysis buffer. PTEN was immunoprecipitated from 75 µg of protein in each sample to quantify specific phosphatase activity. For each phosphatase assay, each sample was incubated with 3 pM PIP3 in duplicate wells for 2 h at 37° C. Next, wells were incubated with Malachite Green, and the absorbance was read, correlating to total amount of free phosphate in solution/well. Each sample set and condition were performed in triplicate (n=3). Results show that 6 nM chemerin increases PTEN phosphatase activity in Mock and Control siRNA transfected cells after 48 h treatment. Although, this increase is lost following CMKLR1 knockdown via siRNA transfection. *$P<0.05$, compared to each vehicle control treated cells for each cell line and transfection subset.
Figure 31B:
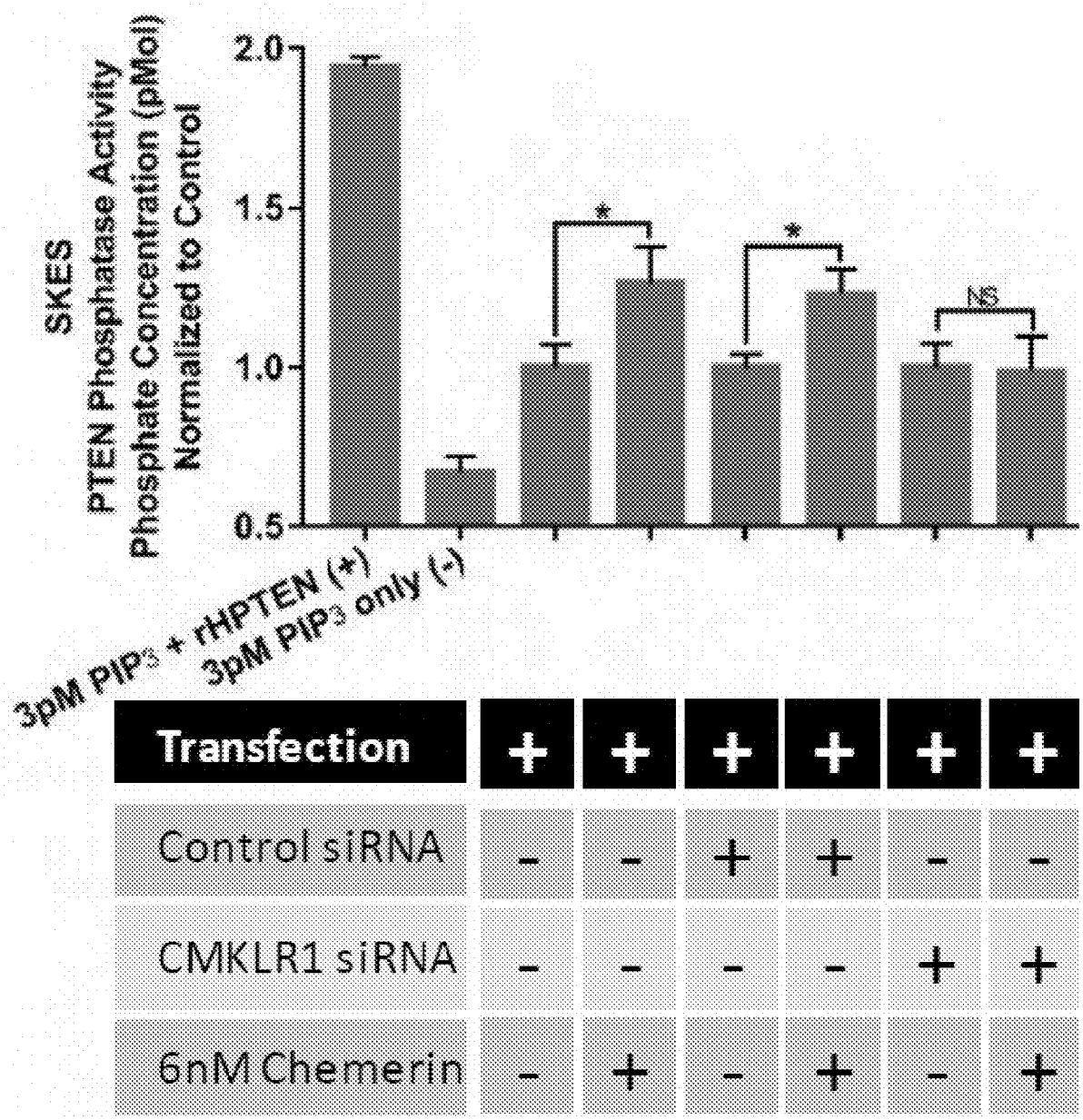
Figure 31C:
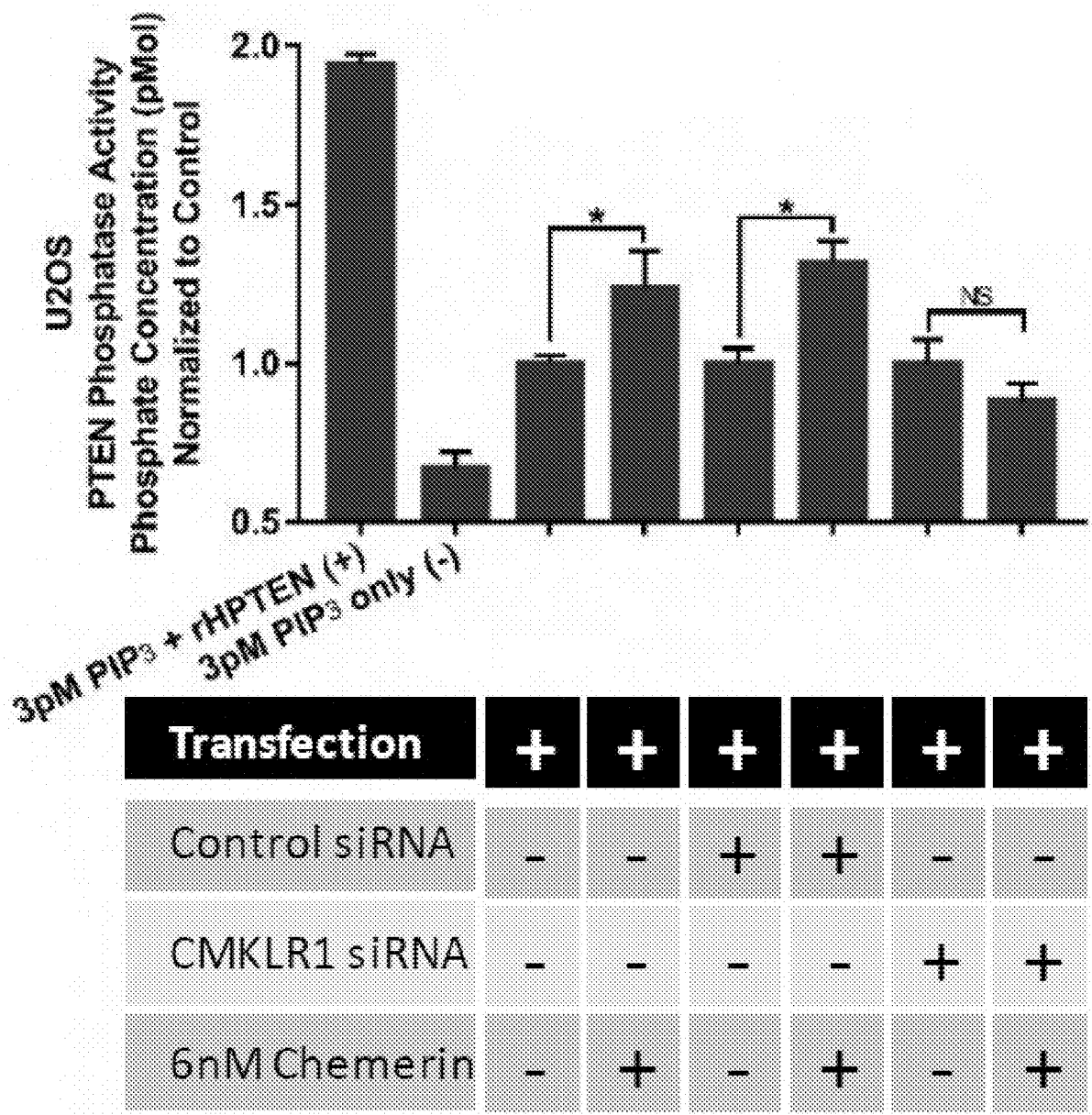
Figure 31D:
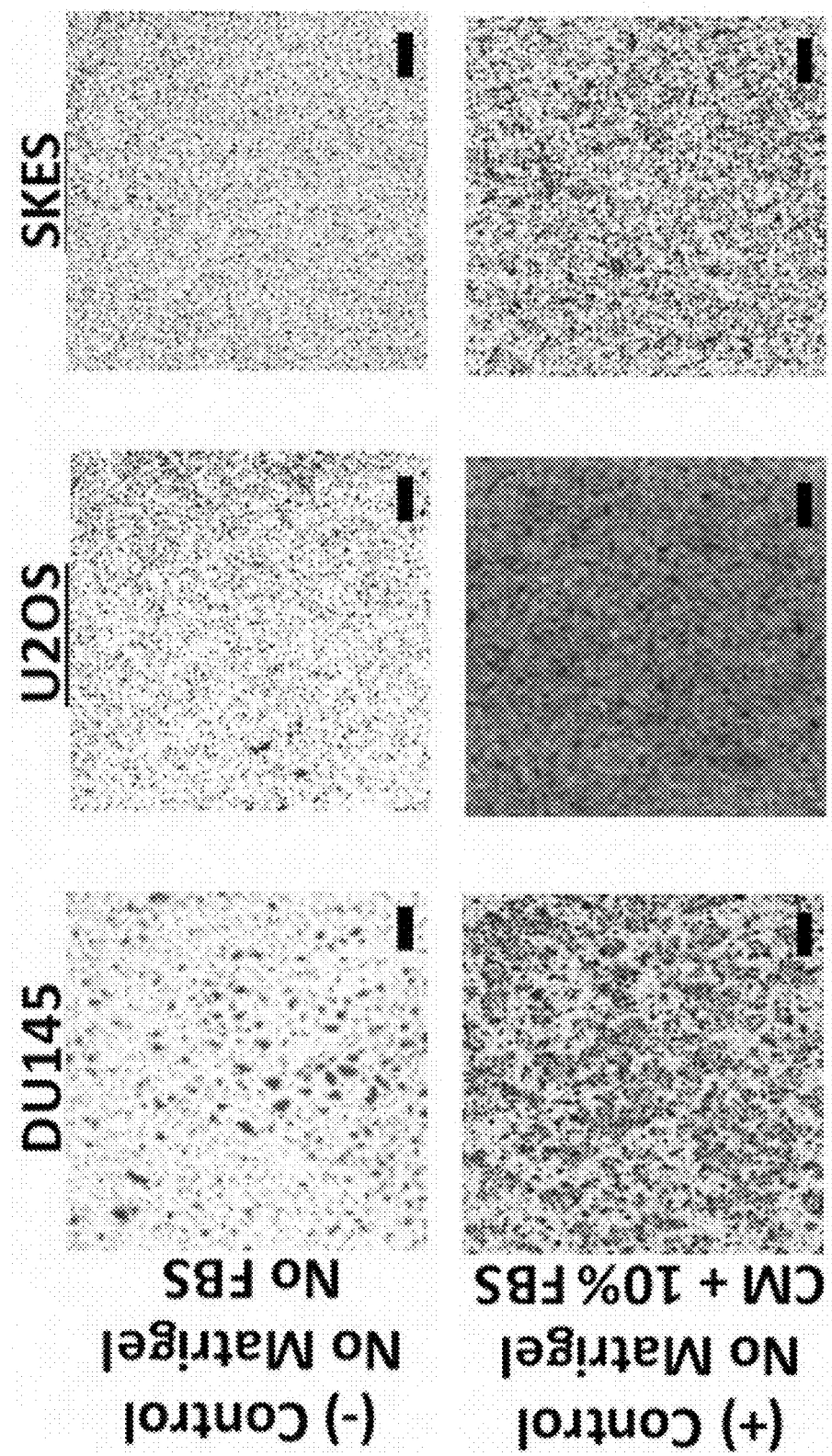
Figure 31E:
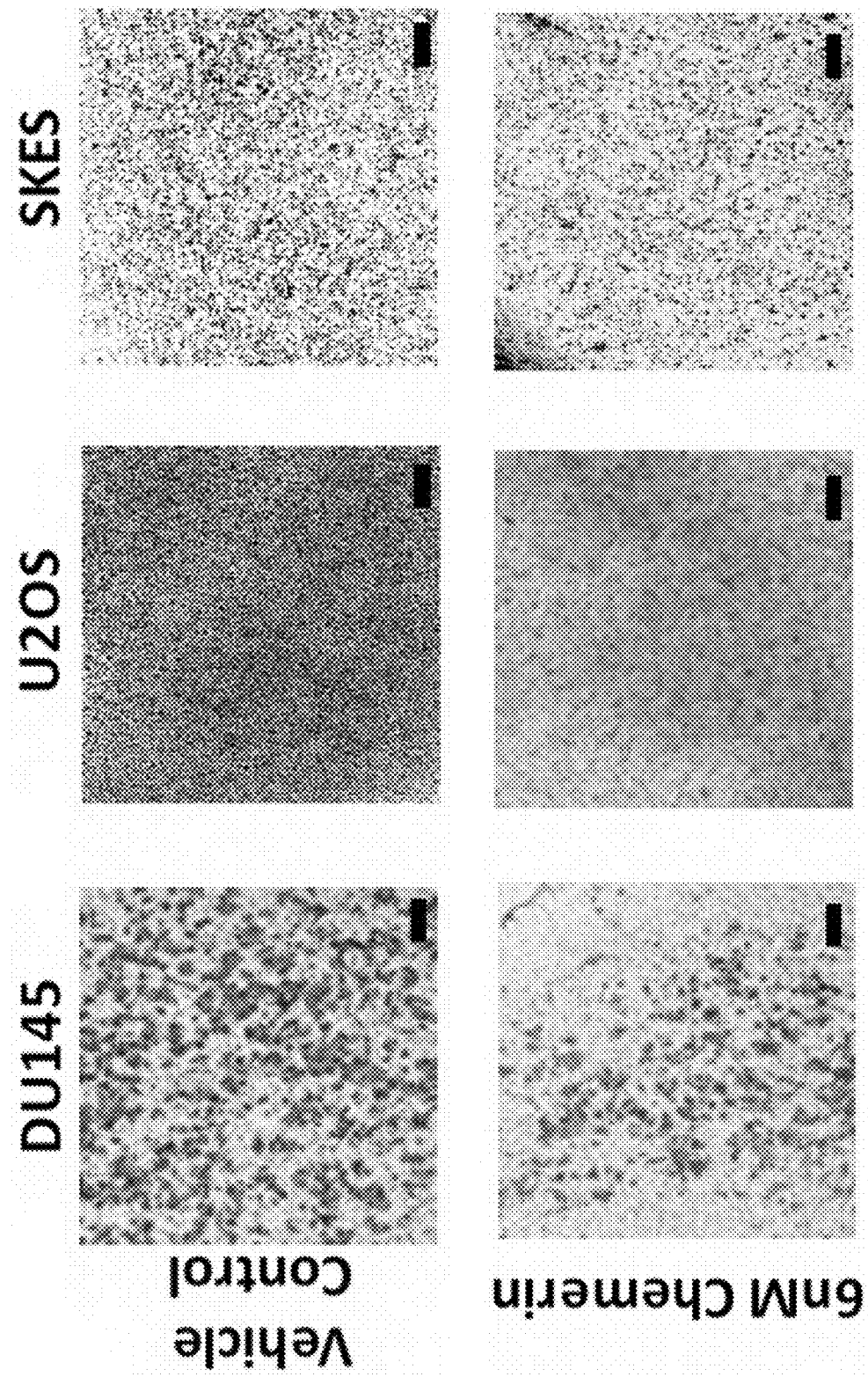
Figure 31F:
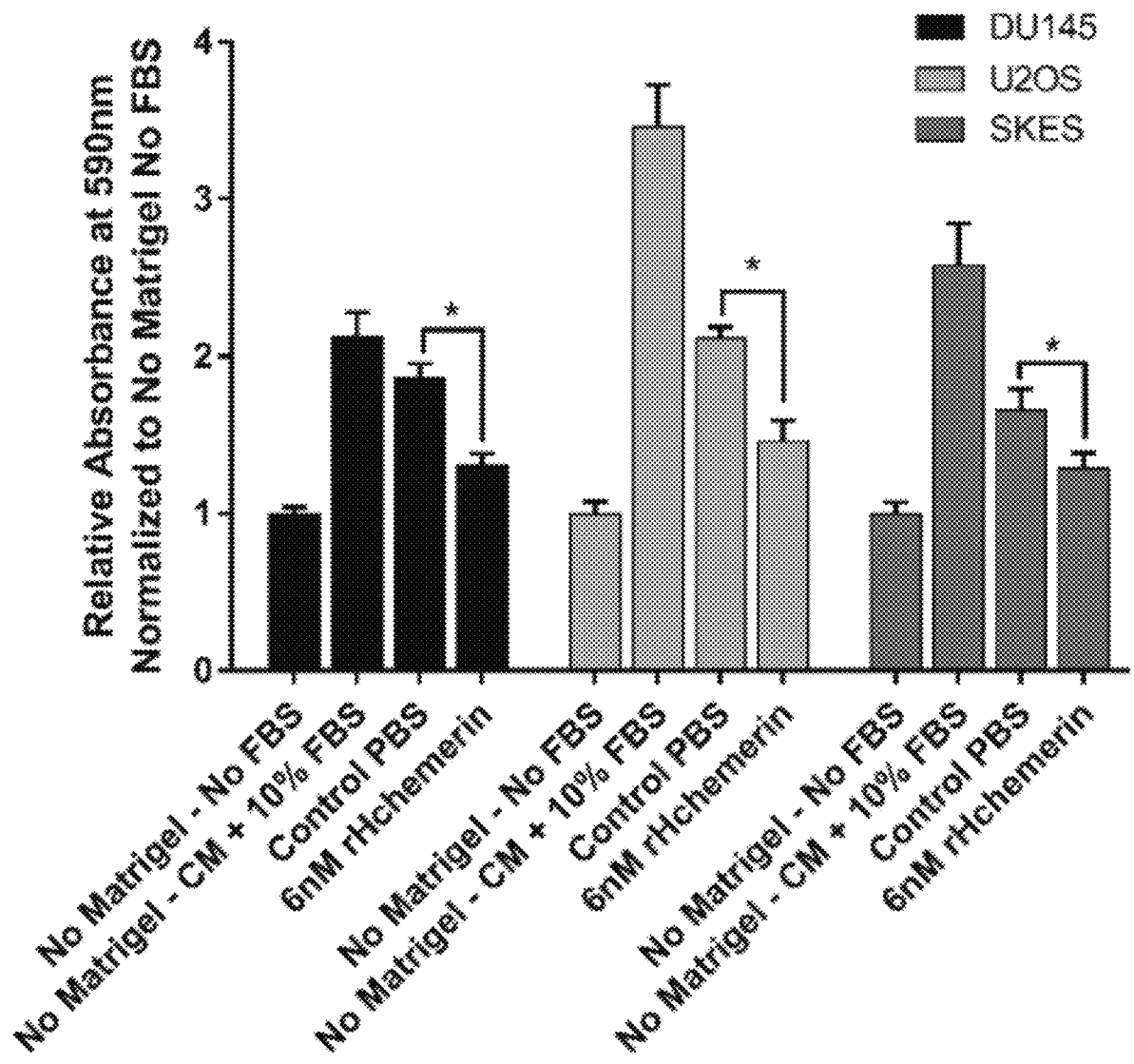
Figure 32A:
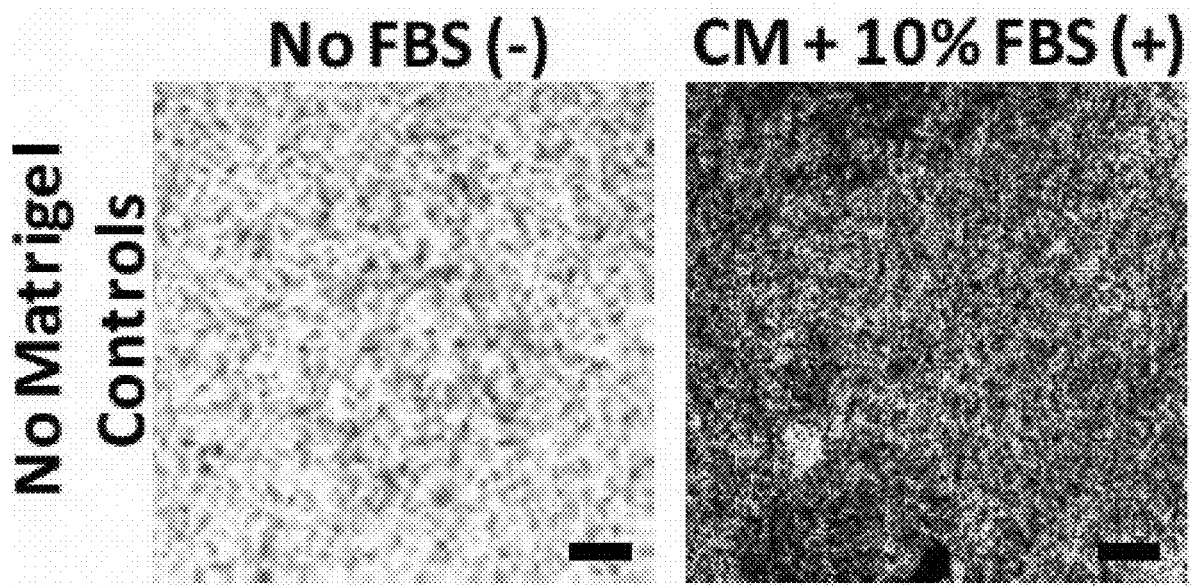
FIG. 32A, FIG. 32B, FIG. 32C, FIG. 32D, FIG. 32E, FIG. 32F, FIG. 32G, FIG. 32H and FIG. 32I depict images and graphs showing CMKLR1 knockdown negates chemerin's ability to decrease DU145 cell invasion.
Figure 32B:
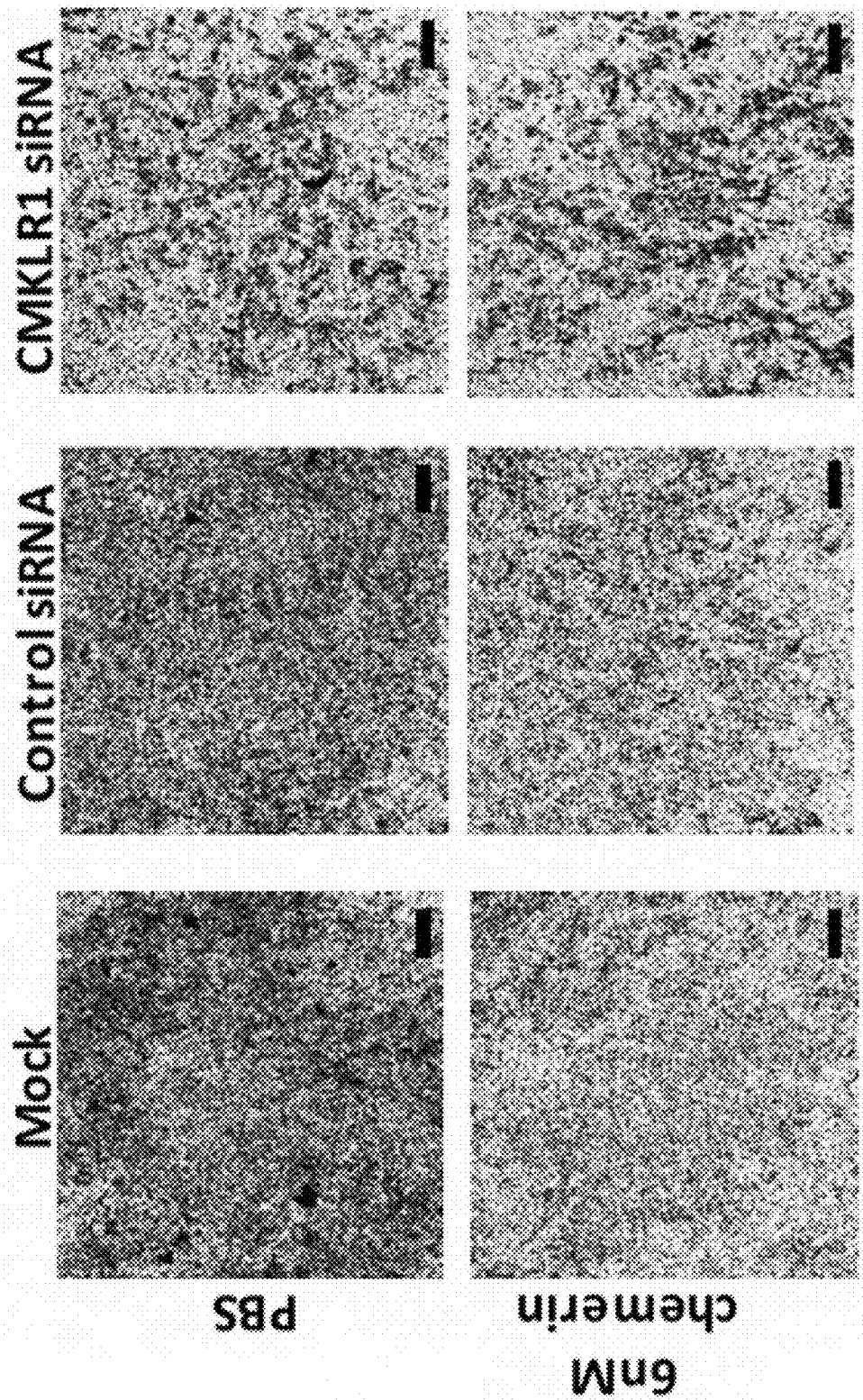
Figure 32C:
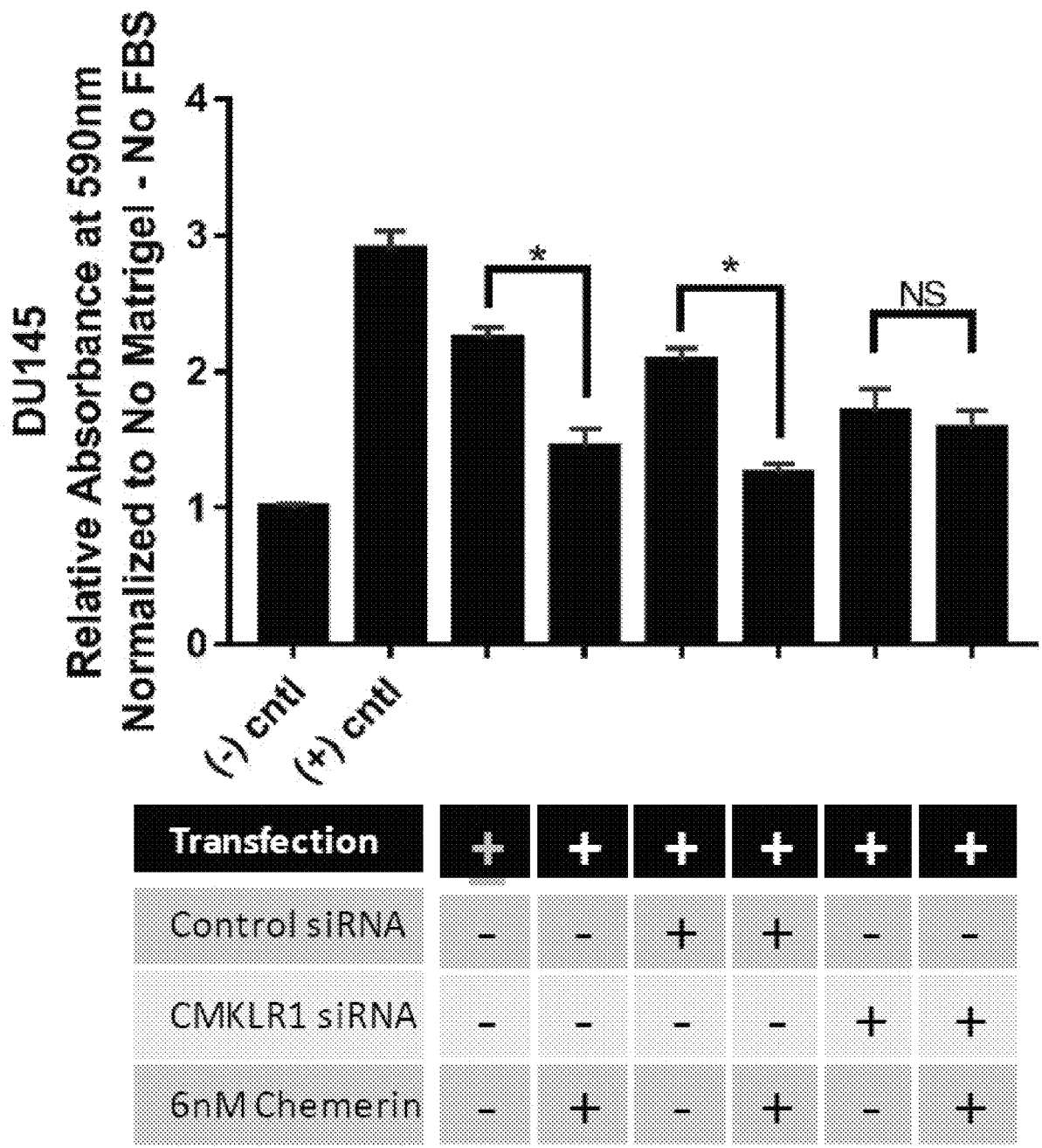
Figure 32D:
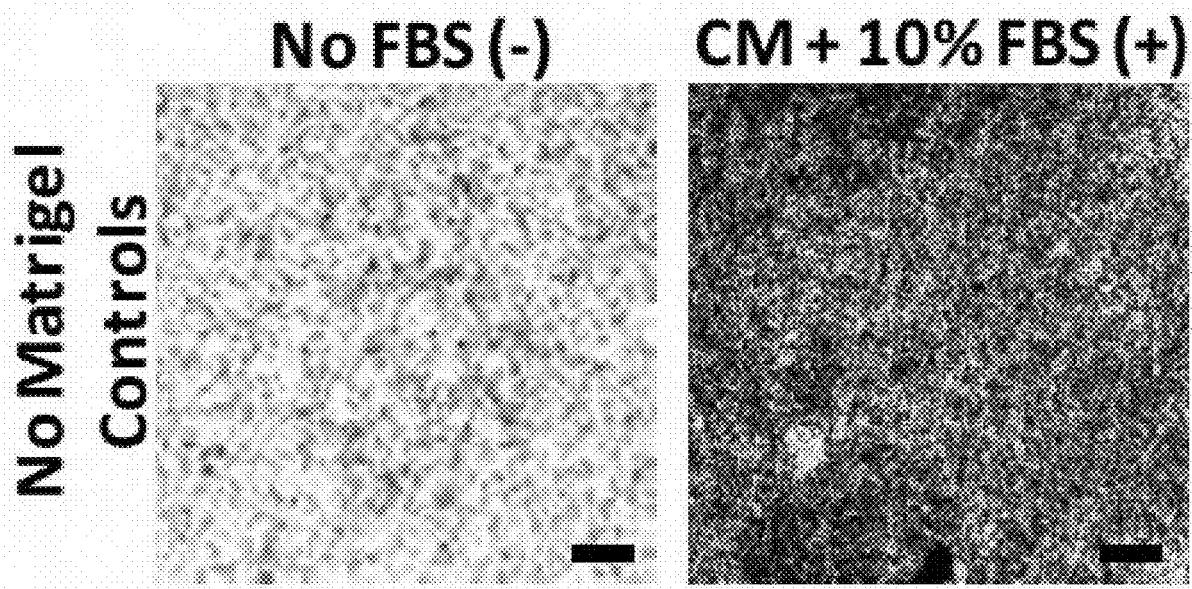
Figure 32E:
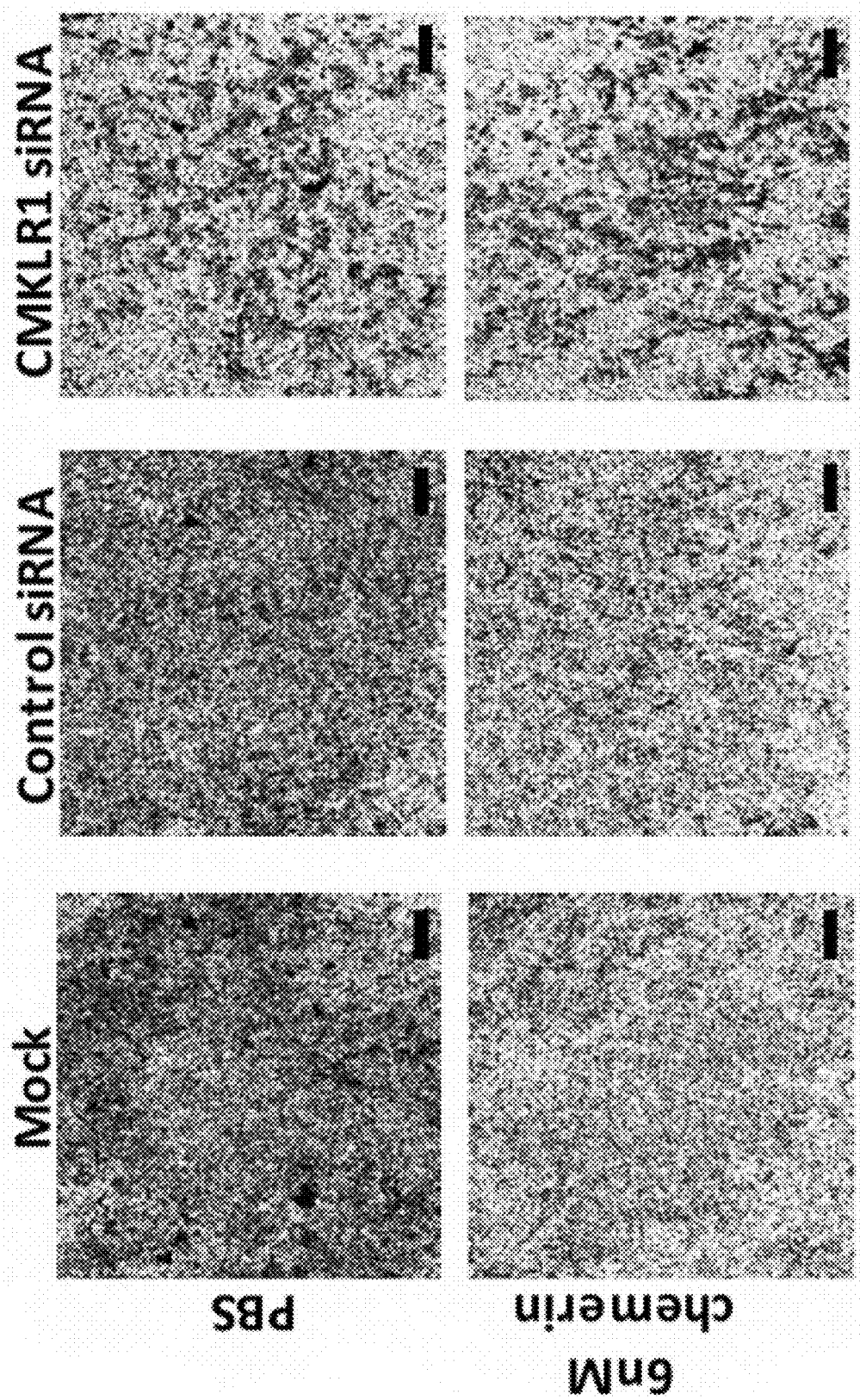
Figure 32F:
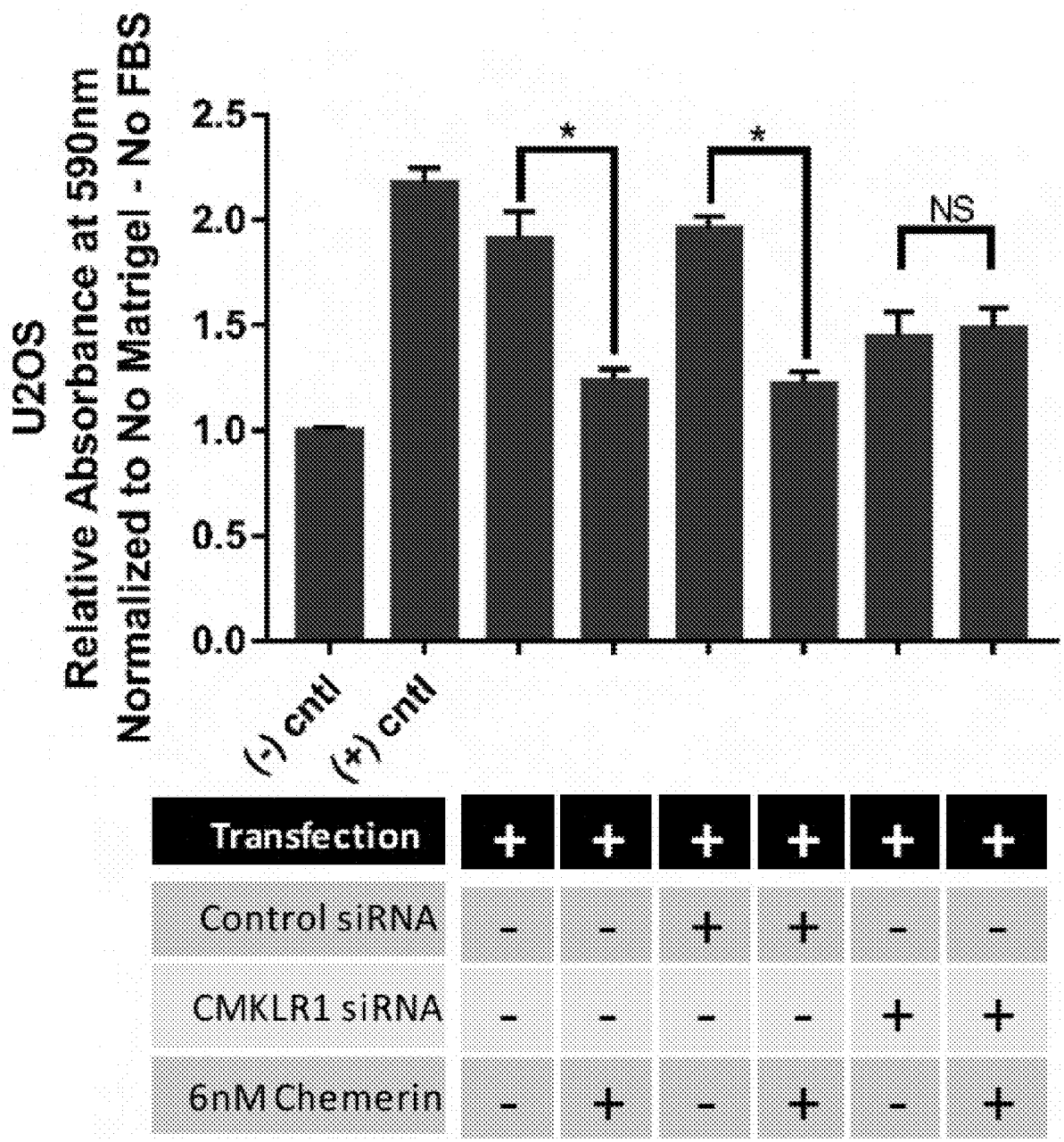
Figure 32G:
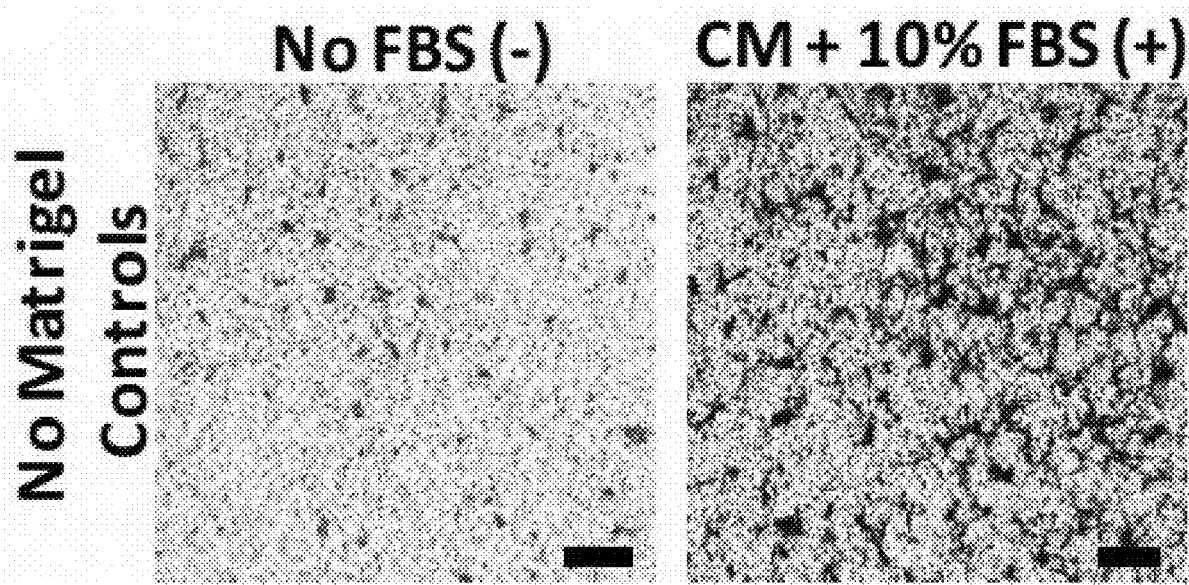
Figure 32H:
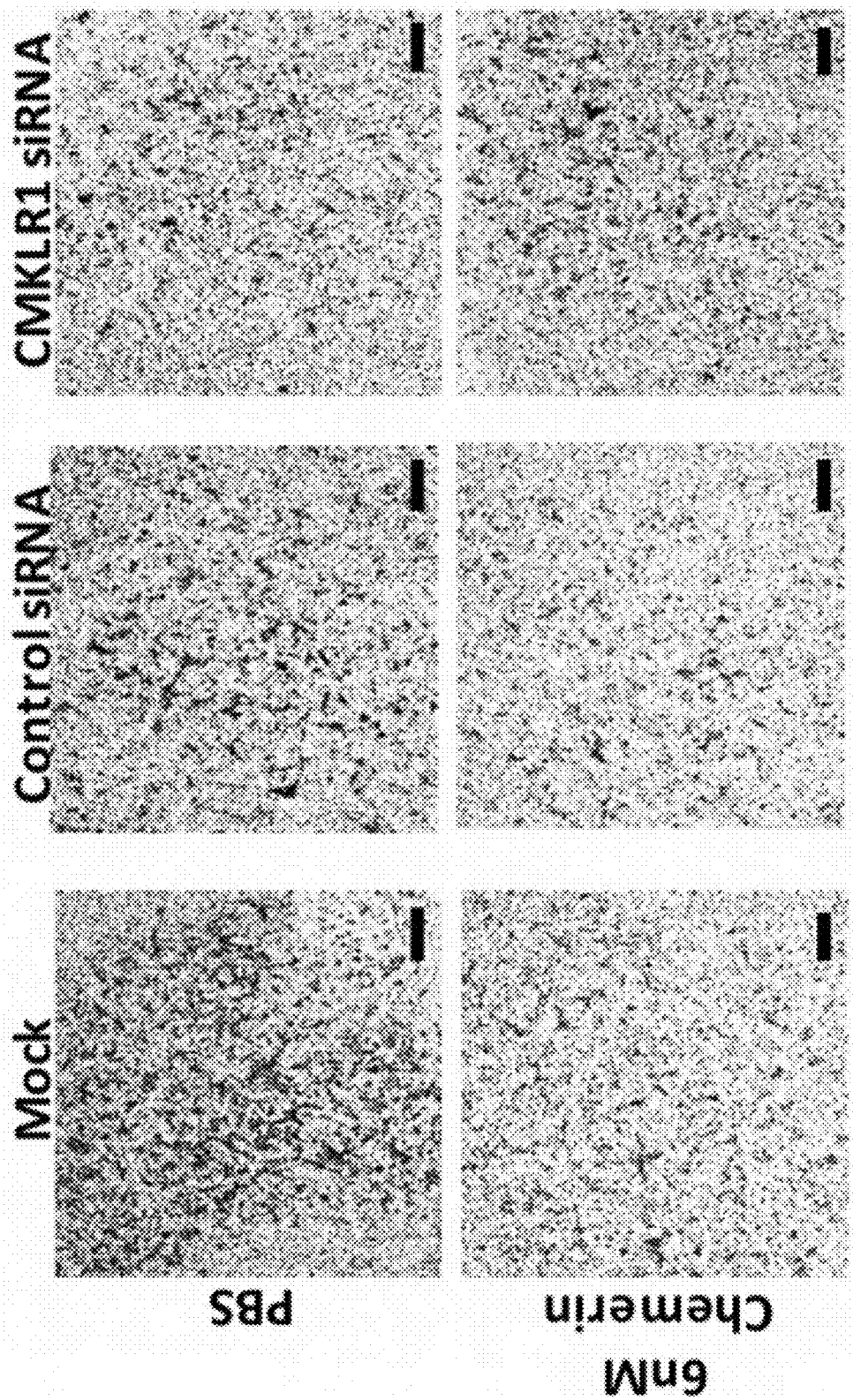
Figure 32I:
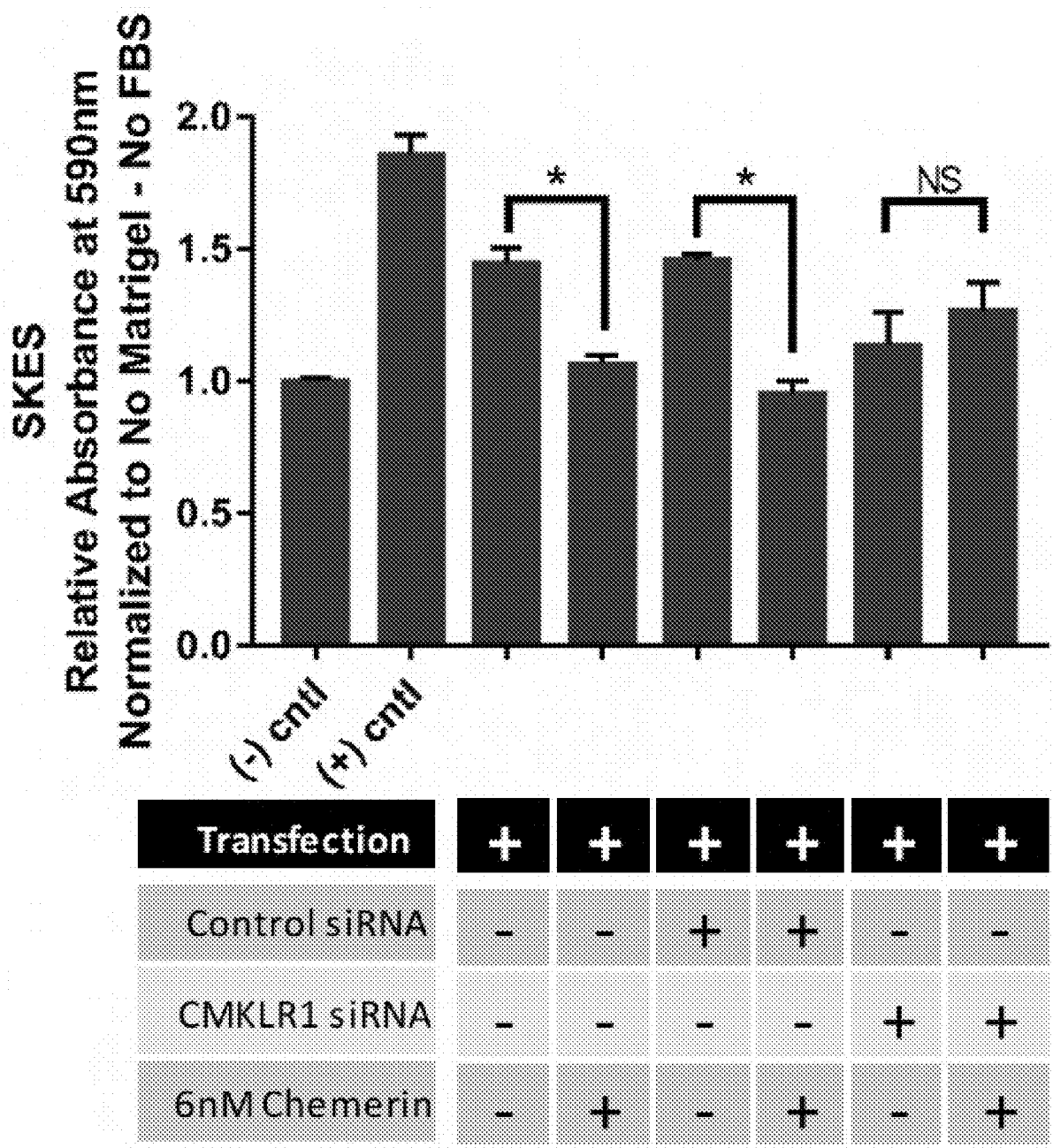
Figure 33A:
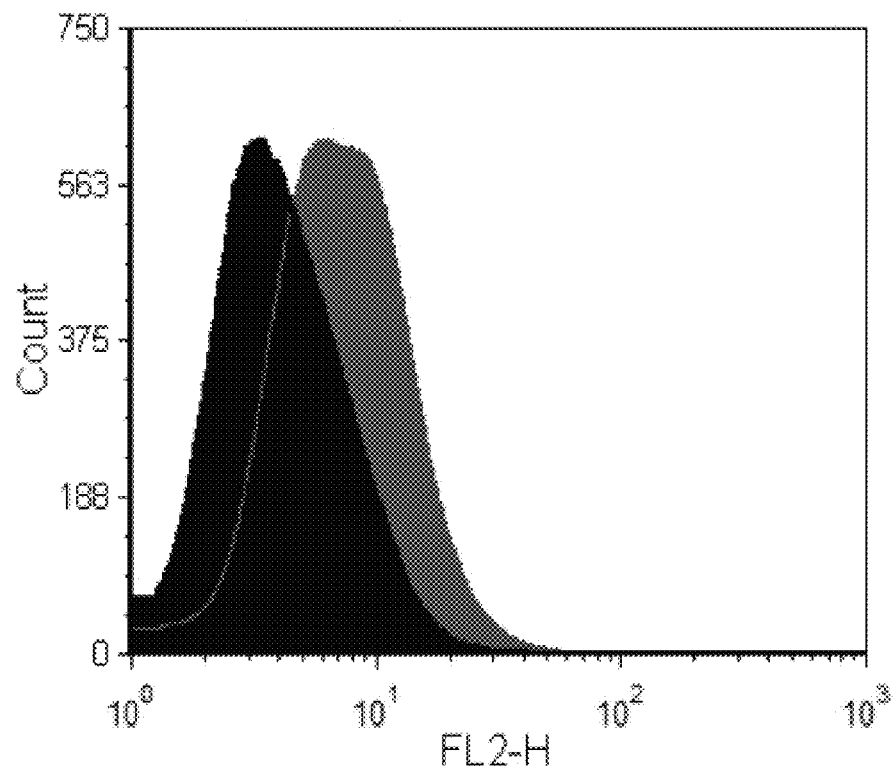
FIG. 33A, FIG. 33B, FIG. 33C, FIG. 33D, FIG. 33E, FIG. 33F, FIG. 33G and FIG. 33H depict flow cytometry plots and immunoblots showing baseline CMKLR1 expression in cell lines.
Figure 33B:
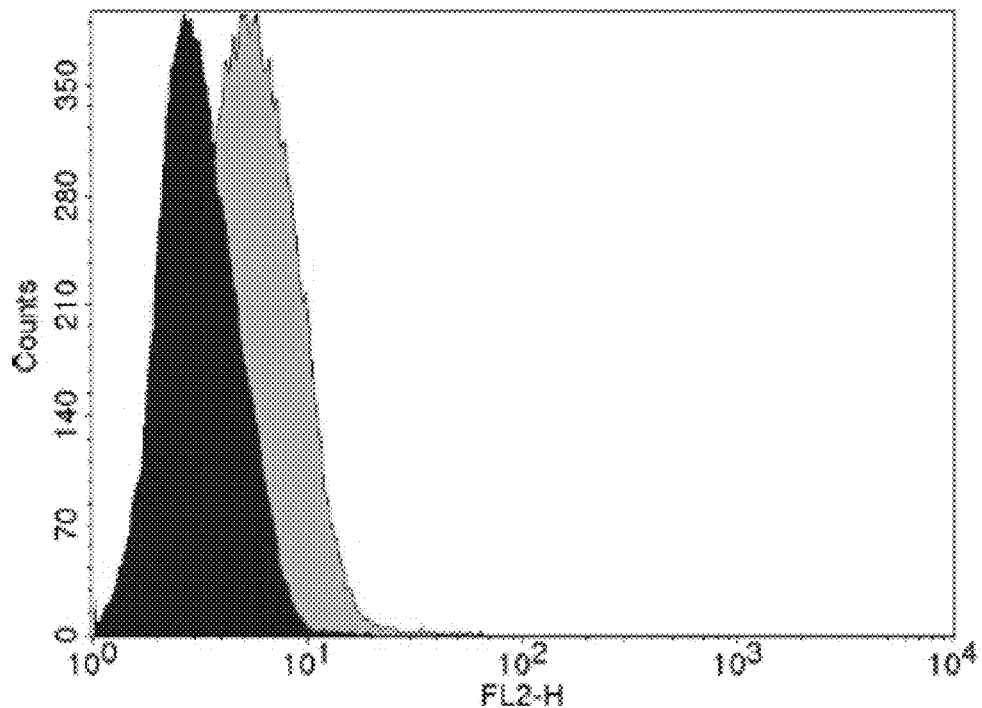
Figure 33C:
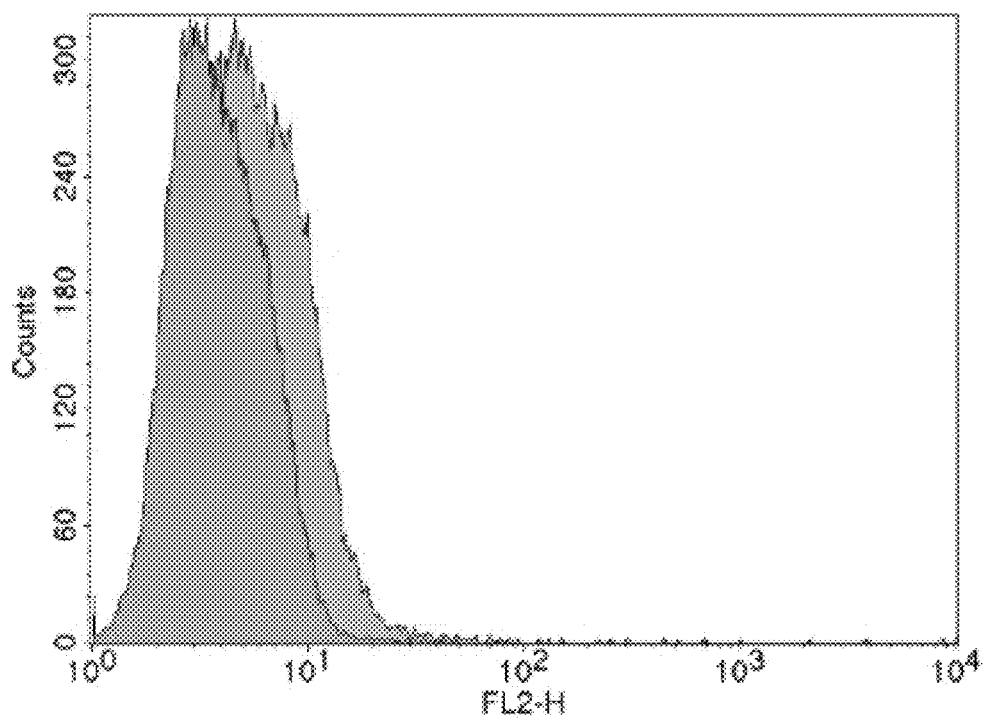
Figure 33D:
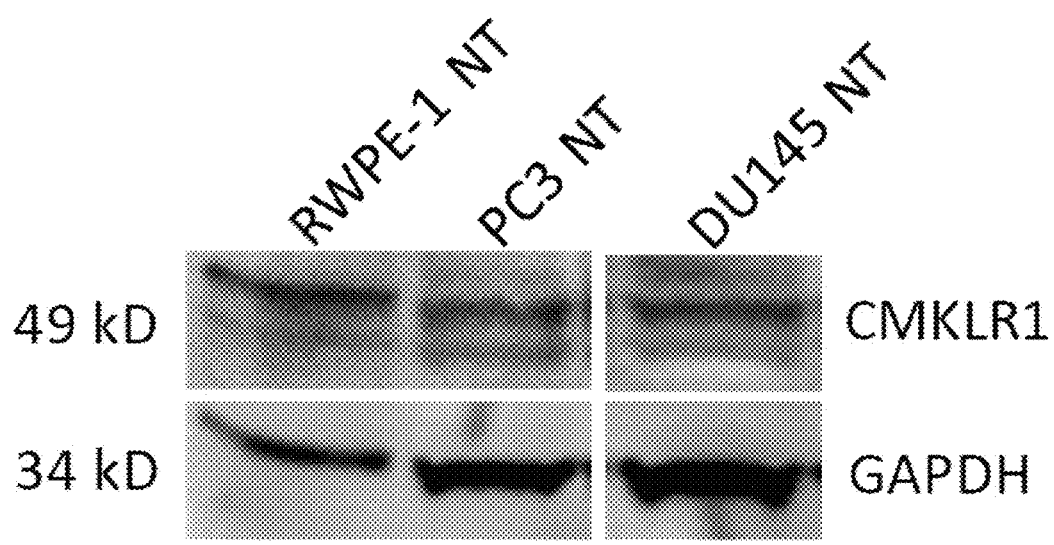
Figure 33E:
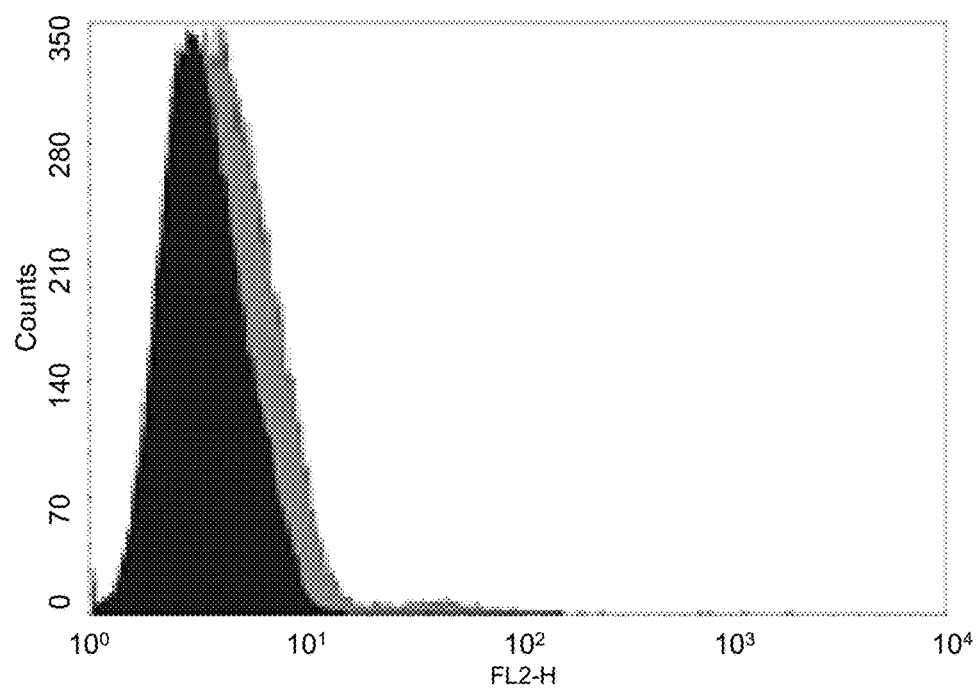
Figure 33F:
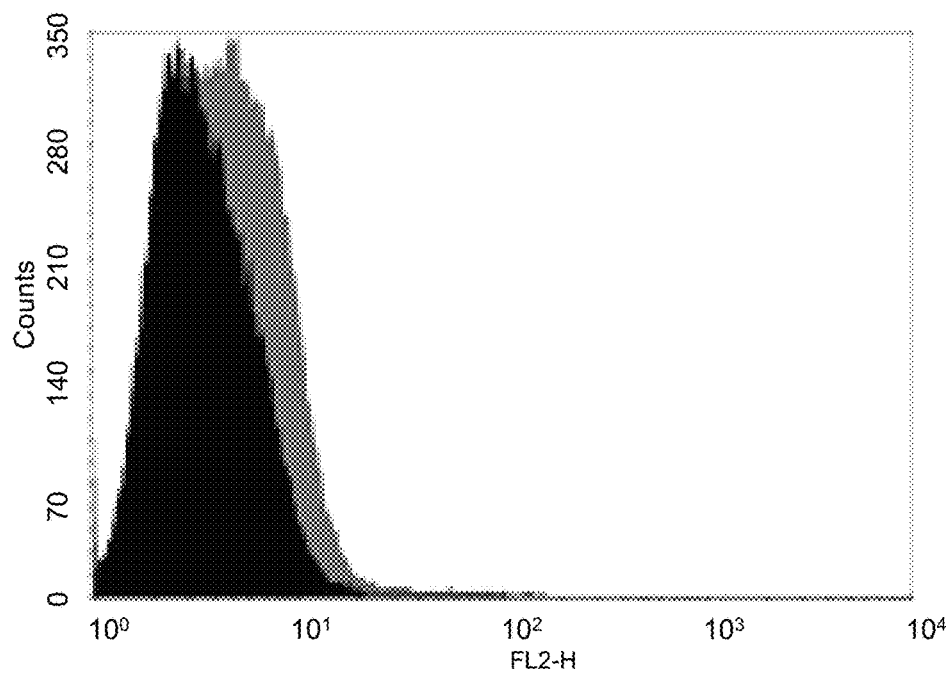
Figure 33G:
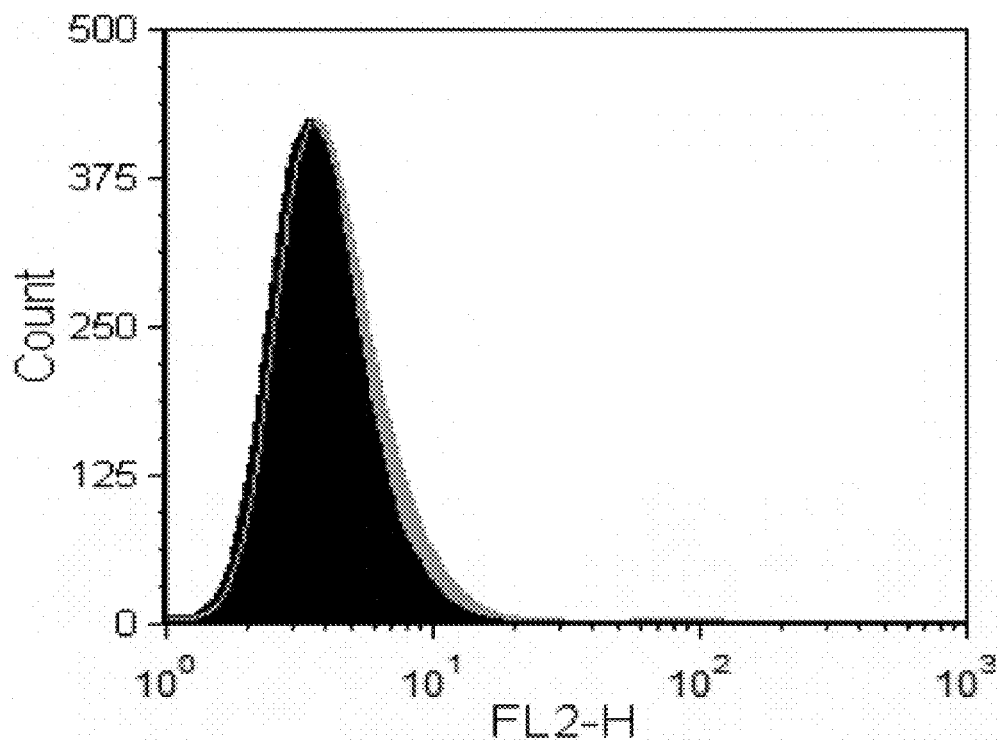
Figure 33H:
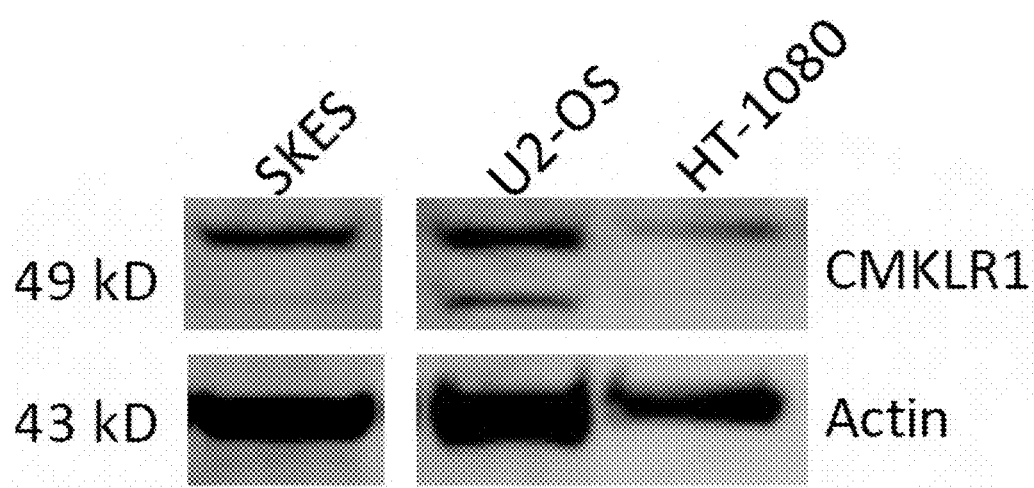

Furthermore, the functional significance of increased PTEN expression by exogenous chemerin was examined. Using a tumor invasion model, the effect of increased PTEN activity in chemerin treated cells was examined. Following a 24 h migration, cells were fixed and stained for analysis. Representative 4× images of each respective cell line and treatment were captured following the experiment and staining protocol (FIG. 31D, FIG. 31E). The results show chemerin treatment significantly decreased overall cell invasion by 29% in DU145 cells, 31% in U2OS cells, and up to 22% in SKES cells (FIG. 31F).

Furthermore, the CMKLR1 siRNA knockdown experiments as stated above were repeated to investigate the effect on tumor cell invasion/migration. After completion, each of the transfected cell subsets were tested using the previously described tumor invasion protocol (FIG. 32). Mock and control siRNA-A cells displayed reduced total tumor cell invasion after chemerin incubation (n=3, P<0.01). In general, CMKLR1 siRNA knockdown decreased overall cell invasion in both treatment groups. Although, decreased CMKLR1 expression diminished the ability of chemerin to slow cancer cell invasion when compared to their PBS-treated counterparts (FIG. 32). Changes in PTEN expression due to chemerin exposure via CMKLR1 binding led to decreased tumor cell invasion. Overall, these studies show that chemerin upregulates PTEN expression to mitigate tumor invasion and migration through a matrigel matrix compared to vehicle control treated cells. Chemerin treatment presents a prospective way to reduce the tumor cell's metastatic potential.

In conclusion, a significant role of chemerin in modulating PTEN expression and activity via CMKLR1 in human tumor cell lines is shown. These novel studies investigate the mechanistic role of the chemerin receptor, CMKLR1, and its potential relationship with the PTEN signaling pathway. This research helps elucidate the interplay between chemerin and PTEN in human tumor cell types. Chemerin-driven increased PTEN expression and activity may help facilitate improved immunotherapy success and the immune systems functional ability to attack cancer cells.

Example 11. Chemerin Downregulates the WNT/β-Catenin Pathway

The WNT/β-catenin pathway is well described as being an active one in multiple tumor types and thus being able to target pharmacologically the WNT/β-catenin pathway is of great interest as an anti-tumor strategy.

Human prostate cancer cells (DU145) were exposed to control protein (0.1% human serum albumin) and recombinant, active chemerin (6 nM). Cells were cultured over 48 hours with fresh media daily. Total RNA was obtained and a Qiagen PCR WNT profiling kit was used to assess the impact of chemerin on the WNT/β-catenin pathway.

Figure 39:
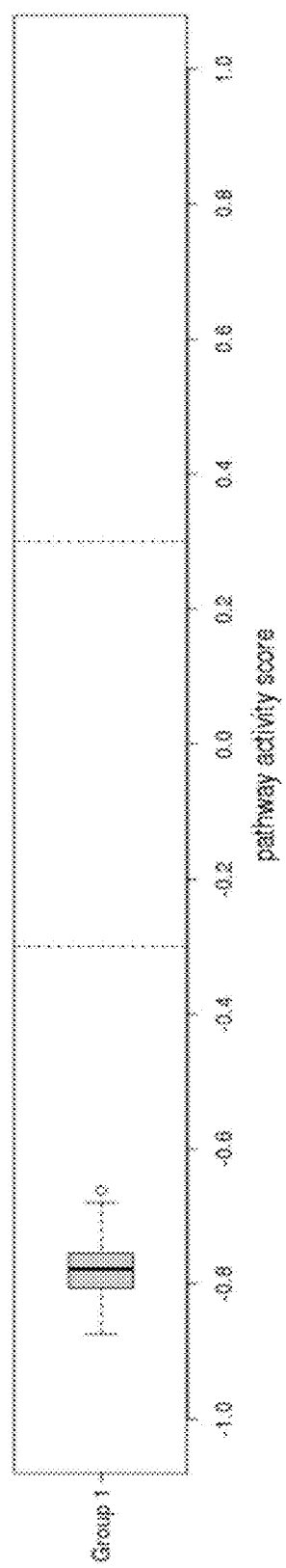
FIG. 39 depicts a diagram showing the pathway activity score of the WNT/β-catenin pathway in the presence of 6 nM chemerin.

FIG. 39 represents 4 independent experiments (n=4) showing that chemerin inhibits WNT/β-catenin signaling in human prostate cancer cells. A positive score indicates stimulation of pathway activity while a negative score indicates repression. The pathway activity score for the WNT/β-catenin signaling pathway was −0.778000 with a p-value of 0.000000.

What is claimed is:

1. A polynucleotide sequence encoding a polypeptide, the polypeptide comprising chemerin linked via a linker to a targeting moiety, wherein the linker comprises SEQ ID NO: 8 and wherein the targeting moiety is capable of directing the chemerin to a target site on a cell.

2. The polynucleotide sequence of claim 1, wherein the chemerin is mature chemerin comprising a nucleotide sequence encoding SEQ ID NO: 3 or prochemerin comprising a nucleotide sequence encoding SEQ ID NO: 2.

3. The polynucleotide sequence of claim 1, wherein the chemerin is mature chemerin comprising a nucleotide sequence encoding SEQ ID NO: 2 with 5, 6, 7, 8 or 9 amino acids absent from the C-terminus of SEQ ID NO: 2.

4. The polynucleotide sequence of claim 1, wherein the targeting moiety is capable of directing the chemerin to a target site on a cancer cell selected from the group consisting of CD20, HER2, EGFR, PSCA and PSMA.

5. The polynucleotide sequence of claim 1, wherein the targeting moiety is selected from the group consisting of an antibody or fragment thereof, an aptamer, or a binding domain derived from a target protein ligand.

6. The polynucleotide sequence of claim 1, wherein the targeting moiety is a CD20 scFv comprising a nucleotide sequence encoding SEQ ID NO: 4 or PSCA scFv comprising a nucleotide sequence encoding SEQ ID NO: 5.

7. A vector comprising a polynucleotide sequence of claim 1.

8. A composition, the composition comprising a polypeptide encoded by the polynucleotide of claim 1.

9. A method to increase phosphatase and tensin homolog (PTEN) expression in a tumor in a subject, the method comprising administering to the subject a composition comprising a chemerin linked via a linker to a targeting moiety, wherein the targeting moiety is capable of directing the chemerin to a target site on a cancer cell of the tumor and wherein the linker comprises SEQ ID NO: 8.

10. A method to treat or stabilize cancer in a subject, the method comprising administering to the subject a composition comprising a chemerin linked via a linker to a targeting moiety, wherein the targeting moiety is capable of directing the chemerin to a target site on a cancer cell of a tumor and thereby recruiting immune cells to the tumor and wherein the linker comprises SEQ ID NO: 8.

11. The method of claim 10, wherein the immune cells include dendritic cells, macrophages, monocytes, and/or natural killer cells.

12. The method of claim 10, wherein the chemerin is mature chemerin comprising SEQ ID NO: 3 or prochemerin comprising SEQ ID NO: 2.

13. The method of claim 10, wherein the chemerin is mature chemerin comprising SEQ ID NO: 2 with 5, 6, 7, 8 or 9 amino acids absent from the C-terminus of SEQ ID NO: 2.

14. The method of claim 10, wherein the target site is a target protein on the surface of the cancer cell and the protein is selected from the group consisting of CD20, HER2, EGFR, PSCA and PSMA.

15. The method of claim 10, wherein the targeting moiety is selected from the group consisting of an antibody or fragment thereof, an aptamer, or a binding domain derived from a target protein ligand.

16. The method of any of claim 9 or 10, wherein the targeting moiety is a CD20 scFv comprising a nucleotide sequence encoding SEQ ID NO: 4 or PSCA scFv comprising a nucleotide sequence encoding SEQ ID NO: 5.

17. The method of claim 10, further comprising administering a checkpoint inhibitor.

* * * * *

```
                        SEQUENCE LISTING

<160> NUMBER OF SEQ ID NOS: 24

<210> SEQ ID NO 1
<211> LENGTH: 163
<212> TYPE: PRT
<213> ORGANISM: Homo sapiens

<400> SEQUENCE: 1

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
                20                  25                  30

Ala Leu Glu Glu Phe His Lys His Pro Pro Val Gln Trp Ala Phe Gln
            35                  40                  45

Glu Thr Ser Val Glu Ser Ala Val Asp Thr Pro Phe Pro Ala Gly Ile
        50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser

<210> SEQ ID NO 2
<211> LENGTH: 143
<212> TYPE: PRT
<213> ORGANISM: Homo sapiens

<400> SEQUENCE: 2

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
        50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95
```

```
Cys Pro Ile Glu Thr Gln Val Leu Arg Glu Ala Glu Glu His Gln Glu
                100                 105                 110

Thr Gln Cys Leu Arg Val Gln Arg Ala Gly Glu Asp Pro His Ser Phe
            115                 120                 125

Tyr Phe Pro Gly Gln Phe Ala Phe Ser Lys Ala Leu Pro Arg Ser
        130                 135                 140

<210> SEQ ID NO 3
<211> LENGTH: 137
<212> TYPE: PRT
<213> ORGANISM: Homo sapiens

<400> SEQUENCE: 3

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
    50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu Glu His Gln Glu
                100                 105                 110

Thr Gln Cys Leu Arg Val Gln Arg Ala Gly Glu Asp Pro His Ser Phe
            115                 120                 125

Tyr Phe Pro Gly Gln Phe Ala Phe Ser
        130                 135

<210> SEQ ID NO 4
<211> LENGTH: 242
<212> TYPE: PRT
<213> ORGANISM: Artificial Sequence
<220> FEATURE:
<223> OTHER INFORMATION: SYNTHESIZED

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Gly Gly Gly Ser Gly Gly
            115                 120                 125

Gly Gly Ser Gly Gly Gly Gly Ser Gln Ile Val Leu Ser Gln Ser Pro
```

```
                130             135             140
Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
            195                 200                 205

Thr Ile Ser Arg Val Glu Ala Glu Asp Ala Ala Thr Tyr Tyr Cys Gln
            210                 215                 220

Gln Trp Thr Ser Asn Pro Pro Thr Phe Gly Gly Gly Thr Lys Leu Glu
225                 230                 235                 240

Ile Lys

<210> SEQ ID NO 5
<211> LENGTH: 238
<212> TYPE: PRT
<213> ORGANISM: Artificial Sequence
<220> FEATURE:
<223> OTHER INFORMATION: SYNTHESIZED

<400> SEQUENCE: 5

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
            35                  40                  45

Gly Asn Ile Asn Pro Asn Asn Gly Gly Thr Thr Tyr Asn Gln Lys Phe
        50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
                100                 105                 110

Val Ser Ser Gly Gly Gly Gly Ser Gly Gly Gly Gly Ser Gly Gly Gly
            115                 120                 125

Gly Ser Asp Ile Val Met Thr Gln Ser His Lys Phe Met Ser Thr Ser
130                 135                 140

Val Gly Asp Arg Val Ser Ile Ile Cys Lys Ala Ser Gln Asp Val Gly
145                 150                 155                 160

Thr Ala Val Asp Trp Tyr Gln Gln Lys Pro Gly Gln Ser Pro Lys Leu
                165                 170                 175

Leu Ile Tyr Trp Ala Ser Thr Arg His Thr Gly Val Pro Asp Arg Phe
            180                 185                 190

Thr Gly Ser Gly Ser Gly Thr Asp Phe Thr Leu Thr Ile Thr Asn Val
        195                 200                 205

Gln Ser Glu Asp Leu Ala Asp Tyr Phe Cys Gln Gln Tyr Asn Ser Tyr
    210                 215                 220

Pro Leu Thr Phe Gly Ala Gly Thr Met Leu Asp Leu Lys
225                 230                 235

<210> SEQ ID NO 6
```

```
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 6

Gly Gly Gly Gly Ala Gly Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 7

Pro Leu Gly Leu Ala Gly
1               5

<210> SEQ ID NO 8
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 8

Gly Gly Gly Gly Ala Gly Gly Gly Gly Pro Leu Gly Leu Ala Gly
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 9

Met Glu Trp Ser Trp Val Phe Leu Phe Phe Leu Ser Val Thr Thr Gly
1               5                   10                  15

Val His Ser

<210> SEQ ID NO 10
<211> LENGTH: 1254
<212> TYPE: DNA
<213> ORGANISM: Artificial Sequence
<220> FEATURE:
<223> OTHER INFORMATION: SYNTHESIZED

<400> SEQUENCE: 10
atggaatgga gctgggtctt tctcttcttc ctgtcagtaa cgactggtgt ccactcccac      60
caccatcatc accatcacca ccatcaccag gtgcagctgc agcagcctgg tgccgagctc     120
gtgaaacctg gcgcctccgt gaagatgtcc tgcaaggcct ccggctacac cttcaccagc     180
tacaacatgc actgggtcaa gcagacccc ggcagaggcc tggaatggat cggcgctatc     240 tacccccggca acggcgacac ctcctacaac cagaagttca agggcaaggc cacccctgacc    300 gccgacaagt cctcttccac cgcctacatg cagctgtcct ccctgacctc cgaggactcc     360
gccgtgtact actgcgcccg gtctacctac tacggcggcg actggtactt caacgtgtgg     420
ggcgctggca ccaccgtgac agtgtctgct ggtggcggag gatctggcgg aggcggtagt     480
ggcggtggcg gatctcagat cgtgctgtcc cagtcccctg ccatcctgtc tgctagccct     540
```

```
ggcgagaaag tgacaatgac ctgccgggcc tcctcctccg tgtcctacat ccactggttc      600
cagcagaagc ccggctccag ccccaagcct tggatctacg ccacctccaa cctggcctct      660
ggcgtgccag tgcggttttc cggctctggc tctggcacct cttacagcct gaccatctcc      720
cgggtggaag ccgaggatgc cgccacctac tactgccagc agtggaccag caaccctccc      780
acctttggag gcggcaccaa gctggaaatc aagggcggag gtggtgcagg aggcggtgga      840
gagctcacgg aagcccagcg ccggggcctg caggtggccc tggaggaatt cacaagcac       900 ccgcccgtgc agtgggcctt ccaggagacc agtgtggaga gcgccgtgga cacgcccttc      960
ccagctggaa tatttgtgag gctggaattt aagctgcagc agacaagctg ccggaagagg     1020
gactggaaga aacccgagtg caaagtcagg cccaatggga ggaaacggaa atgcctggcc     1080
tgcatcaaac tgggctctga ggacaaagtt ctgggccggt tggtccactg ccccatagag     1140
acccaagttc tgcgggaggc tgaggagcac caggagaccc agtgcctcag ggtgcagcgg     1200
gctggtgagg accccacag cttctacttc cctggacagt tcgccttctc ctga           1254
```

<210> SEQ ID NO 11
<211> LENGTH: 1167
<212> TYPE: DNA
<213> ORGANISM: Artificial Sequence
<220> FEATURE:
<223> OTHER INFORMATION: SYNTHESIZED

<400> SEQUENCE: 11

```
caggtgcagc tgcagcagcc tggtgccgag ctcgtgaaac ctggcgcctc cgtgaagatg       60
tcctgcaagg cctccggcta caccttcacc agctacaaca tgcactgggt caagcagacc      120
cccggcagag gcctggaatg gatcggcgct atctaccccg gcaacggcga cacctcctac      180
aaccagaagt tcaagggcaa ggccaccctg accgccgaca gtcctcttc caccgcctac      240 atgcagctgt cctccctgac ctccgaggac tccgccgtgt actactgcgc ccggtctacc      300
tactacggcg gcgactggta cttcaacgtg tggggcgctg gcaccaccgt gacagtgtct      360
gctggtggcg gaggatctgg cggaggcggt agtggcggtg gcggatctca gatcgtgctg      420
tcccagtccc ctgccatcct gtctgctagc cctggcgaga aagtgacaat gacctgccgg      480
gcctcctcct ccgtgtccta catccactgg ttccagcaga gcccggctc cagccccaag      540 ccttggatct acgccacctc caacctggcc tctggcgtgc cagtgcggtt ttccggctct      600
ggctctggca cctcttacag cctgaccatc tccggggtgg aagccgagga tgccgccacc      660
tactactgcc agcagtggac cagcaaccct cccacctttg gaggcggcac caagctggaa      720
atcaagggcg gaggtggtgc aggaggcggt ggagagctca cggaagccca gcgccggggc      780
ctgcaggtgg ccctggagga atttcacaag cacccgcccg tgcagtgggc cttccaggag      840
accagtgtgg agagcgccgt ggacacgccc ttcccagctg gaatatttgt gaggctggaa      900
tttaagctgc agcagacaag ctgccggaag agggactgga gaaacccga gtgcaaagtc      960 aggcccaatg ggaggaaacg gaaatgcctg gcctgcatca aactgggctc tgaggacaaa     1020
gttctgggcc ggttggtcca ctgccccata gagacccaag ttctgcggga ggctgaggag     1080
caccaggaga cccagtgcct cagggtgcag cgggctggtg aggaccccca cagcttctac     1140
ttccctggac agttcgcctt ctcctga                                         1167
```

<210> SEQ ID NO 12
<211> LENGTH: 1272
<212> TYPE: DNA

<213> ORGANISM: Artificial Sequence
<220> FEATURE:
<223> OTHER INFORMATION: SYNTHESIZED

<400> SEQUENCE: 12

| | | | | | |
|---|---|---|---|---|---|
| atggaatgga | gctgggtctt | tctcttcttc | ctgtcagtaa | cgactggtgt | ccactcccac | 60 |
| caccatcatc | accatcacca | ccatcaccag | gtgcagctgc | agcagcctgg | tgccgagctc | 120 |
| gtgaaacctg | gcgcctccgt | gaagatgtcc | tgcaaggcct | ccggctacac | cttcaccagc | 180 |
| tacaacatgc | actgggtcaa | gcagacccccc | ggcagaggcc | tggaatggat | cggcgctatc | 240 |
| taccccggca | acggcgacac | ctcctacaac | cagaagttca | agggcaaggc | caccctgacc | 300 |
| gccgacaagt | cctcttccac | cgcctacatg | cagctgtcct | ccctgacctc | cgaggactcc | 360 |
| gccgtgtact | actgcgcccg | gtctacctac | tacggcggcg | actggtactt | caacgtgtgg | 420 |
| ggcgctggca | ccaccgtgac | agtgtctgct | ggtggcggag | gatctggcgg | aggcggtagt | 480 |
| ggcggtggcg | gatctcagat | cgtgctgtcc | cagtcccctg | ccatcctgtc | tgctagccct | 540 |
| ggcgagaaag | tgacaatgac | ctgccgggcc | tcctcctccg | tgtcctacat | ccactggttc | 600 |
| cagcagaagc | ccggctccag | ccccaagcct | tggatctacg | ccacctccaa | cctggcctct | 660 |
| ggcgtgccag | tgcggttttc | cggctctggc | tctggcacct | cttacagcct | gaccatctcc | 720 |
| cgggtggaag | ccgaggatgc | cgccacctac | tactgccagc | agtggaccag | caaccctccc | 780 |
| acctttggag | cggcaccaa | gctggaaatc | aagggcggag | gtggtgcagg | aggcggtgga | 840 |
| gagctcacgg | aagcccagcg | ccggggcctg | caggtggccc | tggaggaatt | tcacaagcac | 900 |
| ccgcccgtgc | agtgggcctt | ccaggagacc | agtgtggaga | cgccgtgga | cacgcccttc | 960 |
| ccagctggaa | tatttgtgag | gctggaattt | aagctgcagc | agacaagctg | ccggaagagg | 1020 |
| gactggaaga | aacccgagtg | caaagtcagg | cccaatggga | ggaaacggaa | atgcctggcc | 1080 |
| tgcatcaaac | tgggctctga | ggacaaagtt | ctgggccggt | tggtccactg | ccccatagag | 1140 |
| acccaagttc | tgcgggaggc | tgaggagcac | caggagaccc | agtgcctcag | ggtgcagcgg | 1200 |
| gctggtgagg | accccacag | cttctacttc | cctggacagt | tcgccttctc | caaggccctg | 1260 |
| ccccgcagct | ga | | | | | 1272 |

<210> SEQ ID NO 13
<211> LENGTH: 1185
<212> TYPE: DNA
<213> ORGANISM: Artificial Sequence
<220> FEATURE:
<223> OTHER INFORMATION: SYNTHESIZED

<400> SEQUENCE: 13

| | | | | | |
|---|---|---|---|---|---|
| caggtgcagc | tgcagcagcc | tggtgccgag | ctcgtgaaac | ctggcgcctc | cgtgaagatg | 60 |
| tcctgcaagg | cctccggcta | caccttcacc | agctacaaca | tgcactgggt | caagcagacc | 120 |
| cccggcagag | gcctggaatg | gatcggcgct | atctaccccg | gcaacggcga | cacctcctac | 180 |
| aaccagaagt | tcaagggcaa | ggccaccctg | accgccgaca | gtcctcttc | caccgcctac | 240 |
| atgcagctgt | cctccctgac | ctccgaggac | tccgccgtgt | actactgcgc | ccggtctacc | 300 |
| tactacggcg | gcgactggta | cttcaacgtg | tgggcgctg | gcaccaccgt | gacagtgtct | 360 |
| gctggtggcg | gaggatctgg | cggaggcggt | agtggcggtg | gcggatctca | gatcgtgctg | 420 |
| tcccagtccc | ctgccatcct | gtctgctagc | cctggcgaga | aagtgacaat | gacctgccgg | 480 |
| gcctcctcct | ccgtgtccta | catccactgg | ttccagcaga | agcccggctc | cagccccaag | 540 |
| ccttggatct | acgccacctc | caacctggcc | tctggcgtgc | cagtgcggtt | ttccggctct | 600 |

```
ggctctggca cctcttacag cctgaccatc tcccgggtgg aagccgagga tgccgccacc    660
tactactgcc agcagtggac cagcaaccct cccacctttg gaggcggcac caagctggaa    720
atcaagggcg aggtggtgc aggaggcggt ggagagctca cggaagccca gcgccgggc     780 ctgcaggtgg ccctggagga atttcacaag caccgccg tgcagtgggc cttccaggag      840
accagtgtgg agagcgccgt ggacacgccc ttcccagctg gaatatttgt gaggctggaa    900
tttaagctgc agcagacaag ctgccggaag agggactgga agaaacccga gtgcaaagtc    960
aggcccaatg ggaggaaacg gaaatgcctg gcctgcatca aactgggctc tgaggacaaa   1020
gttctgggcc ggttggtcca ctgccccata gagacccaag ttctgcggga ggctgaggag   1080
caccaggaga cccagtgcct cagggtgcag cgggctggtg aggaccccca cagcttctac   1140
ttccctggac agttcgcctt ctccaaggcc ctgccccgca gctga                   1185
```

<210> SEQ ID NO 14
<211> LENGTH: 417
<212> TYPE: PRT
<213> ORGANISM: Artificial Sequence
<220> FEATURE:
<223> OTHER INFORMATION: SYNTHESIZED

<400> SEQUENCE: 14

```
Met Glu Trp Ser Trp Val Phe Leu Phe Phe Leu Ser Val Thr Thr Gly
1               5                   10                  15

Val His Ser His His His His His His His His Gln Val Gln
            20                  25                  30

Leu Gln Gln Pro Gly Ala Glu Leu Val Lys Pro Gly Ala Ser Val Lys
        35                  40                  45

Met Ser Cys Lys Ala Ser Gly Tyr Thr Phe Thr Ser Tyr Asn Met His
    50                  55                  60

Trp Val Lys Gln Thr Pro Gly Arg Gly Leu Glu Trp Ile Gly Ala Ile
65                  70                  75                  80

Tyr Pro Gly Asn Gly Asp Thr Ser Tyr Asn Gln Lys Phe Lys Gly Lys
                85                  90                  95

Ala Thr Leu Thr Ala Asp Lys Ser Ser Thr Ala Tyr Met Gln Leu
            100                 105                 110

Ser Ser Leu Thr Ser Glu Asp Ser Ala Val Tyr Tyr Cys Ala Arg Ser
        115                 120                 125

Thr Tyr Tyr Gly Gly Asp Trp Tyr Phe Asn Val Trp Gly Ala Gly Thr
    130                 135                 140

Thr Val Thr Val Ser Ala Gly Gly Gly Gly Ser Gly Gly Gly Gly Ser
145                 150                 155                 160

Gly Gly Gly Gly Ser Gln Ile Val Leu Ser Gln Ser Pro Ala Ile Leu
                165                 170                 175

Ser Ala Ser Pro Gly Glu Lys Val Thr Met Thr Cys Arg Ala Ser Ser
            180                 185                 190

Ser Val Ser Tyr Ile His Trp Phe Gln Gln Lys Pro Gly Ser Ser Pro
        195                 200                 205

Lys Pro Trp Ile Tyr Ala Thr Ser Asn Leu Ala Ser Gly Val Pro Val
    210                 215                 220

Arg Phe Ser Gly Ser Gly Ser Gly Thr Ser Tyr Ser Leu Thr Ile Ser
225                 230                 235                 240

Arg Val Glu Ala Glu Asp Ala Ala Thr Tyr Tyr Cys Gln Gln Trp Thr
                245                 250                 255
```

```
Ser Asn Pro Pro Thr Phe Gly Gly Thr Lys Leu Glu Ile Lys Gly
            260                 265                 270
Gly Gly Gly Ala Gly Gly Gly Glu Leu Thr Glu Ala Gln Arg Arg
        275                 280                 285
Gly Leu Gln Val Ala Leu Glu Glu Phe His Lys His Pro Pro Val Gln
    290                 295                 300
Trp Ala Phe Gln Glu Thr Ser Val Glu Ser Ala Val Asp Thr Pro Phe
305                 310                 315                 320
Pro Ala Gly Ile Phe Val Arg Leu Glu Phe Lys Leu Gln Gln Thr Ser
                325                 330                 335
Cys Arg Lys Arg Asp Trp Lys Lys Pro Glu Cys Lys Val Arg Pro Asn
                340                 345                 350
Gly Arg Lys Arg Lys Cys Leu Ala Cys Ile Lys Leu Gly Ser Glu Asp
                355                 360                 365
Lys Val Leu Gly Arg Leu Val His Cys Pro Ile Glu Thr Gln Val Leu
370                 375                 380
Arg Glu Ala Glu Glu His Gln Glu Thr Gln Cys Leu Arg Val Gln Arg
385                 390                 395                 400
Ala Gly Glu Asp Pro His Ser Phe Tyr Phe Pro Gly Gln Phe Ala Phe
                405                 410                 415
Ser
```

<210> SEQ ID NO 15
<211> LENGTH: 388
<212> TYPE: PRT
<213> ORGANISM: Artificial Sequence
<220> FEATURE:
<223> OTHER INFORMATION: SYNTHESIZED

<400> SEQUENCE: 15

```
Gln Val Gln Leu Gln Gln Pro Gly Ala Glu Leu Val Lys Pro Gly Ala
1               5                   10                  15
Ser Val Lys Met Ser Cys Lys Ala Ser Gly Tyr Thr Phe Thr Ser Tyr
                20                  25                  30
Asn Met His Trp Val Lys Gln Thr Pro Gly Arg Gly Leu Glu Trp Ile
            35                  40                  45
Gly Ala Ile Tyr Pro Gly Asn Gly Asp Thr Ser Tyr Asn Gln Lys Phe
        50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ser Thr Tyr Tyr Gly Gly Asp Trp Tyr Phe Asn Val Trp Gly
                100                 105                 110
Ala Gly Thr Thr Val Thr Val Ser Ala Gly Gly Gly Ser Gly Gly
            115                 120                 125
Gly Gly Ser Gly Gly Gly Gly Ser Gln Ile Val Leu Ser Gln Ser Pro
        130                 135                 140
Ala Ile Leu Ser Ala Ser Pro Gly Glu Lys Val Thr Met Thr Cys Arg
145                 150                 155                 160
Ala Ser Ser Ser Val Ser Tyr Ile His Trp Phe Gln Gln Lys Pro Gly
                165                 170                 175
Ser Ser Pro Lys Pro Trp Ile Tyr Ala Thr Ser Asn Leu Ala Ser Gly
                180                 185                 190
Val Pro Val Arg Phe Ser Gly Ser Gly Ser Gly Thr Ser Tyr Ser Leu
```

```
                    195                 200                 205
Thr Ile Ser Arg Val Glu Ala Glu Asp Ala Ala Thr Tyr Tyr Cys Gln
210                 215                 220

Gln Trp Thr Ser Asn Pro Pro Thr Phe Gly Gly Gly Thr Lys Leu Glu
225                 230                 235                 240

Ile Lys Gly Gly Gly Gly Ala Gly Gly Gly Gly Glu Leu Thr Glu Ala
                    245                 250                 255

Gln Arg Arg Gly Leu Gln Val Ala Leu Glu Glu Phe His Lys His Pro
            260                 265                 270

Pro Val Gln Trp Ala Phe Gln Glu Thr Ser Val Glu Ser Ala Val Asp
        275                 280                 285

Thr Pro Phe Pro Ala Gly Ile Phe Val Arg Leu Glu Phe Lys Leu Gln
290                 295                 300

Gln Thr Ser Cys Arg Lys Arg Asp Trp Lys Lys Pro Glu Cys Lys Val
305                 310                 315                 320

Arg Pro Asn Gly Arg Lys Arg Lys Cys Leu Ala Cys Ile Lys Leu Gly
                    325                 330                 335

Ser Glu Asp Lys Val Leu Gly Arg Leu Val His Cys Pro Ile Glu Thr
            340                 345                 350

Gln Val Leu Arg Glu Ala Glu His Gln Glu Thr Gln Cys Leu Arg
        355                 360                 365

Val Gln Arg Ala Gly Glu Asp Pro His Ser Phe Tyr Phe Pro Gly Gln
370                 375                 380

Phe Ala Phe Ser
385

<210> SEQ ID NO 16
<211> LENGTH: 423
<212> TYPE: PRT
<213> ORGANISM: Artificial Sequence
<220> FEATURE:
<223> OTHER INFORMATION: SYNTHESIZED

<400> SEQUENCE: 16

Met Glu Trp Ser Trp Val Phe Leu Phe Leu Ser Val Thr Thr Gly
1               5                   10                  15

Val His Ser His His His His His His His His Gln Val Gln
                20                  25                  30

Leu Gln Gln Pro Gly Ala Glu Leu Val Lys Pro Gly Ala Ser Val Lys
            35                  40                  45

Met Ser Cys Lys Ala Ser Gly Tyr Thr Phe Thr Ser Tyr Asn Met His
50                  55                  60

Trp Val Lys Gln Thr Pro Gly Arg Gly Leu Glu Trp Ile Gly Ala Ile
65                  70                  75                  80

Tyr Pro Gly Asn Gly Asp Thr Ser Tyr Asn Gln Lys Phe Lys Gly Lys
                85                  90                  95

Ala Thr Leu Thr Ala Asp Lys Ser Ser Thr Ala Tyr Met Gln Leu
            100                 105                 110

Ser Ser Leu Thr Ser Glu Asp Ser Ala Val Tyr Tyr Cys Ala Arg Ser
        115                 120                 125

Thr Tyr Tyr Gly Gly Asp Trp Tyr Phe Asn Val Trp Gly Ala Gly Thr
130                 135                 140

Thr Val Thr Val Ser Ala Gly Gly Gly Ser Gly Gly Gly Ser
145                 150                 155                 160

Gly Gly Gly Gly Ser Gln Ile Val Leu Ser Gln Ser Pro Ala Ile Leu
```

```
                    165                 170                 175
Ser Ala Ser Pro Gly Glu Lys Val Thr Met Thr Cys Arg Ala Ser Ser
            180                 185                 190

Ser Val Ser Tyr Ile His Trp Phe Gln Gln Lys Pro Gly Ser Ser Pro
        195                 200                 205

Lys Pro Trp Ile Tyr Ala Thr Ser Asn Leu Ala Ser Gly Val Pro Val
    210                 215                 220

Arg Phe Ser Gly Ser Gly Ser Gly Thr Ser Tyr Ser Leu Thr Ile Ser
225                 230                 235                 240

Arg Val Glu Ala Glu Asp Ala Ala Thr Tyr Tyr Cys Gln Gln Trp Thr
                245                 250                 255

Ser Asn Pro Pro Thr Phe Gly Gly Gly Thr Lys Leu Glu Ile Lys Gly
            260                 265                 270

Gly Gly Gly Ala Gly Gly Gly Gly Glu Leu Thr Glu Ala Gln Arg Arg
        275                 280                 285

Gly Leu Gln Val Ala Leu Glu Glu Phe His Lys His Pro Pro Val Gln
    290                 295                 300

Trp Ala Phe Gln Glu Thr Ser Val Glu Ser Ala Val Asp Thr Pro Phe
305                 310                 315                 320

Pro Ala Gly Ile Phe Val Arg Leu Glu Phe Lys Leu Gln Gln Thr Ser
                325                 330                 335

Cys Arg Lys Arg Asp Trp Lys Lys Pro Glu Cys Lys Val Arg Pro Asn
            340                 345                 350

Gly Arg Lys Arg Lys Cys Leu Ala Cys Ile Lys Leu Gly Ser Glu Asp
        355                 360                 365

Lys Val Leu Gly Arg Leu Val His Cys Pro Ile Glu Thr Gln Val Leu
    370                 375                 380

Arg Glu Ala Glu Glu His Gln Glu Thr Gln Cys Leu Arg Val Gln Arg
385                 390                 395                 400

Ala Gly Glu Asp Pro His Ser Phe Tyr Phe Pro Gly Gln Phe Ala Phe
                405                 410                 415

Ser Lys Ala Leu Pro Arg Ser
            420

<210> SEQ ID NO 17
<211> LENGTH: 394
<212> TYPE: PRT
<213> ORGANISM: Artificial Sequence
<220> FEATURE:
<223> OTHER INFORMATION: SYNTHESIZED

<400> SEQUENCE: 17

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
```

```
                100             105             110
Ala Gly Thr Thr Val Thr Val Ser Ala Gly Gly Gly Ser Gly Gly
            115                 120                 125

Gly Gly Ser Gly Gly Gly Ser Gln Ile Val Leu Ser Gln Ser Pro
    130                 135                 140

Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
        195                 200                 205

Thr Ile Ser Arg Val Glu Ala Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys Gly Gly Gly Gly Ala Gly Gly Gly Gly Glu Leu Thr Glu Ala
                245                 250                 255

Gln Arg Arg Gly Leu Gln Val Ala Leu Glu Glu Phe His Lys His Pro
            260                 265                 270

Pro Val Gln Trp Ala Phe Gln Glu Thr Ser Val Glu Ser Ala Val Asp
        275                 280                 285

Thr Pro Phe Pro Ala Gly Ile Phe Val Arg Leu Glu Phe Lys Leu Gln
    290                 295                 300

Gln Thr Ser Cys Arg Lys Arg Asp Trp Lys Lys Pro Glu Cys Lys Val
305                 310                 315                 320

Arg Pro Asn Gly Arg Lys Arg Lys Cys Leu Ala Cys Ile Lys Leu Gly
                325                 330                 335

Ser Glu Asp Lys Val Leu Gly Arg Leu Val His Cys Pro Ile Glu Thr
            340                 345                 350

Gln Val Leu Arg Glu Ala Glu His Gln Glu Thr Gln Cys Leu Arg
        355                 360                 365

Val Gln Arg Ala Gly Glu Asp Pro His Ser Phe Tyr Phe Pro Gly Gln
    370                 375                 380

Phe Ala Phe Ser Lys Ala Leu Pro Arg Ser
385                 390

<210> SEQ ID NO 18
<211> LENGTH: 409
<212> TYPE: PRT
<213> ORGANISM: Artificial Sequence
<220> FEATURE:
<223> OTHER INFORMATION: SYNTHESIZED

<400> SEQUENCE: 18

Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Lys Lys
            20                  25                  30

Pro Gly Thr Ser Val Arg Ile Ser Cys Lys Thr Ser Gly Tyr Thr Phe
        35                  40                  45

Thr Glu Tyr Thr Ile His Trp Val Lys Gln Ser His Gly Lys Ser Leu
    50                  55                  60

Glu Trp Ile Gly Asn Ile Asn Pro Asn Asn Gly Gly Thr Thr Tyr Asn
```

```
            65                  70                  75                  80
        Gln Lys Phe Glu Asp Lys Ala Thr Leu Thr Val Asp Lys Ser Ser Ser
                        85                  90                  95

Thr Ala Tyr Met Glu Leu Arg Ser Leu Thr Ser Glu Asp Ser Ala Val
                        100                 105                 110

Tyr Tyr Cys Ala Ala Gly Trp Asn Phe Asp Tyr Trp Gly Gln Gly Thr
                        115                 120                 125

Thr Leu Thr Val Ser Ser Gly Gly Gly Gly Ser Gly Gly Gly Gly Ser
        130                     135                 140

Ser Gly Gly Gly Gly Ser Asp Ile Val Met Thr Gln Ser His Lys Phe
        145                 150                 155                 160

Met Ser Thr Ser Val Gly Asp Arg Val Ser Ile Ile Cys Lys Ala Ser
                        165                 170                 175

Gln Asp Val Gly Thr Ala Val Asp Trp Tyr Gln Gln Lys Pro Gly Gln
                        180                 185                 190

Ser Pro Lys Leu Leu Ile Tyr Trp Ala Ser Thr Arg His Thr Gly Val
                        195                 200                 205

Pro Asp Arg Phe Thr Gly Ser Gly Ser Gly Thr Asp Phe Thr Leu Thr
                        210                 215                 220

Ile Thr Asn Val Gln Ser Glu Asp Leu Ala Asp Tyr Phe Cys Gln Gln
        225                 230                 235                 240

Tyr Asn Ser Tyr Pro Leu Thr Phe Gly Ala Gly Thr Met Leu Asp Leu
                        245                 250                 255

Lys Gly Gly Gly Gly Ala Gly Gly Gly Gly Glu Leu Thr Glu Ala Gln
                        260                 265                 270

Arg Arg Gly Leu Gln Val Ala Leu Glu Glu Phe His Lys His Pro Pro
                        275                 280                 285

Val Gln Trp Ala Phe Gln Glu Thr Ser Val Glu Ser Ala Val Asp Thr
                        290                 295                 300

Pro Phe Pro Ala Gly Ile Phe Val Arg Leu Glu Phe Lys Leu Gln Gln
        305                     310                 315                 320

Thr Ser Cys Arg Lys Arg Asp Trp Lys Lys Pro Glu Cys Lys Val Arg
                        325                 330                 335

Pro Asn Gly Arg Lys Arg Lys Cys Leu Ala Cys Ile Lys Leu Gly Ser
                        340                 345                 350

Glu Asp Lys Val Leu Gly Arg Leu Val His Cys Pro Ile Glu Thr Gln
                        355                 360                 365

Val Leu Arg Glu Ala Glu Glu His Gln Glu Thr Gln Cys Leu Arg Val
                        370                 375                 380

Gln Arg Ala Gly Glu Asp Pro His Ser Phe Tyr Phe Pro Gly Gln Phe
        385                     390                 395                 400

Ala Phe Ser Lys Ala Leu Pro Arg Ser
                        405

<210> SEQ ID NO 19
<211> LENGTH: 403
<212> TYPE: PRT
<213> ORGANISM: Artificial Sequence
<220> FEATURE:
<223> OTHER INFORMATION: SYNTHESIZED

<400> SEQUENCE: 19

Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Lys Lys
```

-continued

```
                20                  25                  30
Pro Gly Thr Ser Val Arg Ile Ser Cys Lys Thr Ser Gly Tyr Thr Phe
                35                  40                  45
Thr Glu Tyr Thr Ile His Trp Val Lys Gln Ser His Gly Lys Ser Leu
 50                  55                  60
Glu Trp Ile Gly Asn Ile Asn Pro Asn Asn Gly Thr Thr Tyr Asn
 65                  70                  75                  80
Gln Lys Phe Glu Asp Lys Ala Thr Leu Thr Val Asp Lys Ser Ser Ser
                85                  90                  95
Thr Ala Tyr Met Glu Leu Arg Ser Leu Thr Ser Glu Asp Ser Ala Val
                100                 105                 110
Tyr Tyr Cys Ala Ala Gly Trp Asn Phe Asp Tyr Trp Gly Gln Gly Thr
                115                 120                 125
Thr Leu Thr Val Ser Ser Gly Gly Gly Ser Gly Gly Gly Gly
                130                 135                 140
Ser Gly Gly Gly Gly Ser Asp Ile Val Met Thr Gln Ser His Lys Phe
145                 150                 155                 160
Met Ser Thr Ser Val Gly Asp Arg Val Ser Ile Ile Cys Lys Ala Ser
                165                 170                 175
Gln Asp Val Gly Thr Ala Val Asp Trp Tyr Gln Gln Lys Pro Gly Gln
                180                 185                 190
Ser Pro Lys Leu Leu Ile Tyr Trp Ala Ser Thr Arg His Thr Gly Val
                195                 200                 205
Pro Asp Arg Phe Thr Gly Ser Gly Ser Gly Thr Asp Phe Thr Leu Thr
                210                 215                 220
Ile Thr Asn Val Gln Ser Glu Asp Leu Ala Asp Tyr Phe Cys Gln Gln
225                 230                 235                 240
Tyr Asn Ser Tyr Pro Leu Thr Phe Gly Ala Gly Thr Met Leu Asp Leu
                245                 250                 255
Lys Gly Gly Gly Gly Ala Gly Gly Gly Glu Leu Thr Glu Ala Gln
                260                 265                 270
Arg Arg Gly Leu Gln Val Ala Leu Glu Glu Phe His Lys His Pro Pro
                275                 280                 285
Val Gln Trp Ala Phe Gln Glu Thr Ser Val Glu Ser Ala Val Asp Thr
                290                 295                 300
Pro Phe Pro Ala Gly Ile Phe Val Arg Leu Glu Phe Lys Leu Gln Gln
305                 310                 315                 320
Thr Ser Cys Arg Lys Arg Asp Trp Lys Lys Pro Glu Cys Lys Val Arg
                325                 330                 335
Pro Asn Gly Arg Lys Arg Lys Cys Leu Ala Cys Ile Lys Leu Gly Ser
                340                 345                 350
Glu Asp Lys Val Leu Gly Arg Leu Val His Cys Pro Ile Glu Thr Gln
                355                 360                 365
Val Leu Arg Glu Ala Glu Glu His Gln Glu Thr Gln Cys Leu Arg Val
                370                 375                 380
Gln Arg Ala Gly Glu Asp Pro His Ser Phe Tyr Phe Pro Gly Gln Phe
385                 390                 395                 400
Ala Phe Ser

<210> SEQ ID NO 20
<211> LENGTH: 415
<212> TYPE: PRT
<213> ORGANISM: Artificial Sequence
<220> FEATURE:
```

-continued

<223> OTHER INFORMATION: SYNTHESIZED

<400> SEQUENCE: 20

```
Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Lys Lys
            20                  25                  30

Pro Gly Thr Ser Val Arg Ile Ser Cys Lys Thr Ser Gly Tyr Thr Phe
        35                  40                  45

Thr Glu Tyr Thr Ile His Trp Val Lys Gln Ser His Gly Lys Ser Leu
    50                  55                  60

Glu Trp Ile Gly Asn Ile Asn Pro Asn Asn Gly Gly Thr Thr Tyr Asn
65                  70                  75                  80

Gln Lys Phe Glu Asp Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ala Gly Trp Asn Phe Asp Tyr Trp Gly Gln Gly Thr
        115                 120                 125

Thr Leu Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Gly Gly Gly Gly Ala Gly Gly Gly Gly Pro Leu Gly Leu Ala Gly
            260                 265                 270

Glu Leu Thr Glu Ala Gln Arg Arg Gly Leu Gln Val Ala Leu Glu Glu
        275                 280                 285

Phe His Lys His Pro Pro Val Gln Trp Ala Phe Gln Glu Thr Ser Val
    290                 295                 300

Glu Ser Ala Val Asp Thr Pro Phe Pro Ala Gly Ile Phe Val Arg Leu
305                 310                 315                 320

Glu Phe Lys Leu Gln Gln Thr Ser Cys Arg Lys Arg Asp Trp Lys Lys
                325                 330                 335

Pro Glu Cys Lys Val Arg Pro Asn Gly Arg Lys Arg Lys Cys Leu Ala
            340                 345                 350

Cys Ile Lys Leu Gly Ser Glu Asp Lys Val Leu Gly Arg Leu Val His
        355                 360                 365

Cys Pro Ile Glu Thr Gln Val Leu Arg Glu Ala Glu His Gln Glu
    370                 375                 380

Thr Gln Cys Leu Arg Val Gln Arg Ala Gly Glu Asp Pro His Ser Phe
385                 390                 395                 400
```

Tyr Phe Pro Gly Gln Phe Ala Phe Ser Lys Ala Leu Pro Arg Ser
            405                 410                 415

<210> SEQ ID NO 21
<211> LENGTH: 409
<212> TYPE: PRT
<213> ORGANISM: Artificial Sequence
<220> FEATURE:
<223> OTHER INFORMATION: SYNTHESIZED

<400> SEQUENCE: 21

Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Lys Lys
            20                  25                  30

Pro Gly Thr Ser Val Arg Ile Ser Cys Lys Thr Ser Gly Tyr Thr Phe
        35                  40                  45

Thr Glu Tyr Thr Ile His Trp Val Lys Gln Ser His Gly Lys Ser Leu
    50                  55                  60

Glu Trp Ile Gly Asn Ile Asn Pro Asn Asn Gly Gly Thr Thr Tyr Asn
65                  70                  75                  80

Gln Lys Phe Glu Asp Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ala Gly Trp Asn Phe Asp Tyr Trp Gly Gln Gly Thr
        115                 120                 125

Thr Leu Thr Val Ser Ser Gly Gly Gly Gly Ser Gly Gly Gly Gly
    130                 135                 140

Ser Gly Gly Gly Gly Ser Asp Ile Val Met Thr Gln Ser His Lys Phe
145                 150                 155                 160

Met Ser Thr Ser Val Gly Asp Arg Val Ser Ile Ile Cys Lys Ala Ser
                165                 170                 175

Gln Asp Val Gly Thr Ala Val Asp Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Thr Asn Val Gln Ser Glu Asp Leu Ala Asp Tyr Phe Cys Gln Gln
225                 230                 235                 240

Tyr Asn Ser Tyr Pro Leu Thr Phe Gly Ala Gly Thr Met Leu Asp Leu
                245                 250                 255

Lys Gly Gly Gly Gly Ala Gly Gly Gly Pro Leu Gly Leu Ala Gly
            260                 265                 270

Glu Leu Thr Glu Ala Gln Arg Arg Gly Leu Gln Val Ala Leu Glu Glu
        275                 280                 285

Phe His Lys His Pro Pro Val Gln Trp Ala Phe Gln Glu Thr Ser Val
    290                 295                 300

Glu Ser Ala Val Asp Thr Pro Phe Pro Ala Gly Ile Phe Val Arg Leu
305                 310                 315                 320

Glu Phe Lys Leu Gln Gln Thr Ser Cys Arg Lys Arg Asp Trp Lys Lys
                325                 330                 335

Pro Glu Cys Lys Val Arg Pro Asn Gly Arg Lys Arg Lys Cys Leu Ala
            340                 345                 350

```
Cys Ile Lys Leu Gly Ser Glu Asp Lys Val Leu Gly Arg Leu Val His
            355                 360                 365

Cys Pro Ile Glu Thr Gln Val Leu Arg Glu Ala Glu Glu His Gln Glu
370                 375                 380

Thr Gln Cys Leu Arg Val Gln Arg Ala Gly Glu Asp Pro His Ser Phe
385                 390                 395                 400

Tyr Phe Pro Gly Gln Phe Ala Phe Ser
                405

<210> SEQ ID NO 22
<211> LENGTH: 140
<212> TYPE: PRT
<213> ORGANISM: Mus musculus

<400> SEQUENCE: 22

Glu Leu Ser Glu Thr Gln Arg Arg Ser Leu Gln Val Ala Leu Glu Glu
1               5                   10                  15

Phe His Lys His Pro Pro Val Gln Leu Ala Phe Gln Glu Ile Gly Val
            20                  25                  30

Asp Arg Ala Glu Glu Val Leu Phe Ser Ala Gly Thr Phe Val Arg Leu
        35                  40                  45

Glu Phe Lys Leu Gln Gln Thr Asn Cys Pro Lys Lys Asp Trp Lys Lys
    50                  55                  60

Pro Glu Cys Thr Ile Lys Pro Asn Gly Arg Arg Arg Lys Cys Leu Ala
65                  70                  75                  80

Cys Ile Lys Met Asp Pro Lys Gly Lys Ile Leu Gly Arg Ile Val His
                85                  90                  95

Cys Pro Ile Leu Lys Gln Gly Pro Gln Asp Pro Gln Glu Leu Gln Cys
            100                 105                 110

Ile Lys Ile Ala Gln Ala Gly Glu Asp Pro His Gly Tyr Phe Leu Pro
        115                 120                 125

Gly Gln Phe Ala Phe Ser Arg Ala Leu Arg Thr Lys
    130                 135                 140

<210> SEQ ID NO 23
<211> LENGTH: 134
<212> TYPE: PRT
<213> ORGANISM: Mus musculus

<400> SEQUENCE: 23

Glu Leu Ser Glu Thr Gln Arg Arg Ser Leu Gln Val Ala Leu Glu Glu
1               5                   10                  15

Phe His Lys His Pro Pro Val Gln Leu Ala Phe Gln Glu Ile Gly Val
            20                  25                  30

Asp Arg Ala Glu Glu Val Leu Phe Ser Ala Gly Thr Phe Val Arg Leu
        35                  40                  45

Glu Phe Lys Leu Gln Gln Thr Asn Cys Pro Lys Lys Asp Trp Lys Lys
    50                  55                  60

Pro Glu Cys Thr Ile Lys Pro Asn Gly Arg Arg Arg Lys Cys Leu Ala
65                  70                  75                  80

Cys Ile Lys Met Asp Pro Lys Gly Lys Ile Leu Gly Arg Ile Val His
                85                  90                  95

Cys Pro Ile Leu Lys Gln Gly Pro Gln Asp Pro Gln Glu Leu Gln Cys
            100                 105                 110

Ile Lys Ile Ala Gln Ala Gly Glu Asp Pro His Gly Tyr Phe Leu Pro
        115                 120                 125
```

```
Gly Gln Phe Ala Phe Ser
    130

<210> SEQ ID NO 24
<211> LENGTH: 714
<212> TYPE: DNA
<213> ORGANISM: Artificial Sequence
<220> FEATURE:
<223> OTHER INFORMATION: SYNTHESIZED

<400> SEQUENCE: 24
gaagtccaac tgcaacaaag cggcccggaa ctgaaaaaac cgggtacgtc tgttcgtatt      60
agttgcaaaa cctccggcta tacctttacg gaatacacca tccattgggt caaacagtca     120
cacggtaaat cgctggaatg gattggcaac atcaatccga acaatggcgg caccacgtat     180
aaccaaaaat tcgaagataa agcgaccctg acggtggaca aaagctctag tacggcctac     240
atggaactgc gctcactgac ctcggaagat agcgcagtgt attactgcgc ggccggttgg     300
aattttgact attggggcca gggcaccacg ctgaccgttt cctcatcggg cggtggcggt     360
agcggcggtg gcggttctgg cggtggcggt agtgatattg ttatgacgca gtctcataaa     420
ttcatgagca cctctgtggg tgatcgtgtt tccattatct gtaaagcaag tcaggatgtc     480
ggcaccgctg tggactggta tcagcaaaaa ccgggccaaa gcccgaaact gctgatttac     540
tgggcaagca cgcgtcacac cggcgtcccg gatcgtttta cgggcagtgg ttccggcacc     600
gacttcaccc tgacgatcac caacgttcag agcgaagacc tggctgacta cttttgtcaa     660
caatacaact cctatccgct gacctttggc gctggcacga tgctggacct gaaa           714
```